(12) United States Patent
Worley et al.

(10) Patent No.: US 6,720,175 B1
(45) Date of Patent: Apr. 13, 2004

(54) NUCLEIC ACID MOLECULE ENCODING HOMER 1B PROTEIN

(75) Inventors: Paul F. Worley; Jian Cheng Tu, both of Baltimore; Bo Xiao, Ellicott City; Daniel Leahy, Baltimore; Jutta Beneken, Baltimore; Anthony A. Lanahan, Baltimore; Paul R. Brakeman, Baltimore, all of MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/377,285

(22) Filed: Aug. 18, 1999

Related U.S. Application Data

(60) Provisional application No. 60/097,334, filed on Aug. 18, 1998, provisional application No. 60/138,426, filed on Jun. 10, 1999, provisional application No. 60/138,493, filed on Jun. 10, 1999, and provisional application No. 60/138,494, filed on Jun. 10, 1999.

(51) Int. Cl.[7] ............................ C07H 21/04; C12N 1/20; C12N 5/00; C12N 7/01; C12N 15/00

(52) U.S. Cl. ................. 435/252.3; 536/23.5; 536/23.1; 435/254.11; 435/325; 435/320.1

(58) Field of Search ............................... 536/23.1, 23.5; 530/300, 350; 435/69.1, 70.1, 252.3, 320.1, 325, 4, 235.1, 254.11

(56) References Cited

PUBLICATIONS

Xiao et al. Homer regulates the association of group 1 metabotropic glutamate receptors with multivalent complexes of homer–related, synaptic proteins. Neuron 21(4): 707–716, 1998.*

Tu et al. Homer binds a novel proline–rich motif and links group 1 metabotropic glutamate receptors with IP3 receptors. Neuron 21(4):717–26, 1998.*

Roche et al. Homer 1b regulates the trafficking of Group I metabotropic glutamate receptors. J Biol Chem 274(36): 25953–25957, 1999.*

Nickels et al. Accession No. HSA17829. GenEmbl, direct submission. Jan. 7, 1999.*

Xiao et al. Accession No. AF093262, direct submission, GenEmbl database, Nov. 5, 1998.*

Schoepp et al., "Pharmacological and functional characteristics of metabotropic excitatory amino acid receptors", *TIPS*, Dec. 1990, vol. 11, pp. 508–515.

Brakeman et al., "Homer: a protein that selectively binds metabotropic glutamate receptors", *Nature*, Mar. 20, 1997, vol. 386, pp. 284–288.

Ponting et al., "Identification of homer as a homologue of the Wiskott–Aldrich Syndrome protein suggests a receptor–binding function for WH1 domains," *J. Mol. Med.*, Nov.–Dec. 1997, vol. 75, pp. 769–771.

Abe et al., "Molecular characterization of a novel metabotropic glutamate receptor mGluR5 coupled to inositol phosphate/Ca2+ signal transduction", *J. Biol. Chem.*, Jul. 5, 1992, vol. 267, No. 9, pp. 13361–13368.

Nagase et al., "Prediction of the coding sequences of unidentified human genes. VII. The complete sequence of 100 new cDNA clones from brain which can code for large proteins in vitro." *DNA Res.*, 1997, vol. 4, No. 2, pp. 141–150.

* cited by examiner

*Primary Examiner*—Elizabeth Kemmerer
*Assistant Examiner*—Bridget E. Bunner
(74) *Attorney, Agent, or Firm*—Gray Cary Ware & Freidenrich LLP; Lisa A. Haile

(57) ABSTRACT

A method is provided for identifying a compound that modulates a cellular response associated with Homer and mediated by a cell-surface or an intracellular receptor. A method is further provided for identifying a compound that modulates receptor activated calcium mobilization associated with Homer. A method is provided for identifying a compound that inhibits Homer protein activity based on the crystal structure coordinates of Homer protein binding domain. A method is also provided for identifying a compound that affects the formation of cell surface receptors into clusters. Also provided are nucleic acids encoding Homer proteins as well as Homer proteins, and Homer interacting proteins.

7 Claims, 55 Drawing Sheets

EVH1 Domain (Homer)     PH Domain (Spectrin)     PTB Domain (IRS-1)
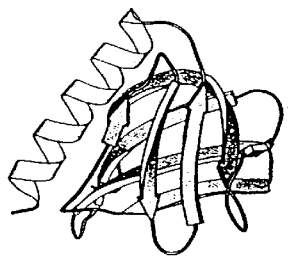 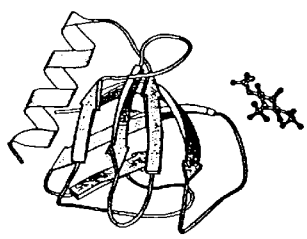 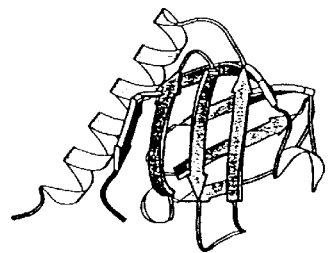
FIG. 4A     FIG. 4B     FIG. 4C
 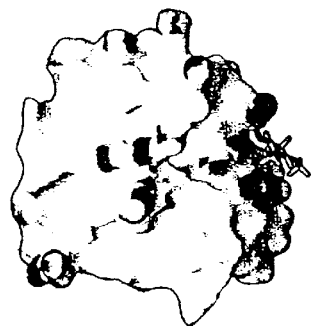 
FIG. 4D     FIG. 4E     FIG. 4F

H-Homer-1a

MGEQPIFSTRAHVFQIDPNTKKNWVPTSKHAVTVSYFYDSTRNVYRIISLDGSKAII
NSTITPNMTFTKTSQKFGQWADSRANTVYGLGFSSEHHLSKFAEKFQEFKEAARL
AKEKSQEKMELTSTPSQESAGGDLQSPLTPESINGTDDERTPDVTQNSEPRAEPTQ
NALPFSHSSAISKHWEAELATLKGNNAKLTAALLESTANVKQWKQQLAAYQEEA
ERLHKRVISGLMSIGI

FIG. 7

H-Homer-1bGenBank

ATGGGGGAGCAGCCGATTTTCAGCACTCGAGCTCATGTCTTCCAAATTGACCCAA
ACACAAAGAAGAACTGGGTACCCACCAGCAAGCATGCAGTTACTGTGTCTTATTT
CTATGACAGCACAAGAAATGTGTATAGGATAATCAGTTTAGATGGCTCAAAGGC
AATAATAAATAGTACCATCACCCCAAACATGACATTTACTAAAACATCTCAGAAG
TTTGGCCAGTGGGCTGATAGCCGGGCAAACACCGTTTATGGATTGGGATTCTCCT
CTGAGCATCATCTTTCGAAATTTGCAGAAAAGTTTCAGGAATTTAAAGAAGCTGC
TCGACTAGCAAAGGAAAAATCACAAGAGAAGATGGAACTTACCAGTACACCTTC
ACAGGAATCCGCAGGCGGGGATCTTCAGTCTCCTTTAACACCGGAAAGTATCAAC
GGGACAGATGATGAAAGAACACCTGATGTGACACAGAACTCAGAGCCAAGGGCT
GAACCAACTCAGAATGCATTGCCATTTTCACATAGTTCAGCAATCAGCAAACATT
GGGAGGCTGAACTGGCTACCCTCAAAGGAAATAATGCCAAACTCACTGCAGCCC
TGCTGGAGTCCACTGCCAATGTGAAACAATGGAAACAGCAACTTGCTGCCTATCA
AGAGGAAGCAGAACGTCTGCACAAGCGGGTGACTGAACTTGAATGTGTTAGTAG
CCAAGCAAATGCAGTACATACTCATAAGACAGAATTAAATCAGACAATACAAGA
ACTGGAAGAGACACTGAAACTGAAGGAAGAGGAAATAGAAAGGTTAAAACAAG
AAATTGATAATGCCAGAGAACTACAAGAACAGAGGGATTCTTTGACTCAGAAAC
TACAGGAAGTAGAAATTCGGAACAAAGACCTGGAGGGACAACTGTCTGACTTAG
AGCAACGTCTGGAGAAAAGTCAGAATGAACAAGAAGCTTTTCGCAATAACCTGA
AGACACTCTTAGAAATTCTGGATGGAAAGATATTTGAACTAACAGAATTACGAG
ATAACTTGGCCAAGCTACTAGAATGCAGCTAAGGAAAGTGAAATTTCAGTGCCA
ATTAATTAAAAGATACACTGTCTCTCTTCATAGGACTGTTTAGCTCTGCATCAAG
ATTGCACAAAAAAAAAAAAAAAAA

FIG. 8

H-Homer-1b

MGEQPIFSTRAHVFQIDPNTKKNWVPTSKHAVTVSYFYDSTRNVYRIISLDGSKAII
NSTITPNMTFTKTSQKFGQWADSRANTVYGLGFSSEHHLSKFAEKFQEFKEAARL
AKEKSQEKMELTSTPSQESAGGDLQSPLTPESINGTDDERTPDVTQNSEPRAEPTQ
NALPFSHSSAISKHWEAELATLKGNNAKLTAALLESTANVKQWKQQLAAYQEEA
ERLHKRVTELECVSSQANAVHTHKTELNQTIQELEETLKLKEEEIERLKQEIDNAR
ELQEQRDSLTQKLQEVEIRNKDLEGQLSDLEQRLEKSQNEQEAFRNNLKTLLEILD
GKIFELTELRDNLAKLLECS*

FIG. 9

H-Homer-2aGenBank

ATGGGGGAGCAGCCGATCTTCACCACCCGAGCGCATGTCTTCCAGATTGACCC
CAACACCAAGAAGAACTGGATGCCTGCGAGCAAGCAGGCGGTCACCGTTTCC
TACTTCTATGATGTCACAAGGAACAGCTATCGGATCATCAGTGTGGACGGAGC
CAAGGTGATCATAAACAGCACAATCACACCGAATATGACCTTCACCAAAACGT
CACAGAAGTTTGGGCAGTGGGCCGACAGCAGAGCCAACACAGTGTTTGGTTTG
GGGTTTTCCTCTGAGCAGCAGCTGACAAAGTTTGCAGAGAAATTCCAGGAGGT
GAAAGAAGCTGCCAAGATAGCCAAAGACAAGACGCAGGAGAAAATCGAGAC
CTCAAGTAATCATTCCCAAGCATCCAGTGTCAACGGGACGGACGAGGAAAAG
GCCTCTCACGCCGGTCCAGCCAACACACAACTGAAGTCTGAGAATGACAAGCT
GAAGATTGCCTTGACGCAGAGCGCAGCCAACGTGAAGAAGTGGGAGATCGAG
CTGCAGACCCTTCGGGAGAGCAATGCACGGCTGACCACAGCACTGCAGGAGT
CGGCAGCCAGTGTGGAGCAGTGGAAGAGGCAGTTCTCCATCTGCCGTGATGA
GAATGACCGGCTCCGCAACAAGATTGATGAGCTGGAAGAACAATGCAGTGAG
ATCAACAGAGAGAAGGAGAAGAACACGCAGCTGAAGAGGAGGATCGAGGAG
CTGGAGGCAGAGCTCCGAGAAAAGGAGACAGAGCTGAAAGATCTCCGAAAAC
AAAGTGAAATCATACCTCAGCTCATGTCAGAGTGCGAATATGTCTCTGAGAAG
CTAGAGGCGGCAGAGAGAGACAATCAAAACCTGGAAGACAAAGTGCGTTCCT
TAAAGACAGACATTGAGGAGAGCAAATACCGACAGCGCCACCTGAAGGTGGA
GTTGAAGAGCTTCCTGGAGGTGCTGGACGGGAAGATTGACGACCTGCATGACT
TCCGCCGAGGGCTCTCCAAGCTGGGCACCGATAACTAGGGCTGGCCGAGGCCC
AGGCCCCGCCCGTGAGTCCCAAGCGTGTGTGCGAGACCAGATAGCTCTAGGAC
GTTCTTCTGTGTGCATTGCTTCTGTAAATGCAGGCGCAGTTTGTCGTGTTTCCA
AACCAGTTGTGCCGTCCACTCACTCCTTTTCAGAATAGAAATCTCCTCTCGCTT
CTCTGGCCTTGTGAGGTTGTGGACAACTGGAAGATTCTGACTCAGGAATCCAG
AACTAGGTCTACCTTCAACATTTATGCAGTCAGGGCAGGGATGTTTATATCTTT
CATAAGGGCTGTTGCAACCATATGAACTGAAAAAACACGCATTTGTAATCCA
AATATTGATATTCTTTACACCAAGCCATCAGGCTCCTTTTATCAAATAGCATTC
AGAGTATTTGAATGTCCACCAGACACCAGCCCCGGGGGGCACAGAGAGAACA
ACATTCCTCTCTGTCAACATCGAGAGGCTTTAAAACAACTGTTTAGTGGAAAC
TTTCTGAGAGATGGAAAACAAGCTTCTGGTGGGTGCATTTTCTGGCCCGGAGT
TGCCTGCATCCACGCTACTGCCCCCTGCCCCCCGCCCCCCCAGTTTGTACGGTT
GCAACAGTGTTCCTTTTCTTGGTTTTAATTTCTGAGCAGATGATTTGCTGTGGG
AACAGCACACAGTGAGGGTGCCTAGCACAATGTCTGGCACAAAGTAGGTGCT
TAATAAATATTTGTTCAATTAAAAAAA

FIG. 10

H-Homer-2a

MGEQPIFTTRAHVFQIDPNTKKNWMPASKQAVTVSYFYDVTRNSYRIISVDGAKV
IINSTITPNMTFTKTSQKFGQWADSRANTVFGLGFSSEQQLTKFAEKFQEVKEAAK
IAKDKTQEKIETSSNHSQASSVNGTDEEKASHAGPANTQLKSENDKLKIALTQSAA
NVKKWEIELQTLRESNARLTTALQESAASVEQWKRQFSICRDENDRLRNKIDELE
EQCSEINREKEKNTQLKRRIEELEAELREKETELKDLRKQSEIIPQLMSECEYVSEK
LEAAERDNQNLEDKVRSLKTDIEESKYRQRHLKVELKSFLEVLDGKIDDLHDFRR
GLSKLGTDN*

FIG. 11

H-Homer-2bGenBank

ATGGGGGAGCAGCCGATCTTCACCACCCGAGCGCATGTCTTCCAGATTGACCC
CAACACCAAGAAGAACTGGATGCCTGCGAGCAAGCAGGCGGTCACCGTTTCC
TACTTCTATGATGTCACAAGGAACAGCTATCGGATCATCAGTGTGGACGGAGC
CAAGGTGATCATAAACAGCACAATCACACCGAATATGACCTTCACCAAAACGT
CACAGAAGTTTGGGCAGTGGGCCGACAGCAGAGCCAACACAGTGTTTGGTTTG
GGGTTTTCCTCTGAGCAGCAGCTGACAAAGTTTGCAGAGAAATTCCAGGAGGT
GAAAGAAGCTGCCAAGATAGCCAAAGACAAGACGCAGGAGAAAATCGAGAC
CTCAAGTAATCATTCCCAAGAATCTGGGCGTGAAACCCCATCTTCTACTCAGG
CATCCAGTGTCAACGGGACGGACGAGGAAAAGGCCTCTCACGCCGGTCCAGC
CAACACACAACTGAAGTCTGAGAATGACAAGCTGAAGATTGCCTTGACGCAG
AGCGCAGCCAACGTGAAGAAGTGGGAGATCGAGCTGCAGACCCTTCGGGAGA
GCAATGCACGGCTGACCACAGCACTGCAGGAGTCGGCAGCCAGTGTGGAGCA
GTGGAAGAGGCAGTTCTCCATCTGCCGTGATGAGAATGACCGGCTCCGCAACA
AGATTGATGAGCTGGAAGAACAATGCAGTGAGATCAACAGAGAGAAGGAGA
AGAACACGCAGCTGAAGAGGAGGATCGAGGAGCTGGAGGCAGAGCTCCGAG
AAAAGGAGACAGAGCTGAAAGATCTCCGAAAACAAAGTGAAATCATACCTCA
GCTCATGTCAGAGTGCGAATATGTCTCTGAGAAGCTAGAGGCGGCAGAGAGA
GACAATCAAAACCTGGAAGACAAAGTGCGTTCCTTAAAGACAGACATTGAGG
AGAGCAAATACCGACAGCGCCACCTGAAGGTGGAGTTGAAGAGCTTCCTGGA
GGTGCTGGACGGGAAGATTGACGACCTGCATGACTTCCGCCGAGGGCTCTCCA
AGCTGGGCACCGATAACTAGGGCTGGCCGAGGCCCAGGCCCCGCCCGTGAGT
CCCAAGCGTGTGTGCGAGACCAGATAGCTCTAGGACGTTCTTCTGTGTGCATT
GCTTCTGTAAATGCAGGCGCAGTTTGTCGTGTTTCCAAACCAGTTGTGCCGTCC
ACTCACTCCTTTTCAGAATAGAAATCTCCTCTCGCTTCTCTGGCCTTGTGAGGT
TGTGGACAACTGGAAGATTCTGACTCAGGAATCCAGAACTAGGTCTACCTTCA
ACATTTATGCAGTCAGGGCAGGGATGTTTATATCTTTCATAAGGGCTGTTGCA
ACCATATGAACTGAAAAAACACGCATTTTGTAATCCAAATATTGATATTCTTT
ACACCAAGCCATCAGGCTCCTTTTATCAAATAGCATTCAGAGTATTTGAATGT
CCACCAGACACCAGCCCCGGGGGGCACAGAGAGAACAACATTCCTCTCTGTC
AACATCGAGAGGCTTTAAAACAACTGTTTAGTGGAAACTTTCTGAGAGATGGA
AAACAAGCTTCTGGTGGGTGCATTTTCTGGCCCGGAGTTGCCTGCATCCACGC
TACTGCCCCCTGCCCCCCGCCCCCCAGTTTGTACGGTTGCAACAGTGTTCCTT
TTCTTGGTTTTAATTTCTGAGCAGATGATTTGCTGTGGGAACAGCACACAGTGA
GGGTGCCTAGCACAATGTCTGGCACAAAGTAGGTGCTTAATAAATATTTGTTC
AATTAAAAAAA

FIG. 12

H-Homer-2b

MGEQPIFTTRAHVFQIDPNTKKNWMPASKQAVTVSYFYDVTRNSYRIISVDGAKV
IINSTITPNMTFTKTSQKFGQWADSRANTVFGLGFSSEQQLTKFAEKFQEVKEAAK
IAKDKTQEKIETSSNHSQESGRETPSSTQASSVNGTDEEKASHAGPANTQLKSEND
KLKIALTQSAANVKKWEIELQTLRESNARLTTALQESAASVEQWKRQFSICRDEN
DRLRNKIDELEEQCSEINREKEKNTQLKRRIEELEAELREKETELKDLRKQSEIIPQL
MSECEYVSEKLEAAERDNQNLEDKVRSLKTDIEESKYRQRHLKVELKSFLEVLDG
KIDDLHDFRRGLSKLGTDN*

FIG. 13

H-Homer-3GenBank

GCACGAGGGCGCATGACTAGTTGGGGCCAAACCAGTGCTCCTGCCACCTCTCT
GGCTGCCCCCTAGAGCCTGCCCATCCCAGCCTGACCAATGTCCACAGCCAGGG
AGCAGCCAATCTTCAGCACACGGGCGCACGTGTTCCAAATTGACCCAGCCACC
AAGCGAAACTGGATCCCAGCGGGCAAGCACGCACTCACTGTCTCCTATTTCTA
CGATGCCACCCGCAATGTGTACCGCATCATCAGCATCGGAGGCGCCAAGGCCA
TCATCAACAGCACTGTCACTCCCAACATGACCTTCACCAAAACTTCCCAGAAG
TTCGGGCAGTGGGCCGACAGTCGCGCCAACACAGTCTACGGCCTGGGCTTTGC
CTCTGAACAGCATCTGACACAGTTTGCCGAGAAGTTCCAGGAAGTGAAGGAA
GCAGCCAGGCTGGCCAGGGAGAAATCTCAGGATGGCGGGGAGCTCACCAGTC
CAGCCCTGGGGCTCGCCTCCCACCAGGTCCCCCCGAGCCCTCTCGTCAGTGCC
AACGGCCCCGGCGAGGAAAAACTGTTCCGCAGCCAGAGCGCTGATGCCCCCG
GCCCCACAGAGCGCGAGCGGCTAAAGAAGATGTTGTCTGAGGGCTCCGTGGG
CGAGGTACAGTGGGAGGCCGAGTTTTTCGCACTGCAGGACAGCAACAACAAG
CTGGCAGGCGCCCTGCGAGAGGCCAACGCCGCCGCAGCCCAGTGGAGGCAGC
AGCTGGAGGCTCAGCGTGCAGAGGCCGAGCGGCTGCGGCAGCGGGTGGCTGA
GCTGGAGGCTCAGGCAGCTTCAGAGGTGACCCCCACCGGTGAGAAGGAGGGG
CTGGGCCAGGGCCAGTCGCTGGAACAGCTGGAAGCTCTGGTGCAAACCAAGG
ACCAGGAGATTCAGACCCTGAAGAGTCAGACTGGGGGGCCCCGCGAGGCCCT
GGAGGCTGCCGAGCGTGAGGAGACTCAGCAGAAGGTGCAGACCCGCAATGCG
GAGTTGGAGCACCAGCTGCGGGCGATGGAGCGCAGCCTGGAGGAGGCACGGG
CAGAGCGGGAGCGGGCGCGGGCTGAGGTGGGCCGGGCAGCGCAGCTGCTGGA
CGTCAGCCTGTTTGAGCTGAGTGAGCTGCGTGAGGGCCTGGCCCGCCTGGCTG
AGGCTGCGCCCTGAGCCGGGGCTGGTTTTCTATGAACGATTCCGGCCTGGGAT
GCGGGCCAGGCTGCAGGCGGCATAGTTGGGCCCATTCGTCCTGGAAAGGGAC
TGGGGGGTCCCAACTTAGCCCTGGGTGGGCCGGGCCGGGNTGGGCTGGGGTG
GGCCCCAGTCGGCTCTGGTTGTTGGCAGCTTTGGGGCTGTTTTGAGCTTCTCA
TTGTGTAGAATTTCTAGATCCCCCGATTACATTTCTAAGCGTGAAAAAAAAAA
AAAAAAAAAAA

FIG. 14

H-Homer-3

MSTAREQPIFSTRAHVFQIDPATKRNWIPAGKHALTVSYFYDATRNVYRIISIGGA
KAIINSTVTPNMTFTKTSQKFGQWADSRANTVYGLGFASEQHLTQFAEKFQEVKE
AARLAREKSQDGGELTSPALGLASHQVPPSPLVSANGPGEEKLFRSQSADAPGPTE
RERLKKMLSEGSVGEVQWEAEFFALQDSNNKLAGALREANAAAAQWRQQLEAQ
RAEAERLRQRVAELEAQAASEVTPTGEKEGLGQGQSLEQLEALVQTKDQEIQTLK
SQTGGPREALEAAEREETQQKVQTRNAELEHQLRAMERSLEEARAERERARAEV
GRAAQLLDVSLFELSELREGLARLAEAAP

FIG. 15 r-i30

CACGCGTCCGTGGCGGAGCTGCAGCAGCTGCAGCAGTTGCAGGAGTTCGATAT
CCCCACGGGCCGGGAGGCTCTGCGGGGCAACCACAGCGCCCTGCTACGGGTGG
CCAACTACTGTGAGGATAACTACTTGCAGGCCACAGACAAGCGGAAGGCGCTG
GAAGAGACGATGGCTTTCACCACCCAGGCCCTGGCCAGTGTAGCCTATCAAGTG
GGTAACCTGGCGGGGCACACGCTTCGAATGCTGGATCTACAGGGTGCTGCCCTG
CGGCAGGTGGAAGCCAAGATGAGCACACTGGGCCAGATGGTGAACATGCACCT
GGAGAAAGTAGCCAGAAGGGAGATTGGCACGTTGGCCACTGTCGTGCGGCTGC
CCCCTAGCCAGAAGGTCATCCCTCCTGAGAGCCTGCCTCCCCTCACTCCCTACT
GCAGAAAACCCCTCAACTTTGCCTGCTTGGATGATGTTGGCCATGGAGTCAAGG
ACTTGAGCACACAGCTGTCACGGACCGGGACCCTGTCTCGCAAGAGCATAAAG
GCGCCCGCTACACCTGCCTCTGCCACGCTGGGGAGACCACCCCGGATCCCTGAG
CCGGTGCAGCTCCCAGCGGTGCCAGACGGCAAGCTCTCCGCTGCCTCCTCTGTG
TCTTCCTTGGCCTCCGCAGGCAGTGCAGAAGGTGCCAGTGGGATCCCCAGTCC
AAGGGACAGGTAGCACCTGCAACCCCGCCTCCTCCACCTATAGCGCCTGTAACT
CCACCTCCTCCACCATTGCCTGCTGAGATCTTCTTGCTGCCCCCTCCGATGGAGG
AGTCCCAGCCCCCTCCGGAAACAGAGTTGCCCCTGCCTCCTCCTCCGGCTCTAC
AGGGGGATGAACTGGGGCTGCTGCCTCCGCCTCCACCAGGTTTTGGACCGGATG
AGCCCAGCTGGGTCCCTGCTGCCTACTTGGAGAAAGTGGTGACGCTGTACCCAT
ACACCCGGCAGAAGGACAATGAGCTCTCCTTTTCTGAAGGAACCGTCATCTGTG
TCACTCGACGCTACTCAGATGGCTGGTGTGAGGGTGTCAGCTCAGAGGGCACTG
GATTCTTCCAGGGAACTATGTGGAGCCCAGCTGCTGACAGCCCAGATCTGTCC
CTGCCTCTTTGGTGGGCCTCTTGAGCCCCAAGAAGCCACCTTCCACTCAAAGCT
GGACTAAGGACCTGTCTACCTCTTGGGCTGTGAACTGTGTTCAGTCCCACACAG
CAGTAGGAAGGGGTATGGGATGGGCTAGAGAGTGGTGGTACTGAGGACGATTG
CTCCAGATGGCAAGAACAAAACAAAACAAACCAAGAAGTTAAGTTTAAGCACC
TTGCCCAGAGGACCCCCTAGCTCATGCACCGATCGCCAGCATTGAATAAAACTG
TTGACCTCCAGGATTGTT

FIG. 16 r-i30(1)

HASVAELQQLQQLQEFDIPTGREALRGNHSALLRVANYCEDNYLQATDKRKALEETMAFT
TQALASVAYQVGNLAGHTLRMLDLQGAALRQVEAKMSTLGQMVNMHLEKVARREIGTL
ATVVRLPPSQKVIPPESLPPLTPYCRKPLNFACLDDVGHGVKDLSTQLSRTGTLSRKSIKAPA
TPASATLGRPPRIPEPVQLPAVPDGKLSAASSVSSLASAGSAEGASGIPQSKGQVAPATPPPPP
IAPVTPPPPPLPAEIFLLPPPMEESQPPPETELPLPPPPALQGDELGLLPPPPPGFGPDEPSWVPA
AYLEKVVTLYPYTRQKDNELSFSEGTVICVTRRYSDGWCEGVSSEGTGFFPGNYVEPSC*

ATGATGACAAACCGAGATGGACGTGACTACTTCATCAATCACATGACACAGGCAATCC
CATTTGATGACCCTCGGTTTGACAGCTGCCAAATCATTCCCCCAGCTCCACGGAAGGTG
GAGATGAGGAGGGACCCTGTGCTGGGCTTTGGGTTCGTGGCAGGGAGTGAAAAGCCA
GTGGTCGTTCGATCGGTAACACCAGGTGGCCCTTCAGAAGGCAAGCTGATCCCGGGAG
ATCAAATTGTAATGATTAATGATGAACCAGTCAGCGCTGCGCCAAGAGAGAGGGTCAT
CGACCTGGTCAGGAGCTGCAAAGAATCGATTCTGTTCACTGTCATCCAGCCTTATCCTT
CTCCCAAATCAGCATTTATTAGTGCTGCTAAAAAGGCAAGATTGAAGTCCAATCCAGT
CAAAGTACGCTTTTCCGAAGAGGTCATCATCAATGGTCAGGTGTCGGAAACTGTTAAA
GACAATTCACTTCTTTTTATGCCAAATGTTTGAAAGTCTACTTGGAAAATGGACAGAC
CAAATCCTTTCGCTTTGACTGCAGCACTTCCATTAAGGATGTCATCTTAACTCTGCAAG
AGAAGCTGTCTATCAAAGGCATTGAGCACTTCTCTCTCATGCTGGAGCAGAGAACTGA
AGGGGCCGGCACCAAGCTGCTCTTACTTCATGAACAGGAGACACTCACTCAGGTGACA
CAGAGGCCGAGTTCCCATAAGATGAGGTGTCTTTTCCGAATCAGTTTTGTTCCCAAGGA
TCCCATTGACCTGTTAAGGAGAGATCCAGTTGCTTTCGAGTATCTCTATGTTCAGAGCT
GTAACGATGTCGTTCAGGAGCGATTTGGACCAGAGCTGAAATACGACATTGCCTTGCG
GCTGGCCGCTTTACAAATGTACATTGCTACTGTCACCACCAAACAGACGCAGAAAATC
TCCCTCAAGTACATTGAGAAAGAATGGGGACTAGAGACTTTCCTTCCATCTGCTGTACT
TCAGAGCATGAAAGAGAAGAACATCAAGAAAGCGCTCTCCCACCTTGTCAAAGCAAA
TCAAAACTTGGTACCACCGGGTAAAAAGCTCTCTGCACTACAAGCTAAGGTCCACTAT
CTCAAGTTCCTCAGTGACCTGCGACTATACGGGGCCGTGTGTTCAAGGCAACATTAG
TGCAGGCAGAGAAGCGCTCAGAAGTGACTCTTCTGGTGGGTCCCCGGTATGGCATAAG
CCATGTCATAAACACCAAAACCAACCTGGTGGCTCTTTTAGCTGACTTCAGCCATGTCA
ACAGGATTGAAATGTTTACTGAAGAGGAGAGTTTGGTGAGGGTGGAGTTGCATGTGCT
CGATGTGAAGCCCATTACACTCCTTATGGAGTCATCAGATGCCATGAACCTGGCCTGTC
TGACAGCTGGATACTACCGGTTGCTCGTGGACTCCAGGAGGTCAATATTTAACATGGC
CAACAAGAAAAATGCAGGCACACAGGACACAGGAACGGAAAATAAAGGCAAGCATA
ATCTCCTTGGTCCTGACTGGAACTGTATGCCCCAGATGACGACCTTCATTGGCGAAGG
GGAACAAGAAGCCCAAATCACTTATATAGATTCTAAGCAGAAGGCAGTTGAGATGAC
AGACAGCACCTTGTGTCCCAAAGAGCACCGGCACTTATATATCGACAACACATACAGT
TCAGATGAACTTAGCCAGCCGCTGACTCAGCCAGGTGATGCACCCTGTGAGGCCGACT
ATAGAAGCCTAGCTCAGCGGTCCCTTTTGACCCTCTCAGGACCAGACACTCTGAAGAA
AGCACAGGAATCTCCGCGAGGAGCTAAAGTGTCCTTTATTTTTGGAGATCTTGCCTTAG
ATGATGGCATGAGTCCCCCAACTCTAGGCTATGAAAGAATGTTAGATGAGAATCCAGA
AATGCTGGAGAAGCAGAGGAATCTCTACATCAGCAGTGCCAATGATATGAAAAACCT
GGACCTCACTCCAGACACAGACAGCATCCAGTTTGTGGCAAATTCAGTATATGCAAAC
ATAGGTGATGTGAAGAACTTTGAAGCCCCTGAGGGAATAGAGGAGCCCCTCTTACATG
ACATCTGTTATGCTGAAAACACAGATGATGCAGAAGATGAAGATGAGGTGAGCTGCG
AGGAGGATCTCGTGGTGAGTGAAATCAACCAACCAGCCATCCTTGACCTGTCTGGGTC
AAGTGATGATATTATTGACCTTACAACACTGCCTCCTCCAGAAGGAGATGACAATGAG
GATGACTTCCTCCTGCGTTCTCTGAACATGGCCATTGCTGCTCCCCCACCTGGTTTTAG
AGACAGTTCTGATGAAGAGGACACTCAGAGCCAGGCAACATCCTTCCATGAGAACAA
AGAACAAGGCAGCAGCCTGCAGAATGAGGAGATCCCTGTGTCCCTCATTGATGCTGTG
CCCACCAGTGCAGAGGGCAAGTGTGAGAAGGGACTGGACCCTACCGTCGTTTCCACAC
TAGAAGCCCTAGAAGCTCTTTCAGAAGAACAGCAGAAGAGTGAAAATTCAGGTGTAG
CCATCTTGCGGGCTTATAGTCCCGAGTCTTCCTCAGACTCGGGCAATGAGACTAACTCT
TCTGAAATGACAGAGGGTTCTGAACTAGCTGCAGCACAGAAGCAGTCGGAAAGCCTCT
CCCGCATGTTCTTGGCCACTCATGAAGGTTATCACCCTCTGGCAGAAGAACAGACAGA
GTTCCCCACCTCCAAAACCCCCTCTGTGGGCTTGCCTCCAAAGTCCTCTCATGGCCTGG
CTGCTCGCCCAGCGACCGACCTCCACCCAAAGTTGTGCCTTCCAAGCAGATCCTTCAC
TCAGATCACATGGAAATGGAGCCAGAAACCATGGAGACCAAGTCAGTCACTGACTATT

FIG. 18a

```
TTAGCAAACTGCACATGGGGTCAGTGGCATATTCCTGTACCAGCAAAAGGAAAAGCAA
GCTTGCTGAGGGAGAGGGGAAATGCCCCCTGAGTGGGAATGTACCAGGGAAAAAACA
GCAAGGAACCAAAATAGCAGAGACGGAGGAGGACACCAAAGGCAAAGTTGGCACTGT
ATCTTCAAGAGACAATCCACACCTCAGCACTTTTAACCTGGAGAGAACTGCCTTTCGCA
AGGACAGCCAAAGATGGTATGTGGCCTCTGATGGTGGGGTGGTAGAGAAAAGTGGAG
TGGAAGCACCAGCCATGAAAGCCTTTCCCAGAGGTCCTGGTCTGGGGAACAGAGAGGC
TGAAGGGAAAGAGGATGGCACTATGGAAGGAGAGGCTGATGATGCTTCAGGACTTGG
TCAAGGGGAACGCTTCCTGTCAGATATGGCCTGTGTAGCCTCAGCCAAAGACTTAGAC
AACCCTGAAGACACTGACTCTCCCACTTGTGACCATGCCACTAAGCTTCCTGAGGCTGA
AGACAATGTGGCCCGCCTTTGTGACTACCATTTGGCCAAGCGAATGTCATCCCTGCAG
AGTGAGGGCCATTTTTCTCTACAGAGCTCTCAAGGCTCTTCAGTGGACACAGGCTGTGG
CCCAGGCAGCAGTAGCAGTGCCTGTGCCACTCCTGTGGAATCGCCCCTCTGCCCATCCA
TGGGAAAGCACCTGATTCCAGATGCTTCTGGGAAAGGTGGGAGTTACATTTCACCAGA
GGAGAGAGTCGCTGGTCATCCCAACCATGGAGCCACCTTCAAGGAACTGCACCCACAG
ACAGAAGGGATGTGTCCACGCATGACAGTGCCTGCTCTGCACACAGCCATTAATGCCG
ACCCCCTGTTTGGCACTTTGAGAGATGGATGCCATCGACTGCCCAAGATTAAGGAAAC
CACAGTGTAG
```

FIG. 18b r-i-42pr

MMTNRDGRDYFINHMTQAIPFDDPRFDSCQIIPPAPRKVEMRRDPVLGFGFVAGSE
KPVVVRSVTPGGPSEGKLIPGDQIVMINDEPVSAAPRERVIDLVRSCKESILFTVIQPY
PSPKSAFISAAKKARLKSNPVKVRFSEEVIINGQVSETVKDNSLLFMPNVLKVYLEN
GQTKSFRFDCSTSIKDVILTLQEKLSIKGIEHFSLMLEQRTEGAGTKLLLLHEQETLTQ
VTQRPSSHKMRCLFRISFVPKDPIDLLRRDPVAFEYLYVQSCNDVVQERFGPELKYD
IALRLAALQMYIATVTTKQTQKISLKYIEKEWGLETFLPSAVLQSMKEKNIKKALSH
LVKANQNLVPPGKKLSALQAKVHYLKFLSDLRLYGGRVFKATLVQAEKRSEVTLL
VGPRYGISHVINTKTNLVALLADFSHVNRIEMFTEEESLVRVELHVLDVKPITLLMES
SDAMNLACLTAGYYRLLVDSRRSIFNMANKKNAGTQDTGTENKGKHNLLGPDWN
CMPQMTTFIGEGEQEAQITYIDSKQKAVEMTDSTLCPKEHRHLYIDNTYSSDELSQP
LTQPGDAPCEADYRSLAQRSLLTLSGPDTLKKAQESPRGAKVSFIFGDLALDDGMSP
PTLGYERMLDENPEMLEKQRNLYISSANDMKNLDLTPDTDSIQFVANSVYANIGDV
KNFEAPEGIEEPLLHDICYAENTDDAEDEDEVSCEEDLVVSEINQPAILDLSGSSDDII
DLTTLPPPEGDDNEDDFLLRSLNMAIAAPPPGFRDSSDEEDTQSQATSFHENKEQGS
SLQNEEIPVSLIDAVPTSAEGKCEKGLDPTVVSTLEALEALSEEQQKSENSGVAILRA
YSPESSSDSGNETNSSEMTEGSELAAAQKQSESLSRMFLATHEGYHPLAEEQTEFPT
SKTPSVGLPPKSSHGLAARPATDLPPKVVPSKQILHSDHMEMEPETMETKSVTDYFS
KLHMGSVAYSCTSKRKSKLAEGEGKCPLSGNVPGKKQQGTKIAETEEDTKGKVGT
VSSRDNPHLSTFNLERTAFRKDSQRWYVASDGGVVEKSGVEAPAMKAFPRGPGLG
NREAEGKEDGTMEGEADDASGLGQGERFLSDMACVASAKDLDNPEDTDSPTCDH
ATKLPEAEDNVARLCDYHLAKRMSSLQSEGHFSLQSSQGSSVDTGCGPGSSSSACA
TPVESPLCPSMGKHLIPDASGKGGSYISPEERVAGHPNHGATFKELHPQTEGMCPRM
TVPALHTAINADPLFGTLRDGCHRLPKIKETTV*

FIG. 19 h-i30

```
GGCACGAGTGAGCATGCCTGCCCTTTGCAAGCAGGTTTGGGTCTCACGCAGAG
GAAACCAAAAGCAATAAGAGGGAGGGAAGGCAGAGCAACCAATCAAGGGCA
GGGTGAGACTCAAAACGAGCGGGCTCCCTGGGGAGCCAGACAGAGGCTGGGG
GTGATGGCGGAGCTACAGCAGCTGCAGGAGTTTGAGATCCCCACTGGCCGGG
AGGCTCTGAGGGGCAACCACAGTGCCCTGCTGCGGGTCGCTGACTACTGCGAG
GACAACTATGTGCAGGCCACAGACAAGCGGAAGGCGCTGGAGGAGACCATGG
CCTTCACTACCCAGGCACTGGCCAGCGTGGCCTACCAGGTGGGCAACCTGGCC
GGGCACACTCTGCGCATGTTGGACCTGCAGGGGCCGCCCTGCGGCAGGTGG
AAGCCCGTGTAAGCACGCTGGGCCAGATGGTGAACATGCATATGGAGAAGGT
GGCCCGAAGGGAGATCGGCACCTTAGCCACTGTCCAACGGCTGCCCCCGGCC
AGAAGGTCATCGCCCCAGAGAACCTACCCCCTCTCACGCCCTACTGCAGGAGA
ACCCTCAACTTTGGCTGCCTGGACGACATTGGCCATGGGATCAAGGACCTCAG
CACGCAGCTGTCAAGAACAGGCACCCTGTCTCGAAAGAGCATCAAGGCCCCT
GCCACACCCGCCTCCGCCACCTTGGGGAGACCACCCCGGATTCCCGAGCCAGT
GCACCTGCCGGTGGTGCCCGACGGCAGACTCTCCGCCGCCTCCTCTGCGTCTTC
CCTGGCCTCGGCCGGCAGCGCCGAAGGTGTCGGTGGGGCCCCACGCCCAAG
GGGCAGGCAGCACCTCCAGCCCCACCTCTCCCCAGCTCCTTGGACCCACCTCC
TCCACCAGCAGCCGTCGAGGTGTTCCAGCGGCCTCCCACGCTGGAGGAGTTGT
CCCCACCCCCACCGGACGAAGAGCTGCCCCTGCCACTGGACCTGCCTCCTCCT
CCACCCCTGGATGGAGATGAATTGGGGCTGCCTCCACCCCCACCAGGATTTGG
GCCTGATGAGCCCAGCTGGGTGCCTGCCTCATACTTGGAGAAAGTGGTGACAC
TGTACCCATACACCAGCCAGAAGGACAATGAGCTCTCCTTCTCTGAGGGCACT
GTCATCTGTGTCACTCGCCGCTACTCCGATGGCTGGTGCGAGGGCGTCAGCTC
AGAGGGGACTGGATTCTTCCCTGGGAACTATGTGGAGCCCAGCTGCTGACAGC
CCAGGGCTCTCTGGGCAGCTGATGTCTGCACTGAGTGGGTTTCATGAGCCCCA
AGCCAAAACCAGCTCCAGTCACAGCTGGACTGGGTCTGCCCACCTCTTGGGCT
GTGAGCTGTGTTCTGTCCTTCCTCCCATCGGAGGGAGAAGGGGTCCTGGGGAG
AGAGAATTTATCCAGAGGCCTGCTGCAGATGGGGAAGAGCTGGAAACCAAGA
AGTTTGTCAACAGAGGACCCCTACTCCATGCAGGACAGGGTCTCCTGCTGCAA
GTCCCAACTTTGAATAAAACAGATGATGTCCTGTGAAAAAAAAAAAAAAAA
AAA
```

MAELQQLQEFEIPTGREALRGNHSALLRVADYCEDNYVQATDKRKALEETMAFTTQALA
SVAYQVGNLAGHTLRMLDLQGAALRQVEARVSTLGQMVNMHMEKVARREIGTLATVQR
LPPGQKVIAPENLPPLTPYCRRTLNFGCLDDIGHGIKDLSTQLSRTGTLSRKSIKAPATPASA
TLGRPPRIPEPVHLPVVPDGRLSAASSASSLASAGSAEGVGGAPTPKGQAAPPAPPLPSSLD
PPPPPAAVEVFQRPPTLEELSPPPPDEELPLPLDLPPPPPLDGDELGLPPPPPGFGPDEPSWVP
ASYLEKVVTLYPYTSQKDNELSFSEGTVICVTRRYSDGWCEGVSSEGTGFFPGNYVEPSC*

TTTCCAGCCAACGCCAAACAGTGACTGTTGACAATTTCATATTGTCATCAGGGGAACC
AAGGCTTATTCAGATGCCTATTTCAGAACCTAGGACAGTTCCATTGAAAAGGCGCAGG
CGTTCGGGCTGGCTGACTAGATGGATCAGGCCTGGCTGCCTGATGGCTATATTCCTCCT
TCCTCCCTCTCCACTTCCATCTCAACCCTTGAGGCTGCATATTGAATAGTTGGAGAATT
CAGTGAACTAAGAGATGCAAATGCACAGTACAAAATTCAAATGTCCAATTCGGGGCA
GGGCTGCATCTAACTTTAATGGCAACCACTGCATGTGATGTCTGGGGACTCTATAGAT
ACATGGCCTCAGACCCTGAAGACATCTGGATTCTGTCACTGGATTGTTCACAAAGTGA
GGCTGAACTTTCCACAGGACGAAGTCTTCAGGCTGGCCGCCTCCCTCGGGAACCTGGG
GCTTGAGCCAGGTGCCGCCCTATGGATGGGAGATGACGGCAAACCGAGATGGGCGAG
ACTACTTCATCAATCACATGACACAGGCAATCCCTTTTGACGACCCTCGGTTAGAGAG
CTGCCAAATCATCCCTCCGGCTCCTCGGAAGGTGGAGATGAGAAGGGACCCCGTGCTG
GGATTTGGTTTTGTGGCAGGCAGTGAAAAGCCAGTGGTCGTTCGCTCAGTAACACCAG
GTGGCCCCTCTGAAGGCAAGCTGATCCCGGGAGATCAGATTGTAATGATTAATGATGA
ACCGGTCAGCGCTGCACCCAGAGAGCGGGTCATCGATCGGTCAGAAGCTGCAAAGA
ATCGATACTCCTCACTGTCATTCAGCCTTACCCTTCTCCCAAATCAGCATTTATTAGTGC
TGCAAAAAAGGCAAGATTAAAGTCCAATCCTGTCAAAGTACGCTTCTCTGAGGAGGTC
ATCATCAACGGCCAAGTGTCGGAAACTGTTAAGGACAACTCACTTCTTTTTATGCCAA
ATGTTTTGAAAGTCTATCTGGAAAATGGGCAGACCAAATCATTTCGTTTTGACTGCAGC
ACTTCCATTAAGGATGTCATCTTAACCCTTCAAGAGAAGCTCTCCATCAAAGGCATTGA
ACACTTCTCTCATGCTGGAGCAGAGGACAGAAGGGGCTGGAACGAAGCTGCTCTTG
CTTCATGAACAGGAGACTCTAACTCAGGTGACACAGAGGCCCAGCTCCCATAAGATGA
GATGTCTTTTCCGAATTAGCTTCGTCCCAAAAGATCCAATTGACCTTTTAAGGAGAGAT
CCAGTTGCTTTCGAGTATCTCTATGTTCAGAGTTGTAACGATGTGGTTCAGGAGCGATT
TGGGCCGGAGCTGAAATATGACATAGCCCTGCGGCTGGCCGCATTACAAATGTACATT
GCAACCGTTACCACCAAGCAAACGCAGAAAATCTCCCTCAAATACATCGAAAAGAA
TGGGGATTAGAGACTTTTCTTCCCTCTGCTGTGCTGCAAAGCATGAAAGAGAAGAACA
TAAAGAAAGCACTTTCACACCTTGTCAAAGCAAATCAAAACTTGGTACCACCGGGTAA
AAAGCTCTCTGCACTACAAGCCAAGGTCCATTATCTCAAGTTCCTCAGTGACCTACGAT
GTATGGGGCCGTGTGTTCAAGGCAACATTAGTGCAGGCAGAAAAGCGCTCGGAAGT
GACTCTCCTGGTTGGGCCCCGGTATGGCATAAGCCATGTCATCAACACCAAAACCAAT
CTGGTGGCTCTTTTAGCCGACTTTAGCCACGTCAACAGGATCGAAATGTTTTCCGAGGA
GGAGAGCTTGGTGCGGGTAGAACTCCACGTGCTAGATGTGAAGCCTATCACGCTTCTG
ATGGAATCCTCAGATGCCATGAACCTGGCCTGCTTGACGGCTGGATACTACCGGCTGC
TTGTTGATTCCAGGAGGTCGATATTTAACATGGCCAACAAGAAAAACACAGCGACCCA
GGAAACAGGACCTGAAAACAAGGGGAAGCATAACCTCCTTGGCCCAGATTGGAACTG
TATACCCCAAATGACCACCTTTATTGGCGAAGGGGAACAAGAAGCCCAGATAACATAC
ATAGATTCAAAGCAGAAGACGGTGGAGATCACAGACAGCACCATGTGTCCAAAAGAG
CACCGGCACTTGTACATAGACAATGCCTATAGTTCAGATGGACTTAACCAGCAGCTGA
GCCAGCCCGGGGAGGCCCCTGTGAGGCAGACTACAGAAGTCTAGCTCAGCGGTCCCT
ATTGACCCTCTCAGGACCAGAAACTCTGAAGAAAGCACAGGAATCTCCGAGAGGAGC
TAAAGTGTCCTTTATTTTTGGAGACTTCGCCTTGGATGATGGTATTAGTCCCCCAACCC
TTGGCTATGAAACGCTACTAGATGAGGGTCCTGAAATGCTGGAGAAGCAGAGAAATCT
CTACATTGGCAGTGCCAATGACATGAAGGGCCTGGATCTCACTCCAGAGGCAGAGGGC

ATCCAGTTTGTGGAAAATTCTGTTTATGCAAACATAGGCGATGTGAAGAGCTTCCAGG
CCGCGGAGGGGATCGAGGAACCCCTCTTGCATGACATCTGTTATGCAGAAAACACTGA
TGACGCGGAGGACGAGGACGAGGTGAGCTGCGAGGAGGACCTCGTGGTGGGGGAGAT
GAACCAGCCGGCCATCCTCAACCTGTCTGGGTCAAGCGATGACATCATTGACCTCACA
TCCCTGCCCCCTCCAGAAGGTGATGACAATGAGGATGACTTCCTGTTGCGTTCCTTGAA
CATGGCCATTGCCGCACCCCCACCTGGCTTTAGAGACAGTTCAGATGAAGAGGACTCT
CAGAGCCAGGCAGCTTCCTTCCCCGAGGACAAGGAGAAAGGCAGCAGCCTGCAAAAT
GATGAGATCCCCGTGTCCCTCATTGACGCTGTGCCCACCAGCGCCGAAGGCAAGTGTG
AGAAGGGACTGGATAATGCCGTCGTCTCCACGCTGGGAGCTCTAGAGGCTCTATCCGT
GTCAGAAGAACAGCAGACCAGTGACAATTCAGGTGTAGCCATCTTGCGGGCTTATAGT
CCTGAGTCTTCGTCAGACTCGGGCAATGAAACTAACTCTTCTGAAATGACTGAGAGTT
CTGAACTGGCCACAGCACAAAAACAGTCAGAAAACCTCTCCCGCATGTTCTTGGCCAC
TCACGAAGGCTACCACCCCCTTGCAGAAGAGCAGACCGAGTTCCCGGCCTCCAAGACC
CCCGCTGGGGGCTTGCCTCCAAAGTCCTCGCACGCCCTGGCTGCTAGGCCAGCAACCG
ACCTCCCGCCCAAAGTTGTGCCTTCCAAGCAGTTACTTCACTCAGACCACATGGAGAT
GGAGCCTGAAACTATGGAGACTAAGTCGGTCACTGACTATTTTAGCAAACTGCACATG
GGGTCGGTGGCATACTCCTGCACTAGCAAAAGGAAAAGCAAGCTGGCCGATGGTGAG
GGGAAGGCACCCCCTAATGGGAACACAACAGGAAAAAAACAGCAGGGGACCAAAAC
GGCAGAGATGGAGGAGGAGGCCAGTGGTAAATTTGGTACTGTGTCTTCACGAGACAGT
CAACACCTGAGCACTTTTAATCTGGAGAGAACTGCCTTTCGCAAGGACAGTCAAAGAT
GGTATGTGGCCACTGAAGGTGGGATGGCTGAAAAAAAGTGGATTAGAAGCAGCAACA
GGGAAAACCTTTCCAAGAGCTTCTGGTCTTGGGGCAAGGGAGGCCGAAGGGAAGGAA
GAAGGAGCTCCTGATGGAGAAACCAGTGATGGCTCAGGACTTGGTCAAGGGGACCGC
TTCTTAACTGACGTGACCTGTGCATCTTCAGCCAAAGACTTAGATAACCCAGAGGACG
CTGACTCGTCCACCTGCGACCATCCTTCCAAGCTTCCTGAGGCTGATGAGAGTGTGGCC
CGCCTTTGTGACTACCACTTGGCCAAGCGGATGTCATCACTGCAAAGCGAGGGCCATT
TTTCTCTGCAGAGCTCCCAAGGCTCTTCAGTGGATGCAGGCTGTGGCACAGGCAGCAG
TGGCAGTGCCTGTGCCACACCCGTGGAGTCGCCGCTCTGCCCCTCCCTGGGGAAGCAC
TTGATTCCTGACGCTTCTGGGAAAGGCGTGAATTACATTCCTTCAGAGGAGAGAGCCC
CTGGGCTTCCCAACCACGGAGCCACCTTTAAGGAACTGCACCCACAGACAGAAGGGAT
GTGTCCACGGATGACAGTGCCTGCTCTGCACACAGCCATTAACACCGAACCCCTGTTT
GGCACATTGAGAGATGGATGCCATCGGCTCCCCAAGATTAAGGAAACCACAGTGTAGC
TTTGACAGAGCCTGGGAAGGAGAGACGAGGAGGCATGCCTTCAGCTTGGTCTAACAT
CCTGAAGCTGATCCCATCCTGCTACCATCAAACATTCACTCGGAATCAAAGGTGCCAA
TTCCAAATCAAGACCCTAATGATTTCTCCCAAGCAAATCAGGCATACGGAGAGGCTGT
GAGCTGGCGGCCACCGGATCTGAGAGGGGGAGCCTCAGGACACCTCCCAGCCAGAA
GGCTCTGAGACATAGCAGCAGTATCCTCTCCGGATCTGTCGATTTGGAGACCTTCCGA
GAGAGAACCAAGGGTGCAGTCAGCTTAAAGTGTCCAGGCATCACAGAAGCACAGGAG
GCCAGTTCTGAAAGGCGAGCAGAACTCCCCCTGGGGAGGAAGCTCACCAAAAGTTTTT
CCCAAAGCTCAATGCACTTGAGCTCTGAGGGGAGGTTTCACAAAAGGTCCCCAGTGGC
TCATAAAGACTCAAAGCTGTATAGGACATTACCCTTGCGGAAGCTGGAGGGCAGCAAT
TGGAGATGCCGGGGACCCTTCAGCTATTGCTTCCTGAACCGAGGGCAGGATGAAGATG
GTGAGGAAGAAGAGGAGAGGGGAGAGGCCACCGTCCAGGTCTCTTGCCTCTATAGAC
CACAGGTGACTCAAGCCATGCCAGAACCAAGCAGCCCATGCCTGGCTGTGGCGATTCA
GAAGCAACGAGGGGAGCTATCCAGAGGGTCAGTGCTGAAGGTCTGGGCAGAAGACCT
GCGAGACCCAGATGACTTGGACTTCAGCAACCTGGCTTTTGATGCCCGGATTGCAAGA

```
ATAAATGCCCTAAAGGAGAGCACATATGCAATGCCTGATGGGTTCCTTGCAGCCCAAA
ATGATGCCAATGAGCTGCTCTGTCTCGTCAGGGCAACCAAGGAGAAGAGGGAGGAGT
CACGCCCTGAAGCGTACGACCTTACACTTTCTCAGTACAAGCAACTGTTATCCATTGAG
TCCAGACAGTTGGGAAGTGCCTGTAGGAAAATGGCGATGGCTGAGAAAAGCCCGGAG
GAGATGCTCCTAGCTATGACTTCCAGCTTTCAAGTGCTCTGTTGCCTAACAGAAGCTTG
CATGCGATTAGTTAAAGTCGTGAACTCAGAAACACAGCGGCAGGAAATTGTAGGGAA
GATCGATGAAGTGGTCATAAATTACATTTGTCTACTGAAAGCTGCCGAAGCAGCCACT
GGAAAGAACCCTGGGGACCCTAATGTTGGACTCTCGGCGCGACACTCAACCACCATGG
CCGCTCTCGTAAGCACACTGACACGTTCTCTCAAGAGGCTTTTAAACAAATAAATATG
GAAGTCACGTCATAATCTACCTTTGCAAAGCCATACATGAACTTTTATTTACTTTGTGT
GTATGATGAACAGATGTCTCCTTTCTTCTCTGTATATTTTGTTATTTTATATAAAATA
GGAGATAAAGTCACACTGATGAAATGTTGAAATGTACTAATCAGATGTATTCTGTTT
ATATTATACATATATACACGTAAAAGAAATATCCAAGAAAGTGATGACATTTGGCT
ATTTTTCATATAGTTAAAACTCCAGGTATATGATGTGAAATTTTAAATTCTACCATGTT
AGAGCAAAACAATGAATCCTATCCCCTTTCTTTCCAAGTAGCTACTTGGAAACCATATC
ATTCATATTTAGAAGTAAAACACAAAACAAAAAGAGAGAGAAAAGAAAAGAAATCA
CAATGTATATAAAACAGTACTTATGTTTTAAAATTATGATTTTTAAGCATTGGAAATAG
CAAAAAGACATTTAAAATTCAAGAAGCTATTATGAATTACTAGAGAATATATCTGTAA
TAAATTAATTTTTTGCTCATAGTATTTGGTTACTGGATGCTTCTTCCAAGAATCCCACA
TATTTAATTTGGGTTTTTGCTACTGGGGCTACAAATTGGTGGGGATGGATTCTACTGTG
TCAGCACAAATGCTCTTCACAGTGGTTCTAGCATTTAAAAAACTTCCCGGGGAGAAGA
ACAGAGGGGATGATGGGCAGTTTCCTAGGTAACACCTAGAGTTATAGAATATCTCATT
ACATAAATGTATGGAATTAATAATACCAAAATTAATTATTTGATGGAAAGATCTGCT
TTGACTAAATGTCAAAAATCTGCAAACCAAAGACATTATCTTCCCCTCATCCCAACTCA
ACTACGAAACTTAAAATTCCCTTTAGAGTGATAGGACATTTAGTAAAGTATTTGCAAA
CTTAAAAAAAGGAACATTTAATGATCATCAAAATTAAGTACAGATTCAGTAATGTAGA
CCAGACCACACACCAGCACCTGTGAGTCTCATCTCAGATCACAGCTCTCAGCATAGGG
CTTCATGCATCACCGCCTCTACAGAGGCTAAGGCTGCCAGTCAAATTTGGAATTATAGC
GTAGTACTGGGACAAAATCTCAAATCTTGGATGTTCCAGAAAATCAGGGAGTGATGGC
TACTGTAATCATGGGAGCCATGAGTAAATAGTTAAGTATTTATTAAATAAATACTTAAT
CTGGATTGGCTGATAAAAATATGAAATCT
```

MTANRDGRDYFINHMTQAIPFDDPRLESCQIIPPAPRKVEMRRDPVLGFGFVAGSE
KPVVVRSVTPGGPSEGKLIPGDQIVMINDEPVSAAPRERVIDLVRSCKESILLTVIQP
YPSPKSAFISAAKKARLKSNPVKVRFSEEVIINGQVSETVKDNSLLFMPNVLKVYL
ENGQTKSFRFDCSTSIKDVILTLQEKLSIKGIEHFSLMLEQRTEGAGTKLLLLHEQE
TLTQVTQRPSSHKMRCLFRISFVPKDPIDLLRRDPVAFEYLYVQSCNDVVQERFGP
ELKYDIALRLAALQMYIATVTTKQTQKISLKYIEKEWGLETFLPSAVLQSMKEKNI
KKALSHLVKANQNLVPPGKKLSALQAKVHYLKFLSDLRLYGGRVFKATLVQAEK
RSEVTLLVGPRYGISHVINTKTNLVALLADFSHVNRIEMFSEEESLVRVELHVLDV
KPITLLMESSDAMNLACLTAGYYRLLVDSRRSIFNMANKKNTATQETGPENKGK
HNLLGPDWNCIPQMTTFIGEGEQEAQITYIDSKQKTVEITDSTMCPKEHRHLYIDN
AYSSDGLNQQLSQPGEAPCEADYRSLAQRSLLTLSGPETLKKAQESPRGAKVSFIF
GDFALDDGISPPTLGYETLLDEGPEMLEKQRNLYIGSANDMKGLDLTPEAEGIQFV
ENSVYANIGDVKSFQAAEGIEEPLLHDICYAENTDDAEDEDEVSCEEDLVVGEMN
QPAILNLSGSSDDIIDLTSLPPPEGDDNEDDFLLRSLNMAIAAPPPGFRDSSDEEDSQ
SQAASFPEDKEKGSSLQNDEIPVSLIDAVPTSAEGKCEKGLDNAVVSTLGALEALS
VSEEQQTSDNSGVAILRAYSPESSSDSGNETNSSEMTESSELATAQKQSENLSRMF
LATHEGYHPLAEEQTEFPASKTPAGGLPPKSSHALAARPATDLPPKVVPSKQLLHS
DHMEMEPETMETKSVTDYFSKLHMGSVAYSCTSKRKSKLADGEGKAPPNGNTTG
KKQQGTKTAEMEEEASGKFGTVSSRDSQHLSTFNLERTAFRKDSQRWYVATEGG
MAEKKWIRSSNRENLSKSFWSWGKGGRREGRRSS

FIG. 23 mHomer-1aGenBank

AGCGGGGCTCCATTGTGCTCGGCGGGGGCCGGGAAGCCAAAGGAGGTGGGC
TCGGGCCCCTGCGCTGCTCCCGGCGGCTGCGCCCCAGCTAGCTGCCAGCC
TGGAAATGGCTCCGCTGCTGCTCCTCGGGAAAACGAATCGATCCTTCCCAGC
CTTCTCTGCCTGCTCTCCACCTCCTCTCTGCTCCGAGTCTTAGGAGGACGAAC
ATTCAAAGGACAGATTCCAATGTGGTGTGCCGTGCACATCGGGAGCGGCTGG
GGTTTGCACTTCGAGATTTCTTCTATATAATTTTTTTTTTTAAACGTAAGGGA
GGCAGTAGCATTGCTGCCTGTAGGATTTTTTATTCAAGTGCACGTCGCGTTGG
GTTGCACGNTCCACCCCCAGGGACCTGGTGTGGTGAAATTTGAACCCACCGC
CTTAGCCCAAAAAGGCCGAGTAACCTGGCTGCCTGAGTGTCGTGGAAGACGT
GAGCGAAATGACCAGCGAACTCATTTTTATCAGACTTGCTGAAGCTGGCTT
TTGCGTTTTTCTACACGTACGCTTAATTTGTGGAATAGTTAAGTGCTATAT
TCTCCGCGCAACCTTTTCAAATTCCAAATGTTTGAACATTTTGGTGTCAGCGC
GAGTGAAATCATTTTACCGACAAGAACTAACTGAATTGTCTGCCTTGTTGAG
TTGCCTCCGGAAAAGATCTCGGGGGTGGAAAAGCAACTGCAAAATAACAGA
CGGAGAAAATTCCTTGGAAGTTATTTCTGTAGCATAAGAGCAGAAACTTCAG
AGCAAGTTTTCATTGGGCAAAATGGGGGAGCAACCTATCTTCAGCACTCGAG
CTCATGTCTTCCAGATTGACCCGAACACAAAGAAGAACTGGGTACCCACCAG
CAAGCATGCAGTTACTGTATCTTATTTTATGACAGCACAAGAAATGTGTAT
AGGATAATCAGTTTAGATGGCTCAAAGGCAATAATAAATAGCACCATCACAC
CAAACATGACATTTACTAAAACATCTCAAAAGTTTGGCCAATGGGCTGATAG
CCGGGCAAACACTGTTTATGGACTGGGATTCTCCTCTGAGCATCATCTTTCAA
AATTCGCAGAAAAGTTTCAGGAATTTAAGGAAGCTGCTCGGCTTGCAAAGGA
GAAGTCGCAGGAGAAGATGGAGCTGACCAGTACCCCTTCACAGGAATCAGC
AGGAGGAGATCTTCAGTCTCCTTTGACACCAGAAAGTATCAATGGGACAGAC
GATGAGAGAACACCCGATGTGACACAGAACTCAGAGCCAAGGGCTGAGCCA
ACTCAGAATGCATTGCCATTTCCACATAGGTACACATTCAATTCAGCAATCA
TGATTAAGTAAGGTGGATAAATATGGAAGTTCATTGGTTTCAGAAACTCTT
GAAGTTACAACCTTTGAGTGAAAAATCTCAGGTCAGACTCCTTTAATTTATTG
TTCTTGGTTGCTCAAGTTGACTGAATTACTATATTTCCATTATCTATGTGGAA
AAAGGAGCATTGAGCTAATTATAGGAGAAATTTTTAAATGGAGAAAATATA
ATTCCTTTCTATCTATATTTTAAAGATCCCTTTTGTTAACCCGTTTTCTGTNTT
TATATATGTTATGTAAGATTTATAATGTGTAATTAGAAACATAGAATTTCTAC
TCTGAAGGAAAGCTTTACCACAGGCCTACAGAGTTTTCACAGAAGACAGGGT
ACCAAGCACGAGCCTGTTAGCATTGATGGCAGATGCCAGCAGAAGGAAGGC
TTGACTTCCTAATTCTGTATTCTAAAAGATACATCATGTTCTAAATGCATTTC
AAACATTAGTTATTGGCCGTACCGTGGCATTACTGGACTGTAAACATGAATG
TGAAATGGCACTATTGAAAATATTTTTTAAAGCCCATCTACCTTAACACTAA
TTTTTACCCTTATTTAAATGCTTTTACTAAATAGTTTTAGGTAAAATTAAGA
AAATAGGGGTTTTTTGACTGCACATTTTTTGAAGAACCAAGTTTTAGAAAAT
TATATTCTTTGACAGATTAAAAATTGCAAAGTGAGATATTTCAAACTCTCCTA
GGTGAGTTTTTATTGTGTTTGAACTTGCATTAATAGGGGCATAGGAT

FIG. 24

M-Homer-1a

MGEQPIFSTRAHVFQIDPNTKKNWVPTSKHAVTVSYFYDSTRNVYRIISLDGSKA
IINSTITPNMTFTKTSQKFGQWADSRANTVYGLGFSSEHHLSKFAEKFQEFKEAA
RLAKEKSQEKMELTSTPSQESAGGDLQSPLTPESINGTDDERTPDVTQNSEPRAE
PTQNALPFPHRYTFNSAIMIK*

FIG. 25 mHomer-1bGenBank

```
GAATTCGGCACGAGTCTGCCTTGTTGAGTTGCCTCCGGAAAAGATCTCGGGG
GTGGAAAAGCAACTGCAAAATAACAGACGGAGAAAATTCCTTGGAAGTTAT
TTCTGTAGCATAAGAGCAGAAACTTCAGAGCAAGTTTTCATTGGGCAAAATG
GGGGAGCAACCTATCTTCAGCACTCGAGCTCATGTCTTCCAGATTGACCCGA
ACACAAAGAAGAACTGGGTACCCACCAGCAAGCATGCAGTTACTGTATCTTA
TTTTTATGACAGCACAAGAAATGTGTATAGGATAATCAGTTTAGATGGCTCA
AAGGCAATAATAAATAGCACCATCACACCAAACATGACATTTACTAAAACAT
CTCAAAGTTTGGCCAATGGGCTGATAGCCGGGCAAACACTGTTTATGGACT
GGGATTCTCCTCTGAGCATCATCTTTCAAAATTCGCAGAAAAGTTTCAGGAA
TTTAAGGAAGCTGCTCGGCTTGCAAAGGAGAAGTCGCAGGAGAAGATGGAG
CTGACCAGTACCCCTTCACAGGAATCAGCAGGAGGAGATCTTCAGTCTCCTT
TGACACCAGAAAGTATCAATGGACAGACGATGAGAGAACACCCGATGTGA
CACAGAACTCAGAGCCAAGGGCTGAGCCAACTCAGAATGCATTGCCATTTCC
ACATAGTTCAGCAATCAGCAAACACTGGGAGGCTGAGCTAGCTACCCTCAAA
GGCAACAATGCCAAACTCACTGCAGCCCTGCTGGAGTCCACTGCCAATGTGA
AGCAGTGGAAGCAACAGCTTGCTGCGTACCAGGAGGAAGCAGAGCGGCTGC
ACAAGCGGGTCACTGAGCTGGAGTGTGTTAGTAGTCAAGCAAACGCTGTGCA
CAGCCACAAGACAGAGCTGAACCAGACAGTGCAGGAACTGGAAGAGACCCT
GAAAGTAAAGGAAGAGGAAATAGAAAGATTAAAACAAGAAATCGATAATG
CCAGAGAACTCCAAGAACAGAGGGACTCTTTGACTCAGAAACTACAGGAAG
TTGAAATTCGAAATAAAGACCTGGAGGGGCAGCTGTCTGACCTAGAACAGC
GCCTGGAGAAGAGCCAGAACGAACAAGAGGCTTTCCGCAGTAACCTGAAGA
CACTCCTAGAAATTCTGGATGGAAAAATATTTGAACTAACAGAATTACGAGA
TAATTTGGCCAAGCTACTGGAATGCAGCTAAAGAGAGTGAAATTTCAGTGCC
AATAGATGGAGAGATGCTGTCTGTCTTCCTAGGACTGTTTGGGCTCCGTACC
AAGATTGCACAAAATTTTTTGAATATCATTCCTCCAGGAGGAGGGTGTTTTG
AAAATTGGAATTGTATATTTCAGTATAAATTTTTGAATTTAGCTTATAGCTAA
TTGGGAAAAAAAAAAAAAAAAAA
```

FIG. 26

M-Homer-1b

---
MGEQPIFSTRAHVFQIDPNTKKNWVPTSKHAVTVSYFYDSTRNVYRIISLDGSKA
IINSTITPNMTFTKTSQKFGQWADSRANTVYGLGFSSEHHLSKFAEKFQEFKEAA
RLAKEKSQEKMELTSTPSQESAGGDLQSPLTPESINGTDDERTPDVTQNSEPRAE
PTQNALPFPHSSAISKHWEAELATLKGNNAKLTAALLESTANVKQWKQQLAAY
QEEAERLHKRVTELECVSSQANAVHSHKTELNQTVQELEETLKVKEEEIERLKQ
EIDNARELQEQRDSLTQKLQEVEIRNKDLEGQLSDLEQRLEKSQNEQEAFRSNLK
TLLEILDGKIFELTELRDNLAKLLECS*

FIG. 27 mHomer-2aGenBank

GGCTTGGCCACGCGTCGACTAGTACGGGGGGGGGGGCGTCGGAGCGGCCGCAC
GAGCAGCGCCGGAGATGGGAGAACAGCCCATCTTCACCACGCGAGCGCACGTC
TTCCAGATTGACCCCAGCACCAAGAAGAACTGGGTGCCGGCAAGCAAGCAGGC
CGTCACGGTTTCCTACTTCTATGATGTCACCAGGAACAGCTATCGGATCATCAGT
GTGGATGGAGCCAAGGTGATCATAAACAGCACTATCACCCCGAACATGACTTTC
ACCAAAACGTCACAGAAGTTCGGGCAGTGGGCTGACAGCAGAGCCAACACCGT
GTTCGGTTTGGGATTCTCCTCCGAGCTGCAGCTCACGAAGTTTGCAGAGAAGTT
CCAGGAGGTAAGAGAAGCTGCCAGGCTAGCCAGAGACAAGTCCCAGGAGAAAA
CCGAGACCTCCAGCAATCATTCCCAAGCATCCAGCGTCAATGGCACAGACGACG
AAAAGGCCTCTCACGCGAGCCCAGCCGACACTCACCTCAAGTCTGAGAATGACA
AGCTGAAGATCGCGCTGACACAGAGTGCTGCCAATGTGAAGAAGTGGGAGATG
GAGCTGCAGACCCTGCGGGAGAGCAACGCCCGGCTGACCACGGCACTGCAGGA
GTCGGCGGCCAGCGTGGAGCAGTGGAAGCGGCAGTTCTCCATCTGCAGGGACG
AGAATGACAGGCTCCGCAGCAAGATCGAGGAGCTGGAAGAACAGTGCAGCGAG
ATAAACAGGGAGAAGGAGAAGAACACACAGCTGAAGAGGAGGATCGAGGAGC
TGGAGTCAGAGGTCCGAGACAAGGAGATGGAGTTGAAAGATCTCCGAAAACAG
AGTGAAATCATACCTCAGCTCATGTCCGAGTGTGAATATGTCTCTGAAGAAGTTA
GAGGCGGCCGAAAGAGACAATCAAAACTTGGAAGACAAAGTGCGGTCTCTAAA
GACAGACATCGAGGAGAGTAAATACCGACAGCGCCACCTGAAGGGGGAGCTGA
AGAGCTTCCTTGAGGTGCTGGATGGAAAGATCGACGACCTCCATGACTTCCGTA
GAGGACTCTCCAAGTTAGGCACAGATAACTAGGGCGGGGCGGAGCAAGTGTGT
GTGAGAGGTGTGGTAGACGTAGGACATTCTCCATTTGCTTCTGTAAATGCAGGT
GCGATCTGTCTGTCTCCAGACCAATTGTGCCGTCCGCTCACTCCTCCAGAATAGG
AAATCTCTCGCTTCTCTGGCTTTGTGAGGTCATGGACAGCTGGAAGCTTCTGACT
CAGGAATCCAGAACTTGGTCTACCTTAGCCGTTTACGCAGTCAGGGCAGGGATG
TTTAGATCTTCCCTTAAGGGCTGTTGTAACCCTATGAACCGGGGATGGGGGAGT
ATTTTCTAATCCAAGTACCATTATCCTTTACAGCAGGCCCTCGGGTGCCTTCTGC
TGCGTGGCATTCAGTGTATGTGACTCTCCAGCAGGTTCTAGACCACGGGCATGT
GGAGGGAGCATCTTTTCCCAGTATGCATTTGTTGCTTTAGCAGATGTGACATGA
CATTGTCAACCACAAAGTTCACACTCAAAAACTGCACAACTGACTTACTCAAAA
AGAAATAATTGTAAAAAAAAAAAAAAAAAA

FIG. 28

M-Homer-2a

MGEQPIFTTRAHVFQIDPSTKKNWVPASKQAVTVSYFYDVTRNSYRIISVDGAK
VIINSTITPNMTFTKTSQKFGQWADSRANTVFGLGFSSELQLTKFAEKFQEVREA
ARLARDKSQEKTETSSNHSQASSVNGTDDEKASHASPADTHLKSENDKLKIALT
QSAANVKKWEMELQTLRESNARLTTALQESAASVEQWKRQFSICRDENDRLRS
KIEELEEQCSEINREKEKNTQLKRRIEELESEVRDKEMELKDLRKQSEIIPQLMSE
CEYVSEKLEAAERDNQNLEDKVRSLKTDIEESKYRQRHLKGELKSFLEVLDGKI
DDLHDFRRGLSKLGTDN*GG

FIG. 29 mHomer-2bGenBank

GGCTTGGCCACGCGTCGACTAGTACGGGGGGGGGGGCGTCGGAGCGGCC
GCACGAGCAGCGCCGGAGATGGGAGAACAGCCCATCTTCACCACGCGAG
CGCACGTCTTCCAGATTGACCCCAGCACCAAGAAGAACTGGGTGCCGGCA
AGCAAGCAGGCCGTCACGGTTTCCTACTTCTATGATGTCACCAGGAACAG
CTATCGGATCATCAGTGTGGATGGAGCCAAGGTGATCATAAACAGCACTA
TCACCCCGAACATGACTTTCACCAAAACGTCACAGAAGTTCGGGCAGTGG
GCTGACAGCAGAGCCAACACCGTGTTCGGTTTGGGATTCTCCTCCGAGCT
GCAGCTCACGAAGTTTGCAGAGAAGTTCCAGGAGGTAAGAGAAGCTGCC
AGGCTAGCCAGAGACAAGTCCCAGGAGAAAACCGAGACCTCCAGCAATC
ATTCCCAAGAATCTGGGTGTGAAACCCCGTCTTCCACTCAGGCATCCAGC
GTCAATGGCACAGACGACGAAAAGGCCTCTCACGCGAGCCCAGCCGACA
CTCACCTCAAGTCTGAGAATGACAAGCTGAAGATCGCGCTGACACAGAGT
GCTGCCAATGTGAAGAAGTGGGAGATGGAGCTGCAGACCCTGCGGGAGA
GCAACGCCCGGCTGACCACGGCACTGCAGGAGTCGGCGGCCAGCGTGGA
GCAGTGGAAGCGGCAGTTCTCCATCTGCAGGGACGAGAATGACAGGCTCC
GCAGCAAGATCGAGGAGCTGGAAGAACAGTGCAGCGAGATAAACAGGGA
GAAGGAGAAGAACACACAGCTGAAGAGGAGGATCGAGGAGCTGGAGTCA
GAGGTCCGAGACAAGGAGATGGAGTTGAAAGATCTCCGAAAACAGAGTG
AAATCATACCTCAGCTCATGTCCGAGTGTGAATATGTCTCTGAGAAGTTAG
AGGCGGCCGAAAGAGACAATCAAAACTTGGAAGACAAAGTGCGGTCTCT
AAAGACAGACATCGAGGAGAGTAAATACCGACAGCGCCACCTGAAGGGG
GAGCTGAAGAGCTTCCTTGAGGTGCTGGATGGAAAGATCGACGACCTCCA
TGACTTCCGTAGAGGACTCTCCAAGTTAGGCACAGATAACTAGGGCGGGG
CGGAGCAAGTGTGTGTGAGAGGTGTGGTAGACGTAGGACATTCTCCATTT
GCTTCTGTAAATGCAGGTGCGATCTGTCTGTCTCCAGACCAATTGTGCCGT
CCGCTCACTCCTCCAGAATAGGAAATCTCTCGCTTCTCTGGCTTTGTGAGG
TCATGGACAGCTGGAAGCTTCTGACTCAGGAATCCAGAACTTGGTCTACC
TTAGCCGTTTACGCAGTCAGGGCAGGGATGTTTAGATCTTCCCTTAAGGGC
TGTTGTAACCCTATGAACCGGGGATGGGGGAGTATTTTCTAATCCAAGTA
CCATTATCCTTTACAGCAGGCCCTCGGGTGCCTTCTGCTGCGTGGCATTCA
GTGTATGTGACTCTCCAGCAGGTTCTAGACCACGGGCATGTGGAGGGAGC
ATCTTTTCCCAGTATGCATTTTGTTGCTTTAGCAGATGTGACATGACATTGT
CAACCACAAAGTTCACACTCAAAAACTGCACAACTGACTTACTCAAAAAG
AAATAATTGTAAAAAAAAAAAAAAAAA

FIG. 30

M-Homer-2b

---
MGEQPIFTTRAHVFQIDPSTKKNWVPASKQAVTVSYFYDVTRNSYRIISVDGA
KVIINSTITPNMTFTKTSQKFGQWADSRANTVFGLGFSSELQLTKFAEKFQEV
REAARLARDKSQEKTETSSNHSQESGCETPSSTQASSVNGTDDEKASHASPAD
THLKSENDKLKIALTQSAANVKKWEMELQTLRESNARLTTALQESAASVEQ
WKRQFSICRDENDRLRSKIEELEEQCSEINREKEKNTQLKRRIEELESEVRDKE
MELKDLRKQSEIIPQLMSECEYVSEKLEAAERDNQNLEDKVRSLKTDIEESKY
RQRHLKGELKSFLEVLDGKIDDLHDFRRGLSKLGTDN*

FIG. 31 mHomer-3GenBank

```
TCCACAGCCAGGGAACAGCCAATCTTCAGCACCCGGGCGCACGTATTCCAGATCGA
CCCCACTACAAAGCGGAACTGGATCCCCGCCGGCAAGCACGCACTTACCGTGTCCTA
TTTCTATGATGCAACCCGAAATGTGTACCGCATCATCAGCATCGGGGGTGCCAAGGC
CATCATCAACAGCACTGTCACTCCCAACATGACCTTCACCAAAACCTCTCAGAAGTT
CGGGCAATGGGCAGACAGTCGAGCCAACACTGTCTACGGCCTAGGCTTTGCCTCTGA
ACAGCAGCTGACCCAGTTTGCTGAGAAGTTTCAGGAGGTGAAAGAAGCTGCCAGGC
TGGCTCGAGAGAAATCTCAAGATGGTGGAGAATTCACTAGTACTGGCCTGGCCCTTG
CCTCCCATCAGGTTCCTCCAAGCCCCTTGGTCAGCACCAATGGTCCAGGCGAGGAAA
AGCTGTTCCGTAGCCAGAGTGCGGACACCCCTGGCCCCACCGAGCGGGAACGGTTG
AAGAAGATGCTGTCAGAAGGCTCTGTAGGGGAAGTCCAGTGGGAAGCAGAGTTCTT
CGCGCTTCAGGACAGCAACCAGAGGTTGGCGGGAGCCCTTCGGGAAGCGAACGCAG
CGGCCACTCAGTGGAGGCAACAACTGGAGGTCCAACGTGCAGAGGCTGAACTCTTG
AGGCAGCGGGTAGCAGAGCTGGAGGCCCAGGTGGCTGTAGAGCCAGTCCGGGCAGG
AGAGAAAGAAGCAACCAGCCAGTCGGTGGAGCAGCTGGAGGCTCGGGTGCAGACC
AAGGACCAGGAGATCCAGACTTTGAAGAATCAGAGCACTGGCACCCGAGAGGCTCC
AGACACTGCCGAGCGCGAAGAGACACAGCAGCAAGTTCAGGACCTGGAGACCCGG
AATGCAGAGCTGGAGCAGCAGCTGCGGGCGATGGAGTGCAACCTGGAGGAGGCGC
GGGCCGAGCGGGAGCGCGCACGGGCGGAGGTGGGCCGGGCTGCGCAGCTGCTGGAT
GTTCGGCTGTTTGAGCTCAGCGAGCTGCGTGAAGGCCTGGCACGCCTGGCAGAGGC
AGCACCCTAGTCTGCCATGGAGTGTCTGCGGCCTCAAGGCGCCCTGGCAGGGGCCA
GGGGACCCCAGCTGTCTCTGAGCTTTGCACTGTGTAGAGTTTTCTAGAATCCTTGGG
CAATGCTTCTACCCAGGTTACATTTCTACGTGTGGCGTTGCTGTCCCTGGCTGCTGCT
GCCCTGCGCCCCAGGGACACTGCGAGGGAAGGCTGCACTAGTCATCCCCATGGGGC
AACAGAGGCTTTGGGATCCTGAGACCTGAAGGCCCTGTACTCATCCCACCCCATTCT
CAAGTCAGACTGACAACTTCAAAGAGTGTTTACTGAAGTCAGGGGCCACCAGCACC
AGGTTTACAGCTCAGTCCTGAGCCTCAGCCTGGGCTGGCTCTTGGGGCCGAGATCTG
GGAGGACGCGACCGTCGGACAGTGCTCCCTGCTTTCTGCCGCCGAAGTGTCTGCCCC
ACTTTCTCCTTGAAGCGTCGGTTTTGTTGCTTGATCTTGGCCAGCTCAGCTTTGCGTTT
GGCCTCCAGGTCTGGGTCCTGCGGAAGGGAGCTGAGAATGTAACTGGGCAGCTTCC
CAGGGACTGGCTCCCCCACCCCTACCCGTCCCCAGGTCCCACCCACCCTTACTGGCC
ACACTCTTATGCCTGTCCCTGCATACCCATGCCTCCCTATACTACCTTCCCCTCCAGG
ATCATCTGTTTCCGCTTGTTGATCTCTTTCTTTTCATCAAAATGCGAAGCCTCCAGTTT
CTAGGGGTGGGGAGGGGAACAGGTCAGTCAGGCCTGGGGCAGGAAGCCCCGCCCAC
CTCACCCCACTCCACCCTACCCTGACAGGCTGGCCACACTTACTATTTCGCACTCCCT
TCGCACTACGTTGACCTGCGTGAGGATTTGTAGAACCTCAGCCTCCTCCACCACCAG
CTCTGCCAGCTGCTGCTCTGCAGGGACAGGAAACACTGAGTTGGGCTGGGAGTGCA
ACCAGCCCTCTGCACCCCAGCTCTGGATGTCTGGATCCAACCAAATGTGGACTGAT
GATATTTAGAAAAAGCAAAATGCTGCCAAGCTTGGCAGCACATGCTTGTCATCACAG
CACTGGGAGGTGGAGGCAGGGGATCACTCGTTTCAGCTGAGTTCCAGGCCAGCTCT
GTAGAGCAAGAATCTGTCTCAAATTAATGACTGAATAAACAAATGAACAAGTAAAA
AAAAAAAAAAAAAAAAAAAAAAAAAAAAAAAA
```

FIG. 32

M-Homer-3

MSTAREQPIFSTRAHVFQIDPTTKRNWIPAGKHALTVSYFYDATRNVYRIISIG
GAKAIINSTVTPNMTFTKTSQKFGQWADSRANTVYGLGFASEQQLTQFAEKF
QEVKEAARLAREKSQDGGEFTSTGLALASHQVPPSPLVSTNGPGEEKLFRSQS
ADTPGPTERERLKKMLSEGSVGEVQWEAEFFALQDSNQRLAGALREANAAA
TQWRQQLEVQRAEAELLRQRVAELEAQVAVEPVRAGEKEATSQSVEQLEAR
VQTKDQEIQTLKNQSTGTREAPDTAEREETQQQVQDLETRNAELEQQLRAME
CNLEEARAERERARAEVGRAAQLLDVRLFELSELREGLARLAEAAP*

FIG. 33

R-Homer1a(nn)

```
GTGCTGTGCACATCGCGAGCGGCTGGGGTTTGCACTTCGAGATTTCTTCTTTATAATTT
TTTTTTTTAATGTAAGGGAGACAGTGGAATTGCTACCCGTAGAATTTTTATTCAAGTG
CACGTCGCGTTGGGTTGCACGCTCCACCCCCAGGGACCTGGTGTGGTGAAATTTGAAC
CCACCGCCTTAGCCCAAAGGCCGAGTAACCTGGCTGCTTGAGTGTCGTGGAAGACGTG
AGCGAAATGATCAGCGAACTCATTTTTTATCAGACTCGCTGAAGCTGGCTTTTGCGTTT
TTCTACACGTACACTAATTTTATGGAATAGTTAAAGTGCTATATTCTCCGCGCAACCTT
TTCAAATTCCAAATGTTTGAACGTTTTGGTGTCAGCGCGAGTGAAATCATTTTACCGAC
AAGAACTAACTGAATTGTCTGCCTCGTTGAGTTGCCTCCGGAAAAGATCTCGGGGGTG
GAAAAGCAACTGCAAAATAACAGACGGAGAAAATTCCTTGGAAGTTATTTCTGTAGCA
TAAGAGCAGAAACTTCAGAGCAAGTTTTCATTGGGCAAAATGGGGGAACAACCTATCT
TCAGCACTCGAGCTCATGTCTTCCAGATCGACCCAAACACAAAGAAGAACTGGGTACC
CACCAGCAAGCATGCAGTTACTGTGTCTTATTCTATGACAGCACAAGGAATGTGTAT
AGGATAATCAGTCTAGACGGCTCAAAGGCAATAATAAATAGCACCATCACTCCAAACA
TGACATTTACTAAAACATCTCAAAAGTTTGGCCAATGGGCTGATAGCCGGGCAAACAC
TGTTTATGGACTGGGATTCTCCTCTGAGCATCATCTCTCAAAATTTGCAGAAAAGTTTC
AGGAATTTAAAGAAGCTGCTCGGCTGGCAAAGGAGAAGTCGCAGGAGAAGATGGAAC
TGACCAGTACCCCTTCACAGGAATCAGCAGGAGGAGATCTTCAGTCTCCTTTAACACC!
AGAAAGTATCAATGGGACAGATGATGAGAGAACACCCGATGTGACACAGAACTCAGA
GCCAAGGGCTGAGCCAGCTCAGAATGCATTGCCATTTTCACATAGGTACACATTCAAT
TCAGCAATCATGATTAAATGAGATGGATAAATATGAAGTTCATTTGGTTTCAGAAACT
CTTGAGTGAAAAATCCCAGGTCAGACTTCTTTAATTAATTAATTGTTTGCTGTTGCTCA
GATTGACTGAATATTTCCATTATCTGTGTAGAAAAAGGAACGTTAATTATAGGAGAAA
CTTTTTCAATGGACAAAACATTCCATTCTATCTATATTTTAAAGATCCCTTTTGCTAACC
AGTTTTCTGATTTTCTACATGTTACGTAAGACTAATAACTTGTGATTAGGATCAATGGA
CTCCTGCTCCAAAGGAAAGCCTTGCCACAGGCCCACAGAGGTGCCACAGAGGACGGG
GCCAGGCAGGAACCCGTCAGCATTGAAGGTTGTTTTTGTATGCCAACAGGAGGAAAGC
TTGAGTTGCTGCTGATTCTTAAAAGAATTCTGTATTCTAAAAGATACACATCATGTTCT
AAATGCATTTTAAACTAGTGACATTAGTTATTGGGCATACTGTGGTATTACTAGACTAC
AAAGAGGAATATGAAGTGGCACCATTGAAAGTATTTTTTAAAAAGCCTGTCTACCTT
AACACTAATTTTTACCCTTATTTAAATGCTTTTTACTAAACAGTTTTAGGTAAAATTAA
GAAAACAGTTTTGTTGACTGCACATCTTTTAGAAGGACCAACTTTTAGAGAATTACATT
CTTTGACAGATTAAAAATTGCAAAGTGAGATATTTCAAACTCTTAAGTGAGTTTTATTG
CCGTTGGACTGCATTAATACGGACATACGATTAAACTTAGTAGACCAACACTGAGGGA
TCTCCTTACCAGGCTGCAGAACAAGGAAATTAAGCAATAAATGGGACTTGTGAATG!
GAAGGACACTCTACTGCTAGTGCTAGTAATTCTGCATAAGATGGTATACATTTTGAAG
A!
AAGCTGCTTTTAATTACTTTTAATAATGATTTTAATTACTCTAGTGCAAGTGCTTCCTCG
AGCTATAAAGGTAGCTGAGCACAGCAGACCTTTACTCCCTCAGTCTGACTTCTGTACTC
ATATTCATTTAGTGAACATAGTCTTTTAACAGAAGACCACAGTTCTTTGATAGCGTTAC
AAAACTTACGTTATTTAAACGTTATAAAGAACGTTATTGTAGGATAAAATGTTAAAAA
CTGTGTCAAGGACAGGAAGAATTCCTATCTATTAAGTAGTGGTTTCCACCCCCACTTAA
GACTGAACTGCACTGAACGGTAACTGTATACTTGGTTTGACACCTCGACTGAGCCATG
CGCACTGAATACTGTGACATTGAGGAGTAAGAACTTTTAAATTTAACATTTAAAGAAG
CTACTTGCAGTTTATGCACCGAAATTTGTCTAAATGTTCTCCATTTTGCTGACCCCGTTG
TATTCATACTGCTCCCCAGAGCCTAGAGTTGTCCTCATCCTGACTTCCTGTGCCTGAGT
GTCTGAGAGGAGTCACTTTCACTGTGAAGACACTGCTTCTGCGCCTCGTAGGGAGGAC
```

FIG. 34a

```
TTGACAGTGCTCCCGTAGAAATCCTACATTATTTCAACCTCAGAGTTACAGTAAAGGCA
GGTTATAACCAGTCTTTCTTATTATTTTAAGAATTTCCAGCCCTAGTGTTTTATGAAAGT
ATTCCTGTGAATTTGACACCTTATGATCCTATATTCATCTAATTCCTTAATGAAATAAAA
ATGTCCATGTGAGGTAGGTTATTTACAGCGATTGCAGGAGACATGGTGTTCTTCAGAGT
TCCCAAACCAGGATAGTTTCAAATAGGTTTTTCATGGCTTCTGACGAAGAAGACCATAA
AGTTCCCTGCAGTGTGTCAGTGATGTGCAAGCTGAATTAGTGCGAAGTGTCACACTGTG
AAAGCACGTGCTTTTGGCTTATTATGAGAAAACGAAATCTTTAAATT!
CAGTTTATGTGTCTTAGGTCCAGTTTACTTTGATTTGACTACTCAGTTCTTCTGACCCCAC
CTAGTATGTATGTATATGTGTGTGTATGTGTGTGTATGTCTGTATGTATACATACATA
TACACACACATTGTATACATATGCTATATATACAGTATGTGTATATATATACTATATATG
AATATATGAATATATATATTCAATTAGTTAATAGTACATTTAAGCCAAATATCCAACAT
AAGCACACTATGTAAGTATCTATCTGGAAAGACCTATATAGAATTGAGATCAACATTTC
ATGAGTTAGAAACAAAGGATTTTATAATTAATATTACTTAAGTCTAAAGTACCCATATA
TTTAAATTAGATATGCAATTTTTCCCTCTTGGCAAAGAAAGACAAAAATCTTGTGTTTAG
AGATGATGTAGATTGTCATTTTTGCCTTTCCTTCCTGAGTACTTGTTTTAACAACAACAA
AAAAAGACTAGTTTAAGAAAAGGGATTGTCCAGTATTTTCTGCTTTGTTAAGTCTAATT
TTACTGTTAAACAGAGAGCAGAATCACTGGAGTACTGGGGGGGTTTTTGTTGTTTTTT
TTTTTTCTTTCTGTTTTTTCGGAGCTGGGGAGCGAACCCAGGGCCTTGCGCTCACTAG
GCAAGCACTCTACCGCTGAGCTAAATCCCCAACCCCTGGAGTATCTGTTTTAAAAGAAA
GCCAGGACCGTTATGATGGCCATACCCAGGGTACATAGTGAAAACAACAGAGACCAAG
CAATGAGAGTGTGAGAGTACCAATCCACCAGTACTGCTGCCGGACATGGCAGCTGCCT
GTGCTTTTCTGAAGAGTCATAGTGTATGCTAAGTCTAGAACCATTACTTAGTAAAGAGG
CTATGACTTTTATTTGGGCCTGACAATTTTAGTGGTGTGGTCATAGTCTATTCTGTATTT
GTAAGCTTTATTTTAAATTACTGTGTTGATTTAGGAAC!
ACAAGAAATGTTTTTATTTTAATTATGAGTGTATATAAGGTTTTCAGATATGCACAGA!
CTACAATAATAGACTCCCATGGAGATACCACTTCAGCCTTAACAGTCAGGGAGAAGGA
GCCTCACTTTATCACCGCACTCACCCTGCTCTCCACTGATCTGTTGTTACTGCGGTGTGG
AGGTCACACGCATGCAGGTCTTCACACATGATGGGTAGGCCCGCACCAAGTGAGCCTC
TCCCAGCCTTGCTGTTTCGTTTTTTTATTTTAATCTTACATGTATGGGTGTTTTGCATCCA
GGCATGTCATGCCTGTGTCCACAGAAGCCAGAAAGGGTATCAGATTCCCTAAAACTGG
AGTTCTCGATGATCGTGAGCGAGCCATTGTGGGTGCTGGGAACTGAAGCTGGGTCCTCT
ACAAGAGCAGCCAGCGCTCTTAACCATTGAGCCACTATCTGCCCTGTGTTTGTTTTATTT
ATTTATTTATTTATTTATTTATTTATTTATTTATTTATTTATTTATTTATTTATTGGTT
CTTTTTTTTGGACTGGGGACCGAAGCCAGGGCCTTGCACTTCCTAGGCAAGCGCTCTA
CCACTGAGCTAAATCCCCAACCCCTTGTTTTATTTTAAAGCAAACGAGATACATAATTT
CAACCATGATAATTTAAGATTATCTTGAACTCTTAAGGAAATGTATATACTAAGCTATT
ATAGTTTTTATTTTCCCTAATTCAGTGGCATAATACCTTACCTTGAGTCGTTTACTACTTT
CTTTGGTTTCTAAAAACTCTACTGCTAAATTACAATGTAAAAACATAGGGCTCGTATAT
ACTGTAGAGTGCTGTAGATGTCCTCGTCATCAACTATGCAATAACAGTCTGATCGACAC
ATTTCAGGAGCGATCACTCTTTGGTGTGCTTCTTTAAATACTTTCAGAAGCTTAGGATGT
GCAAAGCAGGAAGACCGTGGGTGTAAATGTTTACTTATTTCTTTGAGAGTGTTAGTAAG
TCTTTTCTAAATTGCTTTTCTCTTCAAAATTATCGTT!
AACTTAAATGATAATTATCTTTGAGGTTAAACAGAAGCTCATTGACAAACTAAAGTGA
CTTTTTAGGGCATTCTTTGAGATCATAGTCTTATATCTGGGGACTAAAATGTCATTAGA
CCCTAATAGACTAACTTGTATGTTTGTGTGGGGAAACGTTTTCCTCTCTCATTCAAGGT
```

FIG. 34b

```
AACTGTTTGCTGCCTGTTGTTACTTGTGTAGCATTCTAGAAAATGGCTAGGTTTTTTATA
AGATTTAAGACAATAGAAGTAGTTTTATATTATTATAGTTCTGTTGGAATGTGATCCTGA
AATTATTACTGAAAATTAGAATTTTTATTTCGCTAATGACAACCTTGACTCTCAGAGATG
CAGTGTAAATTGATACCTCATCTTTCCGAGAGTTCAGAGCACAGGGCGGCAGTATGTGA
AGCTGCTTTTGCACTGACGCATTTTGATAAGTTTGGCTACTGTAATGGTAAAAGGCTCCT
CAGGCACTGACTGCATTTGGGTTCTTCCGATGGGGGATGATCCGTTCTCGTGGTGCTGCT
GGACTTATGCATTTTGGAGGTACTGCATGTATCTTCCACACTGCTTGACATTTTCTCTGA
TCTGTGTGTTTGCACCAACTCATTAAAAGAAATATGCAGAAATATCTTCTAATTCGTTGA
TCTTCGCTGTATGACAGTTATAATATTAAACACTTGGGTTGATCAAAAAAAAAAAAAAA
AAAAAAAAAA
```

FIG. 34c

R-Homer-1a

MGEQPIFSTRAHVFQIDPNTKKNWVPTSKHAVTVSYFYDSTRNVYRIISLDGS
KAIINSTITPNMTFTKTSQKFGQWADSRANTVYGLGFSSEHHLSKFAEKFQEF
KEAARLAKEKSQEKMELTSTPSQESAGGDLQSPLTPESINGTDDERTPDVTQN
SEPRAEPAQNALPFSHRYTFNSAIMIK*

FIG. 35

R-Homer-1bGenBank

CTAGTGGATCCCCCGGGCTGCAGGAATTCTGCGGCCGCAACACCGCACTGTGGTGGAC
AGTGAGGGCCGGAGAGAGACCACAGTGACCCATCAAGAAGCCCATGACAGTTCCAGA
AGTGATCCAGATCCTCCAAGATCTTCAGCTTTGGATGATCCCTTTTCCATCCTGGACCT
GCTTCTAGGACGTTGGTTTCGGTCCCGATAGCTTTCTTGAACTTCAGAGGCCTTCAGGT
CCTTCCCACCCCCTCCCTCCTGTTGCCCATTGCCAATAAGCATAGCTTTTGCTGTCATC
CTGGGGTCTTAAATGTGTGGAACCCCCCCAGGGACCTGGTGTGGTGAAATTTGAACCC
ACCGCCTTAGCCCAAAGGCCGAGTAACCTGGCTGCTTGAGTGTCGTGGAAGACGTGAG
CGAAATGATCAGCGAACTCATTTTTTATCAGACTCGCTGAAGCTGGCTTTTGCGTTTTT
CTACACGTACACTAATTTTATGGAATAGTTAAAGTGCTATATTCTCCGCGCAACCTTTT
CAAATTCCAAATGTTTGAACGTTTTGGTGTCAGCGCGAGTGAAATCATTTTACCGACAA
GAACTAACTGAATTGTCTGCCTCGTTGAGTTGCCTCCGGAAAAGATCTCGGGGGTGGA
AAAGCAACTGCAAAATAACAGACGGAGAAAATTCCTTGGAAGTTATTTCTGTAGCATA
AGAGCAGAAACTTAAGAGCAAGTTTTCATTGGGCAAAATGGGGGAACAACCTATCTTC
AGCACTCGAGCTCATGTCTTCCAGATCGACCCAAACACAAAGAAGAACTGGGTACCCA
CCAGCAAGCATGCAGTTACTGTGTCTTATTCTATGACAGCACAAGGAATGTGTATAG
GATAATCAGTCTAGACGGCTCAAAGGCAATAATAAATAGCACCATCACTCCAAACATG
ACATTTACTAAAACATCTCAAAAGTTTGGCCAATGGGCTGATAGCCGGGCAAACACTG
TTTATGGACTGGGATTCTCCTCTGAGCATCATCTCTCAAAATTTGCAGAAAAGTTTCAG
GAATTTAAAGAAGCTGCTCGGCTGGCAAAGGAGAAGTCGCAGGAGAAGATGGAACTG
ACCAGTACCCCTTCACAGGAATCAGCAGGAGGAGATCTTCAGTCTCCTTTAACACCAG
AAAGTATCAATGGGACAGATGATGAGAGAACACCCGATGTGACACAGAACTCAGAGC
CAAGGGCTGAGCCAGCTCAGAATGCATTGCCATTTTCACATAGTTCAGCCATCAGCAA
ACACTGGGAGGCTGAACTAGCCACGCTCAAGGGGAACAATGCCAAGCTCACCGCAGC
GCTGCTGGAGTCCACTGCCAACGTGAAGCAGTGGAAGCAACAGCTGGCTGCCTACCAG
GAGGAGGCAGAGCGGCTGCACAAGCGGGTCACGGAGCTGGAATGTGTTAGTAGTCAA
GCAAACGCGGTGCACAGCCACAAGACAGAGCTGAGTCAGACAGTGCAGGAGCTGGAA
GAGACCCTAAAAGTAAAGGAAGAGGAAATAGAAAGATTAAAACAAGAAATTGATAAC
GCCAGAGAACTTCAAGAACAGAGGGACTCTTTGACTCAGAAACTACAGGAAGTTGAG
ATTCGAAATAAAGACCTGGAGGGGCAGCTGTCGGAGCTGGAGCAGCGCCTGGAGAAG
AGCCAGAGCGAGCAGGACGCTTTCCGCAGTAACCTGAAGACTCTCCTAGAGATTCTGG
ACGGGAAAATATTTGAACTAACAGAATTGCGGGATAATTTGGCCAAGCTACTAGAATG
CAGCTAAAGAAAGTGAAATTTCAGTGCCAATAGATGAAGAGATACTGTCTGTCTTCGT
AGGACTGTTTGGGCTCTGTACCAAGATTGCACAAAATTTTTTGAATATCATTCCTCCAG
AAGGAGGGTGTTTTGAAAATTGGAATTGTATATTTCAGTATAAATTTTAGAATTTAGCT
TATAGCTAGTTGGGGGAAAAAAAGACATGAAAAACTTGAACCACAAATTACCTCCATG
TACATTGGCCATAGTTACAATGGGAGAATTAACAATGTCTGGGTCCCTTCTCCTTTTC
TGTTCAACACAGTGAAGATTATCTGCTTTTTAAATTTATTTACGATATCTACAGCTGTG
TTTTGTGTAAAAACTTAGTAATGGAAGCCCTGTCTTTGTTGTTATCTGAATAATTTCTCA
GGATATTTTTTGCTGCTGAGAAAGGGCCATTACCAATTAATCCTTGCCAGGAGTTGGG
GAGCTATGTCTCTAATTGGAATCACTATAACTGGGTGTCTGGAGTTCTTCCCTTTTCGT
ACTGAGAGTGTTCTCACTCTAGTGACTCCTCTGGTACACTCCGTGTTCTCCAATCTTGTC
TGTTGTACTTTACTTTTCCATATTGACTCCATGTATTTATGAGAAGATATTATCTCCCAT
TTTATTATACATTTTGAAGCCAACTAAACAAAGGCAGCTGAGTCCTTCAGATATTTTC
TTTTTAAATTTATAGTAAATTTGACACAGAACTGAAATTCAGCAGTCCGTCTTTGACGG
TTTAGTCTAGCAATGTTAAGGATATTTAGAGAAAATATGCAGTTACGTTTATTTATATA
TTTGGCAAGAAATTTTTCTGGATGATCAATGCTTTTCAATTTATGATAAATAATGGTT
AGGGGGCGCTGTTTATTATAGATAATTTTAAGGTATATAGCTGTTTTCAAGGAGGTCCA
CTTCCGTCTAGCAGCCAAGCAGAGGACTGTATCTAAATCGTGATCGTGGCAGATGGGT
CTTCATAGAAACCATGTCTTTATTCAAACTTCATAGGGCAATATTTTGAACTGTTACCT
AGGCATTTCAAAACAGGAAATACCGTCAACAGACTCTTCTCCAAGAGCAGGTTTTACT

FIG. 36a

GTTGTTTTGATGTAATTTTAAGACATTTAGCAAACATGCATTTCTTTATATGATACATTT
CTTTCACAAAACAATTTAAAAGTAAGCCACGTGCTGTCTGCTCTGCCCGGGTAGGAATT
GCATCAGAATACATATATCTTGCTGTACAATGCCTGTGATATTGAAGAGGGTTCTTTTC
ATGTATGCTTGAGTATCTAACTCTGGAGTCAATGAATGCACTGACTTTTTTTTGTTCGT
ACCCCAAATGATTGAATTGTTAAGTACAAATTAAGCAGATTAACTCATTTTTTCACTCA
TAAACAGATTCTTAGTACTAGTTTTGTTTTATATTTATGTGTATGTATGTAAATACATAC
ATATTAATTTATATTAGAGTGAAAAATAAATTGTTTGTTTCTAACATTAAAAAAAAAAA
AAAAAA

FIG. 36b

R-Homer-1b

MGEQPIFSTRAHVFQIDPNTKKNWVPTSKHAVTVSYFYDSTRNVYRIISLDGSK
AIINSTITPNMTFTKTSQKFGQWADSRANTVYGLGFSSEHHLSKFAEKFQEFKE
AARLAKEKSQEKMELTSTPSQESAGGDLQSPLTPESINGTDDERTPDVTQNSEP
RAEPAQNALPFSHSSAISKHWEAELATLKGNNAKLTAALLESTANVKQWKQQ
LAAYQEEAERLHKRVTELECVSSQANAVHSHKTELSQTVQELEETLKVKEEEIE
RLKQEIDNARELQEQRDSLTQKLQEVEIRNKDLEGQLSELEQRLEKSQSEQDAF
RSNLKTLLEILDGKIFELTELRDNLAKLLECS*

FIG. 37

R-Homer-1cGenBank

GCGGCCGCGTCGACTACGGCTGCGAGAAGACGACAGAAGGGGGCTCCGCTGATGCTC
CTCGTGAGAACGAATCGATCCTTCCCAGCCTTCTCTGCCTGCTCTCCACCTCCTCTCTGC
TCCGAGTCTTAGGAGAACGAACATTCAAAGGACAGATTCCAATGTGGTGTGCTGTGCA
CATCGCGAGCGGCTGGGGTTTGCACTTCGAGATTTCTTCTTTATAATTTTTTTTTTTAA
TGTAAGGGAGACAGTGGAATTGCTACCCGTAGAATTTTATTCAAGTGCACGTCGCGT
TGGGTTGCACGCTCCACCCCCAGGGACCTGGTGTGGTGAAATTTGAACCCACCGCCTT
AGCCCAAAGGCCGAGTAACCTGGCTGCTTGAGTGTCGTGGAAGACGTGAGCGAAATG
ATCAGCGAACTCATTTTTATCAGACTCACTGAAGCTGGCTTTTGCGTTTTCTACACGT
ACACTAATTTTATGGAATAGTTAAAGTGCTATATTCTCCGCGCAACCTTTTCAAATTCC
AAATGTTTGAACGTTTTGGTGTCAGCGCGAGTGAAATCATTTTACCGACAAGAACTAA
CTGAATTGTCTGCCTCGTTGAGTTGCCTCCGGAAAAGATCTCGGGGGTGGAAAAGCAA
CTGCAAAATAACAGACGGAGAAAATTCCTTGGAAGTTATTTCTGTAGCATAAGAGCAG
AAACTTCAGAGCAAGTTTTCATTGGGCAAAATGGGGGAACAACCTATCTTCAGCACTC
GAGCTCATGTCTTCCAGATCGACCCAAACACAAGAAGAACTGGGTACCCACCAGCAA
GCATGCAGTTACTGTGTCTTATTTCTATGACAGCACAAGGAATGTGTATAGGATAATCA
GTCTAGACGGCTCAAAGGCAATAATAAATAGCACCATCACTCCAAACATGACATTTAC
TAAAACATCTCAAAAGTTTGGCCAATGGGCTGATAGCCGGGCAAACACTGTTTATGGA
CTGGGATTCTCCTCTGAGCATCATCTCTCAAAATTTGCAGAAAAGTTTCAGGAATTTAA
AGAAGCTGCTCGGCTGGCAAAGGAGAAGTCGCAGGAGAAGATGGAACTGACCAGTAC
CCCTTCACAGGAATCAGCAGGAGGAGATCTTCAGTCTCCTTTAACACCAGAAAGTATC
AATGGGACAGATGATGAGAGAACACCCGATGTGACACAGAACTCAGAGCCAAGGGCT
GAGCCAGCTCAGAATGCATTGCCATTTTCACATAGTGCCGGGGATCGAACCCAGGGCC
TCTCTCATGCTAGTTCAGCCATCAGCAAACACTGGGAGGCTGAACTAGCCACGCTCAA
GGGGAACAATGCCAAGCTCACCGCAGCGCTGCTGGAGTCCACTGCCAACGTGAAGCA
GTGGAAGCAACAGCTGGCTGCCTACCAGGAGGAGGCAGAGCGGCTGCACAAGCGGGT
CACGGAGCTGGAATGTGTTAGTAGTCAAGCAAACGCGGTGCACAGCCACAAGACAGA
GCTGAGTCAGACAGTGCAGGAGCTGGAAGAGACCCTAAAAGTAAAGGAAGAGGAAAT
AGAAAGATTAAAACAAGAAATTGATAACGCCAGAGAACTTCAAGAACAGAGGGACTC
TTTGACTCAGAAACTACAGGAAGTTGAGATTCGAAATAAAGACCTGGAGGGGCAGCT
GTCGGAGCTGGAGCAGCGCCTGGAGAAGAGCCAGAGCGAGCAGGACGCTTTCCGCAG
TAACCTGAAGACTCTCCTAGAGATTCTGGACGGGAAAATATTTGAACTAACAGAATTG
CGGGATAATTTGGCCAAGCTACTAGAATGCAGCTAAAGAAAGTGAAATTTCAGTGCCA
ATAGATGAAGAGATACTGTCTGTCTTCGTAGGACTGTTTGGGCTCTGTACCAAGATTGC
AAAAAATTTTTTGAATATCATTCCTCCAGAAGGAGGGTGTTTTGAAAATTGGAATTGTA
TATTTCAGTATAAATTTTAGAATTTAGCTTATAGCTAGTTGGGGGAAAAAAAGACATG
AAAAACTTGAACCACAAATAATGCAATCTTTTCCCCTGATAGTAGCCAATGGGAGAAT
TAACAATGTCTGGGTCCCTTCTCCTTTTTCTGTTCAACACAGTGAAGATTATCTGCTTTT
TAAATTTATTTACGATATCTACAGCTGTGTTTTGTGTAAAAACTTAGTAATGGAAGCCC
TGTCTTTGTTGTTATCTGAATAATTTCTCAGGATATTTTTTGCTGCTGAGAAAGGGCCA
TTACCAATTAATCCTTGCCAGGAGTTGGGGAGCTATGTCTCTAATTGGAATCACTATAA
CTGGGTGTCTGGAGTTCTTCCCTTTTCGTACTGAGAGTGTTCTCACTCTAGTGACTACTC
TGGTACACTCCGTGTTCTCCAATCTTGTCTGTTGTACTTTACTTTTCCATATTGACTCCA
TGTATTTATGAGAAGATATTATCTCCCATTTTATTATACATTTTGAAGCCAACTAAACA
AAGGCAGCTGAGTCCTTCAGATATTTTTCTTTTTAAATTTATAGTAAATTTGACACAGA
ACTGAAATTCAGCAGTCCGTCTTTGACGGTTTAGTCTAGCAATGTTAAGGATATTTAGA
GAAAATATGCAGTTACGTTTATTTATATATTTGGCAAGAAATTTTTTCTGGATGATCAA
TGCTTTTCAATTTATGATAAATAATGGTTAGGGGCGCTGTTTATTATAGATAATTTTAA
GGTGTATAGCTGTTTTCAAGGAGGTCCACTCCCGTCTAGCAGCCAAGCAGAGGACTGT
ATCTAAATCGTGATCGTGGCAGATGGGTCTTCATAGAAACCATGTCTTTATTCAAACTT
CATAGGGCAATATTTTGAACTGTTACCTAGGCATTTCAAAACAGGAAATACCGTCAAC

FIG. 38a

```
AGACTCTTCTCCAAGAGCAGGTTTTACTGTTGTTTTGATGTAATTTTAAGACATTTAGC
AAACATGCATTTCTTTATATGATACATTTCTTTCACAAAACAATTTAAAAGTAAGCCAC
GTGCTGTCTGCTCTGCCCGGGTAGGAATTGCATCAGAATACATATATCTTGCTGTACAA
TGCCTGTGATATTGAAGAGGGTTCTTTTCATGTATGCTTGAGTATCTAACTCTGGAGTC
AATGAATGCACTGACTTTTTTTTTGTTCGTACCCCAAATGATTGAATTGTTAAGTACA
AATTAAGCAGATTAACTCATTTTTCACTCATAAACAGATTCTTAGTACTAGTTTTGTTT
TATATTTATGTGTATGTATGTAAATACATACATATTAATTTATATTAGAGTGAAAAATA
AATTGTTTGTTTCTAACATTAGTTTCTACAGTAAGGTGTCTCTGAAACATGTGTGTCAG
ACACTTAGCCACCATGCATTCTATGTGCTACCCCATCATGCCAGTCACCTCCATCGACG
TTAGGGTATTTTCCTTACCTGTCTATTATAAAGAGAATAACTTAGGTACACATGCTCAG
AGCCGAGATATTTCTCTGATAAATCAGGTAATAAAATCTATTTGATGGGTAGAATTTTG
AAAACAGACATGATTTATCTATGAGTTTCTGAATATCAAAGAACACCAGGTTTTCATT
TAAATAGAGGTCTAACACTAGGGATCAGGGAATTTAGTTATGAAGAGTTGAAAAAAA
AAAAAAAAAAAAAAAAAAAAAAAA
```

FIG. 38b

R-Homer-1c

MGEQPIFSTRAHVFQIDPNTKKNWVPTSKHAVTVSYFYDSTRNVYRIISLDGSK
AIINSTITPNMTFTKTSQKFGQWADSRANTVYGLGFSSEHHLSKFAEKFQEFKE
AARLAKEKSQEKMELTSTPSQESAGGDLQSPLTPESINGTDDERTPDVTQNSEP
RAEPAQNALPFSHSAGDRTQGLSHASSAISKHWEAELATLKGNNAKLTAALLE
STANVKQWKQQLAAYQEEAERLHKRVTELECVSSQANAVHSHKTELSQTVQ
ELEETLKVKEEEIERLKQEIDNARELQEQRDSLTQKLQEVEIRNKDLEGQLSEL
EQRLEKSQSEQDAFRSNLKTLLEILDGKIFELTELRDNLAKLLECS*R

FIG. 39

R-SHANK3A(GENBANK)(nn)

CTCTAGAACTAGTGGATCCCCCGGGCTGCAGGATTCTGCGGCCGCGCTAAACCGTGCC
GCCGTCGCCGCCGCCGCTGCGCCTGCGGAGCCCCCGGAGCCGCTGTCCCCCGCGCTGG
CCCCGGCCCCGGCCCCATACGGCCCCCTCCCGCAGTAGCGCGGTCGGCGGGACTCTGG
CGGGGGGTCAGGGGGGGCCAGGGCGCCGCGCGGAGTCCCCGTGCGCTCCTCTCTCCGC
CGGGAACAGTCCGGGCCCCGGCGCTAGCACCGGGATGGACGGCCCCGGGGCCAGCGC
CGTGGTCGTGCGCGTCGGCATCCCGGACCTGCAACAAACGAAGTGCCTGCGTCTGGAT
CCAACCGCGCCCGTGTGGGCCGCCAAGCAGCGTGTGCTCTGCGCCCTCAACCACAGCC
TTCAGGACGCGCTCAACTACGGGCTATTCCAGCCTCCCTCCCGGGGTCGCGCCGGCAA
GTTCCTGGATGAAGAGCGGCTCTTACAGGACTACCCGCCTAACCTGGACACGCCCCTG
CCCTATCTGGAGTTTCGATACAAGCGGAGAGTTTATGCCCAGAACCTCATAGATGACA
AGCAGTTTGCAAAGCTGCACACAAAGGCAAACCTGAAGAAGTTCATGGACTATGTCCA
GCTACACAGCACAGACAAGGTGGCCCGCCTGCTGGACAAGGGGCTGGACCCCAATTTC
CATGACCCTGACTCAGGAGAGTGCCCTCTGAGCCTTGCAGCACAGTTGGACAACGCCA
CTGACCTCCTGAAGGTTCTTCGCAATGGCGGTGCTCATCTGGACTTCCGAACCCGAGAT
GGGCTAACCGCTGTCCACTGCGCCACCCGACAGCGGAATGCGGGAGCATTGACGACCC
TGCTGGACCTGGGGGCTTCACCTGACTACAAGGACAGCCGCGGCCTGACGCCCCTGTA
CCATAGTGCCCTAGGGGGCGGGGATGCCCTCTGCTGTGAGCTGCTTCTCCATGATCACG
CACA!
GTTGGGGACCACTGACGAGAATGGCTGGCAGGAGATCCATCAGGCCTGTCGCTTTGGG
CATGTACAGCACTTGGAGCACCTGCTGTTCTATGGGGCCAACATGGGTGCCCAGAACG
CCTCGGGAAACACAGCCTTGCACATCTGTGCCCTCTATAACCAGGAGAGCTGTGCCCG
CGTCCTGCTTTTCCGTGGTGCCAACAAGGACGTCCGCAATTACAACAGCCAGACAGCC
TTCCAGGTGGCCATTATTGCAGGGAACTTTGAGCTTGCCGAGGTAATCAAGACCCACA
AAGACTCGGATGTCGTACCATTCAGGGAAACCCCCAGCTATGCAAAGCGACGACGTCT
GGCTGGCCCGAGTGGCTTGGCATCCCCTCGGCCCTTACAGCGCTCAGCCAGTGATATC
AACCTGAAGGGTGACCAGCCCGCAGCTTCTCCCGGGCCCACTCTCCGAAGCCTCCCTC
ACCAACTGCTGCTCCAGAGGCTTCAGGAGGAGAAAGACCGGGACAGGGATGGTGAGC
AGGAGAACGACATCAGCGGTCCCTCAGCAGGCAGGGGCGGCCACAGCAAGATCAGCC
CCAGCGGGCCCGGCGGATCCGGCCCCGCGCCCGGCCCCGGCCCGGCGTCTCCCGCGCC
CCCCGCGCCGCCGCCCCGGGGCCCGAAGCGGAAACTTTACAGTGCCGTCCCCGGCCGC
AAGTTCATCGCTGTGAAGGCGCACAGCCCGCAGGGCGAGGGCGAGATCCCGCTGCACC
GCGGCGAGGCCGTGAAGGTGCTCAGCATTGGGGAGGGCGGTTTCTGGGAGGGAACCG
TGAAGGGCCGTACAGGCTGGTTCCCAGCTGACTGTGTGGAGGAAGTGCAGATGCGACA
GTATGACACACGGCATGAAACTCGAGAGGACCGGACGAAGCGTCTTTTCCGCCACTAC
ACTGTGGGTTCCTATGACAGCCTCACTTCACACAGTGATTATGTCATTGATGATAAGGT
GGCTATC!
CTGCAAAAACGGGACCATGAGGGTTTTGGCTTTGTTCTCCGGGGAGCCAAAGCAGAGA
C!
CCCCATTGAGGAGTTTACACCCACACCTGCCTTCCCTGCGCTCCAGTACCTTGAGTCTG
TAGATGTGGAAGGTGTGGCCTGGAAGGCTGGGCTTCGCACTGGGGACTTCCTCATTGA
GGTAAACGGAGTGAACGTCGTGAAGGTTGGACACAAGCAAGTGGTGGGTCTCATCCGT
CAGGGTGGCAACCGTCTGGTCATGAAGGTTGTGTCTGTTACCAGGAAGCCAGAGGAGG
ATAGTGCTCGGCGCAGAGCCCCACCACCTCCCAAGAGGGCCCCCAGCACCACGCTGAC
CCTGCGGTCCAAGTCCATGACGGCTGAGCTCGAGGAACTCGCTTCCATTCGGAGAAGG
AAAGGGGAGAAGTTGGATGAGATCCTGGCGGTTGCTGCGGAACCAACGCTGAGGCCA

FIG. 40a

R-Shank3a(genbank)(nn)

```
GACATTGCAGACGCTGATTCCAGGGCAGCCACTGTCAAGCAGCGGCCCACCAGCCGGA
GGATTACCCCTGCCGAGATCAGCTCATTGTTTGAGCGACAGGGCCTCCCGGGCCCAGA
GAAGCTGCCGGGCTCTCTGCGGAAGGGGATTCCACGGACCAAATCTGTAGGGGAGGAT
GAGAAGCTGGCATCCCTACTGGAAGGGCGTTTCCCACGCAGCACATCAATGCAAGACA
CAGTGCGTGAAGGCCGAGGCATTCCGCCCCCACCGCAGACCGCCCCGCCACCCCCACC
CGCGCCCTACTACTTCGACTCCGGGCCACCCCCCACCTTCTCACCACCGCCACCACCAC
CGGGCCGGGCCTATGACACTGTGCGCTCCAGCTTCAAGCCAGGCCTGGAGGCTCGTCT
GGGTGCAGGGGCAGCTGGCCTGTATGATTCTGGCACACCTCTGGGCCCGCTGCCCTAC
CCTGAGCGCCAGAAGCGTGCACGCTCCATGATCATATTGCAGGACTCTGCGCCAGAAG
TGGGCGATGTACCCCGGCCTGCGCCTGCAGCCACACCGCCTGAGCGCCCCAAGCGCCG
GCCT!
CGGCCGTCAGGCCCTGATAGTCCCTATGCCAACCTGGGCGCCTTCAGTGCCAGCCTCTT
TGCTCCGTCGAAACCGCAGCGCCGCAAGAGTCCGCTGGTGAAGCAGCTTCAGGTGGAG
GACGCTCAGGAGCGCGCGGCGTTGGCCGTGGGTAGCCCGGGACCAGTGGGTGGAAGC
TTTGCACGAGAACCCTCCCCAACGCACCGCGGGCCCCGACCGGGCGGCCTTGACTACA
GCTCTGGAGAAGGCCTGGGGCTCACCTTTGGCGGCCCTAGCCCTGGCCCAGTCAAGGA
GCGGCGCCTGGAGGAGCGACGCCGTTCCACTGTGTTCCTGTCTGTGGGTGCCATCGAG
GGCAACCCTCCCAGCGCGGATCTGCCATCCCTACAACCCTCCCGCTCCATTGATGAGC
GCCTCCTGGGGACAGGCGCCACCACTGGCCGAGATTTGCTGCTCCCCTCCCCTGTCTCT
GCTCTGAAGCCATTGGTCGGTGGTCCCAACCTTGGGCCCTCAAGCTCCACCTTCATCCA
TCCTCTTACTGGCAAACCCTTGGATCCTAGCTCACCCCTAGCTCTTGCTCTGGCTGCCC
GAGAGCGGGCTCTGGCCTCGCAAACACCTTCCCGGTCCCCCACACCCGTGCACAGTCC
TGATGCTGACCGCCCTGGACCCCTCTTTGTGGATGTGCAAACCCGAGACTCCGAGAGA
GGACCCTTGGCCTCCCCAGCCTTCTCCCCTCGGAGTCCAGCCTGGATTCCAGTGCCTGC
TCGCAGAGAGGCAGAGAAGCCCACTCGGGAAGAGCGGAAGTCACCAGAGGACAAGA
AATCCATGATCCTCAGCGTCTTGGACACGTCCTTGCAACGGCCAGCTGGCCTCATTGTT
GTGCATGCCACCAGCAATGGACAGGAGCCCAACAGGCTGGGGGCTGAAGAGGAGCGC
CCGGGTACTCCGGAGCTGGCCCCAACCCCCATGCAGGCAGCAGCTGTGGCAGAGCCCA
TGC!
CAAGCCCACGAGCCCAACCCCCTGGCAACATCCCAGCAGATCCCGGGCCAAGCCAAG
GC!
AACTCAGAGGAGGAGCCAAAGCTGGTATTCGCTGTGAACCTGCCACCTGCTCAACTGT
CCTCCAACGATGAGGAGACCAGAGAGGAGCTGGCCCGCATTGGGCTAGTGCCACCCCC
TGAAGAGTTTGCCAATGGGATCCTGCTGGCCACCCCACCCCCAGGACCGGGCCCCTTG
CCCACCACGGTACCCAGCCCGGCCTCAGGGAAGCCCAGCAGCGAGCTGCCCCCTGCCC
CGGAGTCTGCAGCTGACTCTGGAGTAGAGGAGGCCGACACTCGAAGCTCCAGTGACCC
CCACCTGGAGACCACAAGCACCATTTCCACAGTGTCCAGCATGTCCACCCTGAGCTCG
GAGAGTGGAGAACTCACTGACACCCACACCTCCTTTGCCGATGGACACACTTTTCTACT
CGAGAAGCCACCAGTGCCTCCCAAGCCCAAACTCAAGTCCCCGCTGGGGAAGGGGCC
GGTGACCTTCAGGGGCCCGCTGCTGAAGCAATCCTCGGACAGTGAGCTCATGGCCCAG
CAGCACCATGCCACCTCTACTGGGTTGACTTCTGCTGCTGGGCCTGCCCGCCCTCGCTA
CCTCTTCCAGAGAAGGTCCAAGCTGTGGGGGGACCCCGTGGAGAGTCGGGGGCTCCCT
GGGCCTGAGGATGACAAACCAACTGTGATCAGTGAGCTCAGCTCCCGTCTGCAGCAGC
TGAATAAAGACACTCGCTCCTTGGGGGAGGAACCAGTTGGTGGCCTGGGTAGCCTGCT
GGACCCTGCTAAGAAGTCGCCCATTGCAGCAGCTCGCTGCGCGGTGGTCCCGAGTGCC
```

FIG. 40b

R-Shank3a(genbank)(nn)

```
GGCTGGCTCTTCAGCAGCCTCGGTGAGCTGAGCACCATCTCAGCGCAGCGCAGCCCCG
GGGGCCCGGGCGGAGGGGCCTCCTACTCGGTGCGGCCCAGCGGCCGGTACCCCGTGGC
GAGACGAGCCCCGAGCCCAGTGAAACCCGCATCGCTGGAGCGGGTGGAGGGGCTGGG
GGCGG!
GCGTGGGAGGCGCGGGGCGGCCCTTCGGCCTCACGCCTCCCACCATCCTCAAGTCGTC
CAGCCTCTCCATCCCGCACGAACCCAAGGAAGTGCGCTTCGTGGTGCGAAGTGCGAGT
GCGCGCAGCCGCTCCCCCTCACCATCTCCGCTGCCCTCGCCTTCTCCTGGCTCTGGCCC
CAGTGCCGGCCCGCGTCGGCCATTTCAACAGAAGCCCCTGCAGCTTTGGAGCAAGTTC
GATGTGGGCGACTGGCTGGAGAGCATCCACTTAGGCGAGCACCGAGACCGCTTCGAGG
ACCATGAGATCGAAGGCGCACACCTGCCTGCGCTCACCAAGGAAGACTTCGTGGAGCT
GGGAGTCACACGCGTTGGCCACCGCATGAACATCGAGCGTGCGCTCAGGCAGCTGGAT
GGCAGCTGACGCCCTCTCCCTCTCCTGTTCCTGCTGCGCCCTGCCGGCAGGGCCCCCA
CCCCTACTCCAGGCCGCAGGCTCGGCTCGCCCCTACCACGGCGCCCGGGCCAGGAAT
GTTGCATGAATCGTCCTGTTTGCTGTTGCTTGGAGACTTGCCCTGTACATTGCTTAGTGC
CCTCCCCTGCCGCTGAACCCCACCCAGCACACAGTAAGGGCGCGGACCAGGGGGGCTG
GGTGGAAGGGGGTTGGGGCAGGGTGCTCTGGCCTGACCACCTCCTCCACAGCTCCTGG
TGGCCATTCTTCCAGAGGGGGAACCTAGTCCAGCATGCGAGGTCAGGACACGCCTTGG
TGACTCGGGGGGAGGGGGAGACATTGGGGTTCTCGATAGGGGCCAAGGAGCCCCCT
GTTTTACATATTTTAATCCACTCTATATTTGGAAAGAGAAAAGGAACAAATATCTCTGT
CCGTAACAGTTCCCGCCCTCTTCCCCTCAAGTCCTCTCGCTGGTCCCGCCACAGCTACC
CAGTCTTCCATCTCCGGCCCCTCACTGCCACCCCATATAGGGCAGGGGACACTCCAGC!
TGGCCTGGGGTTAGCCAGGGTCCTGGCAGCCCACCCTGGGGACCCCGGCTCAGCCCCC
T!
TCCCTCGCTGAGCTATAGTATGCCCCACCCACCCTTTAGGTGCTGCTCAGGGGGACGGG
TGGCAGGCATTGCCTGCTGGGCACTAGCAGGGCCAGGTGGCCTGGGAGATTATTGCCC
TGGGGCTGGGCCCCGGTAACCCAACCCCAGCCATCATCTTCACAGGGTCTCTCCCAAA
GGAGGGGTCTAACCTTTCCCCACTTCTTGGGCAACTACAGCAGAGAAGCCTCCCTGCCT
CGCGCCCCAAAGACTCCCCAATTCCTGCCCTGTGTGTGCACCACATGTGTGTGTGCA
CGCCTGCGTGCTTGTGAAAATTGGGTGTGGCTGAGCGCATGGGTGCCCTGTATGTGCTT
GATTGTGGAGTGGTCCCCAGGGGCTGTTCTGGATGGGTGGGAGGTTGAGGAAGCTTGC
ACAGGGGTGCATGCATGGGTGTGTGCCTGTGAAAGGGCCCTGTCTTCTCCAAAGAAAG
GCTGTCCTGCTCTTGGGTCCTGCTGTTTTCTCAGCCTGTTCTCCCTGAACCTCACCCAGC
TTAAGCAGGGGTTCTTGGTGAATCCTTTCAGCTTTGGGAGGCCTCAAGGGCTCCCGTGC
AGGCAGCACCCCTTTGGGCTTCTAAGGGAATTGTGGGGACCACTAAAATCAGGCCACA
ACAGCCCTTGGAGAGAGGCAAAGACTCCTGAGGGTACCCTGGCCCCCCTTACTGTGAC
TCCTCACAATTCAGCAATGACCTGTGGGGCGGGGGGCCTTGGGGCATTTTAACATAG
GGTTTGGAGTCTGGACTAAGCTCCATCCACGTCACTCACAAGTTTCTGTTTCTATTTCTA
GCTTTTTTTAATAAAATATATATATATATATATAAAAGACAGAAAACAGGTGTTTTC
ATGGCCCAGGGGCTTGGCACGCCGGTCTGTGCCCACCCGCCCCGCCCCACCCTGGCCC
ACCGGCCCCATTCCTTAGACACAGAGTCACGCCCACTAACCCTCTTACCAACA!
GAGCAGGTCACACACACAGCAGCGGTCACTGTAACAGACTGCCACATACACAGTCTCA
CATTTACCTGTGGGTTTTTGGTTCTGTTCAGTTTGGGTTTTTAACTTTACAGGGTCAGTT
CCGCTTCATCCCCCTTTTGTATGGAGTTCCATCTCGGGGCTTTCAACCCCCTGCTCCAGT
CCTGAGGCCTCCTGACCCTGACGTTGTGATACACCCCACAGAGATCTATGTTTCTTATA
```

FIG. 40c

R-Shank3a(genbank)(nn)

TTATTATTATTAATAATAATTATTATAATATTATGTAATAAATTTATAAGAAATGAAAA
AAAAAAAAAAAAAA

FIG. 40d r-shan2

MDGPGASAVVVRVGIPDLQQTKCLRLDPTAPVWAAKQRVLCALNHSLQDALNY
GLFQPPSRGRAGKFLDEERLLQDYPPNLDTPLPYLEFRYKRRVYAQNLIDDKQFAK
LHTKANLKKFMDYVQLHSTDKVARLLDKGLDPNFHDPDSGECPLSLAAQLDNAT
DLLKVLRNGGAHLDFRTRDGLTAVHCATRQRNAGALTTLLDLGASPDYKDSRGL
TPLYHSALGGGDALCCELLLHDHAQLGTTDENGWQEIHQACRFGHVQHLEHLLF
YGANMGAQNASGNTALHICALYNQESCARVLLFRGANKDVRNYNSQTAFQVAII
AGNFELAEVIKTHKDSDVVPFRETPSYAKRRRLAGPSGLASPRPLQRSASDINLKG
DQPAASPGPTLRSLPHQLLLQRLQEEKDRDRDGEQENDISGPSAGRGGHSKISPSGP
GGSGPAPGPGPASPAPPAPPPRGPKRKLYSAVPGRKFIAVKAHSPQGEGEIPLHRGE
AVKVLSIGEGGFWEGTVKGRTGWFPADCVEEVQMRQYDTRHETREDRTKRLFRH
YTVGSYDSLTSHSDYVIDDKVAILQKRDHEGFGFVLRGAKAETPIEEFTPTPAFPAL
QYLESVDVEGVAWKAGLRTGDFLIEVNGVNVVKVGHKQVVGLIRQGGNRLVMK
VVSVTRKPEEDSARRRAPPPPKRAPSTTLTRSKSMTAELEELASIRRRKGEKLDEI
LAVAAEPTLRPDIADADSRAATVKQRPTSRRITPAEISSLFERQGLPGPEKLPGSLRK
GIPRTKSVGEDEKLASLLEGRFPRSTSMQDTVREGRGIPPPPQTAPPPPPAPYYFDS
GPPPTFSPPPPPPGRAYDTVRSSFKPGLEARLGAGAAGLYDSGTPLGPLPYPERQKR
ARSMIILQDSAPEVGDVPRPAPAATPPERPKRRPRPSGPDSPYANLGAFSASLFAPS
KPQRRKSPLVKQLQVEDAQERAALAVGSPGPVGGSFAREPSPTHRGPRPGGLDYS
SGEGLGLTFGGPSPGPVKERRLEERRRSTVFLSVGAIEGNPPSADLPSLQPSRSIDER
LLGTGATTGRDLLLPSPVSALKPLVGGPNLGPSSSTFIHPLTGKPLDPSSPLALALAA
RERALASQTPSRSPTPVHSPDADRPGPLFVDVQTRDSERGPLASPAFSPRSPAWIPV
PARREAEKPTREERKSPEDKKSMILSVLDTSLQRPAGLIVVHATSNGQEPNRLGAE
EERPGTPELAPTPMQAAAVAEPMPSPRAQPPGNIPADGPSQGNSEEEPKLVFAVN
LPPAQLSSNDEETREELARIGLVPPPEEFANGILLATPPPGPGPLPTTVPSPASGKPSS
ELPPAPESAADSGVEEADTRSSSDPHLETTSTISTVSSMSTLSSESGELTDTHTSFAD
GHTFLLEKPPVPPKPKLKSPLGKPVTFRGPLLKQSSDSELMAQQHHATSTGLTSA
AGPARPRYLFQRRSKLWGDPVESRGLPGPEDDKPTVISELSSRLQQLNKDTRSLGE
EPVGGLGSLLDPAKKSPIAAARCAVVPSAGWLFSSLGELSTISAQRSPGGPGGGAS
YSVRPSGRYPVARRAPSPVKPASLERVEGLGAGVGGAGRPFGLTPPTILKSSSLSIP
HEPKEVRFVVRSASARSRSPSPSPLPSPSPGSGPSAGPRRPFQQKPLQLWSKFDVGD
WLESIHLGEHRDRFEDHEIEGAHLPALTKEDFVELGVTRVGHRMNIERALRQLDGS

FIG. 41

H-Homer3a

ATGTCCACAGCCAGGGAGCAGCCAATCTTCAGCACACGGGCGCACGTGTTCCA
AATTGACCCAGCCACCAAGCGAAACTGGATCCCAGCGGGCAAGCACGCACTC
ACTGTCTCCTATTTCTACGATGCCACCCGCAATGTGTACCGCATCATCAGCATC
GGAGGCGCCAAGGCCATCATCAACAGCACTGTCACTCCCAACATGACCTTCAC
CAAAACTTCCCAGAAGTTCGGGCAGTGGGCCGACAGTCGCGCCAACACAGTCT
ATGGCCTGGGCTTTGCCTCTGAACAGCATCTGACACAGTTTGCCGAGAAGTTC
CAGGAAGTGAAGGAAGCAGCCAGGCTGGCCAGGGAGAAATCTCAGGATGGCT
GGGGTGGGCCCCAGTCGGCTCTGGTTGTTGGCAGCTTTGGGGCTGTTTTTGAG
CTTCTCATTGTGTAGAATTTCTAGATCCCCCGATTACATTTCTAAGCGTGA

FIG. 42

H-Homer3a[pr]

MSTAREQPIFSTRAHVFQIDPATKRNWIPAGKHALTVSYFYDATRNVYRIISIGGA
KAIINSTVTPNMTFTKTSQKFGQWADSRANTVYGLGFASEQHLTQFAEKFQEVKE
AARLAREKSQDGWGGPQSALVVGSFGAVFELLIV*

FIG. 43 ratina2

CACGCGTCCGGTGTGGTGCACCTTGGCATCTGTAAGCCTTTGGTGGAGGAGGA
GAAGGAGGAGAAGGAGGAACATTTTATTTTCCATTCAAACAACAATGGAGAT
AACAGTGAGTCTCCAGAAACCGTTCACGAGATCCACTCATCTTTAATCCTCGA
GGCACCCCAGGGATTTAGAGATGAGCCGTATCTTGAAGAACTCGTGGATGAAC
CTTTTCTAGATTTGGGAAAGTCTTTGCAGTTCCAACAAAAAGACATGGACAGC
AGCTCAGAAGCCTGGGAAATGCATGAATTCCTGAGCCCTCGGCTGGAGAGAA
GGGGTGAGGAAAGAGAGATGCTTGTTGACGAGGAGTATGAGATCTACCAAGA
CCGCCTCCGGGACATGGAAGCACACCCACCACCTCCTCACATTCGGGAGCCCA
CTTCTGCATCTCCCAGGCTGGATCTCCAGGCCGGCCCCAGTGGCTGCATGCT
GACCTCTCAGGAGGAGAGATACTCGAGTGTCACGACACAGAGTCCATGATGA
CTGCTTATCCCCAGGAGATGCAGGACTATAGCTTCAGCACCACAGACATGATG
AAAGAAACATTTGGCCTTGACTCCCGGCCGCCCATGCCCTCCTCTGAAGGAAA
TGGTCAGCACGGCCGATTTGATGACTTGGAACATCTTCATTCACTAGCAAGCC
ACGGCCTGGATTTAGGCATGATGACTCCAAGTGACTTGCAAGGCCCTGGCGTG
CTTGTAGATCTTCCAGCTGTCACCCCAAGAAGAGGCTGCGGCCGCTAAGTAAG
TAAGACGTCGAGCTCTAAGTAAGTAACGGCCGCCACCGCGGTGGAGCTTTGGA
CTTCTTCGCCAGAGG

FIG. 44 rat inadl

ID  rat INADL          PRT; 286 AA.
SQ  SEQUENCE  286 AA; 31933 MW; 426539 CN;
    HASGVVHLGI CKPLVEEEKE EKEEHFIFHS NNNGDNSESP ETVHEIHSSL ILEAPQGFRD
    EPYLEELVDE PFLDLGKSLQ FQQKDMDSSS EAWEMHEFLS PRLERRGEER EMLVDEEYEI
    YQDRLRDMEA HPPPPHIREP TSASPRLDLQ AGPQWLHADL SGGEILECHD TESMMTAYPQ
    EMQDYSFSTT DMMKETFGLD SRPPMPSSEG NGQHGRFDDL EHLHSLASHG LDLGMMTPSD
    LQGPGVLVDL PAVTPRRGCG R*VSKTSSSK *VTAATAVEL WTSSPE
//

FIG. 45

SEQUENCE LISTING

<160> NUMBER OF SEQ ID NOS: 72

<210> SEQ ID NO 1
<211> LENGTH: 1084
<212> TYPE: DNA
<213> ORGANISM: Homo sapiens
<220> FEATURE:
<221> NAME/KEY: CDS
<222> LOCATION: (76)..(789)

<400> SEQUENCE: 1

```
agacggagaa attcctttgg aagttattcc gtagcataag agctgaaact tcagagcaag      60
ttttcattgg gcaaa atg ggg gaa caa cct atc ttc agc act cga gct cat     111
                Met Gly Glu Gln Pro Ile Phe Ser Thr Arg Ala His
                  1               5                  10 gtc ttc caa att gac cca aac aca aag aag aac tgg gta ccc acc agc      159
Val Phe Gln Ile Asp Pro Asn Thr Lys Lys Asn Trp Val Pro Thr Ser
             15                  20                  25 aag cat gca gtt act gtg tct tat ttc tat gac agc aca aga aat gtg      207
Lys His Ala Val Thr Val Ser Tyr Phe Tyr Asp Ser Thr Arg Asn Val
         30                  35                  40 tat agg ata atc agt tta gat ggc tca aag gca ata ata aat agt acc      255
Tyr Arg Ile Ile Ser Leu Asp Gly Ser Lys Ala Ile Ile Asn Ser Thr
 45                  50                  55                  60 atc acc cca aac atg aca ttt act aaa aca tct cag aag ttt ggc cag      303
Ile Thr Pro Asn Met Thr Phe Thr Lys Thr Ser Gln Lys Phe Gly Gln
                 65                  70                  75 tgg gct gat agc cgg gca aac acc gtt tat gga ttg gga ttc tcc tct      351
Trp Ala Asp Ser Arg Ala Asn Thr Val Tyr Gly Leu Gly Phe Ser Ser
             80                  85                  90 gag cat cat ctt tcg aaa ttt gca gaa aag ttt cag gaa ttt aaa gaa      399
Glu His His Leu Ser Lys Phe Ala Glu Lys Phe Gln Glu Phe Lys Glu
         95                 100                 105 gct gct cga cta gca aag gaa aaa tca caa gag aag atg gaa ctt acc      447
Ala Ala Arg Leu Ala Lys Glu Lys Ser Gln Glu Lys Met Glu Leu Thr
    110                 115                 120 agt aca cct tca cag gaa tcc gca ggc ggg gat ctt cag tct cct tta      495
Ser Thr Pro Ser Gln Glu Ser Ala Gly Gly Asp Leu Gln Ser Pro Leu
125                 130                 135                 140 aca ccg gaa agt atc aac ggg aca gat gat gaa aga aca cct gat gtg      543
Thr Pro Glu Ser Ile Asn Gly Thr Asp Asp Glu Arg Thr Pro Asp Val
                145                 150                 155 aca cag aac tca gag cca agg gct gaa cca act cag aat gca ttg cca      591
Thr Gln Asn Ser Glu Pro Arg Ala Glu Pro Thr Gln Asn Ala Leu Pro
            160                 165                 170
```

```
ttt tca cat agt tca gca atc agc aaa cat tgg gag gct gaa ctg gct      639
Phe Ser His Ser Ser Ala Ile Ser Lys His Trp Glu Ala Glu Leu Ala
        175                 180                 185 acc ctc aaa gga aat aat gcc aaa ctc act gca gcc ctg ctg gag tcc      687
Thr Leu Lys Gly Asn Asn Ala Lys Leu Thr Ala Ala Leu Leu Glu Ser
    190                 195                 200 act gcc aat gtg aaa caa tgg aaa cag caa ctt gct gcc tat caa gag      735
Thr Ala Asn Val Lys Gln Trp Lys Gln Gln Leu Ala Ala Tyr Gln Glu
205                 210                 215                 220 gaa gca gaa cgt ctg cac aag cgg gta att tca ggg ctg atg tct ata      783
Glu Ala Glu Arg Leu His Lys Arg Val Ile Ser Gly Leu Met Ser Ile
                225                 230                 235 ggg att tagggctaac aggttttctt gatcagaaga aatttgcatg tagattcagc       839
Gly Ile acagggatat cttctagttc taggatgtca gaacatagat atgggttgta tgatatgcat    899
ttgtttgatt aagaaaaata ttttccatag tttaatgaga atgaagaata ataccgcctt    959
ttgaagtcaa caaaccatgt tgattcccca tattatccat ggggactagc agtaatgcac    1019
aagtacataa aagcactaat gtattagtgc tagttgatta gtactgacat ggtagttaaa    1079
gtgga                                                                1084

<210> SEQ ID NO 2
<211> LENGTH: 238
<212> TYPE: PRT
<213> ORGANISM: Homo sapiens

<400> SEQUENCE: 2

Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Thr Gln Asn Ala Leu Pro Phe Ser His Ser
                165                 170                 175

Ser Ala Ile Ser Lys His Trp Glu Ala Glu Leu Ala Thr Leu Lys Gly
            180                 185                 190

Asn Asn Ala Lys Leu Thr Ala Ala Leu Leu Glu Ser Thr Ala Asn Val
        195                 200                 205

Lys Gln Trp Lys Gln Gln Leu Ala Ala Tyr Gln Glu Glu Ala Glu Arg
    210                 215                 220
```

```
Leu His Lys Arg Val Ile Ser Gly Leu Met Ser Ile Gly Ile
225                 230                 235

<210> SEQ ID NO 3
<211> LENGTH: 1166
<212> TYPE: DNA
<213> ORGANISM: Homo sapiens
<220> FEATURE:
<221> NAME/KEY: CDS
<222> LOCATION: (1)..(1062)

<400> SEQUENCE: 3 atg ggg gag cag ccg att ttc agc act cga gct cat gtc ttc caa att       48
Met Gly Glu Gln Pro Ile Phe Ser Thr Arg Ala His Val Phe Gln Ile
1                 5                  10                  15 gac cca aac aca aag aag aac tgg gta ccc acc agc aag cat gca gtt       96
Asp Pro Asn Thr Lys Lys Asn Trp Val Pro Thr Ser Lys His Ala Val
             20                  25                  30 act gtg tct tat ttc tat gac agc aca aga aat gta tat agg ata atc      144
Thr Val Ser Tyr Phe Tyr Asp Ser Thr Arg Asn Val Tyr Arg Ile Ile
         35                  40                  45 agt tta gat ggc tca aag gca ata ata aat agt acc atc acc cca aac      192
Ser Leu Asp Gly Ser Lys Ala Ile Ile Asn Ser Thr Ile Thr Pro Asn
     50                  55                  60 atg aca ttt act aaa aca tct cag aag ttt ggc cag tgg gct gat agc      240
Met Thr Phe Thr Lys Thr Ser Gln Lys Phe Gly Gln Trp Ala Asp Ser
65                  70                  75                  80 cgg gca aac acc gtt tat gga ttg gga ttc tcc tct gag cat cat ctt      288
Arg Ala Asn Thr Val Tyr Gly Leu Gly Phe Ser Ser Glu His His Leu
                 85                  90                  95 tcg aaa ttt gca gaa aag ttt cag gaa ttt aaa gaa gct gct cga cta      336
Ser Lys Phe Ala Glu Lys Phe Gln Glu Phe Lys Glu Ala Ala Arg Leu
            100                 105                 110 gca aag gaa aaa tca caa gag aag atg gaa ctt acc agt aca cct tca      384
Ala Lys Glu Lys Ser Gln Glu Lys Met Glu Leu Thr Ser Thr Pro Ser
        115                 120                 125 cag gaa tcc gca ggc ggg gat ctt cag tct cct tta aca ccg gaa agt      432
Gln Glu Ser Ala Gly Gly Asp Leu Gln Ser Pro Leu Thr Pro Glu Ser
    130                 135                 140 atc aac ggg aca gat gat gaa aga aca cct gat gtg aca cag aac tca      480
Ile Asn Gly Thr Asp Asp Glu Arg Thr Pro Asp Val Thr Gln Asn Ser
145                 150                 155                 160 gag cca agg gct gaa cca act cag aat gca ttg cca ttt tca cat agt      528
Glu Pro Arg Ala Glu Pro Thr Gln Asn Ala Leu Pro Phe Ser His Ser
                165                 170                 175 tca gca atc agc aaa cat tgg gag gct gaa ctg gct acc ctc aaa gga      576
Ser Ala Ile Ser Lys His Trp Glu Ala Glu Leu Ala Thr Leu Lys Gly
            180                 185                 190 aat aat gcc aaa ctc act gca gcc ctg ctg gag tcc act gcc aat gtg      624
Asn Asn Ala Lys Leu Thr Ala Ala Leu Leu Glu Ser Thr Ala Asn Val
        195                 200                 205 aaa caa tgg aaa cag caa ctt gct gcc tat caa gag gaa gca gaa cgt      672
Lys Gln Trp Lys Gln Gln Leu Ala Ala Tyr Gln Glu Glu Ala Glu Arg
    210                 215                 220 ctg cac aag cgg gtg act gaa ctt gaa tgt gtt agt agc caa gca aat      720
Leu His Lys Arg Val Thr Glu Leu Glu Cys Val Ser Ser Gln Ala Asn
225                 230                 235                 240 gca gta cat act cat aag aca gaa tta aat cag aca ata caa gaa ctg      768
Ala Val His Thr His Lys Thr Glu Leu Asn Gln Thr Ile Gln Glu Leu
                245                 250                 255 gaa gag aca ctg aaa ctg aag gaa gag gaa ata gaa agg tta aaa caa      816
```

-continued

```
Glu Glu Thr Leu Lys Leu Lys Glu Glu Ile Glu Arg Leu Lys Gln
            260                 265                 270 gaa att gat aat gcc aga gaa cta caa gaa cag agg gat tct ttg act     864
Glu Ile Asp Asn Ala Arg Glu Leu Gln Glu Gln Arg Asp Ser Leu Thr
        275                 280                 285 cag aaa cta cag gaa gta gaa att cgg aac aaa gac ctg gag gga caa     912
Gln Lys Leu Gln Glu Val Glu Ile Arg Asn Lys Asp Leu Glu Gly Gln
    290                 295                 300 ctg tct gac tta gag caa cgt ctg gag aaa agt cag aat gaa caa gaa     960
Leu Ser Asp Leu Glu Gln Arg Leu Glu Lys Ser Gln Asn Glu Gln Glu
305                 310                 315                 320 gct ttt cgc aat aac ctg aag aca ctc tta gaa att ctg gat gga aag    1008
Ala Phe Arg Asn Asn Leu Lys Thr Leu Leu Glu Ile Leu Asp Gly Lys
                325                 330                 335 ata ttt gaa cta aca gaa tta cga gat aac ttg gcc aag cta cta gaa    1056
Ile Phe Glu Leu Thr Glu Leu Arg Asp Asn Leu Ala Lys Leu Leu Glu
            340                 345                 350 tgc agc taaggaaagt gaaatttcag tgccaattaa ttaaaagata cactgtctct    1112
Cys Ser cttcatagga ctgtttagct ctgcatcaag attgcacaaa aaaaaaaaaa aaaa        1166
```

<210> SEQ ID NO 4
<211> LENGTH: 354
<212> TYPE: PRT
<213> ORGANISM: Homo sapiens

<400> SEQUENCE: 4

```
Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Thr Gln Asn Ala Leu Pro Phe Ser His Ser
                165                 170                 175

Ser Ala Ile Ser Lys His Trp Glu Ala Glu Leu Ala Thr Leu Lys Gly
            180                 185                 190

Asn Asn Ala Lys Leu Thr Ala Ala Leu Leu Glu Ser Thr Ala Asn Val
        195                 200                 205

Lys Gln Trp Lys Gln Leu Ala Ala Tyr Gln Glu Glu Ala Glu Arg
    210                 215                 220

Leu His Lys Arg Val Thr Glu Leu Glu Cys Val Ser Ser Gln Ala Asn
```

-continued

```
                225                 230                 235                 240
        Ala Val His Thr His Lys Thr Glu Leu Asn Gln Thr Ile Gln Glu Leu
                            245                 250                 255

Glu Glu Thr Leu Lys Leu Lys Glu Glu Ile Glu Arg Leu Lys Gln
                    260                 265                 270

Glu Ile Asp Asn Ala Arg Glu Leu Gln Glu Gln Arg Asp Ser Leu Thr
                    275                 280                 285

Gln Lys Leu Gln Glu Val Glu Ile Arg Asn Lys Asp Leu Glu Gly Gln
                    290                 295                 300

Leu Ser Asp Leu Glu Gln Arg Leu Glu Lys Ser Gln Asn Glu Gln Glu
        305                 310                 315                 320

Ala Phe Arg Asn Asn Leu Lys Thr Leu Leu Glu Ile Leu Asp Gly Lys
                            325                 330                 335

Ile Phe Glu Leu Thr Glu Leu Arg Asp Asn Leu Ala Lys Leu Leu Glu
                            340                 345                 350

Cys Ser

<210> SEQ ID NO 5
<211> LENGTH: 105
<212> TYPE: PRT
<213> ORGANISM: Homo sapiens

<400> SEQUENCE: 5

Lys Glu Val Trp Gln Val Ile Leu Lys Pro Lys Gly Leu Gly Gln Thr
        1                   5                   10                  15

Lys Asn Leu Ile Gly Ile Tyr Arg Leu Cys Leu Thr Ser Lys Thr Ile
                    20                  25                  30

Ser Phe Val Lys Leu Asn Ser Glu Ala Ala Ala Val Val Leu Gln Leu
                    35                  40                  45

Met Asn Ile Arg Arg Cys Gly His Ser Glu Asn Phe Phe Phe Ile Glu
                    50                  55                  60

Val Gly Arg Ser Ala Val Thr Gly Pro Gly Glu Phe Trp Met Gln Val
        65                  70                  75                  80

Asp Asp Ser Val Val Ala Gln Asn Met His Glu Thr Ile Leu Glu Ala
                            85                  90                  95

Met Arg Ala Met Ser Asp Glu Phe Arg
                    100                 105

<210> SEQ ID NO 6
<211> LENGTH: 106
<212> TYPE: PRT
<213> ORGANISM: Mouse

<400> SEQUENCE: 6

Met Glu Gly Phe Leu Asn Arg Lys His Glu Trp Glu Ala His Asn Lys
        1                   5                   10                  15

Lys Ala Ser Ser Arg Ser Trp His Asn Val Tyr Cys Val Ile Asn Asn
                    20                  25                  30

Gln Glu Met Gly Phe Tyr Lys Asp Ala Lys Ser Ala Ala Ser Gly Ile
                    35                  40                  45

Pro Tyr His Ser Glu Val Pro Val Ser Leu Lys Glu Ala Ile Cys Glu
                    50                  55                  60

Val Ala Leu Asp Tyr Lys Lys Lys His Val Phe Lys Leu Arg Leu
        65                  70                  75                  80

Ser Asp Gly Asn Glu Tyr Leu Phe Gln Ala Lys Asp Asp Glu Glu Met
                            85                  90                  95
```

Asn Thr Trp Ile Gln Ala Ile Ser Ser Ala
            100                 105

<210> SEQ ID NO 7
<211> LENGTH: 1767
<212> TYPE: DNA
<213> ORGANISM: Homo sapiens
<220> FEATURE:
<221> NAME/KEY: CDS
<222> LOCATION: (1)..(1029)

<400> SEQUENCE: 7

| | | | | | | | | | | | | | | | | |
|---|---|---|---|---|---|---|---|---|---|---|---|---|---|---|---|---|
| atg | ggg | gag | cag | ccg | atc | ttc | acc | acc | cga | gcg | cat | gtc | ttc | cag | att | 48 |
| Met | Gly | Glu | Gln | Pro | Ile | Phe | Thr | Thr | Arg | Ala | His | Val | Phe | Gln | Ile | |
| 1 | | | | 5 | | | | | 10 | | | | | 15 | | |
| gac | ccc | aac | acc | aag | aag | aac | tgg | atg | cct | gcg | agc | aag | cag | gcg | gtc | 96 |
| Asp | Pro | Asn | Thr | Lys | Lys | Asn | Trp | Met | Pro | Ala | Ser | Lys | Gln | Ala | Val | |
| | | | 20 | | | | | 25 | | | | | 30 | | | |
| acc | gtt | tcc | tac | ttc | tat | gat | gtc | aca | agg | aac | agc | tat | cgg | atc | atc | 144 |
| Thr | Val | Ser | Tyr | Phe | Tyr | Asp | Val | Thr | Arg | Asn | Ser | Tyr | Arg | Ile | Ile | |
| | | 35 | | | | | 40 | | | | | 45 | | | | |
| agt | gtg | gac | gga | gcc | aag | gtg | atc | ata | aac | agc | aca | atc | aca | ccg | aat | 192 |
| Ser | Val | Asp | Gly | Ala | Lys | Val | Ile | Ile | Asn | Ser | Thr | Ile | Thr | Pro | Asn | |
| | 50 | | | | | 55 | | | | | 60 | | | | | |
| atg | acc | ttc | acc | aaa | acg | tca | cag | aag | ttt | ggg | cag | tgg | gcc | gac | agc | 240 |
| Met | Thr | Phe | Thr | Lys | Thr | Ser | Gln | Lys | Phe | Gly | Gln | Trp | Ala | Asp | Ser | |
| 65 | | | | | 70 | | | | | 75 | | | | | 80 | |
| aga | gcc | aac | aca | gtg | ttt | ggt | ttg | ggg | ttt | tcc | tct | gag | cag | cag | ctg | 288 |
| Arg | Ala | Asn | Thr | Val | Phe | Gly | Leu | Gly | Phe | Ser | Ser | Glu | Gln | Gln | Leu | |
| | | | | 85 | | | | | 90 | | | | | 95 | | |
| aca | aag | ttt | gca | gag | aaa | ttc | cag | gag | gtg | aaa | gaa | gct | gcc | aag | ata | 336 |
| Thr | Lys | Phe | Ala | Glu | Lys | Phe | Gln | Glu | Val | Lys | Glu | Ala | Ala | Lys | Ile | |
| | | | 100 | | | | | 105 | | | | | 110 | | | |
| gcc | aaa | gac | aag | acg | cag | gag | aaa | atc | gag | acc | tca | agt | aat | cat | tcc | 384 |
| Ala | Lys | Asp | Lys | Thr | Gln | Glu | Lys | Ile | Glu | Thr | Ser | Ser | Asn | His | Ser | |
| | | 115 | | | | | 120 | | | | | 125 | | | | |
| caa | gca | tcc | agt | gtc | aac | ggg | acg | gac | gag | gaa | aag | gcc | tct | cac | gcc | 432 |
| Gln | Ala | Ser | Ser | Val | Asn | Gly | Thr | Asp | Glu | Glu | Lys | Ala | Ser | His | Ala | |
| | 130 | | | | | 135 | | | | | 140 | | | | | |
| ggt | cca | gcc | aac | aca | caa | ctg | aag | tct | gag | aat | gac | aag | ctg | aag | att | 480 |
| Gly | Pro | Ala | Asn | Thr | Gln | Leu | Lys | Ser | Glu | Asn | Asp | Lys | Leu | Lys | Ile | |
| 145 | | | | | 150 | | | | | 155 | | | | | 160 | |
| gcc | ttg | acg | cag | agc | gca | gcc | aac | gtg | aag | aag | tgg | gag | atc | gag | ctg | 528 |
| Ala | Leu | Thr | Gln | Ser | Ala | Ala | Asn | Val | Lys | Lys | Trp | Glu | Ile | Glu | Leu | |
| | | | | 165 | | | | | 170 | | | | | 175 | | |
| cag | acc | ctt | cgg | gag | agc | aat | gca | cgg | ctg | acc | aca | gca | ctg | cag | gag | 576 |
| Gln | Thr | Leu | Arg | Glu | Ser | Asn | Ala | Arg | Leu | Thr | Thr | Ala | Leu | Gln | Glu | |
| | | | 180 | | | | | 185 | | | | | 190 | | | |
| tcg | gca | gcc | agt | gtg | gag | cag | tgg | aag | agg | cag | ttc | tcc | atc | tgc | cgt | 624 |
| Ser | Ala | Ala | Ser | Val | Glu | Gln | Trp | Lys | Arg | Gln | Phe | Ser | Ile | Cys | Arg | |
| | | 195 | | | | | 200 | | | | | 205 | | | | |
| gat | gag | aat | gac | cgg | ctc | cgc | aac | aag | att | gat | gag | ctg | gaa | gaa | caa | 672 |
| Asp | Glu | Asn | Asp | Arg | Leu | Arg | Asn | Lys | Ile | Asp | Glu | Leu | Glu | Glu | Gln | |
| | 210 | | | | | 215 | | | | | 220 | | | | | |
| tgc | agt | gag | atc | aac | aga | gag | aag | gag | aag | aac | acg | cag | ctg | aag | agg | 720 |
| Cys | Ser | Glu | Ile | Asn | Arg | Glu | Lys | Glu | Lys | Asn | Thr | Gln | Leu | Lys | Arg | |
| 225 | | | | | 230 | | | | | 235 | | | | | 240 | |
| agg | atc | gag | gag | ctg | gag | gca | gag | ctc | cga | gaa | aag | gag | aca | gag | ctg | 768 |
| Arg | Ile | Glu | Glu | Leu | Glu | Ala | Glu | Leu | Arg | Glu | Lys | Glu | Thr | Glu | Leu | |
| | | | | 245 | | | | | 250 | | | | | 255 | | |

-continued

| | | |
|---|---|---|
| aaa gat ctc cga aaa caa agt gaa atc ata cct cag ctc atg tca gag<br>Lys Asp Leu Arg Lys Gln Ser Glu Ile Ile Pro Gln Leu Met Ser Glu<br>           260                 265                 270 | 816 |
| tgc gaa tat gtc tct gag aag cta gag gcg gca gag aga gac aat caa<br>Cys Glu Tyr Val Ser Glu Lys Leu Glu Ala Ala Glu Arg Asp Asn Gln<br>       275                 280                 285 | 864 |
| aac ctg gaa gac aaa gtg cgt tcc tta aag aca gac att gag gag agc<br>Asn Leu Glu Asp Lys Val Arg Ser Leu Lys Thr Asp Ile Glu Glu Ser<br>   290                 295                 300 | 912 |
| aaa tac cga cag cgc cac ctg aag gtg gag ttg aag agc ttc ctg gag<br>Lys Tyr Arg Gln Arg His Leu Lys Val Glu Leu Lys Ser Phe Leu Glu<br>305                 310                 315                 320 | 960 |
| gtg ctg gac ggg aag att gac gac ctg cat gac ttc cgc cga ggg ctc<br>Val Leu Asp Gly Lys Ile Asp Asp Leu His Asp Phe Arg Arg Gly Leu<br>               325                 330                 335 | 1008 |
| tcc aag ctg ggc acc gat aac tagggctggc cgaggcccag gccccgcccg<br>Ser Lys Leu Gly Thr Asp Asn<br>           340 | 1059 |
| tgagtcccaa gcgtgtgtgc gagaccagat agctctagga cgttcttctg tgtgcattgc | 1119 |
| ttctgtaaat gcaggcgcag tttgtcgtgt tccaaacca gttgtgccgt ccactcactc | 1179 |
| cttttcagaa tagaaatctc ctctcgcttc tctggccttg tgaggttgtg dacaactgga | 1239 |
| agattctgac tcaggaatcc agaactaggt ctaccttcaa catttatgca gtcagggcag | 1299 |
| ggatgtttat atctttcata agggctgttg caaccatatg aactgaaaaa acacgcattt | 1359 |
| tgtaatccaa atattgatat tctttacacc aagccatcag gctcctttta tcaaatagca | 1419 |
| ttcagagtat ttgaatgtcc accagacacc agccccgggg ggcacagaga gaacaacatt | 1479 |
| cctctctgtc aacatcgaga ggctttaaaa caactgttta gtggaaactt tctgagagat | 1539 |
| ggaaaacaag cttctggtgg gtgcattttc tggcccggag ttgcctgcat ccacgctact | 1599 |
| gccccctgcc ccccgccccc ccagtttgta cggttgcaac agtgttcctt ttcttggttt | 1659 |
| taatttctga gcagatgatt tgctgtggga acagcacaca gtgagggtgc ctagcacaat | 1719 |
| gtctggcaca aagtaggtgc ttaataaata tttgttcaat taaaaaaa | 1767 |

<210> SEQ ID NO 8
<211> LENGTH: 343
<212> TYPE: PRT
<213> ORGANISM: Homo sapiens

<400> SEQUENCE: 8

Met Gly Glu Gln Pro Ile Phe Thr Thr Arg Ala His Val Phe Gln Ile
1               5                   10                  15

Asp Pro Asn Thr Lys Lys Asn Trp Met Pro Ala Ser Lys Gln Ala Val
            20                  25                  30

Thr Val Ser Tyr Phe Tyr Asp Val Thr Arg Asn Ser Tyr Arg Ile Ile
        35                  40                  45

Ser Val Asp Gly Ala Lys Val Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Phe Gly Leu Gly Phe Ser Ser Glu Gln Gln Leu
                85                  90                  95

Thr Lys Phe Ala Glu Lys Phe Gln Glu Val Lys Glu Ala Ala Lys Ile
            100                 105                 110

Ala Lys Asp Lys Thr Gln Glu Lys Ile Glu Thr Ser Ser Asn His Ser
        115                 120                 125

```
Gln Ala Ser Ser Val Asn Gly Thr Asp Glu Lys Ala Ser His Ala
        130                 135                 140

Gly Pro Ala Asn Thr Gln Leu Lys Ser Glu Asn Asp Lys Leu Lys Ile
145                 150                 155                 160

Ala Leu Thr Gln Ser Ala Ala Asn Val Lys Lys Trp Glu Ile Glu Leu
                165                 170                 175

Gln Thr Leu Arg Glu Ser Asn Ala Arg Leu Thr Thr Ala Leu Gln Glu
            180                 185                 190

Ser Ala Ala Ser Val Glu Gln Trp Lys Arg Gln Phe Ser Ile Cys Arg
        195                 200                 205

Asp Glu Asn Asp Arg Leu Arg Asn Lys Ile Asp Glu Leu Glu Glu Gln
        210                 215                 220

Cys Ser Glu Ile Asn Arg Glu Lys Glu Lys Asn Thr Gln Leu Lys Arg
225                 230                 235                 240

Arg Ile Glu Glu Leu Glu Ala Glu Leu Arg Glu Lys Glu Thr Glu Leu
                245                 250                 255

Lys Asp Leu Arg Lys Gln Ser Glu Ile Ile Pro Gln Leu Met Ser Glu
            260                 265                 270

Cys Glu Tyr Val Ser Glu Lys Leu Glu Ala Ala Glu Arg Asp Asn Gln
        275                 280                 285

Asn Leu Glu Asp Lys Val Arg Ser Leu Lys Thr Asp Ile Glu Glu Ser
        290                 295                 300

Lys Tyr Arg Gln Arg His Leu Lys Val Glu Leu Lys Ser Phe Leu Glu
305                 310                 315                 320

Val Leu Asp Gly Lys Ile Asp Asp Leu His Asp Phe Arg Arg Gly Leu
                325                 330                 335

Ser Lys Leu Gly Thr Asp Asn
            340

<210> SEQ ID NO 9
<211> LENGTH: 1800
<212> TYPE: DNA
<213> ORGANISM: Homo sapiens
<220> FEATURE:
<221> NAME/KEY: CDS
<222> LOCATION: (1)..(1062)

<400> SEQUENCE: 9 atg ggg gag cag ccg atc ttc acc acc cga gcg cat gtc ttc cag att        48
Met Gly Glu Gln Pro Ile Phe Thr Thr Arg Ala His Val Phe Gln Ile
1               5                   10                  15 gac ccc aac acc aag aag aac tgg atg cct gcg agc aag cag gcg gtc        96
Asp Pro Asn Thr Lys Lys Asn Trp Met Pro Ala Ser Lys Gln Ala Val
                20                  25                  30 acc gtt tcc tac ttc tat gat gtc aca agg aac agc tat cgg atc atc       144
Thr Val Ser Tyr Phe Tyr Asp Val Thr Arg Asn Ser Tyr Arg Ile Ile
            35                  40                  45 agt gtg gac gga gcc aag gtg atc ata aac agc aca atc aca ccg aat       192
Ser Val Asp Gly Ala Lys Val Ile Ile Asn Ser Thr Ile Thr Pro Asn
        50                  55                  60 atg acc ttc acc aaa acg tca cag aag ttt ggg cag tgg gcc gac agc       240
Met Thr Phe Thr Lys Thr Ser Gln Lys Phe Gly Gln Trp Ala Asp Ser
65                  70                  75                  80 aga gcc aac aca gtg ttt ggt ttg ggg ttt tcc tct gag cag cag ctg       288
Arg Ala Asn Thr Val Phe Gly Leu Gly Phe Ser Ser Glu Gln Gln Leu
                85                  90                  95 aca aag ttt gca gag aaa ttc cag gag gtg aaa gaa gct gcc aag ata       336
```

```
                                                                        -continued Thr Lys Phe Ala Glu Lys Phe Gln Glu Val Lys Glu Ala Ala Lys Ile
            100                 105                 110 gcc aaa gac aag acg cag gag aaa atc gag acc tca agt aat cat tcc         384
Ala Lys Asp Lys Thr Gln Glu Lys Ile Glu Thr Ser Ser Asn His Ser
            115                 120                 125 caa gaa tct ggg cgt gaa acc cca tct tct act cag gca tcc agt gtc         432
Gln Glu Ser Gly Arg Glu Thr Pro Ser Ser Thr Gln Ala Ser Ser Val
    130                 135                 140 aac ggg acg gac gag gaa aag gcc tct cac gcc ggt cca gcc aac aca         480
Asn Gly Thr Asp Glu Glu Lys Ala Ser His Ala Gly Pro Ala Asn Thr
145                 150                 155                 160 caa ctg aag tct gag aat gac aag ctg aag att gcc ttg acg cag agc         528
Gln Leu Lys Ser Glu Asn Asp Lys Leu Lys Ile Ala Leu Thr Gln Ser
                165                 170                 175 gca gcc aac gtg aag aag tgg gag atc gag ctg cag acc ctt cgg gag         576
Ala Ala Asn Val Lys Lys Trp Glu Ile Glu Leu Gln Thr Leu Arg Glu
            180                 185                 190 agc aat gca cgg ctg acc aca gca ctg cag gag tcg gca gcc agt gtg         624
Ser Asn Ala Arg Leu Thr Thr Ala Leu Gln Glu Ser Ala Ala Ser Val
        195                 200                 205 gag cag tgg aag agg cag ttc tcc atc tgc cgt gat gag aat gac cgg         672
Glu Gln Trp Lys Arg Gln Phe Ser Ile Cys Arg Asp Glu Asn Asp Arg
    210                 215                 220 ctc cgc aac aag att gat gag ctg gaa gaa caa tgc agt gag atc aac         720
Leu Arg Asn Lys Ile Asp Glu Leu Glu Glu Gln Cys Ser Glu Ile Asn
225                 230                 235                 240 aga gag aag gag aag aac acg cag ctg aag agg agg atc gag gag ctg         768
Arg Glu Lys Glu Lys Asn Thr Gln Leu Lys Arg Arg Ile Glu Glu Leu
                245                 250                 255 gag gca gag ctc cga gaa aag gag aca gag ctg aaa gat ctc cga aaa         816
Glu Ala Glu Leu Arg Glu Lys Glu Thr Glu Leu Lys Asp Leu Arg Lys
            260                 265                 270 caa agt gaa atc ata cct cag ctc atg tca gag tgc gaa tat gtc tct         864
Gln Ser Glu Ile Ile Pro Gln Leu Met Ser Glu Cys Glu Tyr Val Ser
        275                 280                 285 gag aag cta gag gcg gca gag aga gac aat caa aac ctg gaa gac aaa         912
Glu Lys Leu Glu Ala Ala Glu Arg Asp Asn Gln Asn Leu Glu Asp Lys
    290                 295                 300 gtg cgt tcc tta aag aca gac att gag gag agc aaa tac cga cag cgc         960
Val Arg Ser Leu Lys Thr Asp Ile Glu Glu Ser Lys Tyr Arg Gln Arg
305                 310                 315                 320 cac ctg aag gtg gag ttg aag agc ttc ctg gag gtg ctg gac ggg aag        1008
His Leu Lys Val Glu Leu Lys Ser Phe Leu Glu Val Leu Asp Gly Lys
                325                 330                 335 att gac gac ctg cat gac ttc cgc cga ggg ctc tcc aag ctg ggc acc        1056
Ile Asp Asp Leu His Asp Phe Arg Arg Gly Leu Ser Lys Leu Gly Thr
            340                 345                 350 gat aac tagggctggc cgaggcccag ccccgcccg tgagtcccaa gcgtgtgtgc          1112
Asp Asn gagaccagat agctctagga cgttcttctg tgtgcattgc ttctgtaaat gcaggcgcag      1172
tttgtcgtgt ttccaaacca gttgtgccgt ccactcactc cttttcagaa tagaaatctc      1232
ctctcgcttc tctggccttg tgaggttgtg gacaactgga agattctgac tcaggaatcc      1292
agaactaggt ctaccttcaa catttatgca gtcagggcag ggatgtttat atctttcata      1352
agggctgttg caaccatatg aactgaaaaa acacgcattt tgtaatccaa atattgatat      1412
tctttacacc aagccatcag gctccttta tcaaatagca ttcagagtat ttgaatgtcc       1472
accagacacc agccccgggg ggcacagaga gaacaacatt cctctctgtc aacatcgaga     1532
```

```
ggctttaaaa caactgttta gtggaaactt tctgagagat ggaaaacaag cttctggtgg    1592
gtgcattttc tggcccggag ttgcctgcat ccacgctact gccccctgcc cccgccccc    1652 ccagtttgta cggttgcaac agtgttcctt ttcttggttt taatttctga gcagatgatt   1712
tgctgtggga acagcacaca gtgagggtgc ctagcacaat gtctggcaca agtaggtgc    1772 ttaataaata tttgttcaat taaaaaaa                                      1800
```

<210> SEQ ID NO 10
<211> LENGTH: 354
<212> TYPE: PRT
<213> ORGANISM: Homo sapiens

<400> SEQUENCE: 10

```
Met Gly Glu Gln Pro Ile Phe Thr Thr Arg Ala His Val Phe Gln Ile
1               5                   10                  15

Asp Pro Asn Thr Lys Asn Trp Met Pro Ala Ser Lys Gln Ala Val
            20                  25                  30

Thr Val Ser Tyr Phe Tyr Asp Val Thr Arg Asn Ser Tyr Arg Ile Ile
                35                  40                  45

Ser Val Asp Gly Ala Lys Val Ile Ile Asn Ser Thr Ile Thr Pro Asn
50                  55                  60

Met Thr Phe Thr Lys Thr Ser Gln Lys Phe Gly Gln Trp Ala Asp Ser
65                  70                  75                  80

Arg Ala Asn Thr Val Phe Gly Leu Gly Phe Ser Ser Glu Gln Gln Leu
                85                  90                  95

Thr Lys Phe Ala Glu Lys Phe Gln Glu Val Lys Glu Ala Ala Lys Ile
            100                 105                 110

Ala Lys Asp Lys Thr Gln Glu Lys Ile Glu Thr Ser Ser Asn His Ser
        115                 120                 125

Gln Glu Ser Gly Arg Glu Thr Pro Ser Ser Thr Gln Ala Ser Ser Val
    130                 135                 140

Asn Gly Thr Asp Glu Glu Lys Ala Ser His Ala Gly Pro Ala Asn Thr
145                 150                 155                 160

Gln Leu Lys Ser Glu Asn Asp Lys Leu Lys Ile Ala Leu Thr Gln Ser
                165                 170                 175

Ala Ala Asn Val Lys Lys Trp Glu Ile Glu Leu Gln Thr Leu Arg Glu
            180                 185                 190

Ser Asn Ala Arg Leu Thr Thr Ala Leu Gln Glu Ser Ala Ala Ser Val
        195                 200                 205

Glu Gln Trp Lys Arg Gln Phe Ser Ile Cys Arg Asp Glu Asn Asp Arg
    210                 215                 220

Leu Arg Asn Lys Ile Asp Glu Leu Glu Glu Gln Cys Ser Glu Ile Asn
225                 230                 235                 240

Arg Glu Lys Glu Lys Asn Thr Gln Leu Lys Arg Arg Ile Glu Glu Leu
                245                 250                 255

Glu Ala Glu Leu Arg Glu Lys Thr Glu Leu Lys Asp Leu Arg Lys
            260                 265                 270

Gln Ser Glu Ile Ile Pro Gln Leu Met Ser Glu Cys Glu Tyr Val Ser
        275                 280                 285

Glu Lys Leu Glu Ala Ala Glu Arg Asp Asn Gln Asn Leu Glu Asp Lys
    290                 295                 300

Val Arg Ser Leu Lys Thr Asp Ile Glu Gly Ser Lys Tyr Arg Gln Arg
305                 310                 315                 320
```

```
His Leu Lys Val Glu Leu Lys Ser Phe Leu Glu Val Leu Asp Gly Lys
                325                 330                 335

Ile Asp Asp Leu His Asp Phe Arg Arg Gly Leu Ser Lys Leu Gly Thr
            340                 345                 350

Asp Asn

<210> SEQ ID NO 11
<211> LENGTH: 1429
<212> TYPE: DNA
<213> ORGANISM: Homo sapiens
<220> FEATURE:
<221> NAME/KEY: misc_feature
<222> LOCATION: (1)..(1429)
<223> OTHER INFORMATION: n is either a, c, g, or t
<221> NAME/KEY: CDS
<222> LOCATION: (91)..(1164)

<400> SEQUENCE: 11
gcacgagggc gcatgactag ttggggccaa accagtgctc ctgccacctc tctggctgcc      60
ccctagagcc tgcccatccc agcctgacca atg tcc aca gcc agg gag cag cca     114
                                 Met Ser Thr Ala Arg Glu Gln Pro
                                   1               5 atc ttc agc aca cgg gcg cac gtg ttc caa att gac cca gcc acc aag     162
Ile Phe Ser Thr Arg Ala His Val Phe Gln Ile Asp Pro Ala Thr Lys
    10                  15                  20 cga aac tgg atc cca gcg ggc aag cac gca ctc act gtc tcc tat ttc     210
Arg Asn Trp Ile Pro Ala Gly Lys His Ala Leu Thr Val Ser Tyr Phe
 25                  30                  35                  40 tac gat gcc acc cgc aat gtg tac cgc atc atc agc atc gga ggc gcc     258
Tyr Asp Ala Thr Arg Asn Val Tyr Arg Ile Ile Ser Ile Gly Gly Ala
                45                  50                  55 aag gcc atc atc aac agc act gtc act ccc aac atg acc ttc acc aaa     306
Lys Ala Ile Ile Asn Ser Thr Val Thr Pro Asn Met Thr Phe Thr Lys
             60                  65                  70 act tcc cag aag ttc ggg cag tgg gcc gac agt cgc gcc aac aca gtc     354
Thr Ser Gln Lys Phe Gly Gln Trp Ala Asp Ser Arg Ala Asn Thr Val
         75                  80                  85 tac ggc ctg ggc ttt gcc tct gaa cag cat ctg aca cag ttt gcc gag     402
Tyr Gly Leu Gly Phe Ala Ser Glu Gln His Leu Thr Gln Phe Ala Glu
     90                  95                 100 aag ttc cag gaa gtg aag gaa gca gcc agg ctg gcc agg gag aaa tct     450
Lys Phe Gln Glu Val Lys Glu Ala Ala Arg Leu Ala Arg Glu Lys Ser
105                 110                 115                 120 cag gat ggc ggg gag ctc acc agt cca gcc ctg ggg ctc gcc tcc cac     498
Gln Asp Gly Gly Glu Leu Thr Ser Pro Ala Leu Gly Leu Ala Ser His
                125                 130                 135 cag gtc ccc ccg agc cct ctc gtc agt gcc aac ggc ccc ggc gag gaa     546
Gln Val Pro Pro Ser Pro Leu Val Ser Ala Asn Gly Pro Gly Glu Glu
            140                 145                 150 aaa ctg ttc cgc agc cag agc gct gat gcc ccc ggc ccc aca gag cgc     594
Lys Leu Phe Arg Ser Gln Ser Ala Asp Ala Pro Gly Pro Thr Glu Arg
        155                 160                 165 gag cgg cta aag aag atg ttg tct gag ggc tcc gtg ggc gag gta cag     642
Glu Arg Leu Lys Lys Met Leu Ser Glu Gly Ser Val Gly Glu Val Gln
    170                 175                 180 tgg gag gcc gag ttt ttc gca ctg cag gac agc aac aac aag ctg gca     690
Trp Glu Ala Glu Phe Phe Ala Leu Gln Asp Ser Asn Asn Lys Leu Ala
185                 190                 195                 200 ggc gcc ctg cga gag gcc aac gcc gcc gca gcc cag tgg agg cag cag     738
Gly Ala Leu Arg Glu Ala Asn Ala Ala Ala Ala Gln Trp Arg Gln Gln
                205                 210                 215
```

```
ctg gag gct cag cgt gca gag gcc gag cgg ctg cgg cag cgg gtg gct    786
Leu Glu Ala Gln Arg Ala Glu Ala Glu Arg Leu Arg Gln Arg Val Ala
            220                 225                 230 gag ctg gag gct cag gca gct tca gag gtg acc ccc acc ggt gag aag    834
Glu Leu Glu Ala Gln Ala Ala Ser Glu Val Thr Pro Thr Gly Glu Lys
        235                 240                 245 gag ggg ctg ggc cag ggc cag tcg ctg gaa cag ctg gaa gct ctg gtg    882
Glu Gly Leu Gly Gln Gly Gln Ser Leu Glu Gln Leu Glu Ala Leu Val
    250                 255                 260 caa acc aag gac cag gag att cag acc ctg aag agt cag act ggg ggg    930
Gln Thr Lys Asp Gln Glu Ile Gln Thr Leu Lys Ser Gln Thr Gly Gly
265                 270                 275                 280 ccc cgc gag gcc ctg gag gct gcc gag cgt gag gag act cag cag aag    978
Pro Arg Glu Ala Leu Glu Ala Ala Glu Arg Glu Glu Thr Gln Gln Lys
                285                 290                 295 gtg cag acc cgc aat gcg gag ttg gag cac cag ctg cgg gcg atg gag   1026
Val Gln Thr Arg Asn Ala Glu Leu Glu His Gln Leu Arg Ala Met Glu
            300                 305                 310 cgc agc ctg gag gag gca cgg gca gag cgg gag cgg gcg cgg gct gag   1074
Arg Ser Leu Glu Glu Ala Arg Ala Glu Arg Glu Arg Ala Arg Ala Glu
        315                 320                 325 gtg ggc cgg gca gcg cag ctg ctg gac gtc agc ctg ttt gag ctg agt   1122
Val Gly Arg Ala Ala Gln Leu Leu Asp Val Ser Leu Phe Glu Leu Ser
    330                 335                 340 gag ctg cgt gag ggc ctg gcc cgc ctg gct gag gct gcg ccc            1164
Glu Leu Arg Glu Gly Leu Ala Arg Leu Ala Glu Ala Ala Pro
345                 350                 355 tgagccgggg ctggttttct atgaacgatt ccggcctggg atgcgggcca ggctgcaggc   1224
ggcatagttg ggcccattcg tcctggaaag ggactggggg gtcccaactt agccctgggt   1284
gggccgggcc gggntgggct ggggtgggcc ccagtcggct ctggttgttg gcagctttgg   1344
ggctgttttt gagcttctca ttgtgtagaa tttctagatc ccccgattac atttctaagc   1404
gtgaaaaaaa aaaaaaaaaa aaaaa                                          1429

<210> SEQ ID NO 12
<211> LENGTH: 358
<212> TYPE: PRT
<213> ORGANISM: Homo sapiens
<220> FEATURE:
<221> NAME/KEY: misc_feature
<222> LOCATION: (1)..(1429)
<223> OTHER INFORMATION: n is either a, c, g, or t

<400> SEQUENCE: 12

Met Ser Thr Ala Arg Glu Gln Pro Ile Phe Ser Thr Arg Ala His Val
1               5                   10                  15

Phe Gln Ile Asp Pro Ala Thr Lys Arg Asn Trp Ile Pro Ala Gly Lys
            20                  25                  30

His Ala Leu Thr Val Ser Tyr Phe Tyr Asp Ala Thr Arg Asn Val Tyr
        35                  40                  45

Arg Ile Ile Ser Ile Gly Gly Ala Lys Ala Ile Ile Asn Ser Thr Val
    50                  55                  60

Thr Pro Asn Met Thr Phe Thr Lys Thr Ser Gln Lys Phe Gly Gln Trp
65                  70                  75                  80

Ala Asp Ser Arg Ala Asn Thr Val Tyr Gly Leu Gly Phe Ala Ser Glu
                85                  90                  95

Gln His Leu Thr Gln Phe Ala Glu Lys Phe Gln Glu Val Lys Glu Ala
            100                 105                 110
```

```
Ala Arg Leu Ala Arg Glu Lys Ser Gln Asp Gly Gly Glu Leu Thr Ser
        115                 120                 125

Pro Ala Leu Gly Leu Ala Ser His Gln Val Pro Pro Ser Pro Leu Val
        130                 135                 140

Ser Ala Asn Gly Pro Gly Glu Lys Leu Phe Arg Ser Gln Ser Ala
145                 150                 155                 160

Asp Ala Pro Gly Pro Thr Glu Arg Glu Arg Leu Lys Lys Met Leu Ser
                165                 170                 175

Glu Gly Ser Val Gly Glu Val Gln Trp Glu Ala Glu Phe Phe Ala Leu
            180                 185                 190

Gln Asp Ser Asn Asn Lys Leu Ala Gly Ala Leu Arg Glu Ala Asn Ala
        195                 200                 205

Ala Ala Ala Gln Trp Arg Gln Gln Leu Glu Ala Gln Arg Ala Glu Ala
    210                 215                 220

Glu Arg Leu Arg Gln Arg Val Ala Glu Leu Glu Ala Gln Ala Ala Ser
225                 230                 235                 240

Glu Val Thr Pro Thr Gly Glu Lys Glu Gly Leu Gly Gln Gly Gln Ser
                245                 250                 255

Leu Glu Gln Leu Glu Ala Leu Val Gln Thr Lys Asp Gln Glu Ile Gln
            260                 265                 270

Thr Leu Lys Ser Gln Thr Gly Gly Pro Arg Glu Ala Leu Glu Ala Ala
        275                 280                 285

Glu Arg Glu Glu Thr Gln Gln Lys Val Gln Thr Arg Asn Ala Glu Leu
    290                 295                 300

Glu His Gln Leu Arg Ala Met Glu Arg Ser Leu Glu Glu Ala Arg Ala
305                 310                 315                 320

Glu Arg Glu Arg Ala Arg Ala Glu Val Gly Arg Ala Ala Gln Leu Leu
                325                 330                 335

Asp Val Ser Leu Phe Glu Leu Ser Glu Leu Arg Glu Gly Leu Ala Arg
            340                 345                 350

Leu Ala Glu Ala Ala Pro
        355

<210> SEQ ID NO 13
<211> LENGTH: 6
<212> TYPE: PRT
<213> ORGANISM: Artificial sequence
<220> FEATURE:
<223> OTHER INFORMATION: core region for peptide binding
<221> NAME/KEY: VARIANT
<222> LOCATION: (1)..(6)
<223> OTHER INFORMATION: Xaa is any amino acid

<400> SEQUENCE: 13

Pro Pro Xaa Xaa Phe Arg
1               5

<210> SEQ ID NO 14
<211> LENGTH: 10
<212> TYPE: PRT
<213> ORGANISM: Artificial sequence
<220> FEATURE:
<223> OTHER INFORMATION: extended region for peptide binding

<400> SEQUENCE: 14

Ala Leu Thr Pro Pro Ser Pro Phe Arg Asp
1               5                   10
```

-continued

```
<210> SEQ ID NO 15
<211> LENGTH: 1415
<212> TYPE: DNA
<213> ORGANISM: Rattus norvegicus
<220> FEATURE:
<221> NAME/KEY: CDS
<222> LOCATION: (1)..(1110)

<400> SEQUENCE: 15 cac gcg tcc gtg gcg gag ctg cag cag ctg cag cag ttg cag gag ttc      48
His Ala Ser Val Ala Glu Leu Gln Gln Leu Gln Gln Leu Gln Glu Phe
1               5                   10                  15 gat atc ccc acg ggc cgg gag gct ctg cgg ggc aac cac agc gcc ctg      96
Asp Ile Pro Thr Gly Arg Glu Ala Leu Arg Gly Asn His Ser Ala Leu
                20                  25                  30 cta cgg gtg gcc aac tac tgt gag gat aac tac ttg cag gcc aca gac     144
Leu Arg Val Ala Asn Tyr Cys Glu Asp Asn Tyr Leu Gln Ala Thr Asp
            35                  40                  45 aag cgg aag gcg ctg gaa gag acg atg gct ttc acc acc cag gcc ctg     192
Lys Arg Lys Ala Leu Glu Glu Thr Met Ala Phe Thr Thr Gln Ala Leu
        50                  55                  60 gcc agt gta gcc tat caa gtg ggt aac ctg gcg ggg cac acg ctt cga     240
Ala Ser Val Ala Tyr Gln Val Gly Asn Leu Ala Gly His Thr Leu Arg
65                  70                  75                  80 atg ctg gat cta cag ggt gct gcc ctg cgg cag gtg gaa gcc aag atg     288
Met Leu Asp Leu Gln Gly Ala Ala Leu Arg Gln Val Glu Ala Lys Met
                85                  90                  95 agc aca ctg ggc cag atg gtg aac atg cac ctg gag aaa gta gcc aga     336
Ser Thr Leu Gly Gln Met Val Asn Met His Leu Glu Lys Val Ala Arg
            100                 105                 110 agg gag att ggc acg ttg gcc act gtc gtg cgg ctg ccc cct agc cag     384
Arg Glu Ile Gly Thr Leu Ala Thr Val Val Arg Leu Pro Pro Ser Gln
        115                 120                 125 aag gtc atc cct cct gag agc ctg cct ccc ctc act ccc tac tgc aga     432
Lys Val Ile Pro Pro Glu Ser Leu Pro Pro Leu Thr Pro Tyr Cys Arg
    130                 135                 140 aaa ccc ctc aac ttt gcc tgc ttg gat gat gtt ggc cat gga gtc aag     480
Lys Pro Leu Asn Phe Ala Cys Leu Asp Asp Val Gly His Gly Val Lys
145                 150                 155                 160 gac ttg agc aca cag ctg tca cgg acc ggg acc ctg tct cgc aag agc     528
Asp Leu Ser Thr Gln Leu Ser Arg Thr Gly Thr Leu Ser Arg Lys Ser
                165                 170                 175 ata aag gcg ccc gct aca cct gcc tct gcc acg ctg ggg aga cca ccc     576
Ile Lys Ala Pro Ala Thr Pro Ala Ser Ala Thr Leu Gly Arg Pro Pro
            180                 185                 190 cgg atc cct gag ccg gtg cag ctc cca gcg gtg cca gac ggc aag ctc     624
Arg Ile Pro Glu Pro Val Gln Leu Pro Ala Val Pro Asp Gly Lys Leu
        195                 200                 205 tcc gct gcc tcc tct gtg tct tcc ttg gcc tcc gca ggc agt gca gaa     672
Ser Ala Ala Ser Ser Val Ser Ser Leu Ala Ser Ala Gly Ser Ala Glu
    210                 215                 220 ggt gcc agt ggg atc ccc cag tcc aag gga cag gta gca cct gca acc     720
Gly Ala Ser Gly Ile Pro Gln Ser Lys Gly Gln Val Ala Pro Ala Thr
225                 230                 235                 240 ccg cct cct cca cct ata gcg cct gta act cca cct cct cca ttg         768
Pro Pro Pro Pro Pro Ile Ala Pro Val Thr Pro Pro Pro Pro Leu
                245                 250                 255 cct gct gag atc ttc ttg ctg ccc cct ccg atg gag gag tcc cag ccc     816
Pro Ala Glu Ile Phe Leu Leu Pro Pro Pro Met Glu Glu Ser Gln Pro
            260                 265                 270 cct ccg gaa aca gag ttg ccc ctg cct cct cct ccg gct cta cag ggg     864
```

-continued

```
                Pro Pro Glu Thr Glu Leu Pro Leu Pro Pro Pro Ala Leu Gln Gly
                        275                 280                 285 gat gaa ctg ggg ctg ctg cct ccg cct cca cca ggt ttt gga ccg gat        912
Asp Glu Leu Gly Leu Leu Pro Pro Pro Pro Pro Gly Phe Gly Pro Asp
    290                 295                 300 gag ccc agc tgg gtc cct gct gcc tac ttg gag aaa gtg gtg acg ctg        960
Glu Pro Ser Trp Val Pro Ala Ala Tyr Leu Glu Lys Val Val Thr Leu
305                 310                 315                 320 tac cca tac acc cgg cag aag gac aat gag ctc tcc ttt tct gaa gga       1008
Tyr Pro Tyr Thr Arg Gln Lys Asp Asn Glu Leu Ser Phe Ser Glu Gly
                325                 330                 335 acc gtc atc tgt gtc act cga cgc tac tca gat ggc tgg tgt gag ggt       1056
Thr Val Ile Cys Val Thr Arg Arg Tyr Ser Asp Gly Trp Cys Glu Gly
            340                 345                 350 gtc agc tca gag ggc act gga ttc ttc cca ggg aac tat gtg gag ccc       1104
Val Ser Ser Glu Gly Thr Gly Phe Phe Pro Gly Asn Tyr Val Glu Pro
        355                 360                 365 agc tgc tgacagccca gatctgtccc tgcctctttg gtgggcctct tgagccccaa        1160
Ser Cys
    370 gaagccacct tccactcaaa gctggactaa ggacctgtct acctcttggg ctgtgaactg     1220 tgttcagtcc cacacagcag taggaagggg tatgggatgg gctagagagt ggtggtactg     1280 aggacgattg ctccagatgg caagaacaaa acaaaacaaa ccaagaagtt aagtttaagc     1340 accttgccca gaggaccccc tagctcatgc accgatcgcc agcattgaat aaaactgttg     1400 acctccagga ttgtt                                                      1415

<210> SEQ ID NO 16
<211> LENGTH: 370
<212> TYPE: PRT
<213> ORGANISM: Rattus norvegicus

<400> SEQUENCE: 16

His Ala Ser Val Ala Glu Leu Gln Gln Leu Gln Gln Leu Gln Glu Phe
1               5                   10                  15

Asp Ile Pro Thr Gly Arg Glu Ala Leu Arg Gly Asn His Ser Ala Leu
            20                  25                  30

Leu Arg Val Ala Asn Tyr Cys Glu Asp Asn Tyr Leu Gln Ala Thr Asp
        35                  40                  45

Lys Arg Lys Ala Leu Glu Glu Thr Met Ala Phe Thr Thr Gln Ala Leu
    50                  55                  60

Ala Ser Val Ala Tyr Gln Val Gly Asn Leu Ala Gly His Thr Leu Arg
65                  70                  75                  80

Met Leu Asp Leu Gln Gly Ala Ala Leu Arg Gln Val Glu Ala Lys Met
                85                  90                  95

Ser Thr Leu Gly Gln Met Val Asn Met His Leu Glu Lys Val Ala Arg
            100                 105                 110

Arg Glu Ile Gly Thr Leu Ala Thr Val Val Arg Leu Pro Pro Ser Gln
        115                 120                 125

Lys Val Ile Pro Pro Glu Ser Leu Pro Pro Leu Thr Pro Tyr Cys Arg
    130                 135                 140

Lys Pro Leu Asn Phe Ala Cys Leu Asp Asp Val Gly His Gly Val Lys
145                 150                 155                 160

Asp Leu Ser Thr Gln Leu Ser Arg Thr Gly Thr Leu Ser Arg Lys Ser
                165                 170                 175

Ile Lys Ala Pro Ala Thr Pro Ala Ser Ala Thr Leu Gly Arg Pro Pro
```

```
                    180                 185                 190
Arg Ile Pro Glu Pro Val Gln Leu Pro Ala Val Pro Asp Gly Lys Leu
        195                 200                 205

Ser Ala Ser Ser Val Ser Ser Leu Ala Ser Ala Gly Ser Ala Glu
    210                 215                 220

Gly Ala Ser Gly Ile Pro Gln Ser Lys Gly Gln Val Ala Pro Ala Thr
225                 230                 235                 240

Pro Pro Pro Pro Ile Ala Pro Val Thr Pro Pro Pro Pro Leu
                245                 250                 255

Pro Ala Glu Ile Phe Leu Leu Pro Pro Met Glu Glu Ser Gln Pro
            260                 265                 270

Pro Pro Glu Thr Glu Leu Pro Leu Pro Pro Pro Ala Leu Gln Gly
        275                 280                 285

Asp Glu Leu Gly Leu Leu Pro Pro Pro Pro Gly Phe Gly Pro Asp
        290                 295                 300

Glu Pro Ser Trp Val Pro Ala Ala Tyr Leu Glu Lys Val Val Thr Leu
305                 310                 315                 320

Tyr Pro Tyr Thr Arg Gln Lys Asp Asn Glu Leu Ser Phe Ser Glu Gly
                325                 330                 335

Thr Val Ile Cys Val Thr Arg Arg Tyr Ser Asp Gly Trp Cys Glu Gly
                340                 345                 350

Val Ser Ser Glu Gly Thr Gly Phe Phe Pro Gly Asn Tyr Val Glu Pro
            355                 360                 365

Ser Cys
    370

<210> SEQ ID NO 17
<211> LENGTH: 3843
<212> TYPE: DNA
<213> ORGANISM: Rattus norvegicus
<220> FEATURE:
<221> NAME/KEY: CDS
<222> LOCATION: (1)..(3840)

<400> SEQUENCE: 17 atg atg aca aac cga gat gga cgt gac tac ttc atc aat cac atg aca      48
Met Met Thr Asn Arg Asp Gly Arg Asp Tyr Phe Ile Asn His Met Thr
1               5                   10                  15 cag gca atc cca ttt gat gac cct cgg ttt gac agc tgc caa atc att      96
Gln Ala Ile Pro Phe Asp Asp Pro Arg Phe Asp Ser Cys Gln Ile Ile
            20                  25                  30 ccc cca gct cca cgg aag gtg gag atg agg agg gac cct gtg ctg ggc     144
Pro Pro Ala Pro Arg Lys Val Glu Met Arg Arg Asp Pro Val Leu Gly
        35                  40                  45 ttt ggg ttc gtg gca ggg agt gaa aag cca gtg gtc gtt cga tcg gta     192
Phe Gly Phe Val Ala Gly Ser Glu Lys Pro Val Val Val Arg Ser Val
    50                  55                  60 aca cca ggt ggc cct tca gaa ggc aag ctg atc ccg gga gat caa att     240
Thr Pro Gly Gly Pro Ser Glu Gly Lys Leu Ile Pro Gly Asp Gln Ile
65                  70                  75                  80 gta atg att aat gat gaa cca gtc agc gct gcg cca aga gag agg gtc     288
Val Met Ile Asn Asp Glu Pro Val Ser Ala Ala Pro Arg Glu Arg Val
                85                  90                  95 atc gac ctg gtc agg agc tgc aaa gaa tcg att ctg ttc act gtc atc     336
Ile Asp Leu Val Arg Ser Cys Lys Glu Ser Ile Leu Phe Thr Val Ile
            100                 105                 110 cag cct tat cct tct ccc aaa tca gca ttt att agt gct gct aaa aag     384
Gln Pro Tyr Pro Ser Pro Lys Ser Ala Phe Ile Ser Ala Ala Lys Lys
```

|     |     |     |     |     |     |     |     |     |     |     |     |     |     |     |     |     |
|---|---|---|---|---|---|---|---|---|---|---|---|---|---|---|---|---|
|     |     | 115 |     |     |     |     | 120 |     |     |     |     |     | 125 |     |     |     |
| gca | aga | ttg | aag | tcc | aat | cca | gtc | aaa | gta | cgc | ttt | tcc | gaa | gag | gtc | 432 |
| Ala | Arg | Leu | Lys | Ser | Asn | Pro | Val | Lys | Val | Arg | Phe | Ser | Glu | Glu | Val |  |
|     | 130 |     |     |     | 135 |     |     |     |     | 140 |     |     |     |     |     |  |
| atc | atc | aat | ggt | cag | gtg | tcg | gaa | act | gtt | aaa | gac | aat | tca | ctt | ctt | 480 |
| Ile | Ile | Asn | Gly | Gln | Val | Ser | Glu | Thr | Val | Lys | Asp | Asn | Ser | Leu | Leu |  |
| 145 |     |     |     |     | 150 |     |     |     |     | 155 |     |     |     |     | 160 |  |
| ttt | atg | cca | aat | gtt | ttg | aaa | gtc | tac | ttg | gaa | aat | gga | cag | acc | aaa | 528 |
| Phe | Met | Pro | Asn | Val | Leu | Lys | Val | Tyr | Leu | Glu | Asn | Gly | Gln | Thr | Lys |  |
|     |     |     |     | 165 |     |     |     |     | 170 |     |     |     |     | 175 |     |  |
| tcc | ttt | cgc | ttt | gac | tgc | agc | act | tcc | att | aag | gat | gtc | atc | tta | act | 576 |
| Ser | Phe | Arg | Phe | Asp | Cys | Ser | Thr | Ser | Ile | Lys | Asp | Val | Ile | Leu | Thr |  |
|     |     |     | 180 |     |     |     |     | 185 |     |     |     |     | 190 |     |     |  |
| ctg | caa | gag | aag | ctg | tct | atc | aaa | ggc | att | gag | cac | ttc | tct | ctc | atg | 624 |
| Leu | Gln | Glu | Lys | Leu | Ser | Ile | Lys | Gly | Ile | Glu | His | Phe | Ser | Leu | Met |  |
|     |     | 195 |     |     |     |     | 200 |     |     |     |     | 205 |     |     |     |  |
| ctg | gag | cag | aga | act | gaa | ggg | gcc | ggc | acc | aag | ctg | ctc | tta | ctt | cat | 672 |
| Leu | Glu | Gln | Arg | Thr | Glu | Gly | Ala | Gly | Thr | Lys | Leu | Leu | Leu | Leu | His |  |
|     | 210 |     |     |     |     | 215 |     |     |     |     | 220 |     |     |     |     |  |
| gaa | cag | gag | aca | ctc | act | cag | gtg | aca | cag | agg | ccg | agt | tcc | cat | aag | 720 |
| Glu | Gln | Glu | Thr | Leu | Thr | Gln | Val | Thr | Gln | Arg | Pro | Ser | Ser | His | Lys |  |
| 225 |     |     |     |     | 230 |     |     |     |     | 235 |     |     |     |     | 240 |  |
| atg | agg | tgt | ctt | ttc | cga | atc | agt | ttt | gtt | ccc | aag | gat | ccc | att | gac | 768 |
| Met | Arg | Cys | Leu | Phe | Arg | Ile | Ser | Phe | Val | Pro | Lys | Asp | Pro | Ile | Asp |  |
|     |     |     |     | 245 |     |     |     |     | 250 |     |     |     |     | 255 |     |  |
| ctg | tta | agg | aga | gat | cca | gtt | gct | ttc | gag | tat | ctc | tat | gtt | cag | agc | 816 |
| Leu | Leu | Arg | Arg | Asp | Pro | Val | Ala | Phe | Glu | Tyr | Leu | Tyr | Val | Gln | Ser |  |
|     |     |     | 260 |     |     |     |     | 265 |     |     |     |     | 270 |     |     |  |
| tgt | aac | gat | gtc | gtt | cag | gag | cga | ttt | gga | cca | gag | ctg | aaa | tac | gac | 864 |
| Cys | Asn | Asp | Val | Val | Gln | Glu | Arg | Phe | Gly | Pro | Glu | Leu | Lys | Tyr | Asp |  |
|     |     | 275 |     |     |     |     | 280 |     |     |     |     | 285 |     |     |     |  |
| att | gcc | ttg | cgg | ctg | gcc | gct | tta | caa | atg | tac | att | gct | act | gtc | acc | 912 |
| Ile | Ala | Leu | Arg | Leu | Ala | Ala | Leu | Gln | Met | Tyr | Ile | Ala | Thr | Val | Thr |  |
|     | 290 |     |     |     |     | 295 |     |     |     |     | 300 |     |     |     |     |  |
| acc | aaa | cag | acg | cag | aaa | atc | tcc | ctc | aag | tac | att | gag | aaa | gaa | tgg | 960 |
| Thr | Lys | Gln | Thr | Gln | Lys | Ile | Ser | Leu | Lys | Tyr | Ile | Glu | Lys | Glu | Trp |  |
| 305 |     |     |     |     | 310 |     |     |     |     | 315 |     |     |     |     | 320 |  |
| gga | cta | gag | act | ttc | ctt | cca | tct | gct | gta | ctt | cag | agc | atg | aaa | gag | 1008 |
| Gly | Leu | Glu | Thr | Phe | Leu | Pro | Ser | Ala | Val | Leu | Gln | Ser | Met | Lys | Glu |  |
|     |     |     |     | 325 |     |     |     |     | 330 |     |     |     |     | 335 |     |  |
| aag | aac | atc | aag | aaa | gcg | ctc | tcc | cac | ctt | gtc | aaa | gca | aat | caa | aac | 1056 |
| Lys | Asn | Ile | Lys | Lys | Ala | Leu | Ser | His | Leu | Val | Lys | Ala | Asn | Gln | Asn |  |
|     |     |     | 340 |     |     |     |     | 345 |     |     |     |     | 350 |     |     |  |
| ttg | gta | cca | ccg | ggt | aaa | aag | ctc | tct | gca | cta | caa | gct | aag | gtc | cac | 1104 |
| Leu | Val | Pro | Pro | Gly | Lys | Lys | Leu | Ser | Ala | Leu | Gln | Ala | Lys | Val | His |  |
|     |     | 355 |     |     |     |     | 360 |     |     |     |     | 365 |     |     |     |  |
| tat | ctc | aag | ttc | ctc | agt | gac | ctg | cga | cta | tac | ggg | ggc | cgt | gtg | ttc | 1152 |
| Tyr | Leu | Lys | Phe | Leu | Ser | Asp | Leu | Arg | Leu | Tyr | Gly | Gly | Arg | Val | Phe |  |
|     | 370 |     |     |     |     | 375 |     |     |     |     | 380 |     |     |     |     |  |
| aag | gca | aca | tta | gtg | cag | gca | gag | aag | cgc | tca | gaa | gtg | act | ctt | ctg | 1200 |
| Lys | Ala | Thr | Leu | Val | Gln | Ala | Glu | Lys | Arg | Ser | Glu | Val | Thr | Leu | Leu |  |
| 385 |     |     |     |     | 390 |     |     |     |     | 395 |     |     |     |     | 400 |  |
| gtg | ggt | ccc | cgg | tat | ggc | ata | agc | cat | gtc | ata | aac | acc | aaa | acc | aac | 1248 |
| Val | Gly | Pro | Arg | Tyr | Gly | Ile | Ser | His | Val | Ile | Asn | Thr | Lys | Thr | Asn |  |
|     |     |     |     | 405 |     |     |     |     | 410 |     |     |     |     | 415 |     |  |
| ctg | gtg | gct | ctt | tta | gct | gac | ttc | agc | cat | gtc | aac | agg | att | gaa | atg | 1296 |
| Leu | Val | Ala | Leu | Leu | Ala | Asp | Phe | Ser | His | Val | Asn | Arg | Ile | Glu | Met |  |
|     |     |     | 420 |     |     |     |     | 425 |     |     |     |     | 430 |     |     |  |
| ttt | act | gaa | gag | gag | agt | ttg | gtg | agg | gtg | gag | ttg | cat | gtg | ctc | gat | 1344 |

```
                -continued

Phe Thr Glu Glu Glu Ser Leu Val Arg Val Glu Leu His Val Leu Asp
        435                 440                 445 gtg aag ccc att aca ctc ctt atg gag tca tca gat gcc atg aac ctg         1392
Val Lys Pro Ile Thr Leu Leu Met Glu Ser Ser Asp Ala Met Asn Leu
450                 455                 460 gcc tgt ctg aca gct gga tac tac cgg ttg ctc gtg gac tcc agg agg         1440
Ala Cys Leu Thr Ala Gly Tyr Tyr Arg Leu Leu Val Asp Ser Arg Arg
465                 470                 475                 480 tca ata ttt aac atg gcc aac aag aaa aat gca ggc aca cag gac aca         1488
Ser Ile Phe Asn Met Ala Asn Lys Lys Asn Ala Gly Thr Gln Asp Thr
                485                 490                 495 gga acg gaa aat aaa ggc aag cat aat ctc ctt ggt cct gac tgg aac         1536
Gly Thr Glu Asn Lys Gly Lys His Asn Leu Leu Gly Pro Asp Trp Asn
            500                 505                 510 tgt atg ccc cag atg acg acc ttc att ggc gaa ggg gaa caa gaa gcc         1584
Cys Met Pro Gln Met Thr Thr Phe Ile Gly Glu Gly Glu Gln Glu Ala
        515                 520                 525 caa atc act tat ata gat tct aag cag aag gca gtt gag atg aca gac         1632
Gln Ile Thr Tyr Ile Asp Ser Lys Gln Lys Ala Val Glu Met Thr Asp
    530                 535                 540 agc acc ttg tgt ccc aaa gag cac cgg cac tta tat atc gac aac aca         1680
Ser Thr Leu Cys Pro Lys Glu His Arg His Leu Tyr Ile Asp Asn Thr
545                 550                 555                 560 tac agt tca gat gaa ctt agc cag ccg ctg act cag cca ggt gat gca         1728
Tyr Ser Ser Asp Glu Leu Ser Gln Pro Leu Thr Gln Pro Gly Asp Ala
                565                 570                 575 ccc tgt gag gcc gac tat aga agc cta gct cag cgg tcc ctt ttg acc         1776
Pro Cys Glu Ala Asp Tyr Arg Ser Leu Ala Gln Arg Ser Leu Leu Thr
            580                 585                 590 ctc tca gga cca gac act ctg aag aaa gca cag gaa tct ccg cga gga         1824
Leu Ser Gly Pro Asp Thr Leu Lys Lys Ala Gln Glu Ser Pro Arg Gly
        595                 600                 605 gct aaa gtg tcc ttt att ttt gga gat ctt gcc tta gat gat ggc atg         1872
Ala Lys Val Ser Phe Ile Phe Gly Asp Leu Ala Leu Asp Asp Gly Met
    610                 615                 620 agt ccc cca act cta ggc tat gaa aga atg tta gat gag aat cca gaa         1920
Ser Pro Pro Thr Leu Gly Tyr Glu Arg Met Leu Asp Glu Asn Pro Glu
625                 630                 635                 640 atg ctg gag aag cag agg aat ctc tac atc agc agt gcc aat gat atg         1968
Met Leu Glu Lys Gln Arg Asn Leu Tyr Ile Ser Ser Ala Asn Asp Met
                645                 650                 655 aaa aac ctg gac ctc act cca gac aca gac agc atc cag ttt gtg gca         2016
Lys Asn Leu Asp Leu Thr Pro Asp Thr Asp Ser Ile Gln Phe Val Ala
            660                 665                 670 aat tca gta tat gca aac ata ggt gat gtg aag aac ttt gaa gcc cct         2064
Asn Ser Val Tyr Ala Asn Ile Gly Asp Val Lys Asn Phe Glu Ala Pro
        675                 680                 685 gag gga ata gag gag ccc ctc tta cat gac atc tgt tat gct gaa aac         2112
Glu Gly Ile Glu Glu Pro Leu Leu His Asp Ile Cys Tyr Ala Glu Asn
    690                 695                 700 aca gat gat gca gaa gat gaa gat gag gtg agc tgc gag gag gat ctc         2160
Thr Asp Asp Ala Glu Asp Glu Asp Glu Val Ser Cys Glu Glu Asp Leu
705                 710                 715                 720 gtg gtg agt gaa atc aac caa cca gcc atc ctt gac ctg tct ggg tca         2208
Val Val Ser Glu Ile Asn Gln Pro Ala Ile Leu Asp Leu Ser Gly Ser
                725                 730                 735 agt gat gat att att gac ctt aca aca ctg cct cct cca gaa gga gat         2256
Ser Asp Asp Ile Ile Asp Leu Thr Thr Leu Pro Pro Pro Glu Gly Asp
            740                 745                 750
```

-continued

```
gac aat gag gat gac ttc ctc ctg cgt tct ctg aac atg gcc att gct    2304
Asp Asn Glu Asp Asp Phe Leu Leu Arg Ser Leu Asn Met Ala Ile Ala
        755                 760                 765 gct ccc cca cct ggt ttt aga gac agt tct gat gaa gag gac act cag    2352
Ala Pro Pro Pro Gly Phe Arg Asp Ser Ser Asp Glu Glu Asp Thr Gln
770                 775                 780 agc cag gca aca tcc ttc cat gag aac aaa gaa caa ggc agc agc ctg    2400
Ser Gln Ala Thr Ser Phe His Glu Asn Lys Glu Gln Gly Ser Ser Leu
785                 790                 795                 800 cag aat gag gag atc cct gtg tcc ctc att gat gct gtg ccc acc agt    2448
Gln Asn Glu Glu Ile Pro Val Ser Leu Ile Asp Ala Val Pro Thr Ser
        805                 810                 815 gca gag ggc aag tgt gag aag gga ctg gac cct acc gtc gtt tcc aca    2496
Ala Glu Gly Lys Cys Glu Lys Gly Leu Asp Pro Thr Val Val Ser Thr
        820                 825                 830 cta gaa gcc cta gaa gct ctt tca gaa gaa cag cag aag agt gaa aat    2544
Leu Glu Ala Leu Glu Ala Leu Ser Glu Glu Gln Gln Lys Ser Glu Asn
        835                 840                 845 tca ggt gta gcc atc ttg cgg gct tat agt ccc gag tct tcc tca gac    2592
Ser Gly Val Ala Ile Leu Arg Ala Tyr Ser Pro Glu Ser Ser Ser Asp
850                 855                 860 tcg ggc aat gag act aac tct tct gaa atg aca gag ggt tct gaa cta    2640
Ser Gly Asn Glu Thr Asn Ser Ser Glu Met Thr Glu Gly Ser Glu Leu
865                 870                 875                 880 gct gca gca cag aag cag tcg gaa agc ctc tcc cgc atg ttc ttg gcc    2688
Ala Ala Ala Gln Lys Gln Ser Glu Ser Leu Ser Arg Met Phe Leu Ala
            885                 890                 895 act cat gaa ggt tat cac cct ctg gca gaa gaa cag aca gag ttc ccc    2736
Thr His Glu Gly Tyr His Pro Leu Ala Glu Glu Gln Thr Glu Phe Pro
        900                 905                 910 acc tcc aaa acc ccc tct gtg ggc ttg cct cca aag tcc tct cat ggc    2784
Thr Ser Lys Thr Pro Ser Val Gly Leu Pro Pro Lys Ser Ser His Gly
        915                 920                 925 ctg gct gct cgc cca gcg acc gac ctc cca ccc aaa gtt gtg cct tcc    2832
Leu Ala Ala Arg Pro Ala Thr Asp Leu Pro Pro Lys Val Val Pro Ser
930                 935                 940 aag cag atc ctt cac tca gat cac atg gaa atg gag cca gaa acc atg    2880
Lys Gln Ile Leu His Ser Asp His Met Glu Met Glu Pro Glu Thr Met
945                 950                 955                 960 gag acc aag tca gtc act gac tat ttt agc aaa ctg cac atg ggg tca    2928
Glu Thr Lys Ser Val Thr Asp Tyr Phe Ser Lys Leu His Met Gly Ser
            965                 970                 975 gtg gca tat tcc tgt acc agc aaa agg aaa agc aag ctt gct gag gga    2976
Val Ala Tyr Ser Cys Thr Ser Lys Arg Lys Ser Lys Leu Ala Glu Gly
        980                 985                 990 gag ggg aaa tgc ccc ctg agt ggg  aat gta cca ggg aaa  aaa cag caa   3024
Glu Gly Lys Cys Pro Leu Ser Gly  Asn Val Pro Gly Lys  Lys Gln Gln
        995                 1000                1005 gga acc  aaa ata gca gag acg  gag gag gac acc aaa  ggc aaa gtt      3069
Gly Thr  Lys Ile Ala Glu Thr  Glu Glu Asp Thr Lys  Gly Lys Val
    1010                1015                1020 ggc act  gta tct tca aga gac  aat cca cac ctc agc  act ttt aac      3114
Gly Thr  Val Ser Ser Arg Asp  Asn Pro His Leu Ser  Thr Phe Asn
    1025                1030                1035 ctg gag  aga act gcc ttt cgc  aag gac agc caa aga  tgg tat gtg      3159
Leu Glu  Arg Thr Ala Phe Arg  Lys Asp Ser Gln Arg  Trp Tyr Val
    1040                1045                1050 gcc tct  gat ggt ggg gtg gta  gag aaa agt gga gtg  gaa gca cca      3204
Ala Ser  Asp Gly Gly Val Val  Glu Lys Ser Gly Val  Glu Ala Pro
    1055                1060                1065
```

```
gcc atg aaa gcc ttt ccc aga ggt cct ggt ctg ggg aac aga gag      3249
Ala Met Lys Ala Phe Pro Arg Gly Pro Gly Leu Gly Asn Arg Glu
    1070                1075                1080 gct gaa ggg aaa gag gat ggc act atg gaa gga gag gct gat gat      3294
Ala Glu Gly Lys Glu Asp Gly Thr Met Glu Gly Glu Ala Asp Asp
1085                1090                1095 gct tca gga ctt ggt caa ggg gaa cgc ttc ctg tca gat atg gcc      3339
Ala Ser Gly Leu Gly Gln Gly Glu Arg Phe Leu Ser Asp Met Ala
    1100                1105                1110 tgt gta gcc tca gcc aaa gac tta gac aac cct gaa gac act gac      3384
Cys Val Ala Ser Ala Lys Asp Leu Asp Asn Pro Glu Asp Thr Asp
    1115                1120                1125 tct ccc act tgt gac cat gcc act aag ctt cct gag gct gaa gac      3429
Ser Pro Thr Cys Asp His Ala Thr Lys Leu Pro Glu Ala Glu Asp
    1130                1135                1140 aat gtg gcc cgc ctt tgt gac tac cat ttg gcc aag cga atg tca      3474
Asn Val Ala Arg Leu Cys Asp Tyr His Leu Ala Lys Arg Met Ser
    1145                1150                1155 tcc ctg cag agt gag ggc cat ttt tct cta cag agc tct caa ggc      3519
Ser Leu Gln Ser Glu Gly His Phe Ser Leu Gln Ser Ser Gln Gly
    1160                1165                1170 tct tca gtg gac aca ggc tgt ggc cca ggc agc agt agc agt gcc      3564
Ser Ser Val Asp Thr Gly Cys Gly Pro Gly Ser Ser Ser Ser Ala
    1175                1180                1185 tgt gcc act cct gtg gaa tcg ccc ctc tgc cca tcc atg gga aag      3609
Cys Ala Thr Pro Val Glu Ser Pro Leu Cys Pro Ser Met Gly Lys
    1190                1195                1200 cac ctg att cca gat gct tct ggg aaa ggt ggg agt tac att tca      3654
His Leu Ile Pro Asp Ala Ser Gly Lys Gly Gly Ser Tyr Ile Ser
    1205                1210                1215 cca gag gag aga gtc gct ggt cat ccc aac cat gga gcc acc ttc      3699
Pro Glu Glu Arg Val Ala Gly His Pro Asn His Gly Ala Thr Phe
    1220                1225                1230 aag gaa ctg cac cca cag aca gaa ggg atg tgt cca cgc atg aca      3744
Lys Glu Leu His Pro Gln Thr Glu Gly Met Cys Pro Arg Met Thr
    1235                1240                1245 gtg cct gct ctg cac aca gcc att aat gcc gac ccc ctg ttt ggc      3789
Val Pro Ala Leu His Thr Ala Ile Asn Ala Asp Pro Leu Phe Gly
    1250                1255                1260 act ttg aga gat gga tgc cat cga ctg ccc aag att aag gaa acc      3834
Thr Leu Arg Asp Gly Cys His Arg Leu Pro Lys Ile Lys Glu Thr
    1265                1270                1275 aca gtg tag                                                       3843
Thr Val
    1280

<210> SEQ ID NO 18
<211> LENGTH: 1280
<212> TYPE: PRT
<213> ORGANISM: Rattus norvegicus

<400> SEQUENCE: 18

Met Met Thr Asn Arg Asp Gly Arg Asp Tyr Phe Ile Asn His Met Thr
1               5                   10                  15

Gln Ala Ile Pro Phe Asp Asp Pro Arg Phe Asp Ser Cys Gln Ile Ile
            20                  25                  30

Pro Pro Ala Pro Arg Lys Val Glu Met Arg Arg Asp Pro Val Leu Gly
        35                  40                  45

Phe Gly Phe Val Ala Gly Ser Glu Lys Pro Val Val Val Arg Ser Val
```

```
            50                  55                  60
Thr Pro Gly Gly Pro Ser Glu Gly Lys Leu Ile Pro Gly Asp Gln Ile
 65                  70                  75                  80

Val Met Ile Asn Asp Glu Pro Val Ser Ala Pro Arg Glu Arg Val
                 85                  90                  95

Ile Asp Leu Val Arg Ser Cys Lys Glu Ser Ile Leu Phe Thr Val Ile
                100                 105                 110

Gln Pro Tyr Pro Ser Pro Lys Ser Ala Phe Ile Ser Ala Ala Lys Lys
            115                 120                 125

Ala Arg Leu Lys Ser Asn Pro Val Lys Val Arg Phe Ser Glu Val
130                 135                 140

Ile Ile Asn Gly Gln Val Ser Glu Thr Val Lys Asp Asn Ser Leu Leu
145                 150                 155                 160

Phe Met Pro Asn Val Leu Lys Val Tyr Leu Glu Asn Gly Gln Thr Lys
                165                 170                 175

Ser Phe Arg Phe Asp Cys Ser Thr Ser Ile Lys Asp Val Ile Leu Thr
                180                 185                 190

Leu Gln Glu Lys Leu Ser Ile Lys Gly Ile Glu His Phe Ser Leu Met
            195                 200                 205

Leu Glu Gln Arg Thr Glu Gly Ala Gly Thr Lys Leu Leu Leu His
            210                 215                 220

Glu Gln Glu Thr Leu Thr Gln Val Thr Gln Arg Pro Ser Ser His Lys
225                 230                 235                 240

Met Arg Cys Leu Phe Arg Ile Ser Phe Val Pro Lys Asp Pro Ile Asp
                245                 250                 255

Leu Leu Arg Arg Asp Pro Val Ala Phe Glu Tyr Leu Tyr Val Gln Ser
                260                 265                 270

Cys Asn Asp Val Val Gln Glu Arg Phe Gly Pro Glu Leu Lys Tyr Asp
            275                 280                 285

Ile Ala Leu Arg Leu Ala Ala Leu Gln Met Tyr Ile Ala Thr Val Thr
290                 295                 300

Thr Lys Gln Thr Gln Lys Ile Ser Leu Lys Tyr Ile Glu Lys Glu Trp
305                 310                 315                 320

Gly Leu Glu Thr Phe Leu Pro Ser Ala Val Leu Gln Ser Met Lys Glu
                325                 330                 335

Lys Asn Ile Lys Lys Ala Leu Ser His Leu Val Lys Ala Asn Gln Asn
            340                 345                 350

Leu Val Pro Pro Gly Lys Lys Leu Ser Ala Leu Gln Ala Lys Val His
            355                 360                 365

Tyr Leu Lys Phe Leu Ser Asp Leu Arg Leu Tyr Gly Gly Arg Val Phe
            370                 375                 380

Lys Ala Thr Leu Val Gln Ala Glu Lys Arg Ser Glu Val Thr Leu Leu
385                 390                 395                 400

Val Gly Pro Arg Tyr Gly Ile Ser His Val Ile Asn Thr Lys Thr Asn
                405                 410                 415

Leu Val Ala Leu Leu Ala Asp Phe Ser His Val Asn Arg Ile Glu Met
                420                 425                 430

Phe Thr Glu Glu Glu Ser Leu Val Arg Val Glu Leu His Val Leu Asp
            435                 440                 445

Val Lys Pro Ile Thr Leu Leu Met Glu Ser Ser Asp Ala Met Asn Leu
            450                 455                 460

Ala Cys Leu Thr Ala Gly Tyr Tyr Arg Leu Leu Val Asp Ser Arg Arg
465                 470                 475                 480
```

-continued

```
Ser Ile Phe Asn Met Ala Asn Lys Lys Asn Ala Gly Thr Gln Asp Thr
            485                 490                 495
Gly Thr Glu Asn Lys Gly Lys His Asn Leu Leu Gly Pro Asp Trp Asn
            500                 505                 510
Cys Met Pro Gln Met Thr Thr Phe Ile Gly Glu Gly Glu Gln Glu Ala
            515                 520                 525
Gln Ile Thr Tyr Ile Asp Ser Lys Gln Lys Ala Val Glu Met Thr Asp
            530                 535                 540
Ser Thr Leu Cys Pro Lys Glu His Arg His Leu Tyr Ile Asp Asn Thr
545                 550                 555                 560
Tyr Ser Ser Asp Glu Leu Ser Gln Pro Leu Thr Gln Pro Gly Asp Ala
            565                 570                 575
Pro Cys Glu Ala Asp Tyr Arg Ser Leu Ala Gln Arg Ser Leu Leu Thr
            580                 585                 590
Leu Ser Gly Pro Asp Thr Leu Lys Lys Ala Gln Glu Ser Pro Arg Gly
            595                 600                 605
Ala Lys Val Ser Phe Ile Phe Gly Asp Leu Ala Leu Asp Asp Gly Met
            610                 615                 620
Ser Pro Pro Thr Leu Gly Tyr Glu Arg Met Leu Asp Glu Asn Pro Glu
625                 630                 635                 640
Met Leu Glu Lys Gln Arg Asn Leu Tyr Ile Ser Ser Ala Asn Asp Met
            645                 650                 655
Lys Asn Leu Asp Leu Thr Pro Asp Thr Asp Ser Ile Gln Phe Val Ala
            660                 665                 670
Asn Ser Val Tyr Ala Asn Ile Gly Asp Val Lys Asn Phe Glu Ala Pro
            675                 680                 685
Glu Gly Ile Glu Glu Pro Leu Leu His Asp Ile Cys Tyr Ala Glu Asn
            690                 695                 700
Thr Asp Asp Ala Glu Asp Glu Asp Glu Val Ser Cys Glu Glu Asp Leu
705                 710                 715                 720
Val Val Ser Glu Ile Asn Gln Pro Ala Ile Leu Asp Leu Ser Gly Ser
            725                 730                 735
Ser Asp Asp Ile Ile Asp Leu Thr Thr Leu Pro Pro Pro Glu Gly Asp
            740                 745                 750
Asp Asn Glu Asp Asp Phe Leu Leu Arg Ser Leu Asn Met Ala Ile Ala
            755                 760                 765
Ala Pro Pro Pro Gly Phe Arg Asp Ser Ser Asp Glu Glu Asp Thr Gln
            770                 775                 780
Ser Gln Ala Thr Ser Phe His Glu Asn Lys Glu Gln Gly Ser Ser Leu
785                 790                 795                 800
Gln Asn Glu Glu Ile Pro Val Ser Leu Ile Asp Ala Val Pro Thr Ser
            805                 810                 815
Ala Glu Gly Lys Cys Glu Lys Gly Leu Asp Pro Thr Val Val Ser Thr
            820                 825                 830
Leu Glu Ala Leu Glu Ala Leu Ser Glu Glu Gln Gln Lys Ser Glu Asn
            835                 840                 845
Ser Gly Val Ala Ile Leu Arg Ala Tyr Ser Pro Glu Ser Ser Ser Asp
            850                 855                 860
Ser Gly Asn Glu Thr Asn Ser Ser Glu Met Thr Glu Gly Ser Glu Leu
865                 870                 875                 880
Ala Ala Ala Gln Lys Gln Ser Glu Ser Leu Ser Arg Met Phe Leu Ala
            885                 890                 895
```

-continued

```
Thr His Glu Gly Tyr His Pro Leu Ala Glu Glu Gln Thr Glu Phe Pro
        900                 905                 910
Thr Ser Lys Thr Pro Ser Val Gly Leu Pro Pro Lys Ser Ser His Gly
        915                 920                 925
Leu Ala Ala Arg Pro Ala Thr Asp Leu Pro Pro Lys Val Val Pro Ser
930                 935                 940
Lys Gln Ile Leu His Ser Asp His Met Glu Met Glu Pro Glu Thr Met
945                 950                 955                 960
Glu Thr Lys Ser Val Thr Asp Tyr Phe Ser Lys Leu His Met Gly Ser
                965                 970                 975
Val Ala Tyr Ser Cys Thr Ser Lys Arg Lys Ser Lys Leu Ala Glu Gly
                980                 985                 990
Glu Gly Lys Cys Pro Leu Ser Gly Asn Val Pro Gly Lys Lys Gln Gln
                995                1000                1005
Gly Thr Lys Ile Ala Glu Thr Glu Glu Asp Thr Lys Gly Lys Val
        1010                1015                1020
Gly Thr Val Ser Ser Arg Asp Asn Pro His Leu Ser Thr Phe Asn
        1025                1030                1035
Leu Glu Arg Thr Ala Phe Arg Lys Asp Ser Gln Arg Trp Tyr Val
        1040                1045                1050
Ala Ser Asp Gly Gly Val Val Glu Lys Ser Gly Val Glu Ala Pro
        1055                1060                1065
Ala Met Lys Ala Phe Pro Arg Gly Pro Gly Leu Gly Asn Arg Glu
        1070                1075                1080
Ala Glu Gly Lys Glu Asp Gly Thr Met Glu Gly Glu Ala Asp Asp
        1085                1090                1095
Ala Ser Gly Leu Gly Gln Gly Glu Arg Phe Leu Ser Asp Met Ala
        1100                1105                1110
Cys Val Ala Ser Ala Lys Asp Leu Asp Asn Pro Glu Asp Thr Asp
        1115                1120                1125
Ser Pro Thr Cys Asp His Ala Thr Lys Leu Pro Glu Ala Glu Asp
        1130                1135                1140
Asn Val Ala Arg Leu Cys Asp Tyr His Leu Ala Lys Arg Met Ser
        1145                1150                1155
Ser Leu Gln Ser Glu Gly His Phe Ser Leu Gln Ser Ser Gln Gly
        1160                1165                1170
Ser Ser Val Asp Thr Gly Cys Gly Pro Gly Ser Ser Ser Ser Ala
        1175                1180                1185
Cys Ala Thr Pro Val Glu Ser Pro Leu Cys Pro Ser Met Gly Lys
        1190                1195                1200
His Leu Ile Pro Asp Ala Ser Gly Lys Gly Gly Ser Tyr Ile Ser
        1205                1210                1215
Pro Glu Glu Arg Val Ala Gly His Pro Asn His Gly Ala Thr Phe
        1220                1225                1230
Lys Glu Leu His Pro Gln Thr Glu Gly Met Cys Pro Arg Met Thr
        1235                1240                1245
Val Pro Ala Leu His Thr Ala Ile Asn Ala Asp Pro Leu Phe Gly
        1250                1255                1260
Thr Leu Arg Asp Gly Cys His Arg Leu Pro Lys Ile Lys Glu Thr
        1265                1270                1275
Thr Val
        1280
```

-continued

```
<210> SEQ ID NO 19
<211> LENGTH: 1583
<212> TYPE: DNA
<213> ORGANISM: Homo sapiens
<220> FEATURE:
<221> NAME/KEY: CDS
<222> LOCATION: (160)..(1257)

<400> SEQUENCE: 19
```

| | | |
|---|---|---|
| ggcacgagtg agcatgcctg ccctttgcaa gcaggtttgg gtctcacgca gaggaaacca | 60 |
| aaagcaataa gagggaggga aggcagagca accaatcaag gcagggtga gactcaaaac | 120 |
| gagcgggctc cctggggagc cagacagagg ctggggggtg atg gcg gag cta cag<br>                                                                                  Met Ala Glu Leu Gln<br>                                                                                  1                   5 | 174 |

```
cag ctg cag gag ttt gag atc ccc act ggc cgg gag gct ctg agg ggc      222
Gln Leu Gln Glu Phe Glu Ile Pro Thr Gly Arg Glu Ala Leu Arg Gly
             10                  15                  20 aac cac agt gcc ctg ctg cgg gtc gct gac tac tgc gag gac aac tat      270
Asn His Ser Ala Leu Leu Arg Val Ala Asp Tyr Cys Glu Asp Asn Tyr
 25                  30                  35 gtg cag gcc aca gac aag cgg aag gcg ctg gag gag acc atg gcc ttc      318
Val Gln Ala Thr Asp Lys Arg Lys Ala Leu Glu Glu Thr Met Ala Phe
         40                  45                  50 act acc cag gca ctg gcc agc gtg gcc tac cag gtg ggc aac ctg gcc      366
Thr Thr Gln Ala Leu Ala Ser Val Ala Tyr Gln Val Gly Asn Leu Ala
     55                  60                  65 ggg cac act ctg cgc atg ttg gac ctg cag ggg gcc gcc ctg cgg cag      414
Gly His Thr Leu Arg Met Leu Asp Leu Gln Gly Ala Ala Leu Arg Gln
 70                  75                  80                  85 gtg gaa gcc cgt gta agc acg ctg ggc cag atg gtg aac atg cat atg      462
Val Glu Ala Arg Val Ser Thr Leu Gly Gln Met Val Asn Met His Met
                 90                  95                 100 gag aag gtg gcc cga agg gag atc ggc acc tta gcc act gtc caa cgg      510
Glu Lys Val Ala Arg Arg Glu Ile Gly Thr Leu Ala Thr Val Gln Arg
             105                 110                 115 ctg ccc ccc ggc cag aag gtc atc gcc cca gag aac cta ccc cct ctc      558
Leu Pro Pro Gly Gln Lys Val Ile Ala Pro Glu Asn Leu Pro Pro Leu
         120                 125                 130 acg ccc tac tgc agg aga acc ctc aac ttt ggc tgc ctg gac gac att      606
Thr Pro Tyr Cys Arg Arg Thr Leu Asn Phe Gly Cys Leu Asp Asp Ile
     135                 140                 145 ggc cat ggg atc aag gac ctc agc acg cag ctg tca aga aca ggc acc      654
Gly His Gly Ile Lys Asp Leu Ser Thr Gln Leu Ser Arg Thr Gly Thr
150                 155                 160                 165 ctg tct cga aag agc atc aag gcc cct gcc aca ccc gcc tcc gcc acc      702
Leu Ser Arg Lys Ser Ile Lys Ala Pro Ala Thr Pro Ala Ser Ala Thr
                 170                 175                 180 ttg ggg aga cca ccc cgg att ccc gag cca gtg cac ctg ccg gtg gtg      750
Leu Gly Arg Pro Pro Arg Ile Pro Glu Pro Val His Leu Pro Val Val
             185                 190                 195 ccc gac ggc aga ctc tcc gcc gcc tcc tct gcg tct tcc ctg gcc tcg      798
Pro Asp Gly Arg Leu Ser Ala Ala Ser Ser Ala Ser Ser Leu Ala Ser
         200                 205                 210 gcc ggc agc gcc gaa ggt gtc ggt ggg gcc ccc acg ccc aag ggg cag      846
Ala Gly Ser Ala Glu Gly Val Gly Gly Ala Pro Thr Pro Lys Gly Gln
     215                 220                 225 gca gca cct cca gcc cca cct ctc ccc agc tcc ttg gac cca cct cct      894
Ala Ala Pro Pro Ala Pro Pro Leu Pro Ser Ser Leu Asp Pro Pro Pro
230                 235                 240                 245 cca cca gca gcc gtc gag gtg ttc cag cgg cct ccc acg ctg gag gag      942
Pro Pro Ala Ala Val Glu Val Phe Gln Arg Pro Pro Thr Leu Glu Glu
```

-continued

```
                Pro Pro Ala Ala Val Glu Val Phe Gln Arg Pro Pro Thr Leu Glu Glu
                            250                 255                 260 ttg tcc cca ccc cca ccg gac gaa gag ctg ccc ctg cca ctg gac ctg        990
Leu Ser Pro Pro Pro Pro Asp Glu Glu Leu Pro Leu Pro Leu Asp Leu
            265                 270                 275 cct cct cct cca ccc ctg gat gga gat gaa ttg ggg ctg cct cca ccc       1038
Pro Pro Pro Pro Pro Leu Asp Gly Asp Glu Leu Gly Leu Pro Pro Pro
        280                 285                 290 cca cca gga ttt ggg cct gat gag ccc agc tgg gtg cct gcc tca tac       1086
Pro Pro Gly Phe Gly Pro Asp Glu Pro Ser Trp Val Pro Ala Ser Tyr
    295                 300                 305 ttg gag aaa gtg gtg aca ctg tac cca tac acc agc cag aag gac aat       1134
Leu Glu Lys Val Val Thr Leu Tyr Pro Tyr Thr Ser Gln Lys Asp Asn
310                 315                 320                 325 gag ctc tcc ttc tct gag ggc act gtc atc tgt gtc act cgc cgc tac       1182
Glu Leu Ser Phe Ser Glu Gly Thr Val Ile Cys Val Thr Arg Arg Tyr
                330                 335                 340 tcc gat ggc tgg tgc gag ggc gtc agc tca gag ggg act gga ttc ttc       1230
Ser Asp Gly Trp Cys Glu Gly Val Ser Ser Glu Gly Thr Gly Phe Phe
            345                 350                 355 cct ggg aac tat gtg gag ccc agc tgc tgacagccca gggctctctg             1277
Pro Gly Asn Tyr Val Glu Pro Ser Cys
        360                 365 ggcagctgat gtctgcactg agtgggtttc atgagcccca agccaaaacc agctccagtc    1337
acagctggac tgggtctgcc cacctcttgg gctgtgagct gtgttctgtc cttcctccca    1397
tcggagggag aaggggtcct ggggagagag aatttatcca gaggcctgct gcagatgggg    1457
aagagctgga aaccaagaag tttgtcaaca gaggacccct actccatgca ggacagggtc    1517
tcctgctgca agtcccaact tgaataaaaa cagatgatgt cctgtgaaaa aaaaaaaaaa    1577
aaaaaa                                                               1583

<210> SEQ ID NO 20
<211> LENGTH: 366
<212> TYPE: PRT
<213> ORGANISM: Homo sapiens

<400> SEQUENCE: 20

Met Ala Glu Leu Gln Gln Leu Gln Glu Phe Glu Ile Pro Thr Gly Arg
1               5                   10                  15

Glu Ala Leu Arg Gly Asn His Ser Ala Leu Leu Arg Val Ala Asp Tyr
            20                  25                  30

Cys Glu Asp Asn Tyr Val Gln Ala Thr Asp Lys Arg Lys Ala Leu Glu
        35                  40                  45

Glu Thr Met Ala Phe Thr Thr Gln Ala Leu Ala Ser Val Ala Tyr Gln
    50                  55                  60

Val Gly Asn Leu Ala Gly His Thr Leu Arg Met Leu Asp Leu Gln Gly
65                  70                  75                  80

Ala Ala Leu Arg Gln Val Glu Ala Arg Val Ser Thr Leu Gly Gln Met
                85                  90                  95

Val Asn Met His Met Glu Lys Val Ala Arg Arg Glu Ile Gly Thr Leu
            100                 105                 110

Ala Thr Val Gln Arg Leu Pro Pro Gly Gln Lys Val Ile Ala Pro Glu
        115                 120                 125

Asn Leu Pro Pro Leu Thr Pro Tyr Cys Arg Arg Thr Leu Asn Phe Gly
    130                 135                 140

Cys Leu Asp Asp Ile Gly His Gly Ile Lys Asp Leu Ser Thr Gln Leu
```

```
145                 150                 155                 160
Ser Arg Thr Gly Thr Leu Ser Arg Lys Ser Ile Lys Ala Pro Ala Thr
                165                 170                 175

Pro Ala Ser Ala Thr Leu Gly Arg Pro Pro Arg Ile Pro Glu Pro Val
            180                 185                 190

His Leu Pro Val Val Pro Asp Gly Arg Leu Ser Ala Ala Ser Ser Ala
        195                 200                 205

Ser Ser Leu Ala Ser Ala Gly Ser Ala Glu Gly Val Gly Gly Ala Pro
    210                 215                 220

Thr Pro Lys Gly Gln Ala Ala Pro Ala Pro Leu Pro Ser Ser
225                 230                 235                 240

Leu Asp Pro Pro Pro Pro Ala Val Glu Val Phe Gln Arg Pro
                245                 250                 255

Pro Thr Leu Glu Glu Leu Ser Pro Pro Pro Asp Glu Leu Pro
            260                 265                 270

Leu Pro Leu Asp Leu Pro Pro Pro Pro Leu Asp Gly Asp Glu Leu
        275                 280                 285

Gly Leu Pro Pro Pro Pro Gly Phe Gly Pro Asp Glu Pro Ser Trp
    290                 295                 300

Val Pro Ala Ser Tyr Leu Glu Lys Val Val Thr Leu Tyr Pro Tyr Thr
305                 310                 315                 320

Ser Gln Lys Asp Asn Glu Leu Ser Phe Ser Glu Gly Thr Val Ile Cys
                325                 330                 335

Val Thr Arg Arg Tyr Ser Asp Gly Trp Cys Glu Gly Val Ser Ser Glu
            340                 345                 350

Gly Thr Gly Phe Phe Pro Gly Asn Tyr Val Glu Pro Ser Cys
        355                 360                 365

<210> SEQ ID NO 21
<211> LENGTH: 6935
<212> TYPE: DNA
<213> ORGANISM: Homo sapiens
<220> FEATURE:
<221> NAME/KEY: CDS
<222> LOCATION: (498)..(3779)

<400> SEQUENCE: 21
tttccagcca acgccaaaca gtgactgttg acaatttcat attgtcatca ggggaaccaa      60
ggcttattca gatgcctatt tcagaaccta ggacagttcc attgaaaagg cgcaggcgtt     120
cgggctggct gactagatgg atcaggcctg gctgcctgat ggctatattc ctccttcctc     180
cctctccact tccatctcaa cccttgaggc tgcatattga atagttggag aattcagtga     240
actaagagat gcaaatgcac agtacaaaat tcaaatgtcc aattcggggc agggctgcat     300
ctaactttaa tggcaaccac tgcatgtgat gtctggggac tctatagata catgccctca     360
gaccctgaag acatctggat tctgtcactg gattgttcac aaagtgaggc tgaactttcc     420
acaggacgaa gtcttcaggc tggccgcctc cctcgggaac ctggggcttg agccaggtgc     480
cgccctatgg atgggag atg acg gca aac cga gat ggg cga gac tac ttc       530
                    Met Thr Ala Asn Arg Asp Gly Arg Asp Tyr Phe
                      1               5                  10 atc aat cac atg aca cag gca atc cct ttt gac gac cct cgg tta gag       578
Ile Asn His Met Thr Gln Ala Ile Pro Phe Asp Asp Pro Arg Leu Glu
             15                  20                  25 agc tgc caa atc atc cct ccg gct cct cgg aag gtg gag atg aga agg       626
Ser Cys Gln Ile Ile Pro Pro Ala Pro Arg Lys Val Glu Met Arg Arg
         30                  35                  40
```

```
gac ccc gtg ctg gga ttt ggt ttt gtg gca ggc agt gaa aag cca gtg      674
Asp Pro Val Leu Gly Phe Gly Phe Val Ala Gly Ser Glu Lys Pro Val
    45                  50                  55 gtc gtt cgc tca gta aca cca ggt ggc ccc tct gaa ggc aag ctg atc      722
Val Val Arg Ser Val Thr Pro Gly Gly Pro Ser Glu Gly Lys Leu Ile
60                  65                  70                  75 ccg gga gat cag att gta atg att aat gat gaa ccg gtc agc gct gca      770
Pro Gly Asp Gln Ile Val Met Ile Asn Asp Glu Pro Val Ser Ala Ala
                    80                  85                  90 ccc aga gag cgg gtc atc gat ctg gtc aga agc tgc aaa gaa tcg ata      818
Pro Arg Glu Arg Val Ile Asp Leu Val Arg Ser Cys Lys Glu Ser Ile
                95                  100                 105 ctc ctc act gtc att cag cct tac cct tct ccc aaa tca gca ttt att      866
Leu Leu Thr Val Ile Gln Pro Tyr Pro Ser Pro Lys Ser Ala Phe Ile
            110                 115                 120 agt gct gca aaa aag gca aga tta aag tcc aat cct gtc aaa gta cgc      914
Ser Ala Ala Lys Lys Ala Arg Leu Lys Ser Asn Pro Val Lys Val Arg
        125                 130                 135 ttc tct gag gag gtc atc atc aac ggc caa gtg tcg gaa act gtt aag      962
Phe Ser Glu Glu Val Ile Ile Asn Gly Gln Val Ser Glu Thr Val Lys
140                 145                 150                 155 gac aac tca ctt ctt ttt atg cca aat gtt ttg aaa gtc tat ctg gaa     1010
Asp Asn Ser Leu Leu Phe Met Pro Asn Val Leu Lys Val Tyr Leu Glu
                    160                 165                 170 aat ggg cag acc aaa tca ttt cgt ttt gac tgc agc act tcc att aag     1058
Asn Gly Gln Thr Lys Ser Phe Arg Phe Asp Cys Ser Thr Ser Ile Lys
                175                 180                 185 gat gtc atc tta acc ctt caa gag aag ctc tcc atc aaa ggc att gaa     1106
Asp Val Ile Leu Thr Leu Gln Glu Lys Leu Ser Ile Lys Gly Ile Glu
            190                 195                 200 cac ttc tct ctc atg ctg gag cag agg aca gaa ggg gct gga acg aag     1154
His Phe Ser Leu Met Leu Glu Gln Arg Thr Glu Gly Ala Gly Thr Lys
        205                 210                 215 ctg ctc ttg ctt cat gaa cag gag act cta act cag gtg aca cag agg     1202
Leu Leu Leu Leu His Glu Gln Glu Thr Leu Thr Gln Val Thr Gln Arg
220                 225                 230                 235 ccc agc tcc cat aag atg aga tgt ctt ttc cga att agc ttc gtc cca     1250
Pro Ser Ser His Lys Met Arg Cys Leu Phe Arg Ile Ser Phe Val Pro
                    240                 245                 250 aaa gat cca att gac ctt tta agg aga gat cca gtt gct ttc gag tat     1298
Lys Asp Pro Ile Asp Leu Leu Arg Arg Asp Pro Val Ala Phe Glu Tyr
                255                 260                 265 ctc tat gtt cag agt tgt aac gat gtg gtt cag gag cga ttt ggg ccg     1346
Leu Tyr Val Gln Ser Cys Asn Asp Val Val Gln Glu Arg Phe Gly Pro
            270                 275                 280 gag ctg aaa tat gac ata gcc ctg cgg ctg gcc gca tta caa atg tac     1394
Glu Leu Lys Tyr Asp Ile Ala Leu Arg Leu Ala Ala Leu Gln Met Tyr
        285                 290                 295 att gca acc gtt acc acc aag caa acg cag aaa atc tcc ctc aaa tac     1442
Ile Ala Thr Val Thr Thr Lys Gln Thr Gln Lys Ile Ser Leu Lys Tyr
300                 305                 310                 315 atc gaa aaa gaa tgg gga tta gag act ttt ctt ccc tct gct gtg ctg     1490
Ile Glu Lys Glu Trp Gly Leu Glu Thr Phe Leu Pro Ser Ala Val Leu
                    320                 325                 330 caa agc atg aaa gag aag aac ata aag aaa gca ctt tca cac ctt gtc     1538
Gln Ser Met Lys Glu Lys Asn Ile Lys Lys Ala Leu Ser His Leu Val
                335                 340                 345 aaa gca aat caa aac ttg gta cca ccg ggt aaa aag ctc tct gca cta     1586
Lys Ala Asn Gln Asn Leu Val Pro Pro Gly Lys Lys Leu Ser Ala Leu
```

-continued

```
               350                 355                 360
caa gcc aag gtc cat tat ctc aag ttc ctc agt gac cta cga ttg tat   1634
Gln Ala Lys Val His Tyr Leu Lys Phe Leu Ser Asp Leu Arg Leu Tyr
365                 370                 375 ggg ggc cgt gtg ttc aag gca aca tta gtg cag gca gaa aag cgc tcg   1682
Gly Gly Arg Val Phe Lys Ala Thr Leu Val Gln Ala Glu Lys Arg Ser
380                 385                 390                 395 gaa gtg act ctc ctg gtt ggg ccc cgg tat ggc ata agc cat gtc atc   1730
Glu Val Thr Leu Leu Val Gly Pro Arg Tyr Gly Ile Ser His Val Ile
                400                 405                 410 aac acc aaa acc aat ctg gtg gct ctt tta gcc gac ttt agc cac gtc   1778
Asn Thr Lys Thr Asn Leu Val Ala Leu Leu Ala Asp Phe Ser His Val
            415                 420                 425 aac agg atc gaa atg ttt tcc gag gag gag agc ttg gtg cgg gta gaa   1826
Asn Arg Ile Glu Met Phe Ser Glu Glu Glu Ser Leu Val Arg Val Glu
        430                 435                 440 ctc cac gtg cta gat gtg aag cct atc acg ctt ctg atg gaa tcc tca   1874
Leu His Val Leu Asp Val Lys Pro Ile Thr Leu Leu Met Glu Ser Ser
    445                 450                 455 gat gcc atg aac ctg gcc tgc ttg acg gct gga tac tac cgg ctg ctt   1922
Asp Ala Met Asn Leu Ala Cys Leu Thr Ala Gly Tyr Tyr Arg Leu Leu
460                 465                 470                 475 gtt gat tcc agg agg tcg ata ttt aac atg gcc aac aag aaa aac aca   1970
Val Asp Ser Arg Arg Ser Ile Phe Asn Met Ala Asn Lys Lys Asn Thr
                480                 485                 490 gcg acc cag gaa aca gga cct gaa aac aag ggg aag cat aac ctc ctt   2018
Ala Thr Gln Glu Thr Gly Pro Glu Asn Lys Gly Lys His Asn Leu Leu
            495                 500                 505 ggc cca gat tgg aac tgt ata ccc caa atg acc acc ttt att ggc gaa   2066
Gly Pro Asp Trp Asn Cys Ile Pro Gln Met Thr Thr Phe Ile Gly Glu
        510                 515                 520 ggg gaa caa gaa gcc cag ata aca tac ata gat tca aag cag aag acg   2114
Gly Glu Gln Glu Ala Gln Ile Thr Tyr Ile Asp Ser Lys Gln Lys Thr
    525                 530                 535 gtg gag atc aca gac agc acc atg tgt cca aaa gag cac cgg cac ttg   2162
Val Glu Ile Thr Asp Ser Thr Met Cys Pro Lys Glu His Arg His Leu
540                 545                 550                 555 tac ata gac aat gcc tat agt tca gat gga ctt aac cag cag ctg agc   2210
Tyr Ile Asp Asn Ala Tyr Ser Ser Asp Gly Leu Asn Gln Gln Leu Ser
                560                 565                 570 cag ccc ggg gag gcc ccc tgt gag gca gac tac aga agt cta gct cag   2258
Gln Pro Gly Glu Ala Pro Cys Glu Ala Asp Tyr Arg Ser Leu Ala Gln
            575                 580                 585 cgg tcc cta ttg acc ctc tca gga cca gaa act ctg aag aaa gca cag   2306
Arg Ser Leu Leu Thr Leu Ser Gly Pro Glu Thr Leu Lys Lys Ala Gln
        590                 595                 600 gaa tct ccg aga gga gct aaa gtg tcc ttt att ttt gga gac ttc gcc   2354
Glu Ser Pro Arg Gly Ala Lys Val Ser Phe Ile Phe Gly Asp Phe Ala
    605                 610                 615 ttg gat gat ggt att agt ccc cca acc ctt ggc tat gaa acg cta cta   2402
Leu Asp Asp Gly Ile Ser Pro Pro Thr Leu Gly Tyr Glu Thr Leu Leu
620                 625                 630                 635 gat gag ggt cct gaa atg ctg gag aag cag aga aat ctc tac att ggc   2450
Asp Glu Gly Pro Glu Met Leu Glu Lys Gln Arg Asn Leu Tyr Ile Gly
                640                 645                 650 agt gcc aat gac atg aag ggc ctg gat ctc act cca gag gca gag ggc   2498
Ser Ala Asn Asp Met Lys Gly Leu Asp Leu Thr Pro Glu Ala Glu Gly
            655                 660                 665 atc cag ttt gtg gaa aat tct gtt tat gca aac ata ggc gat gtg aag   2546
```

-continued

```
Ile Gln Phe Val Glu Asn Ser Val Tyr Ala Asn Ile Gly Asp Val Lys
                670                 675                 680 agc ttc cag gcc gcg gag ggg atc gag gaa ccc ctc ttg cat gac atc       2594
Ser Phe Gln Ala Ala Glu Gly Ile Glu Glu Pro Leu Leu His Asp Ile
685                 690                 695 tgt tat gca gaa aac act gat gac gcg gag gac gag gac gag gtg agc       2642
Cys Tyr Ala Glu Asn Thr Asp Asp Ala Glu Asp Glu Asp Glu Val Ser
700                 705                 710                 715 tgc gag gag gac ctc gtg gtg ggg gag atg aac cag ccg gcc atc ctc       2690
Cys Glu Glu Asp Leu Val Val Gly Glu Met Asn Gln Pro Ala Ile Leu
                720                 725                 730 aac ctg tct ggg tca agc gat gac atc att gac ctc aca tcc ctg ccc       2738
Asn Leu Ser Gly Ser Ser Asp Asp Ile Ile Asp Leu Thr Ser Leu Pro
            735                 740                 745 cct cca gaa ggt gat gac aat gag gat gac ttc ctg ttg cgt tcc ttg       2786
Pro Pro Glu Gly Asp Asp Asn Glu Asp Asp Phe Leu Leu Arg Ser Leu
                750                 755                 760 aac atg gcc att gcc gca ccc cca cct ggc ttt aga gac agt tca gat       2834
Asn Met Ala Ile Ala Ala Pro Pro Pro Gly Phe Arg Asp Ser Ser Asp
765                 770                 775 gaa gag gac tct cag agc cag gca gct tcc ttc ccc gag gac aag gag       2882
Glu Glu Asp Ser Gln Ser Gln Ala Ala Ser Phe Pro Glu Asp Lys Glu
780                 785                 790                 795 aaa ggc agc agc ctg caa aat gat gag atc ccc gtg tcc ctc att gac       2930
Lys Gly Ser Ser Leu Gln Asn Asp Glu Ile Pro Val Ser Leu Ile Asp
                800                 805                 810 gct gtg ccc acc agc gcc gaa ggc aag tgt gag aag gga ctg gat aat       2978
Ala Val Pro Thr Ser Ala Glu Gly Lys Cys Glu Lys Gly Leu Asp Asn
            815                 820                 825 gcc gtc gtc tcc acg ctg gga gct cta gag gct cta tcc gtg tca gaa       3026
Ala Val Val Ser Thr Leu Gly Ala Leu Glu Ala Leu Ser Val Ser Glu
                830                 835                 840 gaa cag cag acc agt gac aat tca ggt gta gcc atc ttg cgg gct tat       3074
Glu Gln Gln Thr Ser Asp Asn Ser Gly Val Ala Ile Leu Arg Ala Tyr
845                 850                 855 agt cct gag tct tcg tca gac tcg ggc aat gaa act aac tct tct gaa       3122
Ser Pro Glu Ser Ser Ser Asp Ser Gly Asn Glu Thr Asn Ser Ser Glu
860                 865                 870                 875 atg act gag agt tct gaa ctg gcc aca gca caa aaa cag tca gaa aac       3170
Met Thr Glu Ser Ser Glu Leu Ala Thr Ala Gln Lys Gln Ser Glu Asn
                880                 885                 890 ctc tcc cgc atg ttc ttg gcc act cac gaa ggc tac cac ccc ctt gca       3218
Leu Ser Arg Met Phe Leu Ala Thr His Glu Gly Tyr His Pro Leu Ala
            895                 900                 905 gaa gag cag acc gag ttc ccg gcc tcc aag acc ccc gct ggg ggc ttg       3266
Glu Glu Gln Thr Glu Phe Pro Ala Ser Lys Thr Pro Ala Gly Gly Leu
                910                 915                 920 cct cca aag tcc tcg cac gcc ctg gct gct agg cca gca acc gac ctc       3314
Pro Pro Lys Ser Ser His Ala Leu Ala Ala Arg Pro Ala Thr Asp Leu
925                 930                 935 ccg ccc aaa gtt gtg cct tcc aag cag tta ctt cac tca gac cac atg       3362
Pro Pro Lys Val Val Pro Ser Lys Gln Leu Leu His Ser Asp His Met
940                 945                 950                 955 gag atg gag cct gaa act atg gag act aag tcg gtc act gac tat ttt       3410
Glu Met Glu Pro Glu Thr Met Glu Thr Lys Ser Val Thr Asp Tyr Phe
                960                 965                 970 agc aaa ctg cac atg ggg tcg gtg gca tac tcc tgc act agc aaa agg       3458
Ser Lys Leu His Met Gly Ser Val Ala Tyr Ser Cys Thr Ser Lys Arg
            975                 980                 985
```

-continued

| | | | | | | | | | | | | | | |
|---|---|---|---|---|---|---|---|---|---|---|---|---|---|---|
| aaa | agc | aag | ctg | gcc | gat | ggt | gag | ggg | aag | gca | ccc cct | aat | ggg | aac | 3506 |
| Lys | Ser | Lys | Leu | Ala | Asp | Gly | Glu | Gly | Lys | Ala | Pro Pro | Asn | Gly | Asn | |
| | | | 990 | | | | 995 | | | | 1000 | | | | |

| aca | aca | gga | aaa | aaa | cag | cag | ggg | acc | aaa | acg | gca | gag | atg | gag | 3551 |
| Thr | Thr | Gly | Lys | Lys | Gln | Gln | Gly | Thr | Lys | Thr | Ala | Glu | Met | Glu | |
| | | 1005 | | | | | 1010 | | | | | 1015 | | | |

| gag | gag | gcc | agt | ggt | aaa | ttt | ggt | act | gtg | tct | tca | cga | gac | agt | 3596 |
| Glu | Glu | Ala | Ser | Gly | Lys | Phe | Gly | Thr | Val | Ser | Ser | Arg | Asp | Ser | |
| 1020 | | | | | 1025 | | | | | 1030 | | | | | |

| caa | cac | ctg | agc | act | ttt | aat | ctg | gag | aga | act | gcc | ttt | cgc | aag | 3641 |
| Gln | His | Leu | Ser | Thr | Phe | Asn | Leu | Glu | Arg | Thr | Ala | Phe | Arg | Lys | |
| | 1035 | | | | | 1040 | | | | | 1045 | | | | |

| gac | agt | caa | aga | tgg | tat | gtg | gcc | act | gaa | ggt | ggg | atg | gct | gaa | 3686 |
| Asp | Ser | Gln | Arg | Trp | Tyr | Val | Ala | Thr | Glu | Gly | Gly | Met | Ala | Glu | |
| 1050 | | | | | 1055 | | | | | 1060 | | | | | |

| aaa | aag | tgg | att | aga | agc | agc | aac | agg | gaa | aac | ctt | tcc | aag | agc | 3731 |
| Lys | Lys | Trp | Ile | Arg | Ser | Ser | Asn | Arg | Glu | Asn | Leu | Ser | Lys | Ser | |
| | 1065 | | | | | 1070 | | | | | 1075 | | | | |

| ttc | tgg | tct | tgg | ggc | aag | gga | ggc | cga | agg | gaa | gga | aga | agg | agc | 3776 |
| Phe | Trp | Ser | Trp | Gly | Lys | Gly | Gly | Arg | Arg | Glu | Gly | Arg | Arg | Ser | |
| 1080 | | | | | 1085 | | | | | 1090 | | | | | |

| tcc tgatggagaa accagtgatg gctcaggact tggtcaaggg gaccgcttct | 3829 |
|---|---|
| Ser | |

| taactgacgt gacctgtgca tcttcagcca aagacttaga taacccagag gacgctgact | 3889 |
|---|---|
| cgtccacctg cgaccatcct tccaagcttc ctgaggctga tgagagtgtg gcccgccttt | 3949 |
| gtgactacca cttggccaag cggatgtcat cactgcaaag cgagggccat ttttctctgc | 4009 |
| agagctccca aggctcttca gtggatgcag gctgtggcac aggcagcagt ggcagtgcct | 4069 |
| gtgccacacc cgtggagtcg ccgctctgcc cctccctggg gaagcacttg attcctgacg | 4129 |
| cttctgggaa aggcgtgaat tacattcctt cagaggagag agcccctggg cttcccaacc | 4189 |
| acggagccac ctttaaggaa ctgcacccac agacagaagg gatgtgtcca cggatgacag | 4249 |
| tgcctgctct gcacacagcc attaacaccg aaccectgtt tggcacattg agagatggat | 4309 |
| gccatcggct ccccaagatt aaggaaacca cagtgtagct ttgacagagc ctgggaagga | 4369 |
| gagacgagga ggcatgcctt cagcttggtc tcaacatcct gaagctgatc ccatcctgct | 4429 |
| accatcaaac attcactcgg aatcaaaggt gccaattcca aatcaagacc ctaatgattt | 4489 |
| ctcccaagca aatcaggcat acggagaggc tgtgagctgg cggccaccgg atctgagagg | 4549 |
| ggggagcctc aggacacctc ccagccagaa ggctctgaga catagcagca gtatcctctc | 4609 |
| cggatctgtc gatttggaga ccttccgaga gagaaccaag ggtgcagtca gcttaaagtg | 4669 |
| tccaggcatc acagaagcac aggaggccag ttctgaaagg cgagcagaac tccccctggg | 4729 |
| gaggaagctc accaaaagtt tttcccaaag ctcaatgcac ttgagctctg aggggaggtt | 4789 |
| tcacaaaagg tccccagtgg ctcataaaga ctcaaagctg tataggacat tacccttgcg | 4849 |
| gaagctggag ggcagcaatt ggagatgccg ggacccttc agctattgct tcctgaaccg | 4909 |
| agggcaggat gaagatggtg aggaagaaga ggagagggga gaggccaccg tccaggtctc | 4969 |
| ttgcctctat agaccacagg tgactcaagc catgccagaa ccaagcagcc catgcctggc | 5029 |
| tgtggcgatt cagaagcaac gaggggagct atccagaggg tcagtgctga aggtctgggc | 5089 |
| agaagacctg cgagacccag atgacttgga cttcagcaac ctggcttttg atgcccggat | 5149 |
| tgcaagaata aatgccctaa aggagagcac atatgcaatg cctgatgggt tccttgcagc | 5209 |
| ccaaaatgat gccaatgagc tgctctgtct cgtcagggca accaaggaga agaggaggga | 5269 |

-continued

```
gtcacgccct gaagcgtacg accttacact ttctcagtac aagcaactgt tatccattga    5329
gtccagacag ttgggaagtg cctgtaggaa aatggcgatg gctgagaaaa gcccggagga    5389
gatgctccta gctatgactt ccagctttca agtgctctgt tgcctaacag aagcttgcat    5449
gcgattagtt aaagtcgtga actcagaaac acagcggcag gaaattgtag ggaagatcga    5509
tgaagtggtc ataaattaca tttgtctact gaaagctgcc gaagcagcca ctggaaagaa    5569
ccctggggac cctaatgttg gactctcggc gcgacactca accaccatgg ccgctctcgt    5629
aagcacactg acacgttctc tcaagaggct tttaaacaaa taaatatgga agtcacgtca    5689
taatctacct ttgcaaagcc atacatgaac ttttatttac tttgtgtgta tgatgaacag    5749
atgtctcctt tcttctctct gtatattttg ttattttata taaaatagga gataaaagtc    5809
acactgatga aatgttgaaa tgtactaatc agatgtattc tgtttatatt atacatatat    5869
atacacgtaa aagaaatatc caagaaagtg atgacatttg gctattttc atatagttaa     5929 aactccaggt atatgatgtg aaattttaaa ttctaccatg ttagagcaaa acaatgaatc    5989 ctatccctt tctttccaag tagctacttg gaaaccatat cattcatatt tagaagtaaa     6049
acacaaaaca aaaagagag agaaaagaaa agaaatcaca atgtatataa aacagtactt     6109
atgttttaaa attatgattt ttaagcattg gaaatagcaa aaagacattt aaaattcaag    6169
aagctattat gaattactag agaatatatc tgtaataaat taattttttg ctcatagtat    6229
ttggttactg gatgctttct tccaagaatc ccacatattt aatttgggtt tttgctactg    6289
gggctacaaa ttggtgggga tggattctac tgtgtcagca caaatgctct tcacagtggt    6349
tctagcattt aaaaaacttc ccggggagaa gaacagaggg gatgatgggc agtttcctag    6409
gtaacaccta gagttataga atatctcatt acataaaatg tatggaatta ataataccaa    6469
aattaattat ttgatggaaa gatctgcttt gactaaatgt caaaaatctg caaaccaaag    6529
acattatctt cccctcatcc caactcaact acgaaactta aaattcccttt tagagtgata   6589 ggacatttag taaagtattt gcaaacttaa aaaaaggaac atttaatgat catcaaaatt    6649
aagtacagat tcagtaatgt agaccagacc acacaccagc acctgtgagt ctcatctcag    6709
atcacagctc tcagcatagg gcttcatgca tcaccgcctc tacagaggct aaggctgcca    6769
gtcaaatttg gaattatagc gtagtactgg gacaaaatct caaatcttgg atgttccaga    6829
aaatcaggga gtgatggcta ctgtaatcat gggagccatg agtaaatagt taagtattta    6889
ttaaataaat acttaatctg gattggctga taaaaatatg aaatct               6935
```

<210> SEQ ID NO 22
<211> LENGTH: 1094
<212> TYPE: PRT
<213> ORGANISM: Homo sapiens

<400> SEQUENCE: 22

```
Met Thr Ala Asn Arg Asp Gly Arg Asp Tyr Phe Ile Asn His Met Thr
1               5                   10                  15

Gln Ala Ile Pro Phe Asp Asp Pro Arg Leu Glu Ser Cys Gln Ile Ile
            20                  25                  30

Pro Pro Ala Pro Arg Lys Val Glu Met Arg Arg Asp Pro Val Leu Gly
        35                  40                  45

Phe Gly Phe Val Ala Gly Ser Glu Lys Pro Val Val Arg Ser Val
    50                  55                  60

Thr Pro Gly Gly Pro Ser Glu Gly Lys Leu Ile Pro Gly Asp Gln Ile
65                  70                  75                  80
```

```
Val Met Ile Asn Asp Glu Pro Val Ser Ala Pro Arg Glu Arg Val
                85                  90                  95

Ile Asp Leu Val Arg Ser Cys Lys Glu Ser Ile Leu Leu Thr Val Ile
            100                 105                 110

Gln Pro Tyr Pro Ser Pro Lys Ser Ala Phe Ile Ser Ala Ala Lys Lys
            115                 120                 125

Ala Arg Leu Lys Ser Asn Pro Val Lys Val Arg Phe Ser Glu Glu Val
130                 135                 140

Ile Ile Asn Gly Gln Val Ser Glu Thr Val Lys Asp Asn Ser Leu Leu
145                 150                 155                 160

Phe Met Pro Asn Val Leu Lys Val Tyr Leu Glu Asn Gly Gln Thr Lys
                165                 170                 175

Ser Phe Arg Phe Asp Cys Ser Thr Ser Ile Lys Asp Val Ile Leu Thr
            180                 185                 190

Leu Gln Glu Lys Leu Ser Ile Lys Gly Ile Glu His Phe Ser Leu Met
        195                 200                 205

Leu Glu Gln Arg Thr Glu Gly Ala Gly Thr Lys Leu Leu Leu Leu His
        210                 215                 220

Glu Gln Glu Thr Leu Thr Gln Val Thr Gln Arg Pro Ser Ser His Lys
225                 230                 235                 240

Met Arg Cys Leu Phe Arg Ile Ser Phe Val Pro Lys Asp Pro Ile Asp
                245                 250                 255

Leu Leu Arg Arg Asp Pro Val Ala Phe Glu Tyr Leu Tyr Val Gln Ser
            260                 265                 270

Cys Asn Asp Val Val Gln Glu Arg Phe Gly Pro Glu Leu Lys Tyr Asp
            275                 280                 285

Ile Ala Leu Arg Leu Ala Ala Leu Gln Met Tyr Ile Ala Thr Val Thr
        290                 295                 300

Thr Lys Gln Thr Gln Lys Ile Ser Leu Lys Tyr Ile Glu Lys Glu Trp
305                 310                 315                 320

Gly Leu Glu Thr Phe Leu Pro Ser Ala Val Leu Gln Ser Met Lys Glu
                325                 330                 335

Lys Asn Ile Lys Lys Ala Leu Ser His Leu Val Lys Ala Asn Gln Asn
            340                 345                 350

Leu Val Pro Pro Gly Lys Lys Leu Ser Ala Leu Gln Ala Lys Val His
        355                 360                 365

Tyr Leu Lys Phe Leu Ser Asp Leu Arg Leu Tyr Gly Gly Arg Val Phe
370                 375                 380

Lys Ala Thr Leu Val Gln Ala Glu Lys Arg Ser Glu Val Thr Leu Leu
385                 390                 395                 400

Val Gly Pro Arg Tyr Gly Ile Ser His Val Ile Asn Thr Lys Thr Asn
                405                 410                 415

Leu Val Ala Leu Leu Ala Asp Phe Ser His Val Asn Arg Ile Glu Met
            420                 425                 430

Phe Ser Glu Glu Glu Ser Leu Val Arg Val Glu Leu His Val Leu Asp
        435                 440                 445

Val Lys Pro Ile Thr Leu Leu Met Glu Ser Ser Asp Ala Met Asn Leu
        450                 455                 460

Ala Cys Leu Thr Ala Gly Tyr Tyr Arg Leu Leu Val Asp Ser Arg Arg
465                 470                 475                 480

Ser Ile Phe Asn Met Ala Asn Lys Lys Asn Thr Ala Thr Gln Glu Thr
                485                 490                 495

Gly Pro Glu Asn Lys Gly Lys His Asn Leu Leu Gly Pro Asp Trp Asn
```

```
                    500                     505                     510
     Cys Ile Pro Gln Met Thr Thr Phe Ile Gly Glu Gly Glu Gln Glu Ala
                515                     520                     525

Gln Ile Thr Tyr Ile Asp Ser Lys Gln Lys Thr Val Glu Ile Thr Asp
                530                     535                     540

Ser Thr Met Cys Pro Lys Glu His Arg His Leu Tyr Ile Asp Asn Ala
     545                     550                     555                     560

Tyr Ser Ser Asp Gly Leu Asn Gln Gln Leu Ser Gln Pro Gly Glu Ala
                    565                     570                     575

Pro Cys Glu Ala Asp Tyr Arg Ser Leu Ala Gln Arg Ser Leu Leu Thr
                580                     585                     590

Leu Ser Gly Pro Glu Thr Leu Lys Lys Ala Gln Glu Ser Pro Arg Gly
                595                     600                     605

Ala Lys Val Ser Phe Ile Phe Gly Asp Phe Ala Leu Asp Asp Gly Ile
                610                     615                     620

Ser Pro Pro Thr Leu Gly Tyr Glu Thr Leu Leu Asp Glu Gly Pro Glu
     625                     630                     635                     640

Met Leu Glu Lys Gln Arg Asn Leu Tyr Ile Gly Ser Ala Asn Asp Met
                645                     650                     655

Lys Gly Leu Asp Leu Thr Pro Glu Ala Glu Gly Ile Gln Phe Val Glu
                660                     665                     670

Asn Ser Val Tyr Ala Asn Ile Gly Asp Val Lys Ser Phe Gln Ala Ala
                675                     680                     685

Glu Gly Ile Glu Glu Pro Leu Leu His Asp Ile Cys Tyr Ala Glu Asn
                690                     695                     700

Thr Asp Asp Ala Glu Asp Glu Asp Glu Val Ser Cys Glu Glu Asp Leu
     705                     710                     715                     720

Val Val Gly Glu Met Asn Gln Pro Ala Ile Leu Asn Leu Ser Gly Ser
                    725                     730                     735

Ser Asp Asp Ile Ile Asp Leu Thr Ser Leu Pro Pro Pro Glu Gly Asp
                    740                     745                     750

Asp Asn Glu Asp Asp Phe Leu Leu Arg Ser Leu Asn Met Ala Ile Ala
                755                     760                     765

Ala Pro Pro Gly Phe Arg Asp Ser Ser Asp Glu Glu Asp Ser Gln
                770                     775                     780

Ser Gln Ala Ala Ser Phe Pro Glu Asp Lys Glu Lys Gly Ser Ser Leu
     785                     790                     795                     800

Gln Asn Asp Glu Ile Pro Val Ser Leu Ile Asp Ala Val Pro Thr Ser
                    805                     810                     815

Ala Glu Gly Lys Cys Glu Lys Gly Leu Asp Asn Ala Val Val Ser Thr
                820                     825                     830

Leu Gly Ala Leu Glu Ala Leu Ser Val Ser Glu Glu Gln Gln Thr Ser
                835                     840                     845

Asp Asn Ser Gly Val Ala Ile Leu Arg Ala Tyr Ser Pro Glu Ser Ser
     850                     855                     860

Ser Asp Ser Gly Asn Glu Thr Asn Ser Ser Glu Met Thr Glu Ser Ser
     865                     870                     875                     880

Glu Leu Ala Thr Ala Gln Lys Gln Ser Glu Asn Leu Ser Arg Met Phe
                    885                     890                     895

Leu Ala Thr His Glu Gly Tyr His Pro Leu Ala Glu Glu Gln Thr Glu
                    900                     905                     910

Phe Pro Ala Ser Lys Thr Pro Ala Gly Gly Leu Pro Pro Lys Ser Ser
                915                     920                     925
```

His Ala Leu Ala Ala Arg Pro Ala Thr Asp Leu Pro Pro Lys Val Val
    930                 935                 940

Pro Ser Lys Gln Leu Leu His Ser Asp His Met Glu Met Glu Pro Glu
945                 950                 955                 960

Thr Met Glu Thr Lys Ser Val Thr Asp Tyr Phe Ser Lys Leu His Met
                965                 970                 975

Gly Ser Val Ala Tyr Ser Cys Thr Ser Lys Arg Lys Ser Lys Leu Ala
            980                 985                 990

Asp Gly Glu Gly Lys Ala Pro Pro  Asn Gly Asn Thr Thr  Gly Lys Lys
        995                 1000                1005

Gln Gln  Gly Thr Lys Thr Ala  Glu Met Glu Gln Glu  Ala Ser Gly
    1010                1015                1020

Lys Phe  Gly Thr Val Ser Ser  Arg Asp Ser Gln His  Leu Ser Thr
    1025                1030                1035

Phe Asn  Leu Glu Arg Thr Ala  Phe Arg Lys Asp Ser  Gln Arg Trp
    1040                1045                1050

Tyr Val  Ala Thr Glu Gly Gly  Met Ala Glu Lys Lys  Trp Ile Arg
    1055                1060                1065

Ser Ser  Asn Arg Glu Asn Leu  Ser Lys Ser Phe Trp  Ser Trp Gly
    1070                1075                1080

Lys Gly  Gly Arg Arg Glu Gly  Arg Arg Ser Ser
    1085                1090

<210> SEQ ID NO 23
<211> LENGTH: 2139
<212> TYPE: DNA
<213> ORGANISM: Mus musculus
<220> FEATURE:
<221> NAME/KEY: CDS
<222> LOCATION: (806)..(1363)
<221> NAME/KEY: misc_feature
<222> LOCATION: (1)..(2139)
<223> OTHER INFORMATION: n is either a, c, g, or t

<400> SEQUENCE: 23
agcggggctc cattgtgctc ggcgggggcc gggaagccaa aggaggtggg ctcgggcccc      60
tgcgctgctc cccggcggct gcgccccag  ctagctgcca gcctggaaat ggctccgctg     120
ctgctcctcg ggaaaacgaa tcgatccttc ccagccttct ctgcctgctc tccacctcct    180
ctctgctccg agtcttagga ggacgaacat tcaaggaca  gattccaatg tggtgtgccg    240
tgcacatcgg gagcggctgg ggtttgcact tcgagatttc ttctatataa ttttttttt    300 ttaaacgtaa gggaggcagt agcattgctg cctgtaggat ttttttattca agtgcacgtc    360 gcgttgggtt gcacgntcca cccccaggga cctggtgtgg tgaaatttga acccaccgcc    420
ttagcccaaa aaggccgagt aacctggctg cctgagtgtc gtggaagacg tgagcgaaat    480
gaccagcgaa ctcattttt  atcagacttg ctgaagctgg cttttgcgtt ttttctacac    540
gtacgcttaa ttttgtggaa tagttaagtg ctatattctc cgcgcaacct tttcaaattc    600 caaatgttt  aacattttgg tgtcagcgcg agtgaaatca ttttaccgac aagaactaac    660
tgaattgtct gccttgttga gttgcctccg gaaaagatct cggggtgga  aaagcaactg    720 caaaataaca gacggagaaa attccttgga agttatttct gtagcataag agcagaaact    780
tcagagcaag ttttcattgg gcaaa atg ggg gag caa cct atc ttc agc act     832
                         Met Gly Glu Gln Pro Ile Phe Ser Thr
                          1               5 cga gct cat gtc ttc cag att gac ccg aac aca aag aag aac tgg gta     880

```
Arg Ala His Val Phe Gln Ile Asp Pro Asn Thr Lys Lys Asn Trp Val
10                  15                  20                  25 ccc acc agc aag cat gca gtt act gta tct tat ttt tat gac agc aca      928
Pro Thr Ser Lys His Ala Val Thr Val Ser Tyr Phe Tyr Asp Ser Thr
                30                  35                  40 aga aat gtg tat agg ata atc agt tta gat ggc tca aag gca ata ata      976
Arg Asn Val Tyr Arg Ile Ile Ser Leu Asp Gly Ser Lys Ala Ile Ile
            45                  50                  55 aat agc acc atc aca cca aac atg aca ttt act aaa aca tct caa aag     1024
Asn Ser Thr Ile Thr Pro Asn Met Thr Phe Thr Lys Thr Ser Gln Lys
        60                  65                  70 ttt ggc caa tgg gct gat agc cgg gca aac act gtt tat gga ctg gga     1072
Phe Gly Gln Trp Ala Asp Ser Arg Ala Asn Thr Val Tyr Gly Leu Gly
    75                  80                  85 ttc tcc tct gag cat cat ctt tca aaa ttc gca gaa aag ttt cag gaa     1120
Phe Ser Ser Glu His His Leu Ser Lys Phe Ala Glu Lys Phe Gln Glu
90                  95                  100                 105 ttt aag gaa gct gct cgg ctt gca aag gag aag tcg cag gag aag atg     1168
Phe Lys Glu Ala Ala Arg Leu Ala Lys Glu Lys Ser Gln Glu Lys Met
                110                 115                 120 gag ctg acc agt acc cct tca cag gaa tca gca gga gga gat ctt cag     1216
Glu Leu Thr Ser Thr Pro Ser Gln Glu Ser Ala Gly Gly Asp Leu Gln
            125                 130                 135 tct cct ttg aca cca gaa agt atc aat ggg aca gac gat gag aga aca     1264
Ser Pro Leu Thr Pro Glu Ser Ile Asn Gly Thr Asp Asp Glu Arg Thr
        140                 145                 150 ccc gat gtg aca cag aac tca gag cca agg gct gag cca act cag aat     1312
Pro Asp Val Thr Gln Asn Ser Glu Pro Arg Ala Glu Pro Thr Gln Asn
    155                 160                 165 gca ttg cca ttt cca cat agg tac aca ttc aat tca gca atc atg att     1360
Ala Leu Pro Phe Pro His Arg Tyr Thr Phe Asn Ser Ala Ile Met Ile
170                 175                 180                 185 aag taaggtggat aaatatggaa gttcatttgg tttcagaaac tcttgaagtt         1413
Lys acaacctttg agtgaaaaat ctcaggtcag actcctttaa tttattgttc ttggttgctc  1473
aagttgactg aattactata tttccattat ctatgtggaa aaaggagcat tgagctaatt  1533
ataggagaaa ttttttaaat ggagaaaata taattccttt ctatctatat tttaaagatc  1593 cctttgtta acccgttttc tgtntttata tatgttatgt aagatttata atgtgtaatt    1653
agaaacatag aatttctact ctgaaggaaa gctttaccac aggcctacag agttttcaca  1713
gaagacaggg taccaagcac gagcctgtta gcattgatgg cagatgccag cagaaggaag  1773
gcttgacttc ctaattctgt attctaaaag atacatcatg ttctaaatgc atttcaaaca  1833
ttagttattg gccgtaccgt ggcattactg gactgtaaac atgaatgtga aatggcacta  1893
ttgaaaatat ttttttaaag cccatctacc ttaacactaa tttttaccct tatttaaatg  1953 cttttttacta aatagtttta ggtaaaatta agaaaatagg ggttttttga ctgcacattt  2013
ttttgaagaa ccaagtttta gaaaattata ttctttgaca gattaaaaat tgcaaagtga  2073
gatatttcaa actctcctag gtgagttttt attgtgtttg aacttgcatt aatagggca   2133 taggat                                                             2139

<210> SEQ ID NO 24
<211> LENGTH: 186
<212> TYPE: PRT
<213> ORGANISM: Mus musculus
<220> FEATURE:
<221> NAME/KEY: misc_feature
```

```
<222> LOCATION: (1)..(2139)
<223> OTHER INFORMATION: n is either a, c, g, or t

<400> SEQUENCE: 24

Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Thr Gln Asn Ala Leu Pro Phe Pro His Arg
                165                 170                 175

Tyr Thr Phe Asn Ser Ala Ile Met Ile Lys
            180                 185

<210> SEQ ID NO 25
<211> LENGTH: 1418
<212> TYPE: DNA
<213> ORGANISM: Mus musculus
<220> FEATURE:
<221> NAME/KEY: CDS
<222> LOCATION: (153)..(1214)

<400> SEQUENCE: 25
gaattcggca cgagtctgcc ttgttgagtt gcctccggaa aagatctcgg gggtggaaaa      60
gcaactgcaa aataacagac ggagaaaatt ccttggaagt tatttctgta gcataagagc     120
agaaacttca gagcaagttt tcattgggca aa atg ggg gag caa cct atc ttc       173
                                   Met Gly Glu Gln Pro Ile Phe
                                   1               5 agc act cga gct cat gtc ttc cag att gac ccg aac aca aag aag aac       221
Ser Thr Arg Ala His Val Phe Gln Ile Asp Pro Asn Thr Lys Lys Asn
        10                  15                  20 tgg gta ccc acc agc aag cat gca gtt act gta tct tat ttt tat gac       269
Trp Val Pro Thr Ser Lys His Ala Val Thr Val Ser Tyr Phe Tyr Asp
    25                  30                  35 agc aca aga aat gtg tat agg ata atc agt tta gat ggc tca aag gca       317
Ser Thr Arg Asn Val Tyr Arg Ile Ile Ser Leu Asp Gly Ser Lys Ala
40                  45                  50                  55 ata ata aat agc acc atc aca cca aac atg aca ttt act aaa aca tct       365
Ile Ile Asn Ser Thr Ile Thr Pro Asn Met Thr Phe Thr Lys Thr Ser
                60                  65                  70 caa aag ttt ggc caa tgg gct gat agc cgg gca aac act gtt tat gga       413
Gln Lys Phe Gly Gln Trp Ala Asp Ser Arg Ala Asn Thr Val Tyr Gly
            75                  80                  85
```

```
ctg gga ttc tcc tct gag cat cat ctt tca aaa ttc gca gaa aag ttt      461
Leu Gly Phe Ser Ser Glu His His Leu Ser Lys Phe Ala Glu Lys Phe
         90                  95                 100 cag gaa ttt aag gaa gct gct cgg ctt gca aag gag aag tcg cag gag      509
Gln Glu Phe Lys Glu Ala Ala Arg Leu Ala Lys Glu Lys Ser Gln Glu
    105                 110                 115 aag atg gag ctg acc agt acc cct tca cag gaa tca gca gga gga gat      557
Lys Met Glu Leu Thr Ser Thr Pro Ser Gln Glu Ser Ala Gly Gly Asp
120                 125                 130                 135 ctt cag tct cct ttg aca cca gaa agt atc aat ggg aca gac gat gag      605
Leu Gln Ser Pro Leu Thr Pro Glu Ser Ile Asn Gly Thr Asp Asp Glu
                140                 145                 150 aga aca ccc gat gtg aca cag aac tca gag cca agg gct gag cca act      653
Arg Thr Pro Asp Val Thr Gln Asn Ser Glu Pro Arg Ala Glu Pro Thr
            155                 160                 165 cag aat gca ttg cca ttt cca cat agt tca gca atc agc aaa cac tgg      701
Gln Asn Ala Leu Pro Phe Pro His Ser Ser Ala Ile Ser Lys His Trp
        170                 175                 180 gag gct gag cta gct acc ctc aaa ggc aac aat gcc aaa ctc act gca      749
Glu Ala Glu Leu Ala Thr Leu Lys Gly Asn Asn Ala Lys Leu Thr Ala
    185                 190                 195 gcc ctg ctg gag tcc act gcc aat gtg aag cag tgg aag caa cag ctt      797
Ala Leu Leu Glu Ser Thr Ala Asn Val Lys Gln Trp Lys Gln Gln Leu
200                 205                 210                 215 gct gcg tac cag gag gaa gca gag cgg ctg cac aag cgg gtc act gag      845
Ala Ala Tyr Gln Glu Glu Ala Glu Arg Leu His Lys Arg Val Thr Glu
                220                 225                 230 ctg gag tgt gtt agt agt caa gca aac gct gtg cac agc cac aag aca      893
Leu Glu Cys Val Ser Ser Gln Ala Asn Ala Val His Ser His Lys Thr
            235                 240                 245 gag ctg aac cag aca gtg cag gaa ctg gaa gag acc ctg aaa gta aag      941
Glu Leu Asn Gln Thr Val Gln Glu Leu Glu Glu Thr Leu Lys Val Lys
        250                 255                 260 gaa gag gaa ata gaa aga tta aaa caa gaa atc gat aat gcc aga gaa      989
Glu Glu Glu Ile Glu Arg Leu Lys Gln Glu Ile Asp Asn Ala Arg Glu
    265                 270                 275 ctc caa gaa cag agg gac tct ttg act cag aaa cta cag gaa gtt gaa     1037
Leu Gln Glu Gln Arg Asp Ser Leu Thr Gln Lys Leu Gln Glu Val Glu
280                 285                 290                 295 att cga aat aaa gac ctg gag ggg cag ctg tct gac cta gaa cag cgc     1085
Ile Arg Asn Lys Asp Leu Glu Gly Gln Leu Ser Asp Leu Glu Gln Arg
                300                 305                 310 ctg gag aag agc cag aac gaa caa gag gct ttc cgc agt aac ctg aag     1133
Leu Glu Lys Ser Gln Asn Glu Gln Glu Ala Phe Arg Ser Asn Leu Lys
            315                 320                 325 aca ctc cta gaa att ctg gat gga aaa ata ttt gaa cta aca gaa tta     1181
Thr Leu Leu Glu Ile Leu Asp Gly Lys Ile Phe Glu Leu Thr Glu Leu
        330                 335                 340 cga gat aat ttg gcc aag cta ctg gaa tgc agc taaagagagt gaaatttcag   1234
Arg Asp Asn Leu Ala Lys Leu Leu Glu Cys Ser
    345                 350 tgccaataga tggagagatg ctgtctgtct tcctaggact gtttgggctc cgtaccaaga   1294
ttgcacaaaa ttttttgaat atcattcctc caggaggagg gtgttttgaa aattggaatt   1354
gtatatttca gtataaattt ttgaatttag cttatagcta attgggaaaa aaaaaaaaaa   1414
aaaa                                                                1418

<210> SEQ ID NO 26
```

```
<211> LENGTH: 354
<212> TYPE: PRT
<213> ORGANISM: Mus musculus

<400> SEQUENCE: 26

Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Thr Gln Asn Ala Leu Pro Phe Pro His Ser
                165                 170                 175

Ser Ala Ile Ser Lys His Trp Glu Ala Glu Leu Ala Thr Leu Lys Gly
            180                 185                 190

Asn Asn Ala Lys Leu Thr Ala Ala Leu Leu Glu Ser Thr Ala Asn Val
        195                 200                 205

Lys Gln Trp Lys Gln Gln Leu Ala Ala Tyr Gln Glu Glu Ala Glu Arg
    210                 215                 220

Leu His Lys Arg Val Thr Glu Leu Glu Cys Val Ser Ser Gln Ala Asn
225                 230                 235                 240

Ala Val His Ser His Lys Thr Glu Leu Asn Gln Thr Val Gln Glu Leu
                245                 250                 255

Glu Glu Thr Leu Lys Val Lys Glu Glu Ile Glu Arg Leu Lys Gln
            260                 265                 270

Glu Ile Asp Asn Ala Arg Glu Leu Gln Glu Gln Arg Asp Ser Leu Thr
    275                 280                 285

Gln Lys Leu Gln Glu Val Glu Ile Arg Asn Lys Asp Leu Glu Gly Gln
290                 295                 300

Leu Ser Asp Leu Glu Gln Arg Leu Glu Lys Ser Gln Asn Glu Gln Glu
305                 310                 315                 320

Ala Phe Arg Ser Asn Leu Lys Thr Leu Leu Glu Ile Leu Asp Gly Lys
                325                 330                 335

Ile Phe Glu Leu Thr Glu Leu Arg Asp Asn Leu Ala Lys Leu Leu Glu
            340                 345                 350

Cys Ser

<210> SEQ ID NO 27
<211> LENGTH: 1640
<212> TYPE: DNA
<213> ORGANISM: Mus musculus
```

```
<220> FEATURE:
<221> NAME/KEY: CDS
<222> LOCATION: (68)..(1105)

<400> SEQUENCE: 27
ggcttggcca cgcgtcgact agtacggggg gggggcgtc ggagcggccg cacgagcagc      60 gccggag atg gga gaa cag ccc atc ttc acc acg cga gcg cac gtc ttc     109
        Met Gly Glu Gln Pro Ile Phe Thr Thr Arg Ala His Val Phe
        1               5                   10 cag att gac ccc agc acc aag aag aac tgg gtg ccg gca agc aag cag     157
Gln Ile Asp Pro Ser Thr Lys Lys Asn Trp Val Pro Ala Ser Lys Gln
15              20                  25                  30 gcc gtc acg gtt tcc tac ttc tat gat gtc acc agg aac agc tat cgg     205
Ala Val Thr Val Ser Tyr Phe Tyr Asp Val Thr Arg Asn Ser Tyr Arg
                35                  40                  45 atc atc agt gtg gat gga gcc aag gtg atc ata aac agc act atc acc     253
Ile Ile Ser Val Asp Gly Ala Lys Val Ile Ile Asn Ser Thr Ile Thr
            50                  55                  60 ccg aac atg act ttc acc aaa acg tca cag aag ttc ggg cag tgg gct     301
Pro Asn Met Thr Phe Thr Lys Thr Ser Gln Lys Phe Gly Gln Trp Ala
        65                  70                  75 gac agc aga gcc aac acc gtg ttc ggt ttg gga ttc tcc tcc gag ctg     349
Asp Ser Arg Ala Asn Thr Val Phe Gly Leu Gly Phe Ser Ser Glu Leu
    80                  85                  90 cag ctc acg aag ttt gca gag aag ttc cag gag gta aga gaa gct gcc     397
Gln Leu Thr Lys Phe Ala Glu Lys Phe Gln Glu Val Arg Glu Ala Ala
95              100                 105                 110 agg cta gcc aga gac aag tcc cag gag aaa acc gag acc tcc agc aat     445
Arg Leu Ala Arg Asp Lys Ser Gln Glu Lys Thr Glu Thr Ser Ser Asn
                115                 120                 125 cat tcc caa gca tcc agc gtc aat ggc aca gac gac gaa aag gcc tct     493
His Ser Gln Ala Ser Ser Val Asn Gly Thr Asp Asp Glu Lys Ala Ser
            130                 135                 140 cac gcg agc cca gcc gac act cac ctc aag tct gag aat gac aag ctg     541
His Ala Ser Pro Ala Asp Thr His Leu Lys Ser Glu Asn Asp Lys Leu
        145                 150                 155 aag atc gcg ctg aca cag agt gct gcc aat gtg aag aag tgg gag atg     589
Lys Ile Ala Leu Thr Gln Ser Ala Ala Asn Val Lys Lys Trp Glu Met
    160                 165                 170 gag ctg cag acc ctg cgg gag agc aac gcc cgg ctg acc acg gca ctg     637
Glu Leu Gln Thr Leu Arg Glu Ser Asn Ala Arg Leu Thr Thr Ala Leu
175                 180                 185                 190 cag gag tcg gcg gcc agc gtg gag cag tgg aag cgg cag ttc tcc atc     685
Gln Glu Ser Ala Ala Ser Val Glu Gln Trp Lys Arg Gln Phe Ser Ile
                195                 200                 205 tgc agg gac gag aat gac agg ctc cgc agc aag atc gag gag ctg gaa     733
Cys Arg Asp Glu Asn Asp Arg Leu Arg Ser Lys Ile Glu Glu Leu Glu
            210                 215                 220 gaa cag tgc agc gag ata aac agg gag aag gag aag aac aca cag ctg     781
Glu Gln Cys Ser Glu Ile Asn Arg Glu Lys Glu Lys Asn Thr Gln Leu
        225                 230                 235 aag agg agg atc gag gag ctg gag tca gag gtc cga gac aag gag atg     829
Lys Arg Arg Ile Glu Glu Leu Glu Ser Glu Val Arg Asp Lys Glu Met
    240                 245                 250 gag ttg aaa gat ctc cga aaa cag agt gaa atc ata cct cag ctc atg     877
Glu Leu Lys Asp Leu Arg Lys Gln Ser Glu Ile Ile Pro Gln Leu Met
255                 260                 265                 270 tcc gag tgt gaa tat gtc tct gag aag tta gag gcg gcc gaa aga gac     925
Ser Glu Cys Glu Tyr Val Ser Glu Lys Leu Glu Ala Ala Glu Arg Asp
                275                 280                 285
```

-continued

```
aat caa aac ttg gaa gac aaa gtg cgg tct cta aag aca gac atc gag      973
Asn Gln Asn Leu Glu Asp Lys Val Arg Ser Leu Lys Thr Asp Ile Glu
            290                 295                 300 gag agt aaa tac cga cag cgc cac ctg aag ggg gag ctg aag agc ttc     1021
Glu Ser Lys Tyr Arg Gln Arg His Leu Lys Gly Glu Leu Lys Ser Phe
        305                 310                 315 ctt gag gtg ctg gat gga aag atc gac gac ctc cat gac ttc cgt aga    1069
Leu Glu Val Leu Asp Gly Lys Ile Asp Asp Leu His Asp Phe Arg Arg
    320                 325                 330 gga ctc tcc aag tta ggc aca gat aac tag ggc ggg gcggagcaag         1115
Gly Leu Ser Lys Leu Gly Thr Asp Asn     Gly Gly
335                 340                     345 tgtgtgtgag aggtgtggta gacgtaggac attctccatt tgcttctgta aatgcaggtg  1175
cgatctgtct gtctccagac caattgtgcc gtccgctcac tcctccagaa taggaaatct  1235
ctcgcttctc tggctttgtg aggtcatgga cagctggaag cttctgactc aggaatccag  1295
aacttggtct accttagccg tttacgcagt cagggcaggg atgtttagat cttcccttaa  1355
gggctgttgt aaccctatga accggggatg ggggagtatt ttctaatcca agtaccatta  1415
tcctttacag caggccctcg ggtgccttct gctgcgtggc attcagtgta tgtgactctc  1475
cagcaggttc tagaccacgg gcatgtggag ggagcatctt ttcccagtat gcattttgtt  1535
gctttagcag atgtgacatg acattgtcaa ccacaaagtt cacactcaaa aactgcacaa  1595
ctgacttact caaaagaaa taattgtaaa aaaaaaaaa aaaaa                    1640
```

<210> SEQ ID NO 28
<211> LENGTH: 343
<212> TYPE: PRT
<213> ORGANISM: Mus musculus

<400> SEQUENCE: 28

```
Met Gly Glu Gln Pro Ile Phe Thr Thr Arg Ala His Val Phe Gln Ile
1               5                   10                  15

Asp Pro Ser Thr Lys Lys Asn Trp Val Pro Ala Ser Lys Gln Ala Val
            20                  25                  30

Thr Val Ser Tyr Phe Tyr Asp Val Thr Arg Asn Ser Tyr Arg Ile Ile
        35                  40                  45

Ser Val Asp Gly Ala Lys Val Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Phe Gly Leu Gly Phe Ser Ser Glu Leu Gln Leu
                85                  90                  95

Thr Lys Phe Ala Glu Lys Phe Gln Glu Val Arg Glu Ala Ala Arg Leu
            100                 105                 110

Ala Arg Asp Lys Ser Gln Glu Lys Thr Glu Thr Ser Ser Asn His Ser
        115                 120                 125

Gln Ala Ser Ser Val Asn Gly Thr Asp Asp Glu Lys Ala Ser His Ala
    130                 135                 140

Ser Pro Ala Asp Thr His Leu Lys Ser Glu Asn Asp Lys Leu Lys Ile
145                 150                 155                 160

Ala Leu Thr Gln Ser Ala Ala Asn Val Lys Lys Trp Glu Met Glu Leu
                165                 170                 175

Gln Thr Leu Arg Glu Ser Asn Ala Arg Leu Thr Thr Ala Leu Gln Glu
            180                 185                 190
```

```
Ser Ala Ala Ser Val Glu Gln Trp Lys Arg Gln Phe Ser Ile Cys Arg
        195                 200                 205

Asp Glu Asn Asp Arg Leu Arg Ser Lys Ile Glu Glu Leu Glu Glu Gln
        210                 215                 220

Cys Ser Glu Ile Asn Arg Glu Lys Glu Lys Asn Thr Gln Leu Lys Arg
225                 230                 235                 240

Arg Ile Glu Glu Leu Glu Ser Glu Val Arg Asp Lys Glu Met Glu Leu
                245                 250                 255

Lys Asp Leu Arg Lys Gln Ser Glu Ile Ile Pro Gln Leu Met Ser Glu
            260                 265                 270

Cys Glu Tyr Val Ser Glu Lys Leu Glu Ala Ala Glu Arg Asp Asn Gln
        275                 280                 285

Asn Leu Glu Asp Lys Val Arg Ser Leu Lys Thr Asp Ile Glu Glu Ser
        290                 295                 300

Lys Tyr Arg Gln Arg His Leu Lys Gly Glu Leu Lys Ser Phe Leu Glu
305                 310                 315                 320

Val Leu Asp Gly Lys Ile Asp Asp Leu His Asp Phe Arg Arg Gly Leu
                325                 330                 335

Ser Lys Leu Gly Thr Asp Asn
            340
```

<210> SEQ ID NO 29
<211> LENGTH: 1673
<212> TYPE: DNA
<213> ORGANISM: Mus musculus
<220> FEATURE:
<221> NAME/KEY: CDS
<222> LOCATION: (68)..(1129)

<400> SEQUENCE: 29

```
ggcttggcca cgcgtcgact agtacggggg ggggggcgtc ggagcggccg cacgagcagc      60 gccggag atg gga gaa cag ccc atc ttc acc acg cga gcg cac gtc ttc     109
        Met Gly Glu Gln Pro Ile Phe Thr Thr Arg Ala His Val Phe
        1               5                   10 cag att gac ccc agc acc aag aag aac tgg gtg ccg gca agc aag cag     157
Gln Ile Asp Pro Ser Thr Lys Lys Asn Trp Val Pro Ala Ser Lys Gln
15                  20                  25                  30 gcc gtc acg gtt tcc tac ttc tat gat gtc acc agg aac agc tat cgg     205
Ala Val Thr Val Ser Tyr Phe Tyr Asp Val Thr Arg Asn Ser Tyr Arg
                35                  40                  45 atc atc agt gtg gat gga gcc aag gtg atc ata aac agc act atc acc     253
Ile Ile Ser Val Asp Gly Ala Lys Val Ile Ile Asn Ser Thr Ile Thr
            50                  55                  60 ccg aac atg act ttc acc aaa acg tca cag aag ttc ggg cag tgg gct     301
Pro Asn Met Thr Phe Thr Lys Thr Ser Gln Lys Phe Gly Gln Trp Ala
        65                  70                  75 gac agc aga gcc aac acc gtg ttc ggt ttg gga ttc tcc tcc gag ctg     349
Asp Ser Arg Ala Asn Thr Val Phe Gly Leu Gly Phe Ser Ser Glu Leu
    80                  85                  90 cag ctc acg aag ttt gca gag aag ttc cag gag gta aga gaa gct gcc     397
Gln Leu Thr Lys Phe Ala Glu Lys Phe Gln Glu Val Arg Glu Ala Ala
95                  100                 105                 110 agg cta gcc aga gac aag tcc cag gag aaa acc gag acc tcc agc aat     445
Arg Leu Ala Arg Asp Lys Ser Gln Glu Lys Thr Glu Thr Ser Ser Asn
                115                 120                 125 cat tcc caa gaa tct ggg tgt gaa acc ccg tct tcc act cag gca tcc     493
His Ser Gln Glu Ser Gly Cys Glu Thr Pro Ser Ser Thr Gln Ala Ser
            130                 135                 140
```

```
agc gtc aat ggc aca gac gac gaa aag gcc tct cac gcg agc cca gcc     541
Ser Val Asn Gly Thr Asp Asp Glu Lys Ala Ser His Ala Ser Pro Ala
            145                 150                 155 gac act cac ctc aag tct gag aat gac aag ctg aag atc gcg ctg aca     589
Asp Thr His Leu Lys Ser Glu Asn Asp Lys Leu Lys Ile Ala Leu Thr
    160                 165                 170 cag agt gct gcc aat gtg aag aag tgg gag atg gag ctg cag acc ctg     637
Gln Ser Ala Ala Asn Val Lys Lys Trp Glu Met Glu Leu Gln Thr Leu
175                 180                 185                 190 cgg gag agc aac gcc cgg ctg acc acg gca ctg cag gag tcg gcg gcc     685
Arg Glu Ser Asn Ala Arg Leu Thr Thr Ala Leu Gln Glu Ser Ala Ala
                195                 200                 205 agc gtg gag cag tgg aag cgg cag ttc tcc atc tgc agg gac gag aat     733
Ser Val Glu Gln Trp Lys Arg Gln Phe Ser Ile Cys Arg Asp Glu Asn
            210                 215                 220 gac agg ctc cgc agc aag atc gag gag ctg gaa gaa cag tgc agc gag     781
Asp Arg Leu Arg Ser Lys Ile Glu Glu Leu Glu Glu Gln Cys Ser Glu
        225                 230                 235 ata aac agg gag aag gag aag aac aca cag ctg aag agg agg atc gag     829
Ile Asn Arg Glu Lys Glu Lys Asn Thr Gln Leu Lys Arg Arg Ile Glu
    240                 245                 250 gag ctg gag tca gag gtc cga gac aag gag atg gag ttg aaa gat ctc     877
Glu Leu Glu Ser Glu Val Arg Asp Lys Glu Met Glu Leu Lys Asp Leu
255                 260                 265                 270 cga aaa cag agt gaa atc ata cct cag ctc atg tcc gag tgt gaa tat     925
Arg Lys Gln Ser Glu Ile Ile Pro Gln Leu Met Ser Glu Cys Glu Tyr
                275                 280                 285 gtc tct gag aag tta gag gcg gcc gaa aga gac aat caa aac ttg gaa     973
Val Ser Glu Lys Leu Glu Ala Ala Glu Arg Asp Asn Gln Asn Leu Glu
            290                 295                 300 gac aaa gtg cgg tct cta aag aca gac atc gag gag agt aaa tac cga    1021
Asp Lys Val Arg Ser Leu Lys Thr Asp Ile Glu Glu Ser Lys Tyr Arg
        305                 310                 315 cag cgc cac ctg aag ggg gag ctg aag agc ttc ctt gag gtg ctg gat    1069
Gln Arg His Leu Lys Gly Glu Leu Lys Ser Phe Leu Glu Val Leu Asp
    320                 325                 330 gga aag atc gac gac ctc cat gac ttc cgt aga gga ctc tcc aag tta    1117
Gly Lys Ile Asp Asp Leu His Asp Phe Arg Arg Gly Leu Ser Lys Leu
335                 340                 345                 350 ggc aca gat aac tagggcgggg cggagcaagt gtgtgtgaga ggtgtggtag        1169
Gly Thr Asp Asn acgtaggaca ttctccattt gcttctgtaa atgcaggtgc gatctgtctg tctccagacc  1229
aattgtgccg tccgctcact cctccagaat aggaaatctc tcgcttctct ggctttgtga  1289
ggtcatggac agctggaagc ttctgactca ggaatccaga acttggtcta ccttagccgt  1349
ttacgcagtc agggcaggga tgtttagatc ttcccttaag gctgttgta accctatgaa   1409 ccggggatgg gggagtattt tctaatccaa gtaccattat cctttacagc aggccctcgg  1469
gtgccttctg ctgcgtggca ttcagtgtat gtgactctcc agcaggttct agaccacggg  1529
catgtggagg gagcatcttt tcccagtatg cattttgttg ctttagcaga tgtgacatga  1589
cattgtcaac cacaaagttc acactcaaaa actgcacaac tgacttactc aaaaagaaat  1649
aattgtaaaa aaaaaaaaaa aaaa                                         1673

<210> SEQ ID NO 30
<211> LENGTH: 354
<212> TYPE: PRT
<213> ORGANISM: Mus musculus
```

```
<400> SEQUENCE: 30

Met Gly Glu Gln Pro Ile Phe Thr Thr Arg Ala His Val Phe Gln Ile
1               5                   10                  15

Asp Pro Ser Thr Lys Lys Asn Trp Val Pro Ala Ser Lys Gln Ala Val
            20                  25                  30

Thr Val Ser Tyr Phe Tyr Asp Val Thr Arg Asn Ser Tyr Arg Ile Ile
        35                  40                  45

Ser Val Asp Gly Ala Lys Val Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Phe Gly Leu Gly Phe Ser Ser Glu Leu Gln Leu
                85                  90                  95

Thr Lys Phe Ala Glu Lys Phe Gln Glu Val Arg Glu Ala Ala Arg Leu
            100                 105                 110

Ala Arg Asp Lys Ser Gln Glu Lys Thr Glu Thr Ser Ser Asn His Ser
        115                 120                 125

Gln Glu Ser Gly Cys Glu Thr Pro Ser Ser Thr Gln Ala Ser Ser Val
    130                 135                 140

Asn Gly Thr Asp Asp Glu Lys Ala Ser His Ala Ser Pro Ala Asp Thr
145                 150                 155                 160

His Leu Lys Ser Glu Asn Asp Lys Leu Lys Ile Ala Leu Thr Gln Ser
                165                 170                 175

Ala Ala Asn Val Lys Lys Trp Glu Met Glu Leu Gln Thr Leu Arg Glu
            180                 185                 190

Ser Asn Ala Arg Leu Thr Thr Ala Leu Gln Glu Ser Ala Ala Ser Val
        195                 200                 205

Glu Gln Trp Lys Arg Gln Phe Ser Ile Cys Arg Asp Glu Asn Asp Arg
    210                 215                 220

Leu Arg Ser Lys Ile Glu Glu Leu Glu Glu Gln Cys Ser Glu Ile Asn
225                 230                 235                 240

Arg Glu Lys Glu Lys Asn Thr Gln Leu Lys Arg Ile Glu Glu Leu
                245                 250                 255

Glu Ser Glu Val Arg Asp Lys Gly Met Glu Leu Lys Asp Leu Arg Lys
            260                 265                 270

Gln Ser Glu Ile Ile Pro Gln Leu Met Ser Glu Cys Glu Tyr Val Ser
    275                 280                 285

Glu Lys Leu Glu Ala Ala Glu Arg Asp Asn Gln Asn Leu Glu Asp Lys
290                 295                 300

Val Arg Ser Leu Lys Thr Asp Ile Glu Glu Ser Lys Tyr Arg Gln Arg
305                 310                 315                 320

His Leu Lys Gly Glu Leu Lys Ser Phe Leu Glu Val Leu Asp Gly Lys
                325                 330                 335

Ile Asp Asp Leu His Asp Phe Arg Arg Gly Leu Ser Lys Leu Gly Thr
            340                 345                 350

Asp Asn

<210> SEQ ID NO 31
<211> LENGTH: 2297
<212> TYPE: DNA
<213> ORGANISM: Mus musculus
<220> FEATURE:
<221> NAME/KEY: CDS
<222> LOCATION: (1)..(1023)
```

-continued

```
<400> SEQUENCE: 31 tcc aca gcc agg gaa cag cca atc ttc agc acc cgg gcg cac gta ttc      48
Ser Thr Ala Arg Glu Gln Pro Ile Phe Ser Thr Arg Ala His Val Phe
  1               5                  10                  15 cag atc gac ccc act aca aag cgg aac tgg atc ccc gcc ggc aag cac      96
Gln Ile Asp Pro Thr Thr Lys Arg Asn Trp Ile Pro Ala Gly Lys His
             20                  25                  30 gca ctt acc gtg tcc tat ttc tat gat gca acc cga aat gtg tac cgc     144
Ala Leu Thr Val Ser Tyr Phe Tyr Asp Ala Thr Arg Asn Val Tyr Arg
         35                  40                  45 atc atc agc atc ggg ggt gcc aag gcc atc atc aac agc act gtc act     192
Ile Ile Ser Ile Gly Gly Ala Lys Ala Ile Ile Asn Ser Thr Val Thr
     50                  55                  60 ccc aac atg acc ttc acc aaa acc tct cag aag ttc ggg caa tgg gca     240
Pro Asn Met Thr Phe Thr Lys Thr Ser Gln Lys Phe Gly Gln Trp Ala
 65                  70                  75                  80 gac agt cga gcc aac act gtc tac ggc cta ggc ttt gcc tct gaa cag     288
Asp Ser Arg Ala Asn Thr Val Tyr Gly Leu Gly Phe Ala Ser Glu Gln
                 85                  90                  95 cag ctg acc cag ttt gct gag aag ttt cag gag gtg aaa gaa gct gcc     336
Gln Leu Thr Gln Phe Ala Glu Lys Phe Gln Glu Val Lys Glu Ala Ala
            100                 105                 110 agg ctg gct cga gag aaa tct caa gat ggt gga gaa ttc act agt act     384
Arg Leu Ala Arg Glu Lys Ser Gln Asp Gly Gly Glu Phe Thr Ser Thr
        115                 120                 125 ggc ctg gcc ctt gcc tcc cat cag gtt cct cca agc ccc ttg gtc agc     432
Gly Leu Ala Leu Ala Ser His Gln Val Pro Pro Ser Pro Leu Val Ser
    130                 135                 140 acc aat ggt cca ggc gag gaa aag ctg ttc cgt agc cag agt gcg gac     480
Thr Asn Gly Pro Gly Glu Glu Lys Leu Phe Arg Ser Gln Ser Ala Asp
145                 150                 155                 160 acc cct ggc ccc acc gag cgg gaa cgg ttg aag aag atg ctg tca gaa     528
Thr Pro Gly Pro Thr Glu Arg Glu Arg Leu Lys Lys Met Leu Ser Glu
                165                 170                 175 ggc tct gta ggg gaa gtc cag tgg gaa gca gag ttc ttc gcg ctt cag     576
Gly Ser Val Gly Glu Val Gln Trp Glu Ala Glu Phe Phe Ala Leu Gln
            180                 185                 190 gac agc aac cag agg ttg gcg gga gcc ctt cgg gaa gcg aac gca gcg     624
Asp Ser Asn Gln Arg Leu Ala Gly Ala Leu Arg Glu Ala Asn Ala Ala
        195                 200                 205 gcc act cag tgg agg caa caa ctg gag gtc caa cgt gca gag gct gaa     672
Ala Thr Gln Trp Arg Gln Gln Leu Glu Val Gln Arg Ala Glu Ala Glu
    210                 215                 220 ctc ttg agg cag cgg gta gca gag ctg gag gcc cag gtg gct gta gag     720
Leu Leu Arg Gln Arg Val Ala Glu Leu Glu Ala Gln Val Ala Val Glu
225                 230                 235                 240 cca gtc cgg gca gga gag aaa gaa gca acc agc cag tcg gtg gag cag     768
Pro Val Arg Ala Gly Glu Lys Glu Ala Thr Ser Gln Ser Val Glu Gln
                245                 250                 255 ctg gag gct cgg gtg cag acc aag gac cag gag atc cag act ttg aag     816
Leu Glu Ala Arg Val Gln Thr Lys Asp Gln Glu Ile Gln Thr Leu Lys
            260                 265                 270 aat cag agc act ggc acc cga gag gct cca gac act gcc gag cgc gaa     864
Asn Gln Ser Thr Gly Thr Arg Glu Ala Pro Asp Thr Ala Glu Arg Glu
        275                 280                 285 gag aca cag cag caa gtt cag gac ctg gag acc cgg aat gca gag ctg     912
Glu Thr Gln Gln Gln Val Gln Asp Leu Glu Thr Arg Asn Ala Glu Leu
    290                 295                 300 gag cag cag ctg cgg gcg atg gag tgc aac ctg gag gag gcg cgg gcc     960
```

-continued

```
Glu Gln Gln Leu Arg Ala Met Glu Cys Asn Leu Glu Glu Ala Arg Ala
305                 310                 315                 320 gag cgg gag cgc gca cgg gcg gag gtg ggc cgg gct gcg cag ctg ctg      1008
Glu Arg Glu Arg Ala Arg Ala Glu Val Gly Arg Ala Ala Gln Leu Leu
                325                 330                 335 gat gtt cgg ctg ttt gagctcagcg agctgcgtga aggcctggca cgcctggcag      1063
Asp Val Arg Leu Phe
            340 aggcagcacc ctagtctgcc atggagtgtc tgcggcctca aggcgccctg gcaggggcca    1123 ggggacccca gctgtctctg agctttgcac tgtgtagagt tttctagaat ccttgggcaa    1183 tgcttctacc caggttacat ttctacgtgt ggcgttgctg tccctggctg ctgctgccct    1243 gcgcccagg gacactgcga gggaaggctg cactagtcat ccccatgggg caacagaggc    1303 tttgggatcc tgagacctga aggccctgta ctcatcccac cccattctca agtcagactg    1363 acaacttcaa agagtgttta ctgaagtcag gggccaccag caccaggttt acagctcagt    1423 cctgagcctc agcctgggct ggctcttggg gccgagatct gggaggacgc gaccgtcgga    1483 cagtgctccc tgctttctgc cgccgaagtg tctgccccac tttctccttg aagcgtcggt    1543 tttgttgctt gatcttggcc agctcagctt tgcgtttggc ctccaggtct gggtcctgcg    1603 gaagggagct gagaatgtaa ctgggcagct cccagggac tggctccccc acccctaccc    1663 gtccccaggt cccacccacc cttactggcc acactcttat gcctgtccct gcatacccat    1723 gcctccctat actaccttcc cctccaggat catctgtttc cgcttgttga tctctttctt    1783 ttcatcaaaa tgcgaagcct ccagtttcta ggggtgggga ggggaacagg tcagtcaggc    1843 ctggggcagg aagccccgcc cacctcaccc cactccaccc tacctgaca ggctggccac    1903 acttactatt tcgcactccc ttcgcactac gttgacctgc gtgaggattt gtagaacctc    1963 agcctcctcc accaccagct ctgccagctg ctgctctgca gggacaggaa acactgagtt    2023 gggctgggag tgcaaccagc cctctgcacc cccagctctg gatgtctgga tccaaccaaa    2083 tgtggactga tgatatttag aaaaagcaaa atgctgccaa gcttggcagc acatgcttgt    2143 catcacagca ctgggaggtg gaggcagggg gatcactcgt ttcagctgag ttccaggcca    2203 gctctgtaga gcaagaatct gtctcaaatt aatgactgaa taaacaaatg aacaagtaaa    2263 aaaaaaaaaa aaaaaaaaa aaaaaaaaaa aaaa                                 2297
```

<210> SEQ ID NO 32
<211> LENGTH: 341
<212> TYPE: PRT
<213> ORGANISM: Mus musculus

<400> SEQUENCE: 32

```
Ser Thr Ala Arg Glu Gln Pro Ile Phe Ser Thr Arg Ala His Val Phe
1               5                   10                  15

Gln Ile Asp Pro Thr Thr Lys Arg Asn Trp Ile Pro Ala Gly Lys His
                20                  25                  30

Ala Leu Thr Val Ser Tyr Phe Tyr Asp Ala Thr Arg Asn Val Tyr Arg
            35                  40                  45

Ile Ile Ser Ile Gly Gly Ala Lys Ala Ile Ile Asn Ser Thr Val Thr
        50                  55                  60

Pro Asn Met Thr Phe Thr Lys Thr Ser Gln Lys Phe Gly Gln Trp Ala
65                  70                  75                  80

Asp Ser Arg Ala Asn Thr Val Tyr Gly Leu Gly Phe Ala Ser Glu Gln
                85                  90                  95
```

```
Gln Leu Thr Gln Phe Ala Glu Lys Phe Gln Glu Val Lys Glu Ala Ala
            100                 105                 110
Arg Leu Ala Arg Glu Lys Ser Gln Asp Gly Gly Glu Phe Thr Ser Thr
            115                 120                 125
Gly Leu Ala Leu Ala Ser His Gln Val Pro Pro Ser Pro Leu Val Ser
        130                 135                 140
Thr Asn Gly Pro Gly Glu Glu Lys Leu Phe Arg Ser Gln Ser Ala Asp
145                 150                 155                 160
Thr Pro Gly Pro Thr Glu Arg Glu Arg Leu Lys Lys Met Leu Ser Glu
                165                 170                 175
Gly Ser Val Gly Glu Val Gln Trp Glu Ala Glu Phe Phe Ala Leu Gln
            180                 185                 190
Asp Ser Asn Gln Arg Leu Ala Gly Ala Leu Arg Glu Ala Asn Ala Ala
        195                 200                 205
Ala Thr Gln Trp Arg Gln Gln Leu Glu Val Gln Arg Ala Glu Ala Glu
    210                 215                 220
Leu Leu Arg Gln Arg Val Ala Glu Leu Glu Ala Gln Val Ala Val Glu
225                 230                 235                 240
Pro Val Arg Ala Gly Glu Lys Glu Ala Thr Ser Gln Ser Val Glu Gln
                245                 250                 255
Leu Glu Ala Arg Val Gln Thr Lys Asp Gln Glu Ile Gln Thr Leu Lys
            260                 265                 270
Asn Gln Ser Thr Gly Thr Arg Gly Ala Pro Asp Thr Ala Glu Arg Glu
        275                 280                 285
Glu Thr Gln Gln Gln Val Gln Asp Leu Glu Thr Arg Asn Ala Glu Leu
    290                 295                 300
Glu Gln Gln Leu Arg Ala Met Glu Cys Asn Leu Glu Ala Arg Ala
305                 310                 315                 320
Glu Arg Glu Arg Ala Arg Ala Glu Val Gly Arg Ala Ala Gln Leu Leu
                325                 330                 335
Asp Val Arg Leu Phe
            340

<210> SEQ ID NO 33
<211> LENGTH: 5798
<212> TYPE: DNA
<213> ORGANISM: Rattus norvegicus
<220> FEATURE:
<221> NAME/KEY: CDS
<222> LOCATION: (567)..(1124)

<400> SEQUENCE: 33
gtgctgtgca catcgcgagc ggctgggtt tgcacttcga gatttcttct ttataatttt      60
ttttttttaa tgtaagggag acagtggaat tgctacccgt agaatttta ttcaagtgca    120 cgtcgcgttg ggttgcacgc tccaccccca gggacctggt gtggtgaaat ttgaacccac    180
cgccttagcc caaaggccga gtaacctggc tgcttgagtg tcgtggaaga cgtgagcgaa    240
atgatcagcg aactcatttt ttatcagact cgctgaagct ggcttttgcg ttttctaca    300 cgtacactaa ttttatggaa tagttaaagt gctatattct ccgcgcaacc ttttcaaatt    360
ccaaatgttt gaacgttttg gtgtcagcgc gagtgaaatc attttaccga caagaactaa    420
ctgaattgtc tgcctcgttg agttgcctcc ggaaaagatc tcggggtgg aaaagcaact    480 gcaaataaac agacggagaa aattccttgg aagttatttc tgtagcataa agcagaaac     540 ttcagagcaa gttttcattg ggcaaa atg ggg gaa caa cct atc ttc agc act    593
                               Met Gly Glu Gln Pro Ile Phe Ser Thr
```

|   |   |
|---|---|
| cga gct cat gtc ttc cag atc gac cca aac aca aag aag aac tgg gta<br>Arg Ala His Val Phe Gln Ile Asp Pro Asn Thr Lys Lys Asn Trp Val<br>10                  15                    20                 25 | 641 |
| ccc acc agc aag cat gca gtt act gtg tct tat ttc tat gac agc aca<br>Pro Thr Ser Lys His Ala Val Thr Val Ser Tyr Phe Tyr Asp Ser Thr<br>                30                    35                    40 | 689 |
| agg aat gtg tat agg ata atc agt cta gac ggc tca aag gca ata ata<br>Arg Asn Val Tyr Arg Ile Ile Ser Leu Asp Gly Ser Lys Ala Ile Ile<br>              45                    50                  55 | 737 |
| aat agc acc atc act cca aac atg aca ttt act aaa aca tct caa aag<br>Asn Ser Thr Ile Thr Pro Asn Met Thr Phe Thr Lys Thr Ser Gln Lys<br>60                  65                    70 | 785 |
| ttt ggc caa tgg gct gat agc cgg gca aac act gtt tat gga ctg gga<br>Phe Gly Gln Trp Ala Asp Ser Arg Ala Asn Thr Val Tyr Gly Leu Gly<br>75                  80                    85 | 833 |
| ttc tcc tct gag cat cat ctc tca aaa ttt gca gaa aag ttt cag gaa<br>Phe Ser Ser Glu His His Leu Ser Lys Phe Ala Glu Lys Phe Gln Glu<br>90                  95                   100             105 | 881 |
| ttt aaa gaa gct gct cgg ctg gca aag gag aag tcg cag gag aag atg<br>Phe Lys Glu Ala Ala Arg Leu Ala Lys Glu Lys Ser Gln Glu Lys Met<br>                110                    115                    120 | 929 |
| gaa ctg acc agt acc cct tca cag gaa tca gca gga gga gat ctt cag<br>Glu Leu Thr Ser Thr Pro Ser Gln Glu Ser Ala Gly Gly Asp Leu Gln<br>              125                    130                    135 | 977 |
| tct cct tta aca cca gaa agt atc aat ggg aca gat gat gag aga aca<br>Ser Pro Leu Thr Pro Glu Ser Ile Asn Gly Thr Asp Asp Glu Arg Thr<br>140                 145                   150 | 1025 |
| ccc gat gtg aca cag aac tca gag cca agg gct gag cca gct cag aat<br>Pro Asp Val Thr Gln Asn Ser Glu Pro Arg Ala Glu Pro Ala Gln Asn<br>155                 160                   165 | 1073 |
| gca ttg cca ttt tca cat agg tac aca ttc aat tca gca atc atg att<br>Ala Leu Pro Phe Ser His Arg Tyr Thr Phe Asn Ser Ala Ile Met Ile<br>170                 175                   180                   185 | 1121 |
| aaa tgagatggat aaatatgaag ttcatttggt ttcagaaact cttgagtgaa<br>Lys | 1174 |
| aaatcccagg tcagacttct ttaattaatt aattgtttgc tgttgctcag attgactgaa | 1234 |
| tatttccatt atctgtgtag aaaaaggaac gttaattata ggagaaactt tttcaatgga | 1294 |
| caaaacattc cattctatct atattttaaa gatccctttt gctaaccagt tttctgattt | 1354 |
| tctacatgtt acgtaagact aataacttgt gattaggatc aatggactcc tgctccaaag | 1414 |
| gaaagccttg ccacaggccc acagaggtgc cacagaggac ggggccaggc aggaacccgt | 1474 |
| cagcattgaa ggttgttttt gtatgccaac aggaggaaag cttgagttgc tgctgattct | 1534 |
| taaaagaatt ctgtattcta aaagatacac atcatgttct aaatgcattt taaactagtg | 1594 |
| acattagtta ttgggcatac tgtggtatta ctagactaca aagaggaata tgaagtggca | 1654 |
| ccattgaaag tatttttta aaaagcctgt ctaccttaac actaattttt acccttattt | 1714 |
| aaatgctttt tactaaacag ttttaggtaa aattaagaaa acagttttgt tgactgcaca | 1774 |
| tcttttagaa ggaccaactt ttagagaatt acattctttg acagattaaa aattgcaaag | 1834 |
| tgagatattt caaactctta agtgagtttt attgccgttg gactgcatta atacggacat | 1894 |
| acgattaaac ttagtagacc aacactgagg gatctcctta ccaggctgca gaacaaggaa | 1954 |
| attaagcaat aaatgggact tgtgaatgga aggacactct actgctagtg ctagtaattc | 2014 |
| tgcataagat ggtatacatt ttgaagaaag ctgcttttaa ttactttttaa taatgatttt | 2074 |

```
aattactcta gtgcaagtgc ttcctcgagc tataaaggta gctgagcaca gcagacctttt   2134 actccctcag tctgacttct gtactcatat tcatttagtg aacatagtct tttaacagaa   2194
gaccacagtt ctttgatagc gttacaaaac ttacgttatt taaacgttat aaagaacgtt   2254
attgtaggat aaaatgttaa aaactgtgtc aaggacagga agaattccta tctattaagt   2314
agtggtttcc acccccactt aagactgaac tgcactgaac ggtaactgta tacttggttt   2374
gacacctcga ctgagccatg cgcactgaat actgtgacat tgaggagtaa gaacttttaa   2434
atttaacatt taaagaagct acttgcagtt tatgcaccga aatttgtcta aatgttctcc   2494
attttgctga ccccgttgta ttcatactgc tccccagagc ctagagttgt cctcatcctg   2554
acttcctgtg cctgagtgtc tgagaggagt cactttcact gtgaagacac tgcttctgcg   2614
cctcgtaggg aggacttgac agtgctcccg tagaaatcct acattatttc aacctcagag   2674
ttacagtaaa ggcaggttat aaccagtctt tcttattatt ttaagaattt ccagccctag   2734
tgttttatga aagtattcct gtgaatttga caccttatga tcctatattc atctaattcc   2794
ttaatgaaat aaaaatgtcc atgtgaggta ggttatttac agcgattgca ggagacatgg   2854
tgttcttcag agttcccaaa ccaggatagt ttcaaatagg ttttttcatgg cttctgacga   2914 agaagaccat aaagttccct gcagtgtgtc agtgatgtgc aagctgaatt agtgcgaagt   2974
gtcacactgt gaaagcacgt gcttttggct tattatgaga aaacgaaatc tttaaattca   3034
gtttatgtgt cttaggtcca gtttactttg atttgactac tcagttcttc tgaccccacc   3094
tagtatgtat gtatatgtgt gtgtatgtgt gtgtatgtct gtatgtatat acatacatat   3154
acacacacat tgtatacata tgctatatat acagtatgtg tatatatata ctatatatga   3214
atatatgaat atatatattc aattagttaa tagtacattt aagccaaata tccaacataa   3274
gcacactatg taagtatcta tctggaaaga cctatataga attgagatca acatttcatg   3334
agttagaaac aaaggatttt ataattaata ttacttaagt ctaaagtacc catatattta   3394
aattagatat gcaattttttc cctcttggca agaaagaca aaaatcttgt gtttagagat   3454
gatgtagatt gtcattttttg cctttccttc ctgagtactt gttttaacaa caacaaaaaa   3514
agactagttt aagaaaaggg attgtccagt attttttctgc tttgttaagt ctaattttac   3574
tgttaaacag agagcagaat cactggagta ctgggggggt tttttgttgt tttttttttt   3634
ttcttttctg ttttttttcgg agctggggag cgaacccagg gccttgcgct cactaggcaa   3694
gcactctacc gctgagctaa atccccaacc cctggagtat ctgttttaaa agaaagccag   3754
gaccgttatg atggccatac ccagggtaca tagtgaaaac aacagagacc aagcaatgag   3814
agtgtgagag taccaatcca ccagtactgc tgccggacat ggcagctgcc tgtgcttttc   3874
tgaagagtca tagtgtatgc taagtctaga accattactt agtaaagagg ctatgacttt   3934
tatttgggcc tgacaatttt agtggtgtgg tcatagtcta ttctgtattt gtaagctttta   3994 ttttttaaatt actgtgttga tttaggaaca caagaaatgt ttttatttttt aattatgagt   4054 gtatataagg ttttcagata tgcacagact acaataatag actcccatgg agataccact   4114
tcagccttaa cagtcaggga gaaggagcct cacttttatca ccgcactcac cctgctctcc   4174
actgatctgt tgttactgcg gtgtggaggt tcacacgcat gcaggtcttc acacatgatg   4234
ggtaggcccg caccaagtga gcctctccca gccttgctgt ttcgtttttt tatttttaatc   4294 ttacatgtat gggtgttttg catccaggca tgtcatgcct gtgtccacag aagccagaaa   4354
gggtatcaga ttccctaaaa ctggagttct cgatgatcgt gagcgagcca ttgtgggtgc   4414
tgggaactga agctgggtcc tctacaagag cagccagcgc tcttaaccat tgagccacta   4474
```

```
tctgccctgt gtttgtttta tttatttatt tatttattta tttatttatt tatttattta      4534
tttatttatt tatttattta ttggttcttt ttttttggac tggggaccga agccagggcc      4594
ttgcacttcc taggcaagcg ctctaccact gagctaaatc cccaacccct tgttttattt      4654
ttaaagcaaa cgagatacat aatttcaacc atgataattt aagattatct tgaactctta      4714
aggaaatgta tatactaagc tattatagtt tttattttcc ctaattcagt ggcataatac      4774
cttaccttga gtcgtttact actttctttg gtttctaaaa actctactgc taaattacaa      4834
tgtaaaaaca tagggctcgt atatactgta gagtgctgta gatgtcctcg tcatcaacta      4894
tgcaataaca gtctgatcga cacatttcag gagcgatcac tctttggtgt gcttctttaa      4954
atactttcag aagcttagga tgtgcaaagc aggaagaccg tgggtgtaaa tgtttactta      5014
tttctttgag agtgttagta agtcttttct aaattgcttt tctcttcaaa attatcgtta      5074
acttaaatga taattatctt tgaggttaaa cagaagctca ttgacaaact aaagtgactt      5134
tttagggcat tctttgagat catagtctta tatctgggga ctaaaatgtc attagaccct      5194
aatagactaa cttgtatgtt tgtgtgggga aacgttttcc tctctcattc aaggtaactg      5254
tttgctgcct gttgttactt gtgtagcatt ctagaaaatg gctaggtttt ttataagatt      5314
taagacaata gaagtagttt tatattatta tagttctgtt ggaatgtgat cctgaaatta      5374
ttactgaaaa ttagaatttt tatttcgcta atgacaacct tgactctcag agatgcagtg      5434
taaattgata cctcatcttt ccgagagttc agagcacagg gcggcagtat gtgaagctgc      5494
ttttgcactg acgcattttg ataagtttgg ctactgtaat ggtaaaaggc tcctcaggca      5554
ctgactgcat ttgggttctt ccgatggggg atgatccgtt ctcgtggtgc tgctggactt      5614
atgcattttg gaggtactgc atgtatcttc cacactgctt gacattttct ctgatctgtg      5674
tgtttgcacc aactcattaa agaaatatg cagaaatatc ttctaattcg ttgatcttcg      5734
ctgtatgaca gttataatat taaacacttg ggttgatcaa aaaaaaaaaa aaaaaaaaa      5794 aaaa                                                                   5798
```

<210> SEQ ID NO 34
<211> LENGTH: 186
<212> TYPE: PRT
<213> ORGANISM: Rattus norvegicus

<400> SEQUENCE: 34

```
Met Gly Glu Gln Pro Ile Phe Ser Thr Arg Ala His Val Phe Gln Ile
 1               5                  10                  15

Asp Pro Asn Thr Lys Lys Asn Trp Val Pro Thr Ser Lys His Ala Val
                20                  25                  30

Thr Val Ser Tyr Phe Tyr Asp Ser Thr Arg Asn Val Tyr Arg Ile Ile
            35                  40                  45

Ser Leu Asp Gly Ser Lys Ala Ile Ile Asn Ser Thr Ile Thr Pro Asn
        50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125
```

```
Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Ala Gln Asn Ala Leu Pro Phe Ser His Arg
                165                 170                 175

Tyr Thr Phe Asn Ser Ala Ile Met Ile Lys
            180                 185

<210> SEQ ID NO 35
<211> LENGTH: 3339
<212> TYPE: DNA
<213> ORGANISM: Rattus norvegicus
<220> FEATURE:
<221> NAME/KEY: CDS
<222> LOCATION: (740)..(1801)

<400> SEQUENCE: 35
ctagtggatc cccegggctg caggaattct gcggccgcaa caccgcactg tggtggacag      60
tgagggccgg agagagacca cagtgaccca tcaagaagcc catgacagtt ccagaagtga     120
tccagatcct ccaagatctt cagctttgga tgatccettt tccatcctgg acctgcttct     180
aggacgttgg tttcggtccc gatagctttc ttgaacttca gaggccttca ggtccttccc     240
accccctccc tcctgttgc ccattgccaa taagcatagc ttttgctgtc atcctggggt      300
cttaaatgtg tggaaccccc ccagggacct ggtgtggtga aatttgaacc caccgcctta     360
gcccaaaggc cgagtaacct ggctgcttga gtgtcgtgga agacgtgagc gaaatgatca     420
gcgaactcat tttttatcag actcgctgaa gctggctttt gcgttttct acacgtacac      480 taattttatg gaatagttaa agtgctatat tctccgcgca accttttcaa attccaaatg     540
tttgaacgtt ttggtgtcag cgcgagtgaa atcattttac cgacaagaac taactgaatt     600
gtctgcctcg ttgagttgcc tccggaaaag atctcggggg tggaaaagca actgcaaaat     660
aacagacgga gaaattcct tggaagttat ttctgtagca taagagcaga aacttaagag      720
caagttttca ttgggcaaa atg ggg gaa caa cct atc ttc agc act cga gct     772
                     Met Gly Glu Gln Pro Ile Phe Ser Thr Arg Ala
                      1               5                  10 cat gtc ttc cag atc gac cca aac aca aag aag aac tgg gta ccc acc     820
His Val Phe Gln Ile Asp Pro Asn Thr Lys Lys Asn Trp Val Pro Thr
            15                  20                  25 agc aag cat gca gtt act gtg tct tat ttc tat gac agc aca agg aat     868
Ser Lys His Ala Val Thr Val Ser Tyr Phe Tyr Asp Ser Thr Arg Asn
        30                  35                  40 gtg tat agg ata atc agt cta gac ggc tca aag gca ata ata aat agc     916
Val Tyr Arg Ile Ile Ser Leu Asp Gly Ser Lys Ala Ile Ile Asn Ser
 45                  50                  55 acc atc act cca aac atg aca ttt act aaa aca tct caa aag ttt ggc     964
Thr Ile Thr Pro Asn Met Thr Phe Thr Lys Thr Ser Gln Lys Phe Gly
 60                  65                  70                  75 caa tgg gct gat agc cgg gca aac act gtt tat gga ctg gga ttc tcc    1012
Gln Trp Ala Asp Ser Arg Ala Asn Thr Val Tyr Gly Leu Gly Phe Ser
                80                  85                  90 tct gag cat cat ctc tca aaa ttt gca gaa aag ttt cag gaa ttt aaa    1060
Ser Glu His His Leu Ser Lys Phe Ala Glu Lys Phe Gln Glu Phe Lys
             95                 100                 105 gaa gct gct cgg ctg gca aag gag aag tcg cag gag aag atg gaa ctg    1108
Glu Ala Ala Arg Leu Ala Lys Glu Lys Ser Gln Glu Lys Met Glu Leu
        110                 115                 120
```

-continued

| | |
|---|---|
| acc agt acc cct tca cag gaa tca gca gga gga gat ctt cag tct cct<br>Thr Ser Thr Pro Ser Gln Glu Ser Ala Gly Gly Asp Leu Gln Ser Pro<br>    125                          130                          135 | 1156 |
| tta aca cca gaa agt atc aat ggg aca gat gat gag aga aca ccc gat<br>Leu Thr Pro Glu Ser Ile Asn Gly Thr Asp Asp Glu Arg Thr Pro Asp<br>140                          145                          150                          155 | 1204 |
| gtg aca cag aac tca gag cca agg gct gag cca gct cag aat gca ttg<br>Val Thr Gln Asn Ser Glu Pro Arg Ala Glu Pro Ala Gln Asn Ala Leu<br>                        160                          165                          170 | 1252 |
| cca ttt tca cat agt tca gcc atc agc aaa cac tgg gag gct gaa cta<br>Pro Phe Ser His Ser Ser Ala Ile Ser Lys His Trp Glu Ala Glu Leu<br>                175                          180                          185 | 1300 |
| gcc acg ctc aag ggg aac aat gcc aag ctc acc gca gcg ctg ctg gag<br>Ala Thr Leu Lys Gly Asn Asn Ala Lys Leu Thr Ala Ala Leu Leu Glu<br>              190                          195                          200 | 1348 |
| tcc act gcc aac gtg aag cag tgg aag caa cag ctg gct gcc tac cag<br>Ser Thr Ala Asn Val Lys Gln Trp Lys Gln Gln Leu Ala Ala Tyr Gln<br>        205                          210                          215 | 1396 |
| gag gag gca gag cgg ctg cac aag cgg gtc acg gag ctg gaa tgt gtt<br>Glu Glu Ala Glu Arg Leu His Lys Arg Val Thr Glu Leu Glu Cys Val<br>220                          225                          230                          235 | 1444 |
| agt agt caa gca aac gcg gtg cac agc cac aag aca gag ctg agt cag<br>Ser Ser Gln Ala Asn Ala Val His Ser His Lys Thr Glu Leu Ser Gln<br>                        240                          245                          250 | 1492 |
| aca gtg cag gag ctg gaa gag acc cta aaa gta aag gaa gag gaa ata<br>Thr Val Gln Glu Leu Glu Glu Thr Leu Lys Val Lys Glu Glu Glu Ile<br>              255                          260                          265 | 1540 |
| gaa aga tta aaa caa gaa att gat aac gcc aga gaa ctt caa gaa cag<br>Glu Arg Leu Lys Gln Glu Ile Asp Asn Ala Arg Glu Leu Gln Glu Gln<br>        270                          275                          280 | 1588 |
| agg gac tct ttg act cag aaa cta cag gaa gtt gag att cga aat aaa<br>Arg Asp Ser Leu Thr Gln Lys Leu Gln Glu Val Glu Ile Arg Asn Lys<br>        285                          290                          295 | 1636 |
| gac ctg gag ggg cag ctg tcg gag ctg gag cag cgc ctg gag aag agc<br>Asp Leu Glu Gly Gln Leu Ser Glu Leu Glu Gln Arg Leu Glu Lys Ser<br>300                          305                          310                          315 | 1684 |
| cag agc gag cag gac gct ttc cgc agt aac ctg aag act ctc cta gag<br>Gln Ser Glu Gln Asp Ala Phe Arg Ser Asn Leu Lys Thr Leu Leu Glu<br>                        320                          325                          330 | 1732 |
| att ctg gac ggg aaa ata ttt gaa cta aca gaa ttg cgg gat aat ttg<br>Ile Leu Asp Gly Lys Ile Phe Glu Leu Thr Glu Leu Arg Asp Asn Leu<br>              335                          340                          345 | 1780 |
| gcc aag cta cta gaa tgc agc taaagaaagt gaaatttcag tgccaataga<br>Ala Lys Leu Leu Glu Cys Ser<br>        350 | 1831 |
| tgaagagata ctgtctgtct tcgtaggact gtttgggctc tgtaccaaga ttgcacaaaa | 1891 |
| tttttttgaat atcattcctc cagaaggagg gtgttttgaa aattggaatt gtatatttca | 1951 |
| gtataaattt tagaatttag cttatagcta gttgggggaa aaaagacat gaaaaacttg | 2011 |
| aaccacaaat tacctccatg tacattggcc atagttacaa tgggagaatt aacaatgtct | 2071 |
| gggtcccttc tccttttcct gttcaacaca gtgaagatta tctgcttttt aaatttattt | 2131 |
| acgatatcta cagctgtgtt ttgtgtaaaa acttagtaat ggaagccctg tctttgttgt | 2191 |
| tatctgaata atttctcagg atatttttt gctgctgaga aagggccatt accaattaat | 2251 |
| ccttgccagg agttggggag ctatgtctct aattggaatc actataactg ggtgtctgga | 2311 |
| gttcttccct tttcgtactg agagtgttct cactctagtc actcctctgg tacactccgt | 2371 |
| gttctccaat cttgtctgtt gtactttact tttccatatt gactccatgt atttatgaga | 2431 |

-continued

```
agatattatc tcccatttta ttatacattt tgaagccaac taaacaaagg cagctgagtc    2491
cttcagatat ttttctttt aaatttatag taaatttgac acagaactga aattcagcag    2551
tccgtctttg acggtttagt ctagcaatgt taaggatatt tagagaaaat atgcagttac    2611
gtttatttat atatttggca agaaatttt tctggatgat caatgctttt caatttatga    2671
taaataatgg ttaggggggcg ctgtttatta tagataattt taaggtatat agctgttttc    2731
aaggaggtcc acttccgtct agcagccaag cagaggactg tatctaaatc gtgatcgtgg    2791
cagatgggtc ttcatagaaa ccatgtcttt attcaaactt cataggggcaa tattttgaac    2851 tgttacctag gcatttcaaa acaggaaata ccgtcaacag actcttctcc aagagcaggt    2911
tttactgttg ttttgatgta atttaagac atttagcaaa catgcatttc tttatatgat    2971
acatttcttt cacaaaacaa tttaaaagta agccacgtgc tgtctgctct gcccgggtag    3031
gaattgcatc agaatacata tatcttgctg tacaatgcct gtgatattga agagggttct    3091
tttcatgtat gcttgagtat ctaactctgg agtcaatgaa tgcactgact ttttttttgt    3151
tcgtacccca aatgattgaa ttgttaagta caaattaagc agattaactc attttttcac    3211
tcataaacag attcttagta ctagtttttgt tttatattta tgtgtatgta tgtaaataca    3271
tacatattaa tttatattag agtgaaaaat aaattgtttg tttctaacat taaaaaaaaa    3331
aaaaaaaa                                                              3339
```

<210> SEQ ID NO 36
<211> LENGTH: 354
<212> TYPE: PRT
<213> ORGANISM: Rattus norvegicus

<400> SEQUENCE: 36

```
Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Ala Gln Asn Ala Leu Pro Phe Ser His Ser
                165                 170                 175

Ser Ala Ile Ser Lys His Trp Glu Ala Glu Leu Ala Thr Leu Lys Gly
            180                 185                 190

Asn Asn Ala Lys Leu Thr Ala Ala Leu Leu Glu Ser Thr Ala Asn Val
        195                 200                 205
```

-continued

```
Lys Gln Trp Lys Gln Gln Leu Ala Ala Tyr Gln Glu Ala Glu Arg
    210                 215                 220

Leu His Lys Arg Val Thr Glu Leu Glu Cys Val Ser Ser Gln Ala Asn
225                 230                 235                 240

Ala Val His Ser His Lys Thr Glu Leu Ser Gln Thr Val Gln Glu Leu
                245                 250                 255

Glu Glu Thr Leu Lys Val Lys Glu Glu Ile Glu Arg Leu Lys Gln
            260                 265                 270

Glu Ile Asp Asn Ala Arg Glu Leu Gln Glu Gln Arg Asp Ser Leu Thr
            275                 280                 285

Gln Lys Leu Gln Glu Val Glu Ile Arg Asn Lys Asp Leu Glu Gly Gln
    290                 295                 300

Leu Ser Glu Leu Glu Gln Arg Leu Glu Lys Ser Gln Ser Glu Gln Asp
305                 310                 315                 320

Ala Phe Arg Ser Asn Leu Lys Thr Leu Leu Glu Ile Leu Asp Gly Lys
                325                 330                 335

Ile Phe Glu Leu Thr Glu Leu Arg Asp Asn Leu Ala Lys Leu Leu Glu
            340                 345                 350

Cys Ser

<210> SEQ ID NO 37
<211> LENGTH: 3706
<212> TYPE: DNA
<213> ORGANISM: Rattus norvegicus
<220> FEATURE:
<221> NAME/KEY: CDS
<222> LOCATION: (732)..(1835)

<400> SEQUENCE: 37
gcggccgcgt cgactacggc tgcgagaaga cgacagaagg gggctccgct gatgctcctc      60
gtgagaacga atcgatcctt cccagccttc tctgcctgct ctccacctcc tctctgctcc     120
gagtcttagg agaacgaaca ttcaaaggac agattccaat gtggtgtgct gtgcacatcg     180
cgagcggctg gggtttgcac ttcgagattt cttctttata attttttttt tttaatgtaa     240
gggagacagt ggaattgcta cccgtagaat ttttattcaa gtgcacgtcg cgttgggttg     300
cacgctccac ccccagggac ctggtgtggt gaaatttgaa cccaccgcct tagcccaaag     360
gccgagtaac ctggctgctt gagtgtcgtg gaagacgtga gcgaaatgat cagcgaactc     420
attttttatc agactcactg aagctggctt ttgcgttttt ctacacgtac actaattta     480 tggaatagtt aaagtgctat attctccgcg caacctttc aaattccaaa tgtttgaacg      540
ttttggtgtc agcgcgagtg aaatcatttt accgacaaga actaactgaa ttgtctgcct     600
cgttgagttg cctccggaaa agatctcggg ggtggaaaag caactgcaaa ataacagacg     660
gagaaaattc cttggaagtt atttctgtag cataagagca gaaacttcag agcaagtttt     720
cattgggcaa a atg ggg gaa caa cct atc ttc agc act cga gct cat gtc      770
            Met Gly Glu Gln Pro Ile Phe Ser Thr Arg Ala His Val
              1               5                  10 ttc cag atc gac cca aac aca aag aag aac tgg gta ccc acc agc aag      818
Phe Gln Ile Asp Pro Asn Thr Lys Lys Asn Trp Val Pro Thr Ser Lys
 15                  20                  25 cat gca gtt act gtg tct tat ttc tat gac agc aca agg aat gtg tat      866
His Ala Val Thr Val Ser Tyr Phe Tyr Asp Ser Thr Arg Asn Val Tyr
 30                  35                  40                  45 agg ata atc agt cta gac ggc tca aag gca ata ata aat agc acc atc      914
Arg Ile Ile Ser Leu Asp Gly Ser Lys Ala Ile Ile Asn Ser Thr Ile
```

```
                    50                      55                      60
act cca aac atg aca ttt act aaa aca tct caa aag ttt ggc caa tgg     962
Thr Pro Asn Met Thr Phe Thr Lys Thr Ser Gln Lys Phe Gly Gln Trp
                65                      70                      75 gct gat agc cgg gca aac act gtt tat gga ctg gga ttc tcc tct gag    1010
Ala Asp Ser Arg Ala Asn Thr Val Tyr Gly Leu Gly Phe Ser Ser Glu
            80                      85                      90 cat cat ctc tca aaa ttt gca gaa aag ttt cag gaa ttt aaa gaa gct    1058
His His Leu Ser Lys Phe Ala Glu Lys Phe Gln Glu Phe Lys Glu Ala
        95                     100                     105 gct cgg ctg gca aag gag aag tcg cag gag aag atg gaa ctg acc agt    1106
Ala Arg Leu Ala Lys Glu Lys Ser Gln Glu Lys Met Glu Leu Thr Ser
110                     115                     120                 125 acc cct tca cag gaa tca gca gga gga gat ctt cag tct cct tta aca    1154
Thr Pro Ser Gln Glu Ser Ala Gly Gly Asp Leu Gln Ser Pro Leu Thr
                130                     135                     140 cca gaa agt atc aat ggg aca gat gat gag aga aca ccc gat gtg aca    1202
Pro Glu Ser Ile Asn Gly Thr Asp Asp Glu Arg Thr Pro Asp Val Thr
            145                     150                     155 cag aac tca gag cca agg gct gag cca gct cag aat gca ttg cca ttt    1250
Gln Asn Ser Glu Pro Arg Ala Glu Pro Ala Gln Asn Ala Leu Pro Phe
        160                     165                     170 tca cat agt gcc ggg gat cga acc cag ggc ctc tct cat gct agt tca    1298
Ser His Ser Ala Gly Asp Arg Thr Gln Gly Leu Ser His Ala Ser Ser
    175                     180                     185 gcc atc agc aaa cac tgg gag gct gaa cta gcc acg ctc aag ggg aac    1346
Ala Ile Ser Lys His Trp Glu Ala Glu Leu Ala Thr Leu Lys Gly Asn
190                     195                     200                 205 aat gcc aag ctc acc gca gcg ctg ctg gag tcc act gcc aac gtg aag    1394
Asn Ala Lys Leu Thr Ala Ala Leu Leu Glu Ser Thr Ala Asn Val Lys
                210                     215                     220 cag tgg aag caa cag ctg gct gcc tac cag gag gag gca gag cgg ctg    1442
Gln Trp Lys Gln Gln Leu Ala Ala Tyr Gln Glu Glu Ala Glu Arg Leu
            225                     230                     235 cac aag cgg gtc acg gag ctg gaa tgt gtt agt agt caa gca aac gcg    1490
His Lys Arg Val Thr Glu Leu Glu Cys Val Ser Ser Gln Ala Asn Ala
        240                     245                     250 gtg cac agc cac aag aca gag ctg agt cag aca gtg cag gag ctg gaa    1538
Val His Ser His Lys Thr Glu Leu Ser Gln Thr Val Gln Glu Leu Glu
    255                     260                     265 gag acc cta aaa gta aag gaa gag gaa ata gaa aga tta aaa caa gaa    1586
Glu Thr Leu Lys Val Lys Glu Glu Glu Ile Glu Arg Leu Lys Gln Glu
270                     275                     280                 285 att gat aac gcc aga gaa ctt caa gaa cag agg gac tct ttg act cag    1634
Ile Asp Asn Ala Arg Glu Leu Gln Glu Gln Arg Asp Ser Leu Thr Gln
                290                     295                     300 aaa cta cag gaa gtt gag att cga aat aaa gac ctg gag ggg cag ctg    1682
Lys Leu Gln Glu Val Glu Ile Arg Asn Lys Asp Leu Glu Gly Gln Leu
            305                     310                     315 tcg gag ctg gag cag cgc ctg gag aag agc cag agc gag cag gac gct    1730
Ser Glu Leu Glu Gln Arg Leu Glu Lys Ser Gln Ser Glu Gln Asp Ala
        320                     325                     330 ttc cgc agt aac ctg aag act ctc cta gag att ctg gac ggg aaa ata    1778
Phe Arg Ser Asn Leu Lys Thr Leu Leu Glu Ile Leu Asp Gly Lys Ile
    335                     340                     345 ttt gaa cta aca gaa ttg cgg gat aat ttg gcc aag cta cta gaa tgc    1826
Phe Glu Leu Thr Glu Leu Arg Asp Asn Leu Ala Lys Leu Leu Glu Cys
350                     355                     360                 365 agc taa aga aagtgaaatt tcagtgccaa tagatgaaga gatactgtct            1875
Ser
```

```
Ser     Arg gtcttcgtag gactgtttgg gctctgtacc aagattgcaa aaatttttt gaatatcatt    1935 cctccagaag gagggtgttt tgaaaattgg aattgtatat ttcagtataa attttagaat    1995
ttagcttata gctagttggg ggaaaaaaag acatgaaaaa cttgaaccac aaataatgca    2055
atcttttccc ctgatagtag ccaatgggag aattaacaat gtctgggtcc cttctccttt    2115
ttctgttcaa cacagtgaag attatctgct ttttaaattt atttacgata tctacagctg    2175
tgttttgtgt aaaaacttag taatggaagc cctgtctttg ttgttatctg ataaatttct    2235
caggatattt ttttgctgct gagaaagggc cattaccaat taatccttgc caggagttgg    2295
ggagctatgt ctctaattgg aatcactata actgggtgtc tggagttctt cccttttcgt    2355
actgagagtg ttctcactct agtgactact ctggtacact ccgtgttctc caatcttgtc    2415
tgttgtactt tacttttcca tattgactcc atgtatttat gagaagatat tatctcccat    2475
tttattatac attttgaagc caactaaaca aaggcagctg agtccttcag atattttct    2535 ttttaaattt atagtaaatt tgacacagaa ctgaaattca gcagtccgtc tttgacggtt    2595
tagtctagca atgttaagga tatttagaga aaatatgcag ttacgtttat ttatatattt    2655
ggcaagaaat ttttctgga tgatcaatgc ttttcaattt atgataaata atggttaggg    2715
gcgctgttta ttatagataa ttttaaggtg tatagctgtt ttcaaggagg tccactcccg    2775
tctagcagcc aagcagagga ctgtatctaa atcgtgatcg tggcagatgg gtcttcatag    2835
aaaccatgtc tttattcaaa cttcatagg caatattttg aactgttacc taggcatttc    2895
aaaacaggaa ataccgtcaa cagactcttc tccaagagca ggttttactg ttgttttgat    2955
gtaattttaa gacatttagc aaacatgcat ttctttatat gatacatttc tttcacaaaa    3015
caatttaaaa gtaagccacg tgctgtctgc tctgcccggg taggaattgc atcagaatac    3075
atatatcttg ctgtacaatg cctgtgtatat tgaagagggt tcttttcatg tatgcttgag    3135
tatctaactc tggagtcaat gaatgcactg actttttttt ttgttcgtac cccaaatgat    3195
tgaattgtta agtacaaatt aagcagatta actcattttt tcactcataa acagattctt    3255
agtactagtt ttgttttata tttatgtgta tgtatgtaaa tacatacata ttaattata    3315 ttagagtgaa aataaattg tttgtttcta acattagttt ctacagtaag gtgtctctga    3375
aacatgtgtg tcagacactt agccaccatg cattctatgt gctacccat catgccagtc    3435 acctccatcg acgttagggt attttcctta cctgtctatt ataaagagaa taacttaggt    3495
acacatgctc agagccgaga tatttctctg ataaatcagg taataaaatc tatttgatgg    3555
gtagaatttt gaaacagac atgatttat ctatgagttt ctgaatatca aagaacacca    3615
ggttttcatt taaatagagg tctaacacta gggatcaggg aatttagtta tgaagagttg    3675
aaaaaaaaaa aaaaaaaaaa aaaaaaaaaaa a                                 3706
```

<210> SEQ ID NO 38
<211> LENGTH: 366
<212> TYPE: PRT
<213> ORGANISM: Rattus norvegicus

<400> SEQUENCE: 38

```
Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
```

-continued

```
            35                  40                  45
Ser Leu Asp Gly Ser Lys Ala Ile Ile Asn Ser Thr Ile Thr Pro Asn
 50                  55                  60

Met Thr Phe Thr Lys Thr Ser Gln Lys Phe Gly Gln Trp Ala Asp Ser
 65                  70                  75                  80

Arg Ala Asn Thr Val Tyr Gly Leu Gly Phe Ser Ser Glu His His Leu
                 85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Ala Gln Asn Ala Leu Pro Phe Ser His Ser
                165                 170                 175

Ala Gly Asp Arg Thr Gln Gly Leu Ser His Ala Ser Ser Ala Ile Ser
            180                 185                 190

Lys His Trp Glu Ala Glu Leu Ala Thr Leu Lys Gly Asn Asn Ala Lys
        195                 200                 205

Leu Thr Ala Ala Leu Leu Glu Ser Thr Ala Asn Val Lys Gln Trp Lys
    210                 215                 220

Gln Gln Leu Ala Ala Tyr Gln Glu Glu Ala Glu Arg Leu His Lys Arg
225                 230                 235                 240

Val Thr Glu Leu Glu Cys Val Ser Ser Gln Ala Asn Ala Val His Ser
                245                 250                 255

His Lys Thr Glu Leu Ser Gln Thr Val Gln Glu Leu Glu Glu Thr Leu
            260                 265                 270

Lys Val Lys Glu Glu Glu Ile Glu Arg Leu Lys Gln Glu Ile Asp Asn
        275                 280                 285

Ala Arg Glu Leu Gln Glu Gln Arg Asp Ser Leu Thr Gln Lys Leu Gln
    290                 295                 300

Glu Val Glu Ile Arg Asn Lys Asp Leu Glu Gly Gln Leu Ser Glu Leu
305                 310                 315                 320

Glu Gln Arg Leu Glu Lys Ser Gln Ser Glu Gln Asp Ala Phe Arg Ser
                325                 330                 335

Asn Leu Lys Thr Leu Leu Glu Ile Leu Asp Gly Lys Ile Phe Glu Leu
            340                 345                 350

Thr Glu Leu Arg Asp Asn Leu Ala Lys Leu Leu Glu Cys Ser
        355                 360                 365
```

<210> SEQ ID NO 39
<211> LENGTH: 7424
<212> TYPE: DNA
<213> ORGANISM: Rattus norvegicus
<220> FEATURE:
<221> NAME/KEY: CDS
<222> LOCATION: (267)..(5486)

<400> SEQUENCE: 39

```
ctctagaact agtggatccc ccgggctgca ggattctgcg gccgcgctaa accgtgccgc      60
cgtcgccgcc gccgctgcgc ctgcggagcc cccggagccg ctgtccccg cgctggcccc     120
ggccccggcc ccatacggcc ccctcccgca gtagcgcggt cggcgggact ctggcggggg    180
```

-continued

```
gtcaggggg gccagggcgc cgcgcggagt ccccgtgcgc tcctctctcc gccgggaaca        240
gtccgggccc cggcgctagc accggg atg gac ggc ccc ggg gcc agc gcc gtg        293
                             Met Asp Gly Pro Gly Ala Ser Ala Val
                              1               5 gtc gtg cgc gtc ggc atc ccg gac ctg caa caa acg aag tgc ctg cgt        341
Val Val Arg Val Gly Ile Pro Asp Leu Gln Gln Thr Lys Cys Leu Arg
10              15                  20                  25 ctg gat cca acc gcg ccc gtg tgg gcc gcc aag cag cgt gtg ctc tgc        389
Leu Asp Pro Thr Ala Pro Val Trp Ala Ala Lys Gln Arg Val Leu Cys
                30                  35                  40 gcc ctc aac cac agc ctt cag gac gcg ctc aac tac ggg cta ttc cag        437
Ala Leu Asn His Ser Leu Gln Asp Ala Leu Asn Tyr Gly Leu Phe Gln
            45                  50                  55 cct ccc tcc cgg ggt cgc gcc ggc aag ttc ctg gat gaa gag cgg ctc        485
Pro Pro Ser Arg Gly Arg Ala Gly Lys Phe Leu Asp Glu Glu Arg Leu
        60                  65                  70 tta cag gac tac ccg cct aac ctg gac acg ccc ctg ccc tat ctg gag        533
Leu Gln Asp Tyr Pro Pro Asn Leu Asp Thr Pro Leu Pro Tyr Leu Glu
    75                  80                  85 ttt cga tac aag cgg aga gtt tat gcc cag aac ctc ata gat gac aag        581
Phe Arg Tyr Lys Arg Arg Val Tyr Ala Gln Asn Leu Ile Asp Asp Lys
90              95                  100                 105 cag ttt gca aag ctg cac aca aag gca aac ctg aag aag ttc atg gac        629
Gln Phe Ala Lys Leu His Thr Lys Ala Asn Leu Lys Lys Phe Met Asp
                110                 115                 120 tat gtc cag cta cac agc aca gac aag gtg gcc cgc ctg ctg gac aag        677
Tyr Val Gln Leu His Ser Thr Asp Lys Val Ala Arg Leu Leu Asp Lys
            125                 130                 135 ggg ctg gac ccc aat ttc cat gac cct gac tca gga gag tgc cct ctg        725
Gly Leu Asp Pro Asn Phe His Asp Pro Asp Ser Gly Glu Cys Pro Leu
        140                 145                 150 agc ctt gca gca cag ttg gac aac gcc act gac ctc ctg aag gtt ctt        773
Ser Leu Ala Ala Gln Leu Asp Asn Ala Thr Asp Leu Leu Lys Val Leu
    155                 160                 165 cgc aat ggc ggt gct cat ctg gac ttc cga acc cga gat ggg cta acc        821
Arg Asn Gly Gly Ala His Leu Asp Phe Arg Thr Arg Asp Gly Leu Thr
170                 175                 180                 185 gct gtc cac tgc gcc acc cga cag cgg aat gcg gga gca ttg acg acc        869
Ala Val His Cys Ala Thr Arg Gln Arg Asn Ala Gly Ala Leu Thr Thr
                190                 195                 200 ctg ctg gac ctg ggg gct tca cct gac tac aag gac agc cgc ggc ctg        917
Leu Leu Asp Leu Gly Ala Ser Pro Asp Tyr Lys Asp Ser Arg Gly Leu
            205                 210                 215 acg ccc ctg tac cat agt gcc cta ggg ggc ggg gat gcc ctc tgc tgt        965
Thr Pro Leu Tyr His Ser Ala Leu Gly Gly Gly Asp Ala Leu Cys Cys
        220                 225                 230 gag ctg ctt ctc cat gat cac gca cag ttg ggg acc act gac gag aat       1013
Glu Leu Leu Leu His Asp His Ala Gln Leu Gly Thr Thr Asp Glu Asn
    235                 240                 245 ggc tgg cag gag atc cat cag gcc tgt cgc ttt ggg cat gta cag cac       1061
Gly Trp Gln Glu Ile His Gln Ala Cys Arg Phe Gly His Val Gln His
250                 255                 260                 265 ttg gag cac ctg ctg ttc tat ggg gcc aac atg ggt gcc cag aac gcc       1109
Leu Glu His Leu Leu Phe Tyr Gly Ala Asn Met Gly Ala Gln Asn Ala
                270                 275                 280 tcg gga aac aca gcc ttg cac atc tgt gcc ctc tat aac cag gag agc       1157
Ser Gly Asn Thr Ala Leu His Ile Cys Ala Leu Tyr Asn Gln Glu Ser
            285                 290                 295 tgt gcc cgc gtc ctg ctt ttc cgt ggt gcc aac aag gac gtc cgc aat       1205
```

```
                                                          -continued

Cys Ala Arg Val Leu Leu Phe Arg Gly Ala Asn Lys Asp Val Arg Asn
        300                 305                 310 tac aac agc cag aca gcc ttc cag gtg gcc att att gca ggg aac ttt       1253
Tyr Asn Ser Gln Thr Ala Phe Gln Val Ala Ile Ile Ala Gly Asn Phe
315                 320                 325 gag ctt gcc gag gta atc aag acc cac aaa gac tcg gat gtc gta cca       1301
Glu Leu Ala Glu Val Ile Lys Thr His Lys Asp Ser Asp Val Val Pro
330                 335                 340                 345 ttc agg gaa acc ccc agc tat gca aag cga cga cgt ctg gct ggc ccg       1349
Phe Arg Glu Thr Pro Ser Tyr Ala Lys Arg Arg Arg Leu Ala Gly Pro
                350                 355                 360 agt ggc ttg gca tcc cct cgg ccc tta cag cgc tca gcc agt gat atc       1397
Ser Gly Leu Ala Ser Pro Arg Pro Leu Gln Arg Ser Ala Ser Asp Ile
            365                 370                 375 aac ctg aag ggt gac cag ccc gca gct tct ccc ggg ccc act ctc cga       1445
Asn Leu Lys Gly Asp Gln Pro Ala Ala Ser Pro Gly Pro Thr Leu Arg
        380                 385                 390 agc ctc cct cac caa ctg ctg ctc cag agg ctt cag gag gag aaa gac       1493
Ser Leu Pro His Gln Leu Leu Leu Gln Arg Leu Gln Glu Glu Lys Asp
    395                 400                 405 cgg gac agg gat ggt gag cag gag aac gac atc agc ggt ccc tca gca       1541
Arg Asp Arg Asp Gly Glu Gln Glu Asn Asp Ile Ser Gly Pro Ser Ala
410                 415                 420                 425 ggc agg ggc ggc cac agc aag atc agc ccc agc ggg ccc ggc gga tcc       1589
Gly Arg Gly Gly His Ser Lys Ile Ser Pro Ser Gly Pro Gly Gly Ser
                430                 435                 440 ggc ccc gcg ccc ggc ccc ggc ccg gcg tct ccc gcg ccc ccc gcg ccg       1637
Gly Pro Ala Pro Gly Pro Gly Pro Ala Ser Pro Ala Pro Pro Ala Pro
            445                 450                 455 ccg ccc cgg ggc ccg aag cgg aaa ctt tac agt gcc gtc ccc ggc cgc       1685
Pro Pro Arg Gly Pro Lys Arg Lys Leu Tyr Ser Ala Val Pro Gly Arg
        460                 465                 470 aag ttc atc gct gtg aag gcg cac agc ccg cag ggc gag ggc gag atc       1733
Lys Phe Ile Ala Val Lys Ala His Ser Pro Gln Gly Glu Gly Glu Ile
    475                 480                 485 ccg ctg cac cgc ggc gag gcc gtg aag gtg ctc agc att ggg gag ggc       1781
Pro Leu His Arg Gly Glu Ala Val Lys Val Leu Ser Ile Gly Glu Gly
490                 495                 500                 505 ggt ttc tgg gag gga acc gtg aag ggc cgt aca ggc tgg ttc cca gct       1829
Gly Phe Trp Glu Gly Thr Val Lys Gly Arg Thr Gly Trp Phe Pro Ala
                510                 515                 520 gac tgt gtg gag gaa gtg cag atg cga cag tat gac aca cgg cat gaa       1877
Asp Cys Val Glu Glu Val Gln Met Arg Gln Tyr Asp Thr Arg His Glu
            525                 530                 535 act cga gag gac cgg acg aag cgt ctt ttc cgc cac tac act gtg ggt       1925
Thr Arg Glu Asp Arg Thr Lys Arg Leu Phe Arg His Tyr Thr Val Gly
        540                 545                 550 tcc tat gac agc ctc act tca cac agt gat tat gtc att gat gat aag       1973
Ser Tyr Asp Ser Leu Thr Ser His Ser Asp Tyr Val Ile Asp Asp Lys
    555                 560                 565 gtg gct atc ctg caa aaa cgg gac cat gag ggt ttt ggc ttt gtt ctc       2021
Val Ala Ile Leu Gln Lys Arg Asp His Glu Gly Phe Gly Phe Val Leu
570                 575                 580                 585 cgg gga gcc aaa gca gag acc ccc att gag gag ttt aca ccc aca cct       2069
Arg Gly Ala Lys Ala Glu Thr Pro Ile Glu Glu Phe Thr Pro Thr Pro
                590                 595                 600 gcc ttc cct gcg ctc cag tac ctt gag tct gta gat gtg gaa ggt gtg       2117
Ala Phe Pro Ala Leu Gln Tyr Leu Glu Ser Val Asp Val Glu Gly Val
            605                 610                 615
```

```
gcc tgg aag gct ggg ctt cgc act ggg gac ttc ctc att gag gta aac      2165
Ala Trp Lys Ala Gly Leu Arg Thr Gly Asp Phe Leu Ile Glu Val Asn
        620                 625                 630 gga gtg aac gtc gtg aag gtt gga cac aag caa gtg gtg ggt ctc atc      2213
Gly Val Asn Val Val Lys Val Gly His Lys Gln Val Val Gly Leu Ile
635                 640                 645 cgt cag ggt ggc aac cgt ctg gtc atg aag gtt gtg tct gtt acc agg      2261
Arg Gln Gly Gly Asn Arg Leu Val Met Lys Val Val Ser Val Thr Arg
650                 655                 660                 665 aag cca gag gag gat agt gct cgg cgc aga gcc cca cca cct ccc aag      2309
Lys Pro Glu Glu Asp Ser Ala Arg Arg Arg Ala Pro Pro Pro Pro Lys
                670                 675                 680 agg gcc ccc agc acc acg ctg acc ctg cgg tcc aag tcc atg acg gct      2357
Arg Ala Pro Ser Thr Thr Leu Thr Leu Arg Ser Lys Ser Met Thr Ala
            685                 690                 695 gag ctc gag gaa ctc gct tcc att cgg aga agg aaa ggg gag aag ttg      2405
Glu Leu Glu Glu Leu Ala Ser Ile Arg Arg Arg Lys Gly Glu Lys Leu
        700                 705                 710 gat gag atc ctg gcg gtt gct gcg gaa cca acg ctg agg cca gac att      2453
Asp Glu Ile Leu Ala Val Ala Ala Glu Pro Thr Leu Arg Pro Asp Ile
715                 720                 725 gca gac gct gat tcc agg gca gcc act gtc aag cag cgg ccc acc agc      2501
Ala Asp Ala Asp Ser Arg Ala Ala Thr Val Lys Gln Arg Pro Thr Ser
730                 735                 740                 745 cgg agg att acc cct gcc gag atc agc tca ttg ttt gag cga cag ggc      2549
Arg Arg Ile Thr Pro Ala Glu Ile Ser Ser Leu Phe Glu Arg Gln Gly
                750                 755                 760 ctc ccg ggc cca gag aag ctg ccg ggc tct ctg cgg aag ggg att cca      2597
Leu Pro Gly Pro Glu Lys Leu Pro Gly Ser Leu Arg Lys Gly Ile Pro
            765                 770                 775 cgg acc aaa tct gta ggg gag gat gag aag ctg gca tcc cta ctg gaa      2645
Arg Thr Lys Ser Val Gly Glu Asp Glu Lys Leu Ala Ser Leu Leu Glu
        780                 785                 790 ggg cgt ttc cca cgc agc aca tca atg caa gac aca gtg cgt gaa ggc      2693
Gly Arg Phe Pro Arg Ser Thr Ser Met Gln Asp Thr Val Arg Glu Gly
795                 800                 805 cga ggc att ccg ccc cca ccg cag acc gcc ccg cca ccc cca ccc gcg      2741
Arg Gly Ile Pro Pro Pro Pro Gln Thr Ala Pro Pro Pro Pro Pro Ala
810                 815                 820                 825 ccc tac tac ttc gac tcc ggg cca ccc ccc acc ttc tca cca ccg cca      2789
Pro Tyr Tyr Phe Asp Ser Gly Pro Pro Pro Thr Phe Ser Pro Pro Pro
                830                 835                 840 cca cca ccg ggc cgg gcc tat gac act gtg cgc tcc agc ttc aag cca      2837
Pro Pro Pro Gly Arg Ala Tyr Asp Thr Val Arg Ser Ser Phe Lys Pro
            845                 850                 855 ggc ctg gag gct cgt ctg ggt gca ggg gca gct ggc ctg tat gat tct      2885
Gly Leu Glu Ala Arg Leu Gly Ala Gly Ala Ala Gly Leu Tyr Asp Ser
        860                 865                 870 ggc aca cct ctg ggc ccg ctg ccc tac cct gag cgc cag aag cgt gca      2933
Gly Thr Pro Leu Gly Pro Leu Pro Tyr Pro Glu Arg Gln Lys Arg Ala
875                 880                 885 cgc tcc atg atc ata ttg cag gac tct gcg cca gaa gtg ggc gat gta      2981
Arg Ser Met Ile Ile Leu Gln Asp Ser Ala Pro Glu Val Gly Asp Val
890                 895                 900                 905 ccc cgg cct gcg cct gca gcc aca ccg gag cgc ccc aag cgc cgg           3029
Pro Arg Pro Ala Pro Ala Ala Thr Pro Glu Arg Pro Lys Arg Arg
                910                 915                 920 cct cgg ccg tca ggc cct gat agt ccc tat gcc aac ctg ggc gcc ttc      3077
Pro Arg Pro Ser Gly Pro Asp Ser Pro Tyr Ala Asn Leu Gly Ala Phe
            925                 930                 935
```

```
agt gcc agc ctc ttt gct ccg tcg aaa ccg cag cgc cgc aag agt ccg      3125
Ser Ala Ser Leu Phe Ala Pro Ser Lys Pro Gln Arg Arg Lys Ser Pro
        940                 945                 950 ctg gtg aag cag ctt cag gtg gag gac gct cag gag cgc gcg gcg ttg      3173
Leu Val Lys Gln Leu Gln Val Glu Asp Ala Gln Glu Arg Ala Ala Leu
955                 960                 965 gcc gtg ggt agc ccg gga cca gtg ggt gga agc ttt gca cga gaa ccc      3221
Ala Val Gly Ser Pro Gly Pro Val Gly Gly Ser Phe Ala Arg Glu Pro
970                 975                 980                 985 tcc cca acg cac cgc ggg ccc cga ccg ggc ggc ctt gac tac agc tct      3269
Ser Pro Thr His Arg Gly Pro Arg Pro Gly Gly Leu Asp Tyr Ser Ser
                990                 995                 1000 gga gaa ggc ctg ggg ctc acc ttt ggc ggc cct agc cct ggc cca          3314
Gly Glu Gly Leu Gly Leu Thr Phe Gly Gly Pro Ser Pro Gly Pro
            1005                1010                1015 gtc aag gag cgg cgc ctg gag gag cga cgc cgt tcc act gtg ttc          3359
Val Lys Glu Arg Arg Leu Glu Glu Arg Arg Ser Thr Val Phe
1020                1025                1030 ctg tct gtg ggt gcc atc gag ggc aac cct ccc agc gcg gat ctg          3404
Leu Ser Val Gly Ala Ile Glu Gly Asn Pro Pro Ser Ala Asp Leu
        1035                1040                1045 cca tcc cta caa ccc tcc cgc tcc att gat gag cgc ctc ctg ggg          3449
Pro Ser Leu Gln Pro Ser Arg Ser Ile Asp Glu Arg Leu Leu Gly
            1050                1055                1060 aca ggc gcc acc act ggc cga gat ttg ctg ctc ccc tcc cct gtc          3494
Thr Gly Ala Thr Thr Gly Arg Asp Leu Leu Leu Pro Ser Pro Val
                1065                1070                1075 tct gct ctg aag cca ttg gtc ggt ggt ccc aac ctt ggg ccc tca          3539
Ser Ala Leu Lys Pro Leu Val Gly Gly Pro Asn Leu Gly Pro Ser
        1080                1085                1090 agc tcc acc ttc atc cat cct ctt act ggc aaa ccc ttg gat cct          3584
Ser Ser Thr Phe Ile His Pro Leu Thr Gly Lys Pro Leu Asp Pro
            1095                1100                1105 agc tca ccc cta gct ctt gct ctg gct gcc cga gag cgg gct ctg          3629
Ser Ser Pro Leu Ala Leu Ala Leu Ala Ala Arg Glu Arg Ala Leu
        1110                1115                1120 gcc tcg caa aca cct tcc cgg tcc ccc aca ccc gtg cac agt cct          3674
Ala Ser Gln Thr Pro Ser Arg Ser Pro Thr Pro Val His Ser Pro
            1125                1130                1135 gat gct gac cgc cct gga ccc ctc ttt gtg gat gtg caa acc cga          3719
Asp Ala Asp Arg Pro Gly Pro Leu Phe Val Asp Val Gln Thr Arg
                1140                1145                1150 gac tcc gag aga gga ccc ttg gcc tcc cca gcc ttc tcc cct cgg          3764
Asp Ser Glu Arg Gly Pro Leu Ala Ser Pro Ala Phe Ser Pro Arg
        1155                1160                1165 agt cca gcc tgg att cca gtg cct gct cgc aga gag gca gag aag          3809
Ser Pro Ala Trp Ile Pro Val Pro Ala Arg Arg Glu Ala Glu Lys
            1170                1175                1180 ccc act cgg gaa gag cgg aag tca cca gag gac aag aaa tcc atg          3854
Pro Thr Arg Glu Glu Arg Lys Ser Pro Glu Asp Lys Lys Ser Met
        1185                1190                1195 atc ctc agc gtc ttg gac acg tcc ttg caa cgg cca gct ggc ctc          3899
Ile Leu Ser Val Leu Asp Thr Ser Leu Gln Arg Pro Ala Gly Leu
            1200                1205                1210 att gtt gtg cat gcc acc agc aat gga cag gag ccc aac agg ctg          3944
Ile Val Val His Ala Thr Ser Asn Gly Gln Glu Pro Asn Arg Leu
            1215                1220                1225 ggg gct gaa gag gag cgc ccg ggt act ccg gag ctg gcc cca acc          3989
Gly Ala Glu Glu Glu Arg Pro Gly Thr Pro Glu Leu Ala Pro Thr
```

```
                      1230                1235                1240
ccc atg cag gca  gca gct gtg gca  gag ccc atg cca  agc cca cga              4034
Pro Met Gln Ala  Ala Ala Val Ala  Glu Pro Met Pro  Ser Pro Arg
            1245                1250                1255 gcc caa ccc cct  ggc aac atc cca  gca gat ccc ggg  cca agc caa              4079
Ala Gln Pro Pro  Gly Asn Ile Pro  Ala Asp Pro Gly  Pro Ser Gln
            1260                1265                1270 ggc aac tca gag  gag gag cca aag  ctg gta ttc gct  gtg aac ctg              4124
Gly Asn Ser Glu  Glu Glu Pro Lys  Leu Val Phe Ala  Val Asn Leu
            1275                1280                1285 cca cct gct caa  ctg tcc tcc aac  gat gag gag acc  aga gag gag              4169
Pro Pro Ala Gln  Leu Ser Ser Asn  Asp Glu Glu Thr  Arg Glu Glu
            1290                1295                1300 ctg gcc cgc att  ggg cta gtg cca  ccc cct gaa gag  ttt gcc aat              4214
Leu Ala Arg Ile  Gly Leu Val Pro  Pro Pro Glu Glu  Phe Ala Asn
            1305                1310                1315 ggg atc ctg ctg  gcc acc cca ccc  cca gga ccg ggc  ccc ttg ccc              4259
Gly Ile Leu Leu  Ala Thr Pro Pro  Pro Gly Pro Gly  Pro Leu Pro
            1320                1325                1330 acc acg gta ccc  agc ccg gcc tca  ggg aag ccc agc  agc gag ctg              4304
Thr Thr Val Pro  Ser Pro Ala Ser  Gly Lys Pro Ser  Ser Glu Leu
            1335                1340                1345 ccc cct gcc ccg  gag tct gca gct  gac tct gga gta  gag gag gcc              4349
Pro Pro Ala Pro  Glu Ser Ala Ala  Asp Ser Gly Val  Glu Glu Ala
            1350                1355                1360 gac act cga agc  tcc agt gac ccc  cac ctg gag acc  aca agc acc              4394
Asp Thr Arg Ser  Ser Ser Asp Pro  His Leu Glu Thr  Thr Ser Thr
            1365                1370                1375 att tcc aca gtg  tcc agc atg tcc  acc ctg agc tcg  gag agt gga              4439
Ile Ser Thr Val  Ser Ser Met Ser  Thr Leu Ser Ser  Glu Ser Gly
            1380                1385                1390 gaa ctc act gac  acc cac acc tcc  ttt gcc gat gga  cac act ttt              4484
Glu Leu Thr Asp  Thr His Thr Ser  Phe Ala Asp Gly  His Thr Phe
            1395                1400                1405 cta ctc gag aag  cca cca gtg cct  ccc aag ccc aaa  ctc aag tcc              4529
Leu Leu Glu Lys  Pro Pro Val Pro  Pro Lys Pro Lys  Leu Lys Ser
            1410                1415                1420 ccg ctg ggg aag  ggg ccg gtg acc  ttc agg ggc ccg  ctg ctg aag              4574
Pro Leu Gly Lys  Gly Pro Val Thr  Phe Arg Gly Pro  Leu Leu Lys
            1425                1430                1435 caa tcc tcg gac  agt gag ctc atg  gcc cag cag cac  cat gcc acc              4619
Gln Ser Ser Asp  Ser Glu Leu Met  Ala Gln Gln His  His Ala Thr
            1440                1445                1450 tct act ggg ttg  act tct gct gct  ggg cct gcc cgc  cct cgc tac              4664
Ser Thr Gly Leu  Thr Ser Ala Ala  Gly Pro Ala Arg  Pro Arg Tyr
            1455                1460                1465 ctc ttc cag aga  agg tcc aag ctg  tgg ggg gac ccc  gtg gag agt              4709
Leu Phe Gln Arg  Arg Ser Lys Leu  Trp Gly Asp Pro  Val Glu Ser
            1470                1475                1480 cgg ggg ctc cct  ggg cct gag gat  gac aaa cca act  gtg atc agt              4754
Arg Gly Leu Pro  Gly Pro Glu Asp  Asp Lys Pro Thr  Val Ile Ser
            1485                1490                1495 gag ctc agc tcc  cgt ctg cag cag  ctg aat aaa gac  act cgc tcc              4799
Glu Leu Ser Ser  Arg Leu Gln Gln  Leu Asn Lys Asp  Thr Arg Ser
            1500                1505                1510 ttg ggg gag gaa  cca gtt ggt ggc  ctg ggt agc ctg  ctg gac cct              4844
Leu Gly Glu Glu  Pro Val Gly Gly  Leu Gly Ser Leu  Leu Asp Pro
            1515                1520                1525 gct aag aag tcg  ccc att gca gca  gct cgc tgc gcg  gtg gtc ccg              4889
```

-continued

```
                Ala Lys Lys Ser Pro Ile Ala Ala Ala Arg Cys Ala Val Val Pro
                        1530            1535            1540 agt gcc ggc tgg ctc ttc agc agc ctc ggt gag ctg agc acc atc       4934
Ser Ala Gly Trp Leu Phe Ser Ser Leu Gly Glu Leu Ser Thr Ile
        1545            1550            1555 tca gcg cag cgc agc ccc ggg ggc ccg ggc gga ggg gcc tcc tac       4979
Ser Ala Gln Arg Ser Pro Gly Gly Pro Gly Gly Gly Ala Ser Tyr
        1560            1565            1570 tcg gtg cgg ccc agc ggc cgg tac ccc gtg gcg aga cga gcc ccg       5024
Ser Val Arg Pro Ser Gly Arg Tyr Pro Val Ala Arg Arg Ala Pro
        1575            1580            1585 agc cca gtg aaa ccc gca tcg ctg gag cgg gtg gag ggg ctg ggg       5069
Ser Pro Val Lys Pro Ala Ser Leu Glu Arg Val Glu Gly Leu Gly
        1590            1595            1600 gcg ggc gtg gga ggc gcg ggg cgg ccc ttc ggc ctc acg cct ccc       5114
Ala Gly Val Gly Gly Ala Gly Arg Pro Phe Gly Leu Thr Pro Pro
        1605            1610            1615 acc atc ctc aag tcg tcc agc ctc tcc atc ccg cac gaa ccc aag       5159
Thr Ile Leu Lys Ser Ser Ser Leu Ser Ile Pro His Glu Pro Lys
        1620            1625            1630 gaa gtg cgc ttc gtg gtg cga agt gcg agt gcg cgc agc cgc tcc       5204
Glu Val Arg Phe Val Val Arg Ser Ala Ser Ala Arg Ser Arg Ser
        1635            1640            1645 ccc tca cca tct ccg ctg ccc tcg cct tct cct ggc tct ggc ccc       5249
Pro Ser Pro Ser Pro Leu Pro Ser Pro Ser Pro Gly Ser Gly Pro
        1650            1655            1660 agt gcc ggc ccg cgt cgg cca ttt caa cag aag ccc ctg cag ctt       5294
Ser Ala Gly Pro Arg Arg Pro Phe Gln Gln Lys Pro Leu Gln Leu
        1665            1670            1675 tgg agc aag ttc gat gtg ggc gac tgg ctg gag agc atc cac tta       5339
Trp Ser Lys Phe Asp Val Gly Asp Trp Leu Glu Ser Ile His Leu
        1680            1685            1690 ggc gag cac cga gac cgc ttc gag gac cat gag atc gaa ggc gca       5384
Gly Glu His Arg Asp Arg Phe Glu Asp His Glu Ile Glu Gly Ala
        1695            1700            1705 cac ctg cct gcg ctc acc aag gaa gac ttc gtg gag ctg gga gtc       5429
His Leu Pro Ala Leu Thr Lys Glu Asp Phe Val Glu Leu Gly Val
        1710            1715            1720 aca cgc gtt ggc cac cgc atg aac atc gag cgt gcg ctc agg cag       5474
Thr Arg Val Gly His Arg Met Asn Ile Glu Arg Ala Leu Arg Gln
        1725            1730            1735 ctg gat ggc agc tgacgcccct ccctctcc tgttcctgct gcgccctgcc        5526
Leu Asp Gly Ser
        1740 ggcagggccc ccacccctac tccaggccgc aggctcggct cgcccctac cacggcgccc  5586 gggccaggaa tgttgcatga atcgtcctgt ttgctgttgc ttggagactt gccctgtaca  5646 ttgcttagtg ccctccccctg ccgctgaacc ccacccagca cacagtaagg gcgcggacca  5706 gggggggctgg gtggaagggg gttggggcag ggtgctctgg cctgaccacc tcctccacag   5766 ctcctggtgg ccattcttcc agaggggaa cctagtccag catgcgaggt caggacacgc    5826 cttggtgact cggggggagg ggggagacat tgggggttctc gataggggcc aaggagcccc    5886 ctgtttttaca tatttttaatc cactctatat ttggaaagag aaaaggaaca aatatctctg  5946 tccgtaacag ttcccgccct cttcccctca agtcctctcg ctggtccgcc cacagctacc   6006 cagtcttcca tctccggccc ctcactgcca cccccatatag ggcaggggac actccagctg  6066 gcctggggtt agccagggtc ctgcagccc accctgggga ccccggctca gccccccttcc   6126
```

-continued

```
ctcgctgagc tatagtatgc cccacccacc ctttaggtgc tgctcagggg gacgggtggc    6186
aggcattgcc tgctgggcac tagcagggcc aggtggcctg ggagattatt gccctggggc    6246
tgggccccgg taacccaacc ccagccatca tcttcacagg gtctctccca aaggaggggt    6306
ctaacctttc cccacttctt gggcaactac agcagagaag cctccctgcc tcgcgcccca    6366
aagactcccc aattcctgcc ctgtgtgtgt gcaccacatg tgtgtgtgca cgcctgcgtg    6426
cttgtgaaaa ttgggtgtgg ctgagcgcat gggtgccctg tatgtgcttg attgtggagt    6486
ggtccccagg ggctgttctg gatgggtggg aggttgagga agcttgcaca ggggtgcatg    6546
catgggtgtg tgcctgtgaa agggccctgt cttctccaaa gaaaggctgt cctgctcttg    6606
ggtcctgctg ttttctcagc ctgttctccc tgaacctcac ccagcttaag cagggggttct   6666 tggtgaatcc tttcagcttt gggaggcctc aagggctccc gtgcaggcag cacccctttg    6726
ggcttctaag ggaattgtgg ggaccactaa aatcaggcca caacagccct tggagagagg    6786
caaagactcc tgagggtacc ctggcccccc ttactgtgac tcctcacaat tcagcaatga    6846
cctgtggggc gggggggcctt gggcattttt taacataggg tttggagtct ggactaagct    6906
ccatccacgt cactcacaag tttctgtttc tatttctagc ttttttttaat aaaatatata   6966 tatatatata tataaaagac agaaaacagg tgttttcatg gcccaggggc ttggcacgcc    7026
ggtctgtgcc cacccgcccc gccccaccct ggccaccgg ccccattcct tagacacaga    7086
gtcacgccca ctaaccctct taccaacaga gcaggtcaca cacacagcag cggtcactgt    7146
aacagactgc cacatacaca gtctcacatt tacctgtggg tttttggttc tgttcagttt    7206 gggttttttaa ctttacaggg tcagttccgc ttcatccccc ttttgtatgg agttccatct   7266
cggggctttc aaccccctgc tccagtcctg aggcctcctg accctgacgt tgtgatacac    7326
cccacagaga tctatgtttc ttatattatt attattaata ataattatta taatattatg    7386
taataaattt ataagaaatg aaaaaaaaaa aaaaaaa                             7424
```

<210> SEQ ID NO 40
<211> LENGTH: 1740
<212> TYPE: PRT
<213> ORGANISM: Rattus norvegicus

<400> SEQUENCE: 40

```
Met Asp Gly Pro Gly Ala Ser Ala Val Val Arg Val Gly Ile Pro
1               5                   10                  15

Asp Leu Gln Gln Thr Lys Cys Leu Arg Leu Asp Pro Thr Ala Pro Val
            20                  25                  30

Trp Ala Lys Gln Arg Val Leu Cys Ala Leu Asn His Ser Leu Gln
        35                  40                  45

Asp Ala Leu Asn Tyr Gly Leu Phe Gln Pro Pro Ser Arg Gly Arg Ala
    50                  55                  60

Gly Lys Phe Leu Asp Glu Glu Arg Leu Leu Gln Asp Tyr Pro Pro Asn
65                  70                  75                  80

Leu Asp Thr Pro Leu Pro Tyr Leu Glu Phe Arg Tyr Lys Arg Arg Val
                85                  90                  95

Tyr Ala Gln Asn Leu Ile Asp Asp Lys Gln Phe Ala Lys Leu His Thr
            100                 105                 110

Lys Ala Asn Leu Lys Lys Phe Met Asp Tyr Val Gln Leu His Ser Thr
        115                 120                 125

Asp Lys Val Ala Arg Leu Leu Asp Lys Gly Leu Asp Pro Asn Phe His
    130                 135                 140
```

-continued

```
Asp Pro Asp Ser Gly Glu Cys Pro Leu Ser Leu Ala Ala Gln Leu Asp
145                 150                 155                 160

Asn Ala Thr Asp Leu Leu Lys Val Leu Arg Asn Gly Ala His Leu
            165                 170                 175

Asp Phe Arg Thr Arg Asp Gly Leu Thr Ala Val His Cys Ala Thr Arg
                180                 185                 190

Gln Arg Asn Ala Gly Ala Leu Thr Thr Leu Leu Asp Leu Gly Ala Ser
        195                 200                 205

Pro Asp Tyr Lys Asp Ser Arg Gly Leu Thr Pro Leu Tyr His Ser Ala
    210                 215                 220

Leu Gly Gly Asp Ala Leu Cys Cys Glu Leu Leu His Asp His
225                 230                 235                 240

Ala Gln Leu Gly Thr Thr Asp Glu Asn Gly Trp Gln Glu Ile His Gln
                245                 250                 255

Ala Cys Arg Phe Gly His Val Gln His Leu Glu His Leu Leu Phe Tyr
            260                 265                 270

Gly Ala Asn Met Gly Ala Gln Asn Ala Ser Gly Asn Thr Ala Leu His
        275                 280                 285

Ile Cys Ala Leu Tyr Asn Gln Glu Ser Cys Ala Arg Val Leu Leu Phe
290                 295                 300

Arg Gly Ala Asn Lys Asp Val Arg Asn Tyr Asn Ser Gln Thr Ala Phe
305                 310                 315                 320

Gln Val Ala Ile Ile Ala Gly Asn Phe Glu Leu Ala Glu Val Ile Lys
                325                 330                 335

Thr His Lys Asp Ser Asp Val Val Pro Phe Arg Glu Thr Pro Ser Tyr
                340                 345                 350

Ala Lys Arg Arg Arg Leu Ala Gly Pro Ser Gly Leu Ala Ser Pro Arg
        355                 360                 365

Pro Leu Gln Arg Ser Ala Ser Asp Ile Asn Leu Lys Gly Asp Gln Pro
    370                 375                 380

Ala Ala Ser Pro Gly Pro Thr Leu Arg Ser Leu Pro His Gln Leu Leu
385                 390                 395                 400

Leu Gln Arg Leu Gln Glu Glu Lys Asp Arg Asp Arg Asp Gly Glu Gln
                405                 410                 415

Glu Asn Asp Ile Ser Gly Pro Ser Ala Gly Arg Gly His Ser Lys
                420                 425                 430

Ile Ser Pro Ser Gly Pro Gly Ser Gly Pro Ala Pro Gly Pro Gly
        435                 440                 445

Pro Ala Ser Pro Ala Pro Pro Ala Pro Pro Arg Gly Pro Lys Arg
    450                 455                 460

Lys Leu Tyr Ser Ala Val Pro Gly Arg Lys Phe Ile Ala Val Lys Ala
465                 470                 475                 480

His Ser Pro Gln Gly Glu Gly Glu Ile Pro Leu His Arg Gly Glu Ala
            485                 490                 495

Val Lys Val Leu Ser Ile Gly Glu Gly Gly Phe Trp Glu Gly Thr Val
                500                 505                 510

Lys Gly Arg Thr Gly Trp Phe Pro Ala Asp Cys Val Glu Glu Val Gln
        515                 520                 525

Met Arg Gln Tyr Asp Thr Arg His Glu Thr Arg Glu Asp Arg Thr Lys
    530                 535                 540

Arg Leu Phe Arg His Tyr Thr Val Gly Ser Tyr Asp Ser Leu Thr Ser
545                 550                 555                 560

His Ser Asp Tyr Val Ile Asp Asp Lys Val Ala Ile Leu Gln Lys Arg
```

```
                    565                 570                 575
Asp His Glu Gly Phe Gly Phe Val Leu Arg Gly Ala Lys Ala Glu Thr
                580                 585                 590

Pro Ile Glu Glu Phe Thr Pro Thr Pro Ala Phe Pro Ala Leu Gln Tyr
            595                 600                 605

Leu Glu Ser Val Asp Val Glu Gly Val Ala Trp Lys Ala Gly Leu Arg
        610                 615                 620

Thr Gly Asp Phe Leu Ile Glu Val Asn Gly Val Asn Val Val Lys Val
625                 630                 635                 640

Gly His Lys Gln Val Val Gly Leu Ile Arg Gln Gly Gly Asn Arg Leu
                645                 650                 655

Val Met Lys Val Val Ser Val Thr Arg Lys Pro Glu Glu Asp Ser Ala
            660                 665                 670

Arg Arg Arg Ala Pro Pro Pro Lys Arg Ala Pro Ser Thr Thr Leu
        675                 680                 685

Thr Leu Arg Ser Lys Ser Met Thr Ala Glu Leu Glu Glu Leu Ala Ser
690                 695                 700

Ile Arg Arg Arg Lys Gly Glu Lys Leu Asp Glu Ile Leu Ala Val Ala
705                 710                 715                 720

Ala Glu Pro Thr Leu Arg Pro Asp Ile Ala Asp Ala Asp Ser Arg Ala
                725                 730                 735

Ala Thr Val Lys Gln Arg Pro Thr Ser Arg Arg Ile Thr Pro Ala Glu
            740                 745                 750

Ile Ser Ser Leu Phe Glu Arg Gln Gly Leu Pro Gly Pro Glu Lys Leu
        755                 760                 765

Pro Gly Ser Leu Arg Lys Gly Ile Pro Arg Thr Lys Ser Val Gly Glu
    770                 775                 780

Asp Glu Lys Leu Ala Ser Leu Leu Glu Gly Arg Phe Pro Arg Ser Thr
785                 790                 795                 800

Ser Met Gln Asp Thr Val Arg Glu Gly Arg Gly Ile Pro Pro Pro Pro
                805                 810                 815

Gln Thr Ala Pro Pro Pro Pro Ala Pro Tyr Tyr Phe Asp Ser Gly
            820                 825                 830

Pro Pro Pro Thr Phe Ser Pro Pro Pro Pro Gly Arg Ala Tyr
        835                 840                 845

Asp Thr Val Arg Ser Ser Phe Lys Pro Gly Leu Glu Ala Arg Leu Gly
850                 855                 860

Ala Gly Ala Ala Gly Leu Tyr Asp Ser Gly Thr Pro Leu Gly Pro Leu
865                 870                 875                 880

Pro Tyr Pro Glu Arg Gln Lys Arg Ala Arg Ser Met Ile Ile Leu Gln
                885                 890                 895

Asp Ser Ala Pro Glu Val Gly Asp Val Pro Arg Pro Ala Pro Ala Ala
            900                 905                 910

Thr Pro Pro Glu Arg Pro Lys Arg Arg Pro Arg Pro Ser Gly Pro Asp
        915                 920                 925

Ser Pro Tyr Ala Asn Leu Gly Ala Phe Ser Ala Ser Leu Phe Ala Pro
    930                 935                 940

Ser Lys Pro Gln Arg Arg Lys Ser Pro Leu Val Lys Gln Leu Gln Val
945                 950                 955                 960

Glu Asp Ala Gln Glu Arg Ala Ala Leu Ala Val Gly Ser Pro Gly Pro
                965                 970                 975

Val Gly Gly Ser Phe Ala Arg Glu Pro Ser Pro Thr His Arg Gly Pro
            980                 985                 990
```

```
Arg Pro Gly Gly Leu Asp Tyr Ser   Ser Gly Glu Gly Leu   Gly Leu Thr
        995                 1000                1005

Phe Gly Gly Pro Ser Pro Gly   Pro Val Lys Glu Arg   Arg Leu Glu
    1010             1015                 1020

Glu Arg Arg Arg Ser Thr Val   Phe Leu Ser Val Gly   Ala Ile Glu
    1025             1030                 1035

Gly Asn Pro Pro Ser Ala Asp   Leu Pro Ser Leu Gln   Pro Ser Arg
    1040             1045                 1050

Ser Ile Asp Glu Arg Leu Leu   Gly Thr Gly Ala Thr   Thr Gly Arg
    1055             1060                 1065

Asp Leu Leu Leu Pro Ser Pro   Val Ser Ala Leu Lys   Pro Leu Val
    1070             1075                 1080

Gly Gly Pro Asn Leu Gly Pro   Ser Ser Ser Thr Phe   Ile His Pro
    1085             1090                 1095

Leu Thr Gly Lys Pro Leu Asp   Pro Ser Ser Pro Leu   Ala Leu Ala
    1100             1105                 1110

Leu Ala Ala Arg Glu Arg Ala   Leu Ala Ser Gln Thr   Pro Ser Arg
    1115             1120                 1125

Ser Pro Thr Pro Val His Ser   Pro Asp Ala Asp Arg   Pro Gly Pro
    1130             1135                 1140

Leu Phe Val Asp Val Gln Thr   Arg Asp Ser Glu Arg   Gly Pro Leu
    1145             1150                 1155

Ala Ser Pro Ala Phe Ser Pro   Arg Ser Pro Ala Trp   Ile Pro Val
    1160             1165                 1170

Pro Ala Arg Arg Glu Ala Glu   Lys Pro Thr Arg Glu   Glu Arg Lys
    1175             1180                 1185

Ser Pro Glu Asp Lys Lys Ser   Met Ile Leu Ser Val   Leu Asp Thr
    1190             1195                 1200

Ser Leu Gln Arg Pro Ala Gly   Leu Ile Val Val His   Ala Thr Ser
    1205             1210                 1215

Asn Gly Gln Glu Pro Asn Arg   Leu Gly Ala Glu Glu   Arg Pro
    1220             1225                 1230

Gly Thr Pro Glu Leu Ala Pro   Thr Pro Met Gln Ala   Ala Ala Val
    1235             1240                 1245

Ala Glu Pro Met Pro Ser Pro   Arg Ala Gln Pro Pro   Gly Asn Ile
    1250             1255                 1260

Pro Ala Asp Pro Gly Pro Ser   Gln Gly Asn Ser Glu   Glu Glu Pro
    1265             1270                 1275

Lys Leu Val Phe Ala Val Asn   Leu Pro Pro Ala Gln   Leu Ser Ser
    1280             1285                 1290

Asn Asp Glu Glu Thr Arg Glu   Glu Leu Ala Arg Ile   Gly Leu Val
    1295             1300                 1305

Pro Pro Pro Glu Glu Phe Ala   Asn Gly Ile Leu Leu   Ala Thr Pro
    1310             1315                 1320

Pro Pro Gly Pro Gly Pro Leu   Pro Thr Thr Val Pro   Ser Pro Ala
    1325             1330                 1335

Ser Gly Lys Pro Ser Ser Glu   Leu Pro Pro Ala Pro   Glu Ser Ala
    1340             1345                 1350

Ala Asp Ser Gly Val Glu Glu   Ala Asp Thr Arg Ser   Ser Ser Asp
    1355             1360                 1365

Pro His Leu Glu Thr Thr Ser   Thr Ile Ser Thr Val   Ser Ser Met
    1370             1375                 1380
```

-continued

```
Ser Thr Leu Ser Ser Glu Ser Gly Glu Leu Thr Asp Thr His Thr
    1385                1390                1395

Ser Phe Ala Asp Gly His Thr Phe Leu Leu Glu Lys Pro Pro Val
    1400                1405                1410

Pro Pro Lys Pro Lys Leu Lys Ser Pro Leu Gly Lys Gly Pro Val
    1415                1420                1425

Thr Phe Arg Gly Pro Leu Leu Lys Gln Ser Ser Asp Ser Glu Leu
    1430                1435                1440

Met Ala Gln Gln His His Ala Thr Ser Thr Gly Leu Thr Ser Ala
    1445                1450                1455

Ala Gly Pro Ala Arg Pro Arg Tyr Leu Phe Gln Arg Arg Ser Lys
    1460                1465                1470

Leu Trp Gly Asp Pro Val Glu Ser Arg Gly Leu Pro Gly Pro Glu
    1475                1480                1485

Asp Asp Lys Pro Thr Val Ile Ser Glu Leu Ser Ser Arg Leu Gln
    1490                1495                1500

Gln Leu Asn Lys Asp Thr Arg Ser Leu Gly Glu Glu Pro Val Gly
    1505                1510                1515

Gly Leu Gly Ser Leu Leu Asp Pro Ala Lys Lys Ser Pro Ile Ala
    1520                1525                1530

Ala Ala Arg Cys Ala Val Val Pro Ser Ala Gly Trp Leu Phe Ser
    1535                1540                1545

Ser Leu Gly Glu Leu Ser Thr Ile Ser Ala Gln Arg Ser Pro Gly
    1550                1555                1560

Gly Pro Gly Gly Gly Ala Ser Tyr Ser Val Arg Pro Ser Gly Arg
    1565                1570                1575

Tyr Pro Val Ala Arg Arg Ala Pro Ser Pro Val Lys Pro Ala Ser
    1580                1585                1590

Leu Glu Arg Val Glu Gly Leu Gly Ala Gly Val Gly Gly Ala Gly
    1595                1600                1605

Arg Pro Phe Gly Leu Thr Pro Pro Thr Ile Leu Lys Ser Ser Ser
    1610                1615                1620

Leu Ser Ile Pro His Glu Pro Lys Glu Val Arg Phe Val Val Arg
    1625                1630                1635

Ser Ala Ser Ala Arg Ser Arg Ser Pro Ser Pro Ser Pro Leu Pro
    1640                1645                1650

Ser Pro Ser Pro Gly Ser Gly Pro Ser Ala Gly Pro Arg Arg Pro
    1655                1660                1665

Phe Gln Gln Lys Pro Leu Gln Leu Trp Ser Lys Phe Asp Val Gly
    1670                1675                1680

Asp Trp Leu Glu Ser Ile His Leu Gly Glu His Arg Asp Arg Phe
    1685                1690                1695

Glu Asp His Glu Ile Glu Gly Ala His Leu Pro Ala Leu Thr Lys
    1700                1705                1710

Glu Asp Phe Val Glu Leu Gly Val Thr Arg Val Gly His Arg Met
    1715                1720                1725

Asn Ile Glu Arg Ala Leu Arg Gln Leu Asp Gly Ser
    1730                1735                1740

<210> SEQ ID NO 41
<211> LENGTH: 474
<212> TYPE: DNA
<213> ORGANISM: Homo sapiens
<220> FEATURE:
<221> NAME/KEY: CDS
```

<222> LOCATION: (1)..(435)

<400> SEQUENCE: 41

| | | | | | | | | | | | | | | | | |
|---|---|---|---|---|---|---|---|---|---|---|---|---|---|---|---|---|
| atg | tcc | aca | gcc | agg | gag | cag | cca | atc | ttc | agc | aca | cgg | gcg | cac | gtg | 48 |
| Met | Ser | Thr | Ala | Arg | Glu | Gln | Pro | Ile | Phe | Ser | Thr | Arg | Ala | His | Val | |
| 1 | | | | 5 | | | | | 10 | | | | | 15 | | |
| ttc | caa | att | gac | cca | gcc | acc | aag | cga | aac | tgg | atc | cca | gcg | ggc | aag | 96 |
| Phe | Gln | Ile | Asp | Pro | Ala | Thr | Lys | Arg | Asn | Trp | Ile | Pro | Ala | Gly | Lys | |
| | | | 20 | | | | | 25 | | | | | 30 | | | |
| cac | gca | ctc | act | gtc | tcc | tat | ttc | tac | gat | gcc | acc | cgc | aat | gtg | tac | 144 |
| His | Ala | Leu | Thr | Val | Ser | Tyr | Phe | Tyr | Asp | Ala | Thr | Arg | Asn | Val | Tyr | |
| | | | 35 | | | | | 40 | | | | | 45 | | | |
| cgc | atc | atc | agc | atc | gga | ggc | gcc | aag | gcc | atc | atc | aac | agc | act | gtc | 192 |
| Arg | Ile | Ile | Ser | Ile | Gly | Gly | Ala | Lys | Ala | Ile | Ile | Asn | Ser | Thr | Val | |
| | 50 | | | | | 55 | | | | | 60 | | | | | |
| act | ccc | aac | atg | acc | ttc | acc | aaa | act | tcc | cag | aag | ttc | ggg | cag | tgg | 240 |
| Thr | Pro | Asn | Met | Thr | Phe | Thr | Lys | Thr | Ser | Gln | Lys | Phe | Gly | Gln | Trp | |
| 65 | | | | | 70 | | | | | 75 | | | | | 80 | |
| gcc | gac | agt | cgc | gcc | aac | aca | gtc | tat | ggc | ctg | ggc | ttt | gcc | tct | gaa | 288 |
| Ala | Asp | Ser | Arg | Ala | Asn | Thr | Val | Tyr | Gly | Leu | Gly | Phe | Ala | Ser | Glu | |
| | | | | 85 | | | | | 90 | | | | | 95 | | |
| cag | cat | ctg | aca | cag | ttt | gcc | gag | aag | ttc | cag | gaa | gtg | aag | gaa | gca | 336 |
| Gln | His | Leu | Thr | Gln | Phe | Ala | Glu | Lys | Phe | Gln | Glu | Val | Lys | Glu | Ala | |
| | | | 100 | | | | | 105 | | | | | 110 | | | |
| gcc | agg | ctg | gcc | agg | gag | aaa | tct | cag | gat | ggc | tgg | ggt | ggg | ccc | cag | 384 |
| Ala | Arg | Leu | Ala | Arg | Glu | Lys | Ser | Gln | Asp | Gly | Trp | Gly | Gly | Pro | Gln | |
| | | 115 | | | | | 120 | | | | | 125 | | | | |
| tcg | gct | ctg | gtt | gtt | ggc | agc | ttt | ggg | gct | gtt | ttt | gag | ctt | ctc | att | 432 |
| Ser | Ala | Leu | Val | Val | Gly | Ser | Phe | Gly | Ala | Val | Phe | Glu | Leu | Leu | Ile | |
| | 130 | | | | | 135 | | | | | 140 | | | | | | gtg tagaatttct agatccccg attacatttc taagcgtga 474
Val
145

<210> SEQ ID NO 42
<211> LENGTH: 145
<212> TYPE: PRT
<213> ORGANISM: Homo sapiens

<400> SEQUENCE: 42

Met Ser Thr Ala Arg Glu Gln Pro Ile Phe Ser Thr Arg Ala His Val
1               5                  10                  15

Phe Gln Ile Asp Pro Ala Thr Lys Arg Asn Trp Ile Pro Ala Gly Lys
            20                  25                  30

His Ala Leu Thr Val Ser Tyr Phe Tyr Asp Ala Thr Arg Asn Val Tyr
        35                  40                  45

Arg Ile Ile Ser Ile Gly Gly Ala Lys Ala Ile Ile Asn Ser Thr Val
    50                  55                  60

Thr Pro Asn Met Thr Phe Thr Lys Thr Ser Gln Lys Phe Gly Gln Trp
65                  70                  75                  80

Ala Asp Ser Arg Ala Asn Thr Val Tyr Gly Leu Gly Phe Ala Ser Glu
                85                  90                  95

Gln His Leu Thr Gln Phe Ala Glu Lys Phe Gln Glu Val Lys Glu Ala
            100                 105                 110

Ala Arg Leu Ala Arg Glu Lys Ser Gln Asp Gly Trp Gly Gly Pro Gln
        115                 120                 125

Ser Ala Leu Val Val Gly Ser Phe Gly Ala Val Phe Glu Leu Leu Ile
    130                 135                 140

Val
145

<210> SEQ ID NO 43
<211> LENGTH: 859
<212> TYPE: DNA
<213> ORGANISM: Rattus norvegicus
<220> FEATURE:
<221> NAME/KEY: CDS
<222> LOCATION: (1)..(858)

<400> SEQUENCE: 43

| | | | | | | | | | | | | | | | | |
|---|---|---|---|---|---|---|---|---|---|---|---|---|---|---|---|---|
| cac | gcg | tcc | ggt | gtg | gtg | cac | ctt | ggc | atc | tgt | aag | cct | ttg | gtg | gag | 48 |
| His | Ala | Ser | Gly | Val | Val | His | Leu | Gly | Ile | Cys | Lys | Pro | Leu | Val | Glu | |
| 1 | | | | 5 | | | | | 10 | | | | | 15 | | |
| gag | gag | aag | gag | gag | aag | gag | gaa | cat | ttt | att | ttc | cat | tca | aac | aac | 96 |
| Glu | Glu | Lys | Glu | Glu | Lys | Glu | Glu | His | Phe | Ile | Phe | His | Ser | Asn | Asn | |
| | | | 20 | | | | | 25 | | | | | 30 | | | |
| aat | gga | gat | aac | agt | gag | tct | cca | gaa | acc | gtt | cac | gag | atc | cac | tca | 144 |
| Asn | Gly | Asp | Asn | Ser | Glu | Ser | Pro | Glu | Thr | Val | His | Glu | Ile | His | Ser | |
| | | 35 | | | | | 40 | | | | | 45 | | | | |
| tct | tta | atc | ctc | gag | gca | ccc | cag | gga | ttt | aga | gat | gag | ccg | tat | ctt | 192 |
| Ser | Leu | Ile | Leu | Glu | Ala | Pro | Gln | Gly | Phe | Arg | Asp | Glu | Pro | Tyr | Leu | |
| | 50 | | | | | 55 | | | | | 60 | | | | | |
| gaa | gaa | ctc | gtg | gat | gaa | cct | ttt | cta | gat | ttg | gga | aag | tct | ttg | cag | 240 |
| Glu | Glu | Leu | Val | Asp | Glu | Pro | Phe | Leu | Asp | Leu | Gly | Lys | Ser | Leu | Gln | |
| 65 | | | | | 70 | | | | | 75 | | | | | 80 | |
| ttc | caa | caa | aaa | gac | atg | gac | agc | agc | tca | gaa | gcc | tgg | gaa | atg | cat | 288 |
| Phe | Gln | Gln | Lys | Asp | Met | Asp | Ser | Ser | Ser | Glu | Ala | Trp | Glu | Met | His | |
| | | | | 85 | | | | | 90 | | | | | 95 | | |
| gaa | ttc | ctg | agc | cct | cgg | ctg | gag | aga | agg | ggt | gag | gaa | aga | gag | atg | 336 |
| Glu | Phe | Leu | Ser | Pro | Arg | Leu | Glu | Arg | Arg | Gly | Glu | Glu | Arg | Glu | Met | |
| | | | | 100 | | | | | 105 | | | | | 110 | | |
| ctt | gtt | gac | gag | gag | tat | gag | atc | tac | caa | gac | cgc | ctc | cgg | gac | atg | 384 |
| Leu | Val | Asp | Glu | Glu | Tyr | Glu | Ile | Tyr | Gln | Asp | Arg | Leu | Arg | Asp | Met | |
| | | | 115 | | | | | 120 | | | | | 125 | | | |
| gaa | gca | cac | cca | cca | cct | cct | cac | att | cgg | gag | ccc | act | tct | gca | tct | 432 |
| Glu | Ala | His | Pro | Pro | Pro | Pro | His | Ile | Arg | Glu | Pro | Thr | Ser | Ala | Ser | |
| | | 130 | | | | | 135 | | | | | 140 | | | | |
| ccc | agg | ctg | gat | ctc | cag | gcc | ggc | ccc | cag | tgg | ctg | cat | gct | gac | ctc | 480 |
| Pro | Arg | Leu | Asp | Leu | Gln | Ala | Gly | Pro | Gln | Trp | Leu | His | Ala | Asp | Leu | |
| 145 | | | | | 150 | | | | | 155 | | | | | 160 | |
| tca | gga | gga | gag | ata | ctc | gag | tgt | cac | gac | aca | gag | tcc | atg | atg | act | 528 |
| Ser | Gly | Gly | Glu | Ile | Leu | Glu | Cys | His | Asp | Thr | Glu | Ser | Met | Met | Thr | |
| | | | | 165 | | | | | 170 | | | | | 175 | | |
| gct | tat | ccc | cag | gag | atg | cag | gac | tat | agc | ttc | agc | acc | aca | gac | atg | 576 |
| Ala | Tyr | Pro | Gln | Glu | Met | Gln | Asp | Tyr | Ser | Phe | Ser | Thr | Thr | Asp | Met | |
| | | | | 180 | | | | | 185 | | | | | 190 | | |
| atg | aaa | gaa | aca | ttt | ggc | ctt | gac | tcc | cgg | ccg | ccc | atg | ccc | tcc | tct | 624 |
| Met | Lys | Glu | Thr | Phe | Gly | Leu | Asp | Ser | Arg | Pro | Pro | Met | Pro | Ser | Ser | |
| | | | 195 | | | | | 200 | | | | | 205 | | | |
| gaa | gga | aat | ggt | cag | cac | ggc | cga | ttt | gat | gac | ttg | gaa | cat | ctt | cat | 672 |
| Glu | Gly | Asn | Gly | Gln | His | Gly | Arg | Phe | Asp | Asp | Leu | Glu | His | Leu | His | |
| | | | 210 | | | | | 215 | | | | | 220 | | | |
| tca | cta | gca | agc | cac | ggc | ctg | gat | tta | ggc | atg | atg | act | cca | agt | gac | 720 |
| Ser | Leu | Ala | Ser | His | Gly | Leu | Asp | Leu | Gly | Met | Met | Thr | Pro | Ser | Asp | |
| 225 | | | | | 230 | | | | | 235 | | | | | 240 | |
| ttg | caa | ggc | cct | ggc | gtg | ctt | gta | gat | ctt | cca | gct | gtc | acc | cca | aga | 768 |
| Leu | Gln | Gly | Pro | Gly | Val | Leu | Val | Asp | Leu | Pro | Ala | Val | Thr | Pro | Arg | |
| | | | | 245 | | | | | 250 | | | | | 255 | | |
| aga | ggc | tgc | ggc | cgc | taa | gta | agt | aag | acg | tcg | agc | tct | aag | taa | gta | 816 |

```
Arg Gly Cys Gly Arg     Val Ser Lys Thr Ser Ser Lys     Val
            260                     265                 270 acg gcc gcc acc gcg gtg gag ctt tgg act tct tcg cca gag g           859
Thr Ala Ala Thr Ala Val Glu Leu Trp Thr Ser Ser Pro Glu
                275                 280
```

<210> SEQ ID NO 44
<211> LENGTH: 261
<212> TYPE: PRT
<213> ORGANISM: Rattus norvegicus

<400> SEQUENCE: 44

```
His Ala Ser Gly Val His Leu Gly Ile Cys Lys Pro Leu Val Glu
1               5                   10                  15

Glu Lys Glu Lys Glu His Phe Ile Phe His Ser Asn Asn
            20              25              30

Asn Gly Asp Asn Ser Glu Ser Pro Glu Thr Val His Glu Ile His Ser
            35              40                  45

Ser Leu Ile Leu Glu Ala Pro Gln Gly Phe Arg Asp Glu Pro Tyr Leu
        50              55                  60

Glu Glu Leu Val Asp Glu Pro Phe Leu Asp Leu Gly Lys Ser Leu Gln
65                  70                  75                  80

Phe Gln Gln Lys Asp Met Asp Ser Ser Glu Ala Trp Glu Met His
                85              90                  95

Glu Phe Leu Ser Pro Arg Leu Glu Arg Arg Gly Glu Glu Arg Glu Met
                100                 105                 110

Leu Val Asp Glu Glu Tyr Glu Ile Tyr Gln Asp Arg Leu Arg Asp Met
            115                 120                 125

Glu Ala His Pro Pro Pro His Ile Arg Glu Pro Thr Ser Ala Ser
        130                 135                 140

Pro Arg Leu Asp Leu Gln Ala Gly Pro Gln Trp Leu His Ala Asp Leu
145                 150                 155                 160

Ser Gly Gly Glu Ile Leu Glu Cys His Asp Thr Glu Ser Met Met Thr
                165                 170                 175

Ala Tyr Pro Gln Glu Met Gln Asp Tyr Ser Phe Ser Thr Thr Asp Met
                180                 185                 190

Met Lys Glu Thr Phe Gly Leu Asp Ser Arg Pro Pro Met Pro Ser Ser
            195                 200                 205

Glu Gly Asn Gly Gln His Gly Arg Phe Asp Asp Leu Glu His Leu His
        210                 215                 220

Ser Leu Ala Ser His Gly Leu Asp Leu Gly Met Met Thr Pro Ser Asp
225                 230                 235                 240

Leu Gln Gly Pro Gly Val Leu Val Asp Leu Pro Ala Val Thr Pro Arg
                245                 250                 255

Arg Gly Cys Gly Arg
            260
```

<210> SEQ ID NO 45
<211> LENGTH: 8
<212> TYPE: PRT
<213> ORGANISM: Rattus norvegicus

<400> SEQUENCE: 45

```
Val Ser Lys Thr Ser Ser Ser Lys
1               5
```

<210> SEQ ID NO 46

```
<211> LENGTH: 15
<212> TYPE: PRT
<213> ORGANISM: Rattus norvegicus

<400> SEQUENCE: 46

Val Thr Ala Ala Thr Ala Val Glu Leu Trp Thr Ser Ser Pro Glu
1               5                   10                  15

<210> SEQ ID NO 47
<211> LENGTH: 5
<212> TYPE: PRT
<213> ORGANISM: Artificial sequence
<220> FEATURE:
<223> OTHER INFORMATION: optimal ligand

<400> SEQUENCE: 47

Phe Pro Pro Pro Pro
1               5

<210> SEQ ID NO 48
<211> LENGTH: 4
<212> TYPE: PRT
<213> ORGANISM: Artificial sequence
<220> FEATURE:
<223> OTHER INFORMATION: motif ligand

<400> SEQUENCE: 48

Lys Ile Ala Ala
1

<210> SEQ ID NO 49
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 49
gacagcagag ccaacaccgt g                                         21

<210> SEQ ID NO 50
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 50
gtctgcagct ccatctccca c                                         21

<210> SEQ ID NO 51
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 51
cacggtgttg gctctgctgt c                                         21

<210> SEQ ID NO 52
<211> LENGTH: 21
<212> TYPE: DNA
<213> ORGANISM: Artificial sequence
<220> FEATURE:
<223> OTHER INFORMATION: oligonucleotide for PCR
```

<400> SEQUENCE: 52
atgggvgarc arccbatytt c          21

<210> SEQ ID NO 53
<211> LENGTH: 7
<212> TYPE: PRT
<213> ORGANISM: Artificial sequence
<220> FEATURE:
<223> OTHER INFORMATION: conserved amino acid sequence

<400> SEQUENCE: 53

Met Gly Glu Gln Pro Ile Phe
1               5

<210> SEQ ID NO 54
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 54
gagggtagcc agttcagcct c          21

<210> SEQ ID NO 55
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 55
gttgatctca ctgcattgtt c          21

<210> SEQ ID NO 56
<211> LENGTH: 18
<212> TYPE: PRT
<213> ORGANISM: Artificial sequence
<220> FEATURE:
<223> OTHER INFORMATION: peptide from Homer 1b/c

<400> SEQUENCE: 56

Ile Phe Glu Leu Thr Glu Leu Arg Asp Asn Leu Ala Lys Leu Leu Glu
1               5                   10                  15

Cys Ser

<210> SEQ ID NO 57
<211> LENGTH: 20
<212> TYPE: PRT
<213> ORGANISM: Artificial sequence
<220> FEATURE:
<223> OTHER INFORMATION: peptide from Homer 2a/b

<400> SEQUENCE: 57

Gly Lys Ile Asp Asp Leu His Asp Phe Arg Arg Gly Leu Ser Lys Leu
1               5                   10                  15

Gly Thr Asp Asn
            20

<210> SEQ ID NO 58
<211> LENGTH: 19
<212> TYPE: PRT
<213> ORGANISM: Artificial sequence
<220> FEATURE:
<223> OTHER INFORMATION: peptide from Homer 3

```
<400> SEQUENCE: 58

Arg Leu Phe Glu Leu Ser Glu Leu Arg Glu Gly Leu Ala Arg Leu Ala
1               5                   10                  15

Glu Ala Ala

<210> SEQ ID NO 59
<211> LENGTH: 10
<212> TYPE: PRT
<213> ORGANISM: Artificial sequence
<220> FEATURE:
<223> OTHER INFORMATION: peptide with Homer ligand peptide consensus

<400> SEQUENCE: 59

Leu Val Pro Pro Pro Glu Glu Phe Ala Asn
1               5                   10

<210> SEQ ID NO 60
<211> LENGTH: 10
<212> TYPE: PRT
<213> ORGANISM: Artificial sequence
<220> FEATURE:
<223> OTHER INFORMATION: peptide with Homer ligand peptide consensus

<400> SEQUENCE: 60

Pro Leu Pro Pro Pro Leu Glu Phe Ser Asn
1               5                   10

<210> SEQ ID NO 61
<211> LENGTH: 10
<212> TYPE: PRT
<213> ORGANISM: Artificial sequence
<220> FEATURE:
<223> OTHER INFORMATION: peptide with Homer ligand peptide consensus

<400> SEQUENCE: 61

Pro Leu Pro Pro Pro Leu Glu Phe Ala Asn
1               5                   10

<210> SEQ ID NO 62
<211> LENGTH: 10
<212> TYPE: PRT
<213> ORGANISM: Artificial sequence
<220> FEATURE:
<223> OTHER INFORMATION: peptide with Homer ligand peptide consensus

<400> SEQUENCE: 62

Phe Leu Pro Pro Pro Glu Ser Phe Asp Ala
1               5                   10

<210> SEQ ID NO 63
<211> LENGTH: 113
<212> TYPE: PRT
<213> ORGANISM: Rat

<400> SEQUENCE: 63

Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
                20                  25                  30

Thr Val Ser Tyr Phe Tyr Asp Ser Thr Arg Asn Val Tyr Arg Ile Ile
            35                  40                  45

Ser Leu Asp Gly Ser Lys Ala Ile Ile Asn Ser Thr Ile Thr Pro Asn
        50                  55                  60
```

Met Thr Phe Thr Lys Thr Ser Gln Lys Phe Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
                100                 105                 110

Ala

<210> SEQ ID NO 64
<211> LENGTH: 113
<212> TYPE: PRT
<213> ORGANISM: Drosophila

<400> SEQUENCE: 64

Met Gly Glu Gln Pro Ile Phe Thr Cys Gln Ala His Val Phe His Ile
1               5                   10                  15

Asp Pro Lys Thr Lys Arg Thr Trp Ile Thr Ala Ser Met Lys Ala Val
                20                  25                  30

Asn Val Ser Phe Phe Tyr Asp Ser Ser Arg Asn Leu Tyr Arg Ile Ile
                35                  40                  45

Ser Val Glu Gly Thr Lys Ala Val Ile Asn Ser Thr Ile Thr Pro Asn
        50                  55                  60

Met Thr Phe Thr Gln Thr Ser Gln Lys Phe Gly Gln Trp Ser Asp Val
65                  70                  75                  80

Arg Ala Asn Thr Val Tyr Gly Leu Gly Phe Ala Ser Glu Ala Glu Ile
                85                  90                  95

Thr Lys Phe Val Glu Lys Phe Gln Glu Val Lys Glu Ala Thr Lys Asn
                100                 105                 110

Ala

<210> SEQ ID NO 65
<211> LENGTH: 113
<212> TYPE: PRT
<213> ORGANISM: Drosophila

<400> SEQUENCE: 65

Met Thr Glu Gln Ser Ile Ile Gly Ala Arg Ala Ser Val Met Val Tyr
1               5                   10                  15

Asp Asp Asn Gln Lys Lys Trp Val Pro Ser Gly Ser Ser Ser Gly Leu
                20                  25                  30

Ser Lys Val Gln Ile Tyr His His Gln Gln Asn Asn Thr Phe Arg Val
        35                  40                  45

Val Gly Arg Lys Leu Gln Asp His Glu Val Val Ile Asn Cys Ser Ile
    50                  55                  60

Leu Lys Gly Leu Lys Tyr Asn Gln Ala Thr Ala Thr Phe His Gln Trp
65                  70                  75                  80

Arg Asp Ser Lys Phe Val Tyr Gly Leu Asn Phe Ser Ser Gln Asn Ala
                85                  90                  95

Glu Asn Phe Ala Arg Ala Met Met His Ala Leu Glu Val Leu Ser Gly
                100                 105                 110

Arg

<210> SEQ ID NO 66
<211> LENGTH: 114
<212> TYPE: PRT
<213> ORGANISM: Mouse

```
<400> SEQUENCE: 66

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
            100                 105                 110

Ser Gln

<210> SEQ ID NO 67
<211> LENGTH: 115
<212> TYPE: PRT
<213> ORGANISM: Mouse

<400> SEQUENCE: 67

Met Ser Glu Gln Ser Ile Cys Gln Ala Arg Ala Ser Val Met Val Tyr
1               5                   10                  15

Asp Asp Thr Ser Lys Lys Trp Val Pro Ile Lys Pro Gly Gln Gln Gly
            20                  25                  30

Phe Ser Arg Ile Asn Ile Tyr His Asn Thr Ala Ser Ser Thr Phe Arg
        35                  40                  45

Val Val Gly Val Lys Leu Gln Asp Gln Gln Val Val Ile Asn Tyr Ser
    50                  55                  60

Ile Val Lys Gly Leu Lys Tyr Asn Gln Ala Thr Pro Thr Phe His Gln
65                  70                  75                  80

Trp Arg Asp Ala Arg Gln Val Tyr Gly Leu Asn Phe Ala Ser Lys Glu
                85                  90                  95

Glu Ala Thr Thr Phe Ser Asn Ala Met Leu Phe Ala Leu Asn Ile Met
            100                 105                 110

Asn Ser Gln
        115

<210> SEQ ID NO 68
<211> LENGTH: 119
<212> TYPE: PRT
<213> ORGANISM: Drosophila

<400> SEQUENCE: 68

Gly His Leu Leu Ser Ser Phe Arg Leu Trp Ala Glu Val Phe His Val
1               5                   10                  15

Ser Ala Ser Gly Ala Gly Thr Val Lys Trp Gln Gln Val Ser Glu Asp
            20                  25                  30

Leu Val Pro Val Asn Ile Thr Cys Ile Gln Asp Ser Pro Glu Cys Ile
        35                  40                  45

Phe His Ile Thr Ala Tyr Asn Ser Gln Val Asp Lys Ile Leu Asp Val
    50                  55                  60

Arg Leu Val Gln Pro Gly Thr Arg Ile Gly Gln Ala Ser Glu Cys Phe
```

-continued

```
                65                  70                  75                  80
Val Tyr Trp Lys Asp Pro Met Thr Asn Asp Thr Trp Gly Leu Asn Phe
                    85                  90                  95

Thr Ser Pro Ile Asp Ala Lys Gln Phe Arg Glu Cys Cys Ser Pro Ser
                100                 105                 110

Phe Lys Phe Ser Arg Lys Ala
            115

<210> SEQ ID NO 69
<211> LENGTH: 116
<212> TYPE: PRT
<213> ORGANISM: Homo sapiens

<400> SEQUENCE: 69

Met Ser Glu Thr Val Ile Cys Ser Ser Arg Ala Thr Val Met Leu Tyr
1               5                   10                  15

Asp Asp Gly Asn Lys Arg Trp Leu Pro Ala Gly Thr Gly Pro Gln Ala
                20                  25                  30

Phe Ser Arg Val Gln Ile Tyr His Asn Pro Thr Ala Asn Ser Phe Arg
            35                  40                  45

Val Val Gly Arg Lys Met Gln Pro Asp Gln Gln Val Val Ile Asn Cys
        50                  55                  60

Ala Ile Val Arg Gly Val Lys Tyr Asn Gln Ala Thr Pro Asn Phe His
65                  70                  75                  80

Gln Trp Arg Asp Ala Arg Gln Val Trp Gly Leu Asn Phe Gly Ser Lys
                85                  90                  95

Glu Asp Ala Ala Gln Phe Ala Ala Gly Met Ala Ser Ala Leu Glu Ala
                100                 105                 110

Leu Glu Gly Gly
            115

<210> SEQ ID NO 70
<211> LENGTH: 110
<212> TYPE: PRT
<213> ORGANISM: Homo sapiens

<400> SEQUENCE: 70

Phe Leu Gly Lys Lys Cys Val Thr Met Ser Ser Ala Val Val Gln Leu
1               5                   10                  15

Tyr Ala Ala Asp Arg Asn Cys Met Trp Ser Lys Lys Cys Ser Gly Val
                20                  25                  30

Ala Cys Leu Val Lys Asp Asn Pro Gln Arg Ser His Phe Ile Arg Ile
            35                  40                  45

Phe Asp Ile Lys Asp Gly Lys Leu Trp Glu Gln Glu Leu Tyr Asn Asn
        50                  55                  60

Phe Val Tyr Asn Ser Pro Arg Gly Tyr Phe His Thr Phe Ala Gly Asp
65                  70                  75                  80

Thr Cys Gln Val Ala Leu Asn Phe Ala Asn Glu Glu Ala Lys Lys
                85                  90                  95

Phe Arg Lys Ala Val Thr Asp Leu Leu Gly Arg Arg Gln Arg
                100                 105                 110

<210> SEQ ID NO 71
<211> LENGTH: 114
<212> TYPE: PRT
<213> ORGANISM: Homo sapiens

<400> SEQUENCE: 71
```

```
Met Leu Gly Arg Lys Cys Leu Thr Leu Ala Thr Ala Val Val Gln Leu
1               5                   10                  15

Tyr Leu Ala Leu Pro Pro Gly Ala Glu His Trp Thr Lys Glu His Cys
                20                  25                  30

Gly Ala Val Cys Leu Val Lys Asp Asn Pro Gln Lys Ser Tyr Phe Ile
                35                  40                  45

Arg Leu Tyr Gly Leu Gln Ala Gly Arg Leu Leu Trp Glu Gln Glu Leu
        50                  55                  60

Tyr Ser Gln Leu Val Tyr Ser Thr Pro Thr Pro Phe Phe His Thr Phe
65                  70                  75                  80

Ala Gly Asp Asp Cys Gln Ala Gly Leu Asn Phe Ala Asp Glu Asp Glu
                85                  90                  95

Ala Gln Ala Phe Arg Ala Leu Val Gln Glu Lys Ile Gln Lys Arg Asn
                100                 105                 110

Gln Arg

<210> SEQ ID NO 72
<211> LENGTH: 16
<212> TYPE: PRT
<213> ORGANISM: Artificial sequence
<220> FEATURE:
<223> OTHER INFORMATION: Mutations in the EVH1 domain of the WASP gene

<400> SEQUENCE: 72

Pro Trp Met Pro Asp Ile Glu Val Pro Met Asp Cys Arg Ser Lys Lys
1               5                   10                  15
```

NUCLEIC ACID MOLECULE ENCODING HOMER 1B PROTEIN

This application claims the benefit of priority under 35 U.S.C. §119(e) to U.S. Provisional Application No. 60/097,334, filed Aug. 18, 1998, to U.S. Provisional Application No. 60/138,426, filed Jun. 10, 1999, to U.S. Provisional Application No. 60/138,493, filed Jun. 10, 1999, and to U.S. Provisional Application No. 60/138,494, filed Jun. 10, 1999, each of which is incorporated by reference in its entirety herein.

STATEMENT AS TO FEDERALLY SPONSORED RESEARCH

This invention was made with Government support under Grant No. RO1 DA10309, RO1 DA11742 and KO2 MH01152, awarded by the National Institutes of Health. The government may have certain rights in the invention.

FIELD OF THE INVENTION

The present invention relates generally to protein-protein interactions and more specifically to molecules involved in mediating receptor-activated or ion channel-mediated intracellular calcium mobilization or concentration.

BACKGROUND OF THE INVENTION

The mature central nervous system exhibits the capacity to alter cellular interactions as a function of the activity of specific neuronal circuits. This capacity is believed to underlie learning and memory storage, age-related memory loss, tolerance to and dependence on drugs of abuse, recovery from brain injury, epilepsy as well as aspects of postnatal development of the brain (Schatz, C., *Neuron*, 5:745, 1990). Currently, the role of activity-dependent synaptic plasticity is best understood in the context of learning and memory. Cellular mechanisms underlying activity-dependent plasticity are known to be initiated by rapid, transmitter-induced changes in membrane conductance properties and activation of intracellular signaling pathways (Bliss and Collingridge, *Nature*, 361:31, 1993). Several lines of evidence also indicate a role for rapid synthesis of mRNA and protein in long-term neuroplasticity. For example, classical studies of learning and memory demonstrate a requirement for protein synthesis in long-term, but not short-term memory (Flexner, et al., *Science*, 141:57, 1963; Agranoff, B., *Basic Neurochemistry*, 3rd Edition, 1981; Davis and Squire, *Physiol. Bull.*, 96:518, 1984), and long-term enhancement of synaptic connectivity, studied in cultured invertebrate neurons (Montarolo, et al., *Science*, 234:1249, 1986; Bailey, et al., *Neuron*, 9:749, 1992) or in the rodent hippocampus (Frey, et al., *Science*, 260:1661, 1993; Nguyen, et al., *Science*, 265:1104, 1994), is blocked by inhibitors of either RNA or protein synthesis. Importantly, inhibitors of macromolecular synthesis are most effective when administered during a brief time window surrounding the conditioning stimulus indicating a special requirement for molecules that are rapidly induced (Goelet, et al., *Nature*, 322:419, 1986).

Immediate early genes (IEGs) are rapidly induced in neurons by neurotransmitter stimulation and synaptic activity and are hypothesized to be part of the macromolecular response required for long-term plasticity (Goelet, et al., supra; Sheng and Greenberg, *Neuron*, 4:477, 1990; Silva and Giese, *Neurobiology*, 4:413, 1994). To identify cellular mechanisms that may contribute to long-term plasticity in the vertebrate brain, differential cloning techniques have been used to identify genes that are rapidly induced by depolarizing stimuli (Nedivi, et al., *Nature*, 363:713, 1993; Qian, et al., *Nature*, 361:453, 1993; Yamagata, et al., *Neuron*, 11:371, 1993; Yamagata, et al., *Learning and Memory* 1:140, 1994; Yamagata, et al.,*Journal of Biological Chemistry*, 269:16333, 1994; Andreasson and Worley, *Neuroscience*, 69:781, 1995; Lyford, et al., *Neuron*, 14:433, 1995). In contrast to the earlier focus on transcription factors, many of the newly characterized IEGs represent molecules that can directly modify the function of cells and include growth factors (Nedivi, et al., supra; Andreasson and Worley, supra), secreted enzymes that can modify the extracellular matrix, such as tissue plasminogen activator (Qian, et al., supra), enzymes involved in intracellular signaling, such as prostaglandin synthase (Yamagata, et al., supra), and a novel homolog of H-Ras, termed Rheb (Yamagata, et al., supra), as well as a novel cytoskeleton-associated protein, termed Arc (Lyford, et al., supra). The remarkable functional diversity of this set of rapid response genes is representative of the repertoire of cellular mechanisms that are likely to contribute to activity-dependent neuronal plasticity.

Pharmaceutical agents often act by modulating signaling between cells or within cells. For example, Prozac alters the reuptake of the neurotransmitter serotonin and enhances aspects of its signaling function in brain. Nonsteroidal antiinflammatory drugs (NSAIDs) act by inhibiting the activity of cyclooxygenase enzyme, which is involved in the signaling pathways of inflammation. Viagra modifies the intracellular guanylate cyclase response to autonomic neurotransmitters in erectile tissues. These, and other precedent setting pharmaceuticals, validate the notion that specific signaling pathways may be targeted for therapeutic development.

Cellular mechanisms that modify important intracellular signals can involve changes in intracellular calcium. This type of mechanism is used in brain neurons to adapt to changes in intercellular signaling, and is demonstrated to exert powerful effects on cellular responses induced by glutamate. Similar, though distinct, cellular mechanism may be used to modulate intracellular calcium signals in other tissues including heart, lung, liver and skeletal muscle. Compounds that can modify this mechanism can modulate natural transmitter signals and may exert therapeutic effects.

Classical studies demonstrated that activation of receptors on the cell surface evoke changes in the level of specific, diffusable molecules inside the cell. The regulated production of these molecules serves to signal events happening at the membrane surface to intracellular receptors and are therefore termed second messenger signaling pathways. Major second messenger pathways include the phosphoinositide pathway, which regulates intracellular calcium; the adenylate cyclase pathway, which regulates levels of cyclic AMP; the guanylate cyclase pathway, which regulates levels of cGMP; and the nitric oxide pathway which regulates NO.

The regulated release of intracellular calcium is essential to the function of all tissues. Each tissue possesses a distinct physiology that is dependent on receptor/transmitter-regulated release of intracellular calcium. For example, synaptic function is modulated in brain neurons by glutamate receptor regulated release of intracellular calcium. Contractility of cardiac and smooth muscle is also regulated by intracellular calcium. Recent reviews of the role of calcium signaling in cellular responses include: Berridge, *Nature* 386:759 (1997); Berridge, *J. Physiol.* (London) 499:291 (1997); Bootman et al., *Cell* 91:367 (1997).

Recent studies demonstrate that molecules that function together in signaling networks are frequently clustered together in macromolecular complexes. For example, components of the MAP kinase pathway form a complex of cytosolic kinases with their specific substrates (Davis, *Mol. Reprod. Dev.* 42:459 (1995)). Similarly, proteins such as AKAP function as scaffolds for specific kinases and their substrates (Lester and Scott, *Recent Prog. Horm. Res.* 52:409 (1997)). Recently, a multi-PDZ containing protein was identified in Drosophila (termed InaD) that couples the membrane-associated, light-activated ion channel with its effector enzymes (Tsunoda et al., *Nature* 388:243 (1997)). The biochemical consequence of this clustering is that the local concentrations of molecules that convey the signals between proteins are as high as possible. Consequently, signaling takes place efficiently. The clustering activity of these proteins is essential to normal function of the signaling cascade (Lester and Scott, supra 1997; Tsunoda et al., supra 1997). Accordingly, Accordingly, agents that alter these signaling complexes will modify the response due to transmitter or other form of cellular stimulation in a way that mimics more classical receptor agonists or antagonists. For example, a metabotropic glutamate receptor signaling may be blocked either at the receptor by conventional receptor antagonists or by uncoupling the metabotropic receptor from its intracellular IP3 receptor by agents that block the cross-linking activity of Homer family proteins.

The identification of molecules regulating the aggregation of neurotransmitter receptors at synapses is central to understanding the mechanisms of neural development, synaptic plasticity and learning. The most well characterized model for the synaptic aggregation of ionotropic receptors is the neuromuscular junction. Early work showed that contact between the axon of a motor neuron and the surface of a myotube rapidly triggers the accumulation of preexisting surface acetylcholine receptors (Anderson and Cohen, *J Physiol* 268:757–773, 1977; Frank and Fischbach, *J Cell Biol* 83:143–158, 1979). Subsequent work has shown that agrin, a complex glycoprotein secreted by the presynaptic terminal, activates a postsynaptic signal transduction cascade (reviewed by Colledge and Froehner, *Curr Opin Neurobiol* 8:357–63, 1998), that leads to receptor clustering by the membrane associated protein rapsyn.

SUMMARY OF THE INVENTION

Homer proteins, the products of neuronal immediate early genes, selectively bind the carboxy-termini of certain cell-surface receptors (e.g., group 1 metabotropic receptors), certain intracellular receptors and binding proteins (e.g., inositol trisphosphate receptors, ryanodine receptor, Shank proteins, I42). Many forms of Homer proteins contain a "coiled-coil" structure in the carboxy-terminal domain which mediates homo- and heteromultimerization between Homer proteins. The present invention is based on the seminal discovery that Homer plays a significant role in mediating receptor-activated calcium mobilization from internal stores and that Homer proteins regulate aspects of receptor clustering In one embodiment, a method is provided for identifying a compound that modulates a cellular response mediated by a cell-surface receptor. The method includes incubating a test compound and a cell expressing a cell-surface receptor and a Homer protein under conditions sufficient to permit the compound to interact with the cell, and exposing the cell to a cell-surface receptor ligand. A cellular response to the ligand by the cell incubated with the compound is compared with a cellular response of the cell not incubated with the compound wherein a difference in cellular response identify a compound that modulates a Homer-associated cellular response.

In another embodiment, a method is provided for identifying a compound that modulates a cellular response mediated by an intracellular receptor. The method includes incubating the compound, and a cell expressing an intracellular receptor and a Homer protein under conditions sufficient to permit the compound to interact with the cell and exposing the cell to conditions that activate the intracellular receptor. A cellular response by a cell incubated with the compound is compared with a cellular response of a cell not incubated with the compound wherein a difference in a cellular response identifies a compound that modulates a Homer-associated cellular response.

In yet another embodiment, a method is provided for identifying a compound that modulates receptor activated calcium mobilization in a cell. The method includes incubating the compound and a cell expressing a Homer protein under conditions sufficient to permit the compound to interact with the cell and exposing the cell to conditions sufficient to activate calcium mobilization. The receptor-activated calcium mobilization of a cell incubated with said the compound is compared with the receptor-activated calcium mobilization of a cell not incubated with the compound wherein a difference in calcium mobilization is indicative of an effect of the compound on Homer-associated calcium mobilization.

In another embodiment, a method is provided for modulating receptor-mediated calcium mobilization. The method includes exposing a cell expressing Homer protein to a compound in a sufficient amount to modulate the calcium mobilization that typically occurs when a cell is exposed to an amount of ligand sufficient to activate an intercellular signaling pathway that includes Homer protein.

In another embodiment, a method is provided for identifying a compound that inhibits Homer protein activity. The method includes identifying an inhibitor of Homer binding or crosslinking activity and identifying an inhibitor of Homer protein activity that forms covalent or non-covalent bonds with amino acids in a Homer protein binding site, based upon the crystal structure coordinates of Homer protein binding domain. and synthesizing the inhibitor.

In one embodiment, a method is provided for identifying a compound that affects the formation of cell surface receptors into clusters. The method includes incubating the compound and a cell expressing a Homer protein and a Homer interacting protein, e.g., a Shank protein, under conditions sufficient to allow the compound to interact with the cell and determining the effect of the compound on the formation of cell-surface receptors into clusters. The formation of cell-surface receptors into clusters of a cell contacted with the compound is compared to the formation of cell-surface receptors into clusters of a cell not contacted with the compound, wherein a difference in the formation of clusters is indicative of a compound that affects formation of cell surface receptors into clusters.

In another embodiment, a method is provided for treating a disorder associated with glutamate receptors, including metabotropic and NMDA-type glutamate receptors, in a subject. The method includes administering to a subject in need, a therapeutically effective amount of a compound that modulates Homer protein activity.

In another embodiment, a method is provided for treating a disorder associated with Homer protein activity including administering to a subject in need a therapeutically effective amount of a compound that modulates Homer protein activity. The compound may be identified by a method of the invention described herein.

In another embodiment, there is provided an isolated nucleic acid encoding Homer protein 1b, having the nucleotide sequence as set forth in SEQ ID NO:3 as well as an isolated Homer protein having substantially the same amino acid sequence as set forth in SEQ ID NO:4.

In another embodiment, there is provided an isolated nucleic acid encoding Homer protein 1c, having the nucleotide sequence as set forth in SEQ ID NO:5 as well as an isolated Homer protein having substantially the same amino acid sequence as set forth in SEQ ID NO:6.

In another embodiment, there is provided an isolated nucleic acid encoding Homer protein 2a, having the nucleotide sequence as set forth in SEQ ID NO:7 as well as an isolated Homer protein having substantially the same amino acid sequence as set forth in SEQ ID NO:8.

In another embodiment, there is provided an isolated nucleic acid encoding Homer protein 2b, having the nucleotide sequence as set forth in SEQ ID NO:9 as well as an isolated Homer protein having substantially the same amino acid sequence as set forth in SEQ ID NO:10.

In another embodiment, there is provided an isolated nucleic acid encoding Homer protein 3, having the nucleotide sequence as set forth in SEQ ID NO:11 as well as an isolated Homer protein having substantially the same amino acid sequence as set forth in SEQ ID NO:12.

In another embodiment, there is provided an isolated peptide having the amino acid sequence set forth in SEQ ID NO:13 an isolated peptide having the amino acid sequence set forth in SEQ ID NO:14.

In yet another embodiment, there is provided an isolated nucleic acid encoding Homer Interacting Protein, having the nucleotide sequence as set forth in SEQ ID NO:15 or 17 with a deduced amino acid sequence as set forth in SEQ ID NO:16 or 18, respectively.

In another embodiment, there is provided an isolated Homer Interacting Protein having substantially the same amino acid sequence as set forth in SEQ ID NO:19.

In another embodiment, there is provided an isolated Homer Interacting Protein having substantially the same amino acid sequence as set forth in SEQ ID NO:20.

In yet a further embodiment, there is provided a substantially purified polypeptide containing a proline rich region that is specifically capable of specifically binding to polypeptides of the Homer family.

In still another embodiment, there is provided a transgenic non-human animal having a transgene that expresses a Homer protein, e.g., Homer 1a, chromosomally integrated into the germ cells of the animal.

BRIEF DESCRIPTION OF THE DRAWINGS

FIG. 4. Structural Comparison of EVH1, PH, and PTB Domains. Ribbon diagrams (A)–(C) and surface representations (D)–(F) of the Homer 1 EVH1, β-spectrin PH, and IRS-1 PTB domains, respectively, are shown. All molecules are shown in a similar orientation, which is rotated about 45° about the vertical axis from orientations shown in FIG. 3. The β-spectrin PH domain is shown with bound inositol trisphosphate (Hyvonen et al, 1995). The IRS-1 domain is shown complexed to a phosphotyrosine-containing peptide derived from the insulin receptor (ECk et al., 1996).

FIGS. 7 through 45 are described in the following table.

Figure 1:
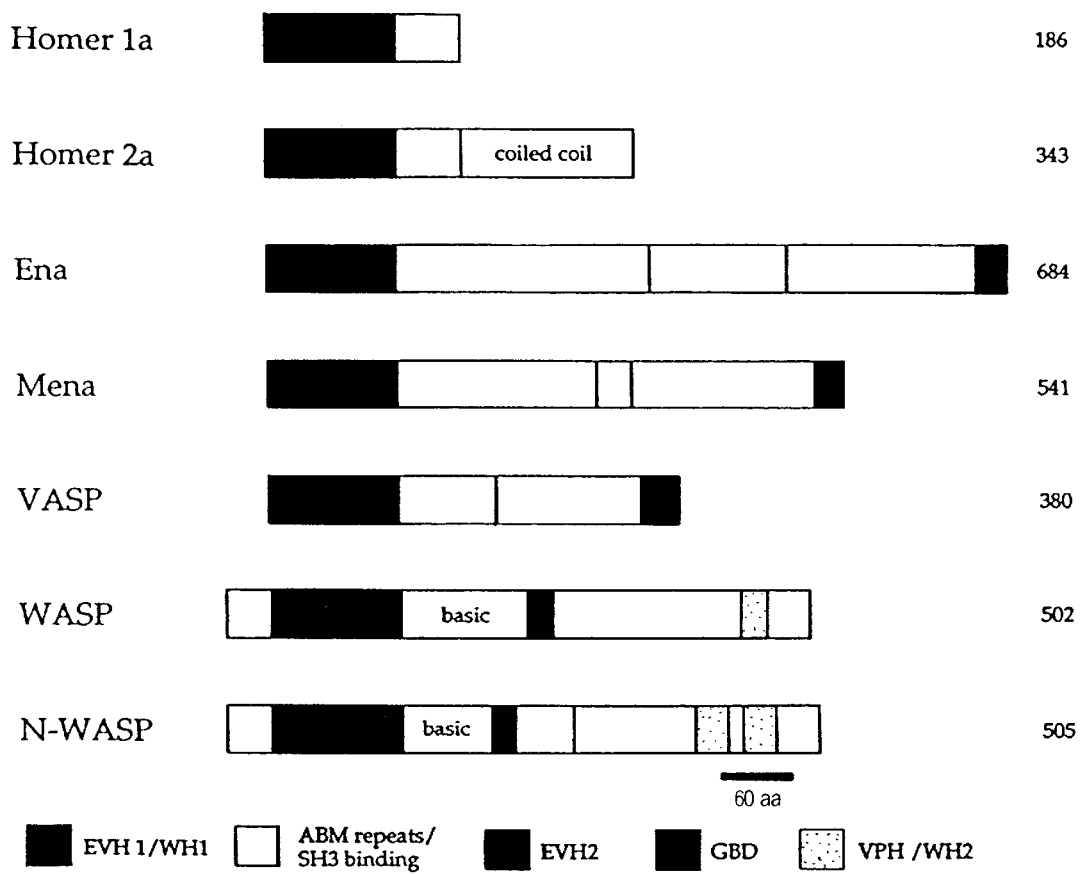
FIG. 1. Schematic Representation of EVH1 Domain-containing Proteins. EVH1 domains are found at or near the N-termini of Homer, Ena, Mena, VASP, and WASP proteins. Homer 1b/2/3 encode a CC domain which mediates multimerization between various Homer proteins. In ENA, Mena, VASP, WASP, and N-WASP, the EVH1 domain is followed by a central proline rich region of variable length. The proteins are drawn to the scale shown, and the respective amino acid lengths are shown at the right.
Figure 2:
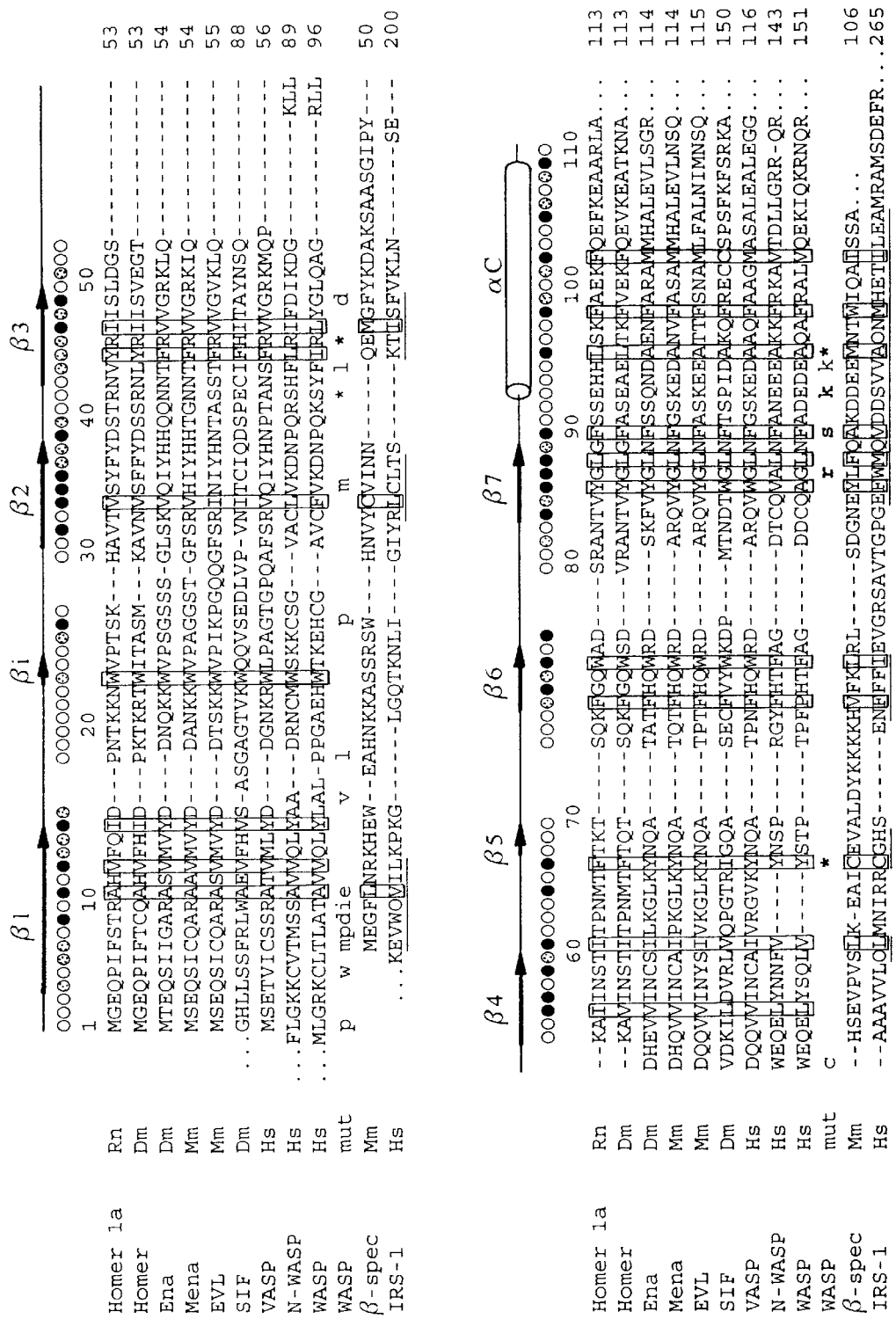
FIG. 2. Structure-Based Alignment of EVH1, PH, and PTB Domain Sequences. A structure-based sequence alignment between EVH1 domain and the β-spectrin PH domain and the IRS-1 PTB domain is shown. Species are indicated by Rn (rat), Hs (human), Mm (mouse), and Dm (Drosophila). Elements of the Homer EVH1 domain secondary structure are represented by arrows (β-strands), cylinders (α-helices), and lines (coils). Conserved residues (among EVH1 domains) are highlighted. The fractional solvent accessibility (FAS) of each residue in Homer 1a is indicated by ovals. Filled ovals=$0 \leq FAS \leq 0.1$ (buried); shaded ovals=$0.1 < FAS \leq 0.4$ (partially accessible); open ovals=$FAS > 0.4$. Mutations in the EVH1 domain of the WASP gene are indicated in lower case letter below the WASP amino acid sequence. Mutations that are associated with the severe WAS phenotype are show in bold letters (Zhu et al, 1997). Sites mutated to more then one residue are indicated by asterisks. Bold asterisk indicate residues that, when mutated, affect the interaction of WASP with WIP (Stewart et al., 1999). Residues of Homer, β-spectrin, and IRS-1 that align well following structural superposition and were used to calculate rms differences in Cα positions between these domains are underlined in the IRS-1 sequence. Gaps are indicated by dashes while continued sequences at amino- and carboxy-termini are indicated by periods. Residue numbering for Homer 1a is shown above its amino acid sequence. The number of the last included residue of each protein is shown it the end of each row. Sequences shown are Homer 1a Rn (SEQ ID NO:63), Homer Dm (SEQ ID NO:64), Ena Dm (SEQ ID NO:65), Mena Mm (SEQ ID NO:66), EVL Mm (SEQ ID NO:67), SIF Dm (SEQ ID NO:68), VASP Hs (SEQ ID NO:69), N-WASP Hs (SEQ ID NO:70), WASP Hs (SEQ ID NO:71), WASP mut (SEQ ID NO:72), β-spec Mm (SEQ ID NO:6), IRS-1 Hs (SEQ ID NO:5).
Figure 3:
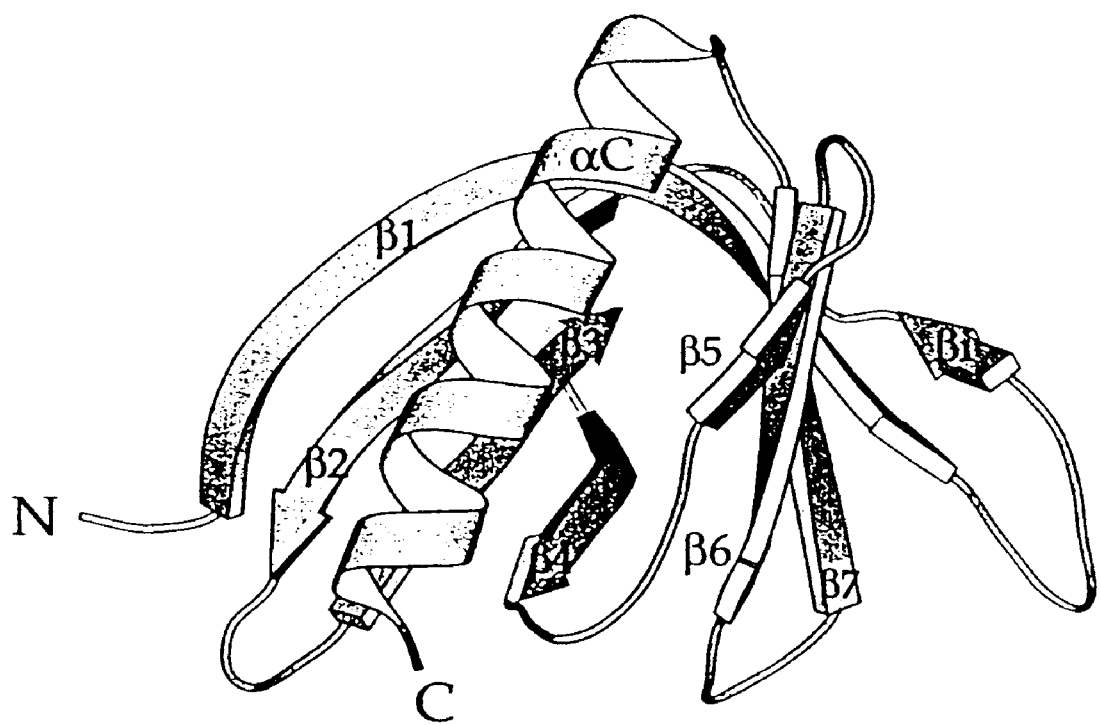
FIG. 3. Ribbon Diagram of the Homer 1a EVH 1 Domain. The amino and carboxy termini are indicated, and elements of secondary structure are labeled to correspond to homologous structures in PH and PTB domains. An additional short region of β-strand between β1 and β2 has been labeled βi.
Figure 5:
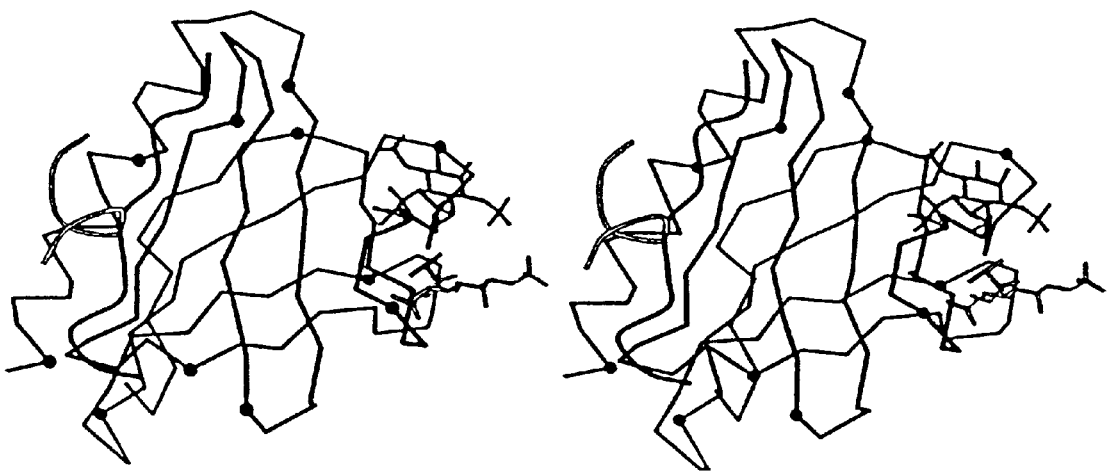
FIG. 5. Versatile Ligand Recognition by PH-Like Domain. Sterodiagram of a backbone trace of Homer 1 EVH1 doamin showing the relative positions of IP3 as bound by the β-spectrin and PLC-δ PH domains, as well as the peptide ligands for the IRS-1 and Numb PTB domains is shown. The orientations of the EVH1 domain is similar to that in FIG. 4. Ligand positions were determined by superimposing the backbone traces of the EVH1, PH and PTB domains in the program) (Jones et al., 1991).
Figure 6B:
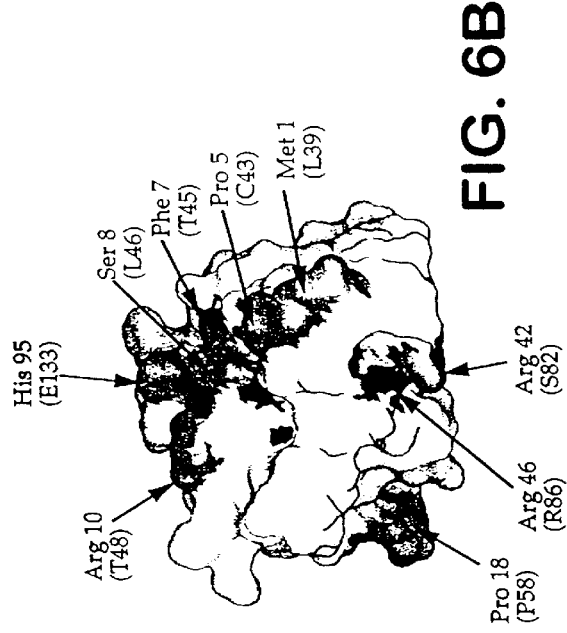
FIG. 6. Mapping of WAS-Causing and Homer Binding Mutations on the EVH1 Surface. (A) and (B) Surface representations of the Homer1 EVH1 doamin with sites homologous to positions of WASP mutations (in parentheses) colored according to solvent accessibility. Solvent exposed residues are shown in magenta, and buried or partially buried residues are shown in blue. Residue assignments are based on the sequence shown in FIG. 2. WASP EVH1 mutations are listed in Table 2. Surface representations of Homer 1 EVH1 domain showing the location of residues targeted by site-directed mutagenesis. Mutations that disrupt binding of Homer EVH1 to ligands in an in vitro binding assay are shown in red, while those that have no effect on binding are shown in light blue (see Table 3). The orientation of the EVH1 domain in panels A and C is identical to that in FIG. 4A and D. IN panels B and D, the molecule is rotated about 180 degrees about the vertical axis.
Figure 6D:
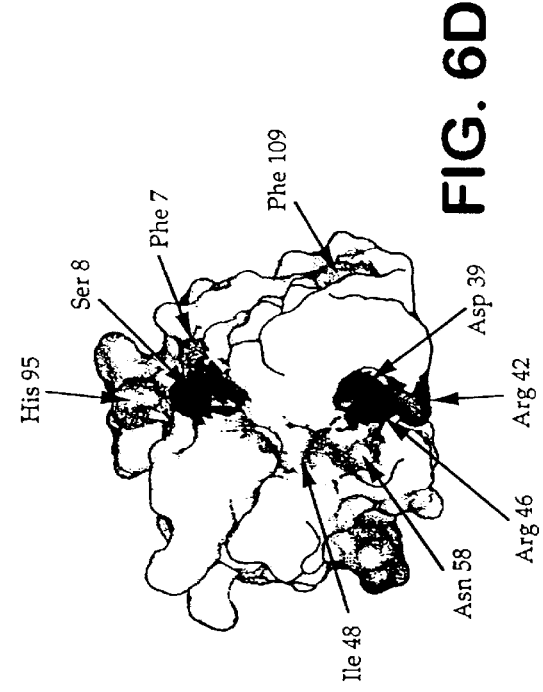
Figure 6A:
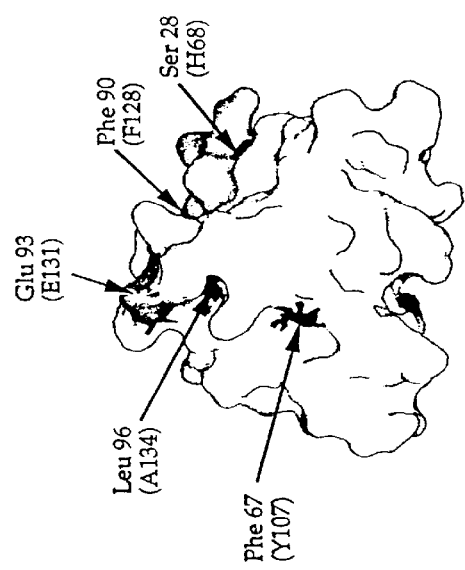
Figure 6C:
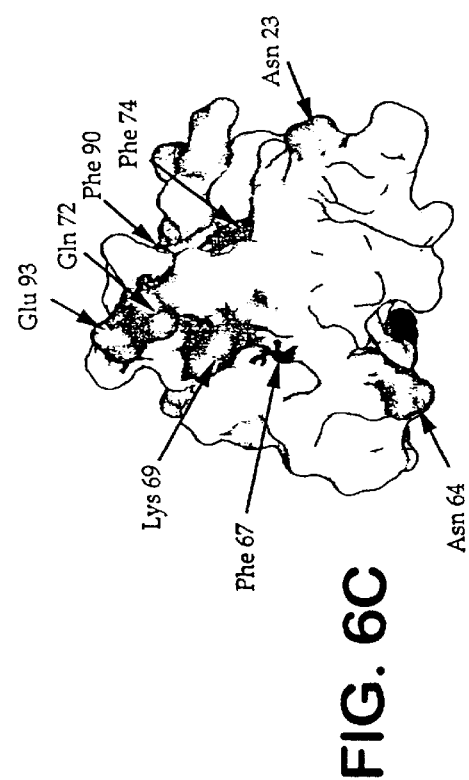

| Figures Homer Family Proteins and Homer Interacting Proteins | | |
|---|---|---|
| FIG. No. | SEQ ID No. | Sequence |
|  | 1 | Human Homer 1a (nucleic acid) |
| 7 | 2 | Human Homer 1a (amino acid) |
| 8 | 3 | Human Homer 1b (nucleic acid) |
| 9 | 4 | Human Homer 1b (amino acid) |
| 2 | 5 | IRS-1 |
| 2 | 6 | β-spectrin |
| 10 | 7 | Human Homer 2a (nucleic acid) |
| 11 | 8 | Human Homer 2a (amino acid) |
| 12 | 9 | Human Homer 2b (nucleic acid) |
| 13 | 10 | Human Homer 2b (amino acid) |
| 14 | 11 | Human Homer 3 (nucleic acid) |
| 15 | 12 | Human Homer 3 (amino acid) |
| 16 | 15 | Homer interacting protein: rat I30 (nucleic acid) |
| 17 | 16 | Homer interacting protein: rat I30 (amino acid) |
| 18-1 to 18-2 | 17 | Homer interacting protein: rat I42 (nucleic acid) |
| 19 | 18 | Homer interacting protein: rat I42 (amino acid) |
| 20 | 19 | Homer interacting protein: human I30 (nucleic acid) |
| 21 | 20 | Homer interacting protein: human I30 (amino acid) |
| 22-1 to 22-3 | 21 | Homer interacting protein: human I42 (nucleic acid) |
| 23 | 22 | Homer interacting protein: human I42 (amino acid) |
| 24 | 23 | Mouse Homer 1a (nucleic acid) |
| 25 | 24 | Mouse Homer 1a (amino acid) |
| 26 | 25 | Mouse Homer 1b (nucleic acid) |
| 27 | 26 | Mouse Homer 1b (amino acid) |
| 28 | 27 | Mouse Homer 2a (nucleic acid) |
| 29 | 28 | Mouse Homer 2a (amino acid) |
| 30 | 29 | Mouse Homer 2b (nucleic acid) |
| 31 | 30 | Mouse Homer 2b (amino acid) |
| 32 | 31 | Mouse Homer 3 (nucleic acid) |
| 33 | 32 | Mouse Homer 3 (amino acid) |
| 34-1 to 34-3 | 33 | Rat Homer 1a (nucleic acid) |
| 35 | 34 | Rat Homer 1a (amino acid) |
| 36-1 to 36-2 | 35 | Rat Homer 1b (nucleic acid) |
| 37 | 36 | Rat Homer 1b (amino acid) |
| 38-1 to 38-2 | 37 | Rat Homer 1c (nucleic acid) |
| 39 | 38 | Rat Homer 1c (amino acid) |
| 40-1 to 40-4 | 39 | Rat Shank 3a (nucleic acid) |
| 41 | 40 | Rat Shank 3a (amino acid) |
| 42 | 41 | Human Homer 3a (nucleic acid) |
| 43 | 42 | Human Homer 3a (amino acid) |
| 44 | 43 | Rat INADL partial nucleic acid sequence |
| 45 | 44 | Rat INADL partial amino acid sequence |

DETAILED DESCRIPTION OF THE INVENTION

Homer represents a family of proteins that selectively binds the carboxy-terminus of group 1 metabotropic receptors and is enriched at excitatory synapses (Brakeman et al., 1997). In the adult brain, Homer is rapidly and transiently induced by physiological synaptic stimuli that evoke ion-term potentiation in the hippocampus (Brakeman et al., 1997; Kato et al., 1997), and is also induced in the striatum by dopaminetic drugs of addiction (Brakeman et al., 1997). The first Homer gene identified, now termed Homer 1a (Brakeman et al., *Nature* 386:2284–288 (1997); GenBank Accession No. U92079), is a member of a family of closely related Homer proteins that are constitutively expressed in brain (Kato et al., 1998; Sun et al., 1998; Xiao et al., 1998). There are now three mammalian genes identified and at least six distinct transcripts expressed in brain (Xiao et al., 1998). All Homer family members, including Homer 1a, contain an amino-terminal region of about 110 amino acids that binds metabotropic glutamate receptors 1a and 5 (mGluR1a and mGluR5) (Xiao et al., 1998). The region of Homer that interacts with mGluR1a or 5 is termed "EVH1 domain", based on homology to similar domains in a family of proteins that include Drosophila Enabled (Gertler et al., 1996), mammalian VASP (Haffner et al., 1995) and the Wescott-Aldrige protein (WASP) (Ponting and Phillips, 1997; Symons et al., 1996). The EVH1 domain of Homer is conserved at a level of about 80% between Drosophila, rodent and human (Xiao et al., 1998) The Homer family EVH1 domain also can bind to intracellular receptors such as the inositol trisphosphate receptor and dyamin III. Binding of Homer proteins in the EVH1 region is mediated by an amino acid sequence motif that is rich in proline residues.

To explore the proline-rich motif and its role in Homer interactions, a deletion mutation strategy was used. A 50-amino acid deletion at the carboxy-terminal end of mGluR5 destroyed binding to Homer. By contrast, a 41 amino acid deletion of mGluR5 retained full binding activity. The intervening sequence is proline rich and shares sequence similarity with the previously described SH3 ligand sequence (Yu, 1994 ). A series of point mutants based on the known structure-function relationship for SH3 ligands was prepared and binding assays confirmed general characteristics of SH3 ligand binding, but also demonstrated that that the Homer binding site is distinct in the positioning of critical amino acids (Tu et al., 1998). A consensus for binding was determined to be PPXXFR, consistent with the observation that mutation of either of the proline residues or the phenylalanine, or a change in their relative position, interrupted binding. The arginine in the last position was preferred over other tested amino acids, but is not essential. Mutations were identically effective in interrupting binding to each of the Homer family members including Homer 1a, 1b/c, 2a/b, 3 and an EVH1 fragment (110 amino acids) of Homer 1. Thus, it was concluded that the interaction with mGluR5 was mediated by the Homer EVH1 domain.

To further explore Homer binding, mutations of mGluR5 were tested using a 250 amino acid carboxy-terminal fragment of the receptor, which had an identical effect on binding when placed in the full length mGluR5 protein (Tu et al., 1998). This exquisite sensitivity of Homer binding to changes in single amino acids within the Homer-ligand site was confirmed in other Homer-interacting proteins including mGluR1a (Tu et al., 1998), Shank (Tu et al., 1999), and 142 (see below). To further confirm that the interaction was mediated by a direct interaction at the Homer-ligand site (as opposed to a secondary allosteric effect on a remote binding site), synthetic 10-mer peptides with either the wild type, or F-to-R mutation were prepared. The wild type peptide blocked binding of mGluR1a or mGluR5 to each of the Homer family members (Tu et al., 1998). Approximately half of the binding was blocked at a peptide concentration of 3.4 micromolar. By contrast, the F-to-R mutant peptide did not alter binding at concentrations as high as 340 micromolar.

Most forms of Homer protein encode a carboxy-terminal domain with a "coiled-coil" structure. This coiled-coil domain mediates homo- and heteromultermization between Homer proteins (Kato et al., 1998; Xiao et al., 1998) and such multimers can be identified in normal brain tissue (Xiao et al., 1998). Homer proteins are enriched in brain tissue fractions from postsynaptic densities and are localized at the ultrastructural level to postsynaptic densities. Homer 1a differs from the other members of the Homer family in that Homer 1a is not constitutively expressed and it does not contain a carboxy terminal coiled-coil domain. Experimental data showing that Homer proteins interact with cell-surface receptors and with intracellular receptors, and form multimeric complexes with other Homer proteins indicates an important role for Homer proteins in intracellular signaling.

An exemplary polynucleotide encoding a Homer protein is set forth as SEQ ID NO: 1. The term "polynucleotide", "nucleic acid", "nucleic acid sequence", or "nucleic acid molecule" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. A polynucleotide encoding Homer includes "degenerate variants", sequences that are degenerate as a result of the genetic code. There are 20 natural amino acids, most of which are specified by more than one codon. Therefore, all degenerate nucleotide sequences are included in the invention as long as the amino acid sequence of a polypeptide encoded by the nucleotide sequence of SEQ ID NO: 1 is functionally unchanged.

A nucleic acid molecule encoding Homer includes sequences encoding functional Homer polypeptides as well as functional fragments thereof. As used herein, the term "functional polypeptide" refers to a polypeptide which possesses biological function or activity which is identified through a defined functional assay (e.g., EXAMPLE 3), and which is associated with a particular biologic, morphologic, or phenotypic alteration in the cell. The term "functional fragments of Homer polypeptide," refers to fragments of a Homer polypeptide that retain a Homer activity, e.g., the ability to interact with cell-surface or intracellular receptors or mediate intracellular calcium mobilization, and the like. Additionally, functional Homer fragments may act as competitive inhibitors of Homer binding, for example, biologically functional fragments, for example, can vary in size from a polypeptide fragment as small as an epitope capable of binding an antibody molecule to a large polypeptide capable of participating in the characteristic induction or programming of phenotypic changes within a cell.

A functional Homer polypeptide includes a polypeptide as set forth in SEQ ID NO:2 and conservative variations thereof. The terms "conservative variation" and "substantially similar" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The terms "conservative variation" and "substantially similar" also include the use of a substituted amino acid in place of an unsubstituted parent amino acid provided that antibodies raised to the substituted polypeptide also immunoreact with the unsubstituted polypeptide.

Also included are other Homer nucleic acid and amino acid sequences, including Homer 1b (SEQ ID NOS:3 and 4); Homer 1c (SEQ ID NOS:5 and 6); Homer 2a (SEQ ID NOS:7 and 8); Homer 2b (SEQ ID NOS:9 and 10); Homer 3 (SEQ ID NOS:11 and 12).

Cell-surface receptors are important intermediaries in intercellular signaling. A "cell-surface receptor" is a protein, usually having at least one binding domain on the outer surface of a cell where specific molecules may bind to, activate, or block the cell surface receptor. Cell surface receptors usually have at least one extracellular domain, a membrane spanning region ("transmembrane") and an intracellular domain. Activation of a cell-surface receptor can lead to changes in the levels of various molecules inside the cell. Several types of cell-surface receptors have been identified in a variety of cell types, including ligand-gated receptors, ligand-gated channels, voltage-activated receptors, voltage-activated channels, ion channels and the like.

One class of cell-surface receptor is excitatory amino acid receptors (EAA receptors) which are the major class of excitatory neurotransmitter receptors in the central nervous system. "EAA receptors" are membrane spanning proteins that mediate the stimulatory actions of glutamate and possibly other endogenous acidic amino acids. EAA are crucial for fast excitatory neurotransmission and they have been implicated in a variety of diseases including Alzheimer's disease, stroke schizophrenia, head trauma and epilepsy. EAA have also been implicated in the process of aging In addition, EAA are integral to the processes of long-term potentiation, one of the synaptic mechanisms underlying learning and memory. There are three main subtypes of EAA receptors: (1) the metabotropic or trans ACPD receptors; (2) the ionotropic NMDA receptors; and (3) the non-NMDA receptors, which include the AMPA receptors and kainate receptors.

Ionotropic glutamate receptors are generally divided into two classes: the NMDA and non-NMDA receptors. Both classes of receptors are linked to integral cation channels and share some amino acid sequence homology. GluR1–4 are termed AMPA ($\alpha$-amino-3-hydroxy-5-methylisoxazole-4-propionic acid) receptors because AMPA preferentially activates receptors composed of these subunits, while GluR5–7 are termed kainate receptors as these are preferentially sensitive to kainic acid. Thus, an "AMPA receptor" is a non-NMDA receptor that can be activated by AMPA. AMPA receptors include the GluR1–4 family, which form homo-oligomeric and hetero-oligomeric complexes which display different current-voltage relations and $Ca^{2+}$ permeability. Polypeptides encoded by GluR1–4 nucleic acid sequences can form functional ligand-gated ion channels. An AMPA receptor includes a receptor having a GluR1, GluR2, GluR3 or GluR4 subunit. NMDA receptor subtypes include class NR2B and NR2D, for example.

Metabotropic glutamate receptors are divided into three groups based on amino acid sequence homology, transduction mechanism and binding selectivity: Group I, Group II and Group III. Each Group of receptors contains one or more types of receptors. For example, Group I includes metabotropic glutamate receptors 1 and 5 (mGluR1 and mGluR5), Group II includes metabotropic glutamate receptors 2 and 3 (mGluR2 and mGluR3) and Group III includes metabotropic glutamate receptors 4, 6, 7 and 8 (mGluR4, mGluR6, mGluR7 and mGluR8). Each mGluR type may be found in several subtypes. For example, subtypes of mGluR1 include mGluR1a, mGluR1b and mGluR1c.

Group I metabotropic glutamate receptors represent a family of seven membrane spanning proteins that couple to G-proteins and activate phospholipase C (Nakanishi, 1994). Members of the family include mGluR1 and mGluR5. Activation of these receptors results in the hydrolysis of membrane phosphatidylinositol bisphosphate to diacylglycerol, which activates protein kinase C. and inositol trisphosphate, which in turn activates the inositol trisphosphate receptor to release intracellular calcium. (Aramori and Nakanishi, 1992; Joly et al., 1995 Kawabata et al., 1998)

Activation of a glutamate receptor on the cell surface results in a cellular response. A "cellular response" is an event or sequence of events that singly or together are a direct or indirect response by a cell to activation of a cell surface receptor. A "cellular response" is also the blockade or activation of selective and non-selective cation channels and potentiation or inhibition of other cell-surface receptor responses. In addition, a "cellular response" may be the activation of an intracellular signaling pathway, including the activation of all steps or any one step in an intracellular signaling pathway.

An "intracellular signaling pathway" is a sequence of events that transduces information about an extracellular event into a signal to intracellular receptors or effector molecules such as enzymes. One type of intracellular signaling pathway is a second messenger signaling pathway. It may begin with the activation of receptors on the cell surface, which activation evokes changes in the level of specific, diffusible molecules inside the cell. The regulated production of these molecules serves to signal events to the intracellular receptors and is therefore termed a second messenger signaling pathway. Major second messenger pathways include the adenylate cyclase pathway, which regulates levels of cyclic AMP, the phosphoinositide pathway, which regulates intracellular calcium, guanylate cyclase, which regulates levels of cGMP, and the nitric oxide pathway, which regulates nitric oxide.

A cellular response mediated by cell surface receptors can also include calcium mobilization. A compound can modulate cellular responses mediated by cell surface receptors by inhibiting or potentiating the release of calcium from intracellular stores. A compound increases calcium mobilization by increasing the release of calcium from intracellular stores. A compound decreases calcium mobilization by inhibiting of the release of calcium from intracellular stores.

Cell-surface receptors are known to mediate cellular responses. Methods for demonstrating cellular responses are well known in the art (e.g. electrophysiological and biochemical methods). (See Examples section for additional methodology). A method is provided for identifying a compound that modulates a cellular response mediated by a cell-surface receptor. The method includes incubating the compound and a cell expressing a cell-surface receptor and a Homer protein under conditions sufficient to permit the compound to interact with the cell. The cell may be any cell of interest, including but not limited to neuronal cells, glial cells, cardiac cells, bronchial cells, uterine cells, testicular cells, liver cells, renal cells, intestinal cells, cells from the thymus and spleen, placental cells, endothelial cells, endocrine cells including thyroid, parathyroid, pituitary and the like, smooth muscle cells and skeletal muscle cells. The cell is exposed to a cell-surface receptor ligand. A "cell surface receptor ligand" is a compound that binds to the binding site of the cell-surface receptor thereby initiating a sequence of events that singly or together embrace a "cellular response". The effect of the compound on the cellular response is determined, either directly or indirectly, and a cellular response is then compared with a cellular response of a control cell. A suitable control includes, but is not limited to, a cellular response of a cell not contacted with the compound. The term "incubating" includes conditions which allow contact between the test compound and the cell of interest. "Contacting" may include in solution or in solid phase.

Compounds which modulate a cellular response can include peptides, peptidomimetics, polypeptides, pharmaceuticals, chemical compounds and biological agents, for example. Antibodies, neurotropic agents, antiepileptic compounds and combinatorial compound libraries can also be tested using the method of the invention. One class of organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

The test agent may also be a combinatorial library for screening a plurality of compounds. Compounds such as peptides identified in the method of the invention can be further cloned, sequenced, and the like, either in solution of after binding to a solid support, by any method usually applied to the isolation of a specific DNA sequence Molecular techniques for DNA analysis (Landegren et al., *Science* 242:229–237, 1988) and cloning have been reviewed (Sambrook et al., *Molecular Cloning: a Laboratory Manual*, 2nd Ed.; Cold Spring Harbor Laboratory Press, Plainview, N.Y., 1998, herein incorporated by reference).

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A variety of other agents may be included in the screening assay. These include agents like salts, neutral proteins, e.g., albumin, detergents, etc. that are used to facilitate optimal protein-protein binding and/or reduce nonspecific or background interactions. Reagents that improve the efficiency of the assay, such as protease inhibitors, nuclease inhibitors, antimicrobial agents and the like may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 h will be sufficient.

In another embodiment, a method is provided for identifying a compound that modulates a cellular response mediated by an intracellular receptor. An "intracellular receptor" is a protein that binds particular intracellular molecules. Intracellular receptors include ryanodine receptors and inositol trisphosphate receptors, for example, an "inositol trisphosphate receptor" is a receptor that binds the compound inositol 1,4,5 trisphosphate, which is an important intracellular second messenger. Inositol 1,4,5 trisphosphate is released from phosphatidyl inositol bisphosphate by the action of a specific phospholipase C enzyme (PLC) and binds to and activates a calcium channel in the endoplasmic reticulum (ER).

A compound can modulate a cellular response mediated by an intracellular receptor by inhibiting or potentiating the release of calcium from intracellular stores, for example, a compound increases calcium mobilization by increasing the release of calcium from intracellular stores. A compound decreases calcium mobilization by inhibiting of the release of calcium from intracellular stores.

The method of the invention includes incubating the compound and a cell expressing an intracellular receptor and a Homer protein under conditions sufficient to permit the compound to interact with the cell, exposing the cell to conditions that activate said intracellular receptor, and comparing a cellular response in a cell incubated with said compound with the response of a cell not incubated with said compound. Methods for determining cellular responses mediated by intracellular signals are well known to one of skill in the art (e.g., biochemical assays) and provided in the Examples as well.

A method is also provided for identifying a compound that modulates receptor-activated calcium mobilization. The term "calcium mobilization" means a change in the amount or concentration of free calcium ($Ca^{+2}$) sequestered in the endoplasmic reticulum, sarcoplasmic reticulum or mitochondria of a cell. The method includes incubating the compound and a cell expressing a Homer protein under conditions sufficient to permit the compound to interact with the cell and exposing the cell to conditions sufficient to activate calcium mobilization. Then, the cellular response of the cell exposed to the compound is compared to the cellular response of a cell not exposed to the compound. A difference in a cellular response is indicative of a compound that modulates receptor-activated calcium mobilization in a cell.

In another embodiment of the invention, a method is provided for modulating receptor-mediated calcium mobilization in a cell including exposing a cell to a compound in a sufficient amount to modulate the calcium mobilization that normally occurs when a cell is exposed to all amount of ligand sufficient to activate an intracellular signaling pathway. Those of skill in the art will understand that "the calcium mobilization that normally occurs" depends on the cell type and on the ligand activating the intracellular pathway (Berridge, 1997 supra; Berridge, 1998 supra; Bootman, 1997 supra). Methods of measuring free calcium flux are well known in the art (e.g., imaging methodology using calcium-sensitive dyes such as fura-2 and the like).

A ligand which activates the intracellular signaling pathway may be an agonist or antagonist of metabotropic glutamate receptors. The terms "agonist" and "antagonist" are meant to include compounds that bind to the receptor and, respectively, activate or block activation of the receptor. Known agonists of metabotropic glutamate receptors include glutamate, quisqualate, Ibotenate, homocysteine sulfinate and the neurotoxin β-N-methylamino-L-alanine. Antagonists of metabotropic glutamate receptors include MCPG. Known agonists of the NMDA type glutamate receptor include glutamate and NMDA and known antagonists include MK-801 and APV.

Another embodiment of the invention includes a method of identifying a compound that inhibits Homer protein activity. The method relies on functional properties of the Homer EVH1 and coiled-coil binding domains that can be used to establish high-throughput screens for molecules that influence these and other functional properties of Homer family members. Homer protein activity may be blocked, partially or completely, by interfering with a protein or other molecule in the intracellular signaling pathway though which Homer proteins act. For example, Homer activity can be modulated, for example, by modulating Homer protein expression, by modifying the activity of the Homer EVH1 domain, by modification of the activity of the Homer CC domain, by modification of Homer crosslinking activity, and the like. Homer activity can also be modulated with by interfering with the expression or activity of Homer Interacting Protein 142, Homer Interacting Protein 130, NR2D, ACK-2, Shank proteins, ryanodine, inositol trisphosphate, and hInaD, and the like.

Homer proteins function as a regulated adapter network that cross-links interacting proteins. Cross-linking is determined by the binding properties of the Homer EVH1 domain, which recognize a unique proline-rich ligand with a core sequence consensus of PXXF. This Homer ligand is present in all identified proteins that naturally associate with Homer, and the ability of Homer proteins to bind can be disrupted by single amino acid changes in this motif. Cross-linking activity of Homer proteins has demonstrated effects on glutamate receptor signaling and this action is due to the formation of signaling complexes that link cell-surface receptors with intracellular receptors. Cross-linking by Homer proteins may also have consequences on receptor trafficking or other cellular functions of the interacting proteins.

Development of agents that modulate activity of the Homer EVH1 domain is furthered by knowledge of the crystal structure of Homer protein. The method includes designing inhibitors of Homer protein that form non-covalent bonds with amino acids in the Homer binding sites based upon the crystal structure co-ordinates of Homer protein binding domain; synthesizing the inhibitor; and determining whether the inhibitor inhibits the activity of Homer protein.

The "Homer protein binding domain" is a conserved sequence of amino acids in the amino-terminal region of the that interacts with other proteins. All Homer proteins possess a conserved region of about 175 amino acids at their amino-termini. The 110 terminal amino acids in this region interact with the carboxy-termini of other proteins, for example metabotropic glutamate receptors, inositol trisphosphate receptors, Shank, and the like. The carboxy-termini region of the proteins to which the Homer protein binding domain may bind usually contains an amino acid sequence that contains a high number of proline residues.

One aspect of the invention resides in the obtaining of crystals of Homer protein of sufficient quality to determine the three dimensional (tertiary) structure of the protein by X-ray diffraction methods. The knowledge obtained concerning Homer proteins may be used in the determination of the three dimensional structure of the binding domain of Homer proteins. The binding domain can also be predicted by various computer models. Upon discovering the three-dimensional protein structure of the binding domain, small molecules which mimic the functional binding of Homer protein to its ligands can be designed and synthesized This is the method of "rational" drug design. Another approach to "rational" drug design is based on a lead compound that is discovered using high thoughput screens; the lead compound is further modified based on a crystal structure of the binding regions of the molecule in question. Accordingly, another aspect of the invention is to provide material which is a starting material in the rational design of drugs which mimic or prevents the action of Homer proteins.

The term "crystal structure coordinates" refers to mathematical coordinates derived from mathematical equations related to the patterns obtained on diffraction of a monochromatic beam of X-rays by the atoms (scattering centers) of a Homer protein molecule in crystal form. The diffraction data are used to calculate an electron density map of the repeating unit of the crystal. The electron density maps are used to establish the positions of the individual atoms within the unit cell of the crystal. The crystal structure coordinates of the Homer protein binding domain are obtained from a Homer protein crystal having orthorhombic space group symmetry P2,212, with a=33.79, b=51.40, and c=66.30 Angstroms. The coordinates of the Homer protein binding domain can also be obtained by means of computational analysis.

The term "selenomethione substitution refers to the method of producing a chemically modified form of the crystal of Homer. The Homer protein is expressed by bacterial in meida that is depleted in methionine and supplement in selenomethionine. Selenium is thereby incorporated into the crystal in place of methionine sulfurs. The location (s) of selenium are determined by X-ray diffraction analysis of the crystal. This information is used to generate the phase information used to construct three-dimensional structure of the protein.

The term "heavy atom derivatization" refers to the method of producing a chemically modified form of the crystal of Homer. A crystal is soaked in a solution containing heavy metal atom salts or organometallic compounds, which can diffuse through the crystal and bind to the surface of the protein. The location(s) of the bound heavy metal atom(s) are determined by X-ray diffraction analysis of the soaked crystal. This information is used to generate the phase information used to construct three-dimensional structure of the protein.

Those of skill in the art understand that a set of structure coordinates determined by X-ray crystallography is not without standard error.

The term "unit cell" refers to the basic parallelipiped shaped block. The entire volume of a crystal may be constructed by regular assembly of such blocks.

The term "space group" refers to the arrangement of symmetry elements of a crystal.

The term "molecular replacement" refers to a method that involves generating a preliminary model of an Homer crystal whose structure coordinates are not known, by orienting and positioning a molecule whose structure coordinates are known. Phases are then calculated from this model and combined with observed amplitudes to give an approximate Fourier synthesis of the structure whose coordinates are known.

The crystal structure coordinates of Homer protein may be used to design compounds that bind to the protein and alter its physical or physiological properties in a variety of ways. The structure coordinates of the protein may also be used to computationally screen small molecule data bases for compounds that bind to the protein. The structure coordinates of Homer mutants (e.g., missense mutations, deletion mutations, and the like, obtained by site-directed mutagenesis, by exposure to mutagenic agents, through selection of naturally occurring mutants, etc.) may also facilitate the identification of related proteins, thereby further leading to novel therapeutic modes for treating or preventing Homer-mediated conditions. A potential inhibitor is designed to form hydrogen bonds with tryptophan$^{24}$, phenylalanine$^{74}$, threonine$^{66}$, threonine$^{68}$, glutamine76, alanine$^{78}$, threonine$^{70}$, and valine$^{85}$ of the Homer binding domain.

A method is also provided for identifying a compound that affects the formation of cell surface receptors into clusters. The method includes incubating the compound and a cell expressing a Homer protein and a Homer Interacting protein, such as a Shank protein, a Homer Interacting Protein, and the like, under conditions sufficient to allow the compound to interact with the cell, determining the effect of the compound on the formation of cell-surface receptors into clusters, and comparing the formation of cell-surface receptors into clusters in cells contacted with the compound with the formation of cell surface receptors into clusters in cells not contacted with the compound.

Shank proteins are a novel family of proteins found at the postsynaptic density (PSD) and which are capable of binding to other proteins. Shank proteins contain multiple protein interaction domains, including ankyrin repeats, SH3 domain, PDZ domain, at least one proline rich domain and at least one SAM domain. The PDZ domain of Shank mediates binding to the carboxy-terminus of guanylate kinase associated protein (GKAP), and this interaction is important in neuronal cells for the synaptic localization of Shank proteins. Shank proteins also interact with Homer proteins and therefore Shank and Homer may serve as a protein bridge that links specific proteins that bind to Homer and specific proteins that bind to Shank. Exemplary Shank proteins include Shank 1a, Shank 1b and Shank 3, and cortactin binding protein, and the like.

A compound can affect the formation of cell-surface receptors into clusters by either stimulating the formation of cell-surface receptors into clusters or by inhibiting the recruitment of cell-surface receptors into clusters. When the effect is "inhibition", cell-surface clustering is decreased as compared with the level in the absence of the test compound. When the effect is "stimulation", cell-surface clustering is increased as compared to a control in the absence of the test compound.

A method is further provided for treating a subject with a disorder associated with metabotropic receptors or ion channel receptors comprising administering to the subject a therapeutically effective amount of a compound that modulates Homer protein activity. In yet another embodiment, a method is provided for treating a subject with a disorder associated with Homer protein activity, comprising administering to the subject a therapeutically effective amount of a compound that modulates Homer protein activity.

Essentially, any disorder that is etiologically linked to a glutamate receptor, an inositol trisphosphate receptor, a ryanodine receptor, a Shank protein, I42 (or other Homer interacting proteins) or to a Homer protein could be considered susceptible to treatment with an agent that modulates Homer protein activity. The disorder may be a neuronal cell disorder. Examples of neuronal cell disorders include but are not limited to Alzheimer's disease, Parkinson's disease, stroke, epilepsy, neurodegenerative disease, Huntington's disease, and brain or spinal cord injury/damage, including ischemic injury. The disorder may also be a disorder of a cardiac disorder, a disorder of musculature, a renal disorder, a uterine disorder or a disorder of bronchial tissue. The disorder may be epilepsy, glutamate toxicity, a disorder of memory, a disorder of learning or a disorder of brain development.

Detection of altered (decreased or increased) levels of "Homer protein activity" can be accomplished by hybridization of nucleic acids isolated from a cell of interest with a Homer polynucleotide of the invention. Analysis, such as Northern Blot analysis, are utilized to quantitate expression of Homer, such as to measure Homer transcripts. Other standard nucleic acid detection techniques will be known to those of skill in the art. Detection of altered levels of Homer can also accomplished using assays designed to detect Homer polypeptide. For example, antibodies or petides that specifically bind a Homer polypeptide can be utilized. Analyses, such as radioimmune assay or immunohistochemistry, are then used to measure Homer, such as to measure protein concentration qualitatively or quantitatively.

Treatment can include modulation of Homer activity by administration of a therapeutically effective amount of a compound that modulates Homer or Homer protein activity. The term "modulate" envisions the suppression of Homer activity or expression when Homer is overexpressed or has an increased activity as compared to a control. The term "modulate" also includes the augmentation of the expression of Homer when it is underexpressed or has a decreased activity as compared to a control. The term "compound" as used herein describes any molecule, e.g., protein, nucleic acid, or pharmaceutical, with the capability of altering the expression of Homer polynucleotide or activity of Homer polypeptide. Treatment may inhibit the interaction of the EVH1 domain of Homer with its target protein, may increase the avidity of this interaction by means of allosteric effects, may block the binding activity of the coiled-coil doamin of Homer or influence other functional properties of Homer proteins.

Candidate agents include nucleic acids encoding a Homer, or that interfere with expression of Homer, such as an antisense nucleic acid, ribozymes, and the like. Candidate agents also encompass numerous chemical classes wherein the agent modulates Homer expression or activity.

Where a disorder is associated with the increased expression of Homer, nucleic acid sequences that interfere with the expression of Homer can be used. In this manner, the coupling of cell-surface and intracellular receptors can be inhibited. This approach also utilizes, for example, antisense nucleic acid, ribozymes, or triplex agents to block transcription or translation of Homer mRNA, either by masking that mRNA with an antisense nucleic acid or triplex agent, or by cleaving it with a ribozyme in disorders associated with increased Homer. Alternatively, a dominant negative form of Homer polypeptide could be administered.

When Homer is overexpressed, candidate agents include antisense nucleic acid sequences. Antisense nucleic acids are DNA or RNA molecules that are complementary to at least a portion of a specific mRNA molecule (Weintraub, 1990, *Scientific American*, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, 1988, *Anal.Biochem.*, 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, *Antisense Res. and Dev.*, 1(3):227; Helene, C., 1991, *Anticancer Drug Design*, 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, *J.Amer.Med. Assn.*, 260:3030). A major advantage of this approach is that, because they are sequence-specific, only mRNAs with particular sequences are inactivated.

There are two basic types of ribozymes namely, tetrahymena-type (Hasselhoff, 1988, *Nature*, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

When a disorder is associated with the decreased expression of Homer, nucleic acid sequences that encode Homer can be used. An agent which modulates Homer expression includes a polynucleotide encoding a polypeptide of SEQ ID NO:2, 4, 6, 8, 10 or 12, or a conservative variant thereof. Alternatively, an agent of use with the subject invention includes agents that increase the expression of a polynucleotide encoding Homer or an agent that increases the activity of Homer polypeptide.

In another embodiment of the invention, there is provided a transgenic non-human animal having a transgene that expresses Homer 1a chromosomally integrated into the germ cells of the animal. Animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty h in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, Jan. 12, 1994) can be utilized whereby the embryo is obtained from a sacrificed hen approximately two and one-half h after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention are murine typically (e.g., mouse). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 8:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 2–98:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode Homer protein-sense and antisense polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. As used herein, the term "transgenic" includes any transgenic technology familiar to those in the art which can produce an organism carrying an introduced transgene or one in which an endogenous gene has been rendered non-functional or "knocked out".

Antibodies of the invention may bind to Homer proteins or Homer interacting proteins provided by the invention to prevent normal interactions of the Homer proteins and Homer Interacting proteins. Binding of antibodies to Homer proteins or Homer Interacting Proteins can interfere with cell-signaling by interfering with an intracellular signaling pathway. Binding of antibodies can interfere with Homer protein binding to extracellular receptors, e.g., to NMDA receptors, to metabotropic receptors, and the like. Binding of antibodies can interfere with Homer protein binding to intracellular receptors, e.g., inositol trisphosphate receptors, and the like. Furthermore, binding to Homer proteins or to Homer Interacting Proteins can interfere with cell-surface receptor clustering mediated by Homer family proteins.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "antibody" as used in this invention includes intact molecules as well as fragments thereof, such as Fab, F(ab')2, and Fv which are capable of binding to an epitopic determinant present in an invention polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, New York (1988), incorporated herein by reference). Monoclonal antibodies are made from antigen containing fragments of the protein by methods well known to those skilled in the art (Kohler, et al., Nature, 256:495, 1975).

Antibodies which bind to an invention polypeptide of the invention can be prepared using an intact polypeptide or fragments containing small peptides of interest as the immunizing antigen. For example, it may be desirable to produce antibodies that specifically bind to the N- or C-terminal domains of an invention polypeptide. The polypeptide or peptide used to immunize an animal is derived from translated cDNA or chemically synthesized and can be conjugated to a carrier protein, if desired. Commonly used carrier proteins which may be chemically coupled to the immunizing peptide include keyhole limpet hemocyanin (KLH), thyroglobulin, bovine serum albumin (BSA), tetanus toxoid, and the like.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See, for example, Coligan, et al., Unit 9, Current Protocols in Immunology, Wiley Interscience, 1994, incorporated by reference).

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyi, puridoxal, and fluorescein, which can react with specific antihapten antibodies.

In using the monoclonal and polyclonal antibodies of the invention for the in vivo detection of antigen, e.g., Homer, the detectably labeled antibody is given a dose which is diagnostically effective. The term "diagnostically effective" means that the amount of detectably labeled antibody is administered in sufficient quantity to enable detection of the site having the antigen comprising a polypeptide of the invention for which the antibodies are specific.

The concentration of detectably labeled antibody which is administered should be sufficient such that the binding to those cells having the polypeptide is detectable compared to the background. Further, it is desirable that the detectably labeled antibody be rapidly cleared from the circulatory system in order to give the best target-to-background signal ratio.

As a rule, the dosage of detectably labeled antibody for in vivo treatment or diagnosis will vary depending on such factors as age, sex, and extent of disease of the individual. Such dosages may vary, for example, depending on whether multiple injections are given, antigenic burden, and other factors known to those of skill in the art.

The following examples are intended to illustrate but not to limit the invention in any manner, shape, or form, either

EXAMPLES

Homer 1a is an IEG and is the original member of a family of proteins that function together as a regulated adapter system that is hypothesized to control the coupling of membrane receptors to intracellular pools of releasable calcium. Homer proteins function at excitatory synapses to couple membrane group 1 metabotropic glutamate receptors (mGluR) to endoplasmic reticulum-associated inositol trisphosphate receptors (IP3R) (Brakeman et al., 1997; Tu et al., 1998; Xiao et al., 1998). Current studies suggest a broader role for Homer proteins in calcium signaling and receptor trafficking. The Shank family of proteins was identified based on their association with Homer (Naisbitt et al., 1999; Tu et al., 1999). Shank, together with Homer, appears to be part of both the NMDA and group 1 mGluR signaling complexes. By virtue of its interaction with Shank, Homer provides a mechanism to couple NMDA Ca2+ influx to intracellular Ca2+-induced Ca2+ release pools. The inventors have identified additional Homer-interacting proteins that provide insight into the role of Homer in trafficking of group 1 mGluR (e.g., SEQ ID NOS:16, 18, 20). Because these Homer-dependent cellular processes are regulated by the IEG form of Homer (Homer 1a), mechanisms by which Homer proteins can modulate Ca2+ dynamics of mGluR and NMDA receptors, as well as regulate receptor trafficking are defined.

Homer family proteins possess an N-terminal EVH1 domain that mediates interactions with mGluRs, IP3R, Shank and other novel proteins. The EVH1 domain has been determined to bind the proline rich motif PPXXFR (Tu et al., 1998). The present invention provides the crystal structure of the Homer EVH1 domain. In complementary studies, genetic approaches were used to identify critical residues in both the EVH1 domain and the ligand that modulate the affinity of the Homer-mGluR (and other Homer-interacting proteins) interaction. This information is essential to an understanding of the integrative cellular actions of Homer proteins,. Together, these studies define the molecular basis of specificity of EVH1 interaction with its ligands, and provide insight into how the EVH1 interaction is regulated, This patent application includes a description of several Homer-interacting proteins that are part of the signaling network that is controlled by Homer (e.g., SEQ ID NOS: 16, 18, 20). Yeast two-hybrid screens and searches of NCBI protein data bases identified a set of known and novel candidate interacting proteins for Homer include the ryanodine receptor, NMDA receptor subunit NR2D, human InaD and novel interacting proteins termed I42 and I30. As described below, current data indicate that agents can be developed that specifically modulate the crosslinking activity of Homer for these various receptors and thereby provide novel theraputics that regulate the output of these receptors on cellular function.

Homer acts in several ways to regulate cellular function. Homer and Homer-related proteins function as an adapter system to couple membrane receptors to intracellular pools of releasable Ca. This "signaling" function of Homer is documented in Xiao et al (1998), Tu et al (1998 and 1999) Naisbett et al. (1999), as well as by studies of the novel Homer-interacting protein termed I42 (see below). By virtue of its crosslinking activity, Homer proteins play a role in synaptogenesis and spatial targeting/trafficking of GluRs to other postsynaptic structural proteins. This function of Homer is supported by observations in Tu et al (1999) and Naisbett et al (1999).

Initial Cloning of Homer; a Novel Brain Immediate Early Gene (IEG)

Homer was cloned in a differential screen of seizure-stimulated hippocampus. Prior work, in which IEG induction was examined in brain provided a detailed understanding of time course and tissue distribution of the IEG response (Cole et al., 1989; Saffen et al., 1988; Worley et al., 1990), and suggested a paradigm to maximally induce novel IEG mRNAs (Lanahan and Worley, 1998; Worley et al., 1990). Once cloned, in situ hybridization was used to screen for IEGs that were regulated in other paradigms that activate neurons including LTP stimulation in the hippocampus (Brakeman et al., 1997) and acute administration of cocaine. In these models, Homer was one of the most highly induced of all of the IEGs (Brakeman et al., 1997). Initial characterization of Homer was challenging in that the mRNA was nearly 7 kb, while the best deduced open reading frame was only 186 aa, and was located near the 5' end of the cDNA (Brakeman et al., 1997). The 3' UTR was over 5 kb. The ORF was confirmed by in vitro transcription and translation of the cDNA, and rabbit polyclonal antisera were generated against bacterially expressed fusion proteins. With these antibodies, we were able to demonstrate that the protein was rapidly and transiently induced in the hippocampus following a seizure (Brakeman et al., 1997). This confirmed the deduced ORF and assured us that the cDNA was indeed translated in brain.

Homer Selectively Binds Group 1 Metabotropic Receptors and is Enriched at Synapses In an effort to discover the function of Homer, a yeast 2-hybrid technique (Chevray and Nathans, 1992; Fields and Song, 1989) was used to screen a cDNA library prepared from rat hippocampus and cortex. The full length Homer IEG was used as bait. Among ~30 confirmed interacting cDNAs, one encoded the C-terminal 250 aa of mGluR5. We initially confirmed that the proteins bind using a GSTHomer in a pulldown assay with either fragments of mGluR5, or full length mGluR5 expressed in heterologous cells (HEK293 cells) (Brakeman et al., 1997). Homer protein also bound to mGluR1a, but not mGluR2, 3, 4, or 7. This was an interesting clue to the function of Homer since mGluR1 and mGluR5 (termed group 1 metabotropic receptors) couple to phospholipase C and active hydrolysis of phosphoinositides to generate inositol trisphosphate and diacylglycerol (Nakanishi et al., 1994). mGluR1a and 5 also share sequence similarity in their long, cytosolically disposed C-terminus. Other metabotropic glutamate receptors (termed group 2 and 3) inhibit adenylate cyclase activity, and have short C-termini that lack homology to group 1 receptors. We proceeded to test whether Homer and mGluR5 naturally associate in brain and confirmed that these proteins co-immunoprecipitate from detergent extracts of hippocampus (Brakeman et al., 1997). The next major clue was provided by the observation that Homer immunoreactivity was enriched at excitatory synapses (Brakeman et al., 1997). In brain, Homer protein was associated with dendrites and showed a punctate pattern consistent with a localization in spines. The binding properties and cellular distribution of Homer suggested a role at the excitatory synapse.

Homer is a Member of a Family of Closely Related Proteins that are Enriched at the Excitatory Synapse A search of the NCBI sequence data base identified several ESTs that showed strong homology to Homer, but were clearly distinct in that they encoded additional C-terminal sequence (Brakeman et al., 1997). Using a combination of screening strategies, a family of 12 cDNAs was identified from rat, mouse, Drosophila, and human (Xiao et al., 1998). All of these cDNAs encoded proteins with a similar protein structure and were deduced to be the products of 3 independent mammalian genes (termed Homer 1, 2, 3) and 1 Drosophilia gene. Like Homer IEG (now termed Homer 1a), all new family members contain an N-terminal, ~110 amino acid domain that binds mGluR1a/5 ((Xiao et al., 1998). The region of Homer that interacts with mGluR1a/5 is termed an EVH1 domain based on its modest homology (20–25% identity) to domains in a family of proteins that include Drosophila Enabled Gertler, 1996, mammalian VASP (Haffner et al., 1995) and the Wiscott-Aldridge protein (WASP) (Ponting and Phillips, 1997; Symons et al., 1996). The EVH1 domains of Homer proteins from Drosophilia, rodent and human are conserved at a level of 80% identity (Xiao et al., 1998). Other than the IEG Homer 1a, all new forms of Homer encode an additional C-terminal domain with predicted coiled-coil (CC) structure.

As the nomenclature suggests, Homer 1 gene encodes both the IEG form (Homer 1a) and splice forms that encode CC domains termed Homer 1b and 1c. The 1b and 1c splice forms differ in their inclusion of an approximately 10 amino acid sequence located between the EVH1 and CC domains. (Homer family members that encode CC domains are also referred to as CC-Homers to distinguish them from Homer 1a, which lacks a CC domain.) Similarly, Homer 2 encodes two CC-Homer splice forms termed Homer 2a and 2b, which also differ by a short internal sequence between EVH1 and CC domains. Homer 3 encodes a single form. The CC domains are less conserved than the EVH1 domain (~40% identity between rat Homer 1, 2 and 3) but they are able to specifically bind to themselves and to CC-domains of other Homer family members (Xiao et al., 1998). Homer CC domains do not interact with other representative CC-domain proteins in GST pulldown assays, and a yeast 2-hybrid screen of brain cDNA with the CC-domain of Homer 1 identified multiple copies of Homer 1, Homer 2 and Homer 3, but not other CC domains (Xiao et al., 1998). As evidence that Homer proteins can naturally self-multimerize, we demonstrated that Homer 1b/Homer 3 heteromultimers co-immunoprecipitate from brain (Xiao et al., 1998). These observations indicate that the Homer CC domains mediate specific self-association.

In contrast to Homer 1a, all CC-containing Homer family members are constitutively expressed in brain (Xiao et al., 1998). This was confirmed using both Northern blot and in situ hybridization assays which compared expression with Homer 1a in the same material. mRNA and protein expression of Homer 1b/c, Homer 2 and Homer 3 are unchanged in hippocampus following a seizure while Homer 1a mRNA and protein are induced at least 10 fold.

Antibodies were generated that specifically recognize each of the CC-Homers. Antibodies were raised against synthetic C-terminal peptide sequences. Because Homer 1b and 1c possess identical C-termini, the C-terminal antibodies recognize both splice forms. Similarly, C-terminal Homer 2 antibodies recognize both Homer 2a and 2b. Accordingly, when using these antibodies to detect Homer proteins, we refer to the immunoreactivity as Homer 1b/c or Homer 2a/b. We used these antibodies to determine that Homer 1b/c and 3 are enriched in a detergent resistant fraction of the postsynaptic density (PSD) (Xiao et al., 1998). Homer 2a/b is also enriched in synaptic fractions, but is relatively more soluble than Homer 1b/c and Homer 3.

Like Homer 1a, each of the CC-Homers co-immunoprecipitates with group 1 mGluRs from brain (Xiao et al., 1998). Immunogold electron microscopy (EM) demonstrated that Homer 1b/c and Homer 3 are ultrastructurally localized at the PSD (Xiao et al., 1998). These observations suggest that CC-Homer proteins function as multivalent adapter complexes that bind mGluRs at postsynaptic sites.

Homer 1a Functions as a Natural Dominant Negative Protein

The fact that Homer 1a lacks a CC domain suggested that it may function as a natural dominant negative to disrupt cross-linking of CC-Homers. In this model, the EVH1 domain of Homer 1a can bind and compete for the same target proteins as CC-Homers (such as mGluR5), but because Homer 1a lacks the CC-domain, it cannot self-associate and cannot cross-link. To test the dominant negative hypothesis, we generated a transgenic mouse that constitutively expressed Homer 1a in brain neurons under the control of a modified Thy-1 promoter Aigner, 1995 #200. We confirmed transgene expression in hippocampus, cerebellum and cortex in two independent lines (Xiao et al., 1998). The level of transgene expression in the hippocampus was similar to natural Homer 1a expression induced by a seizure. In contract to the natural Homer 1a, however, the transgene was constitutively expressed in the unstimulated mouse. A prediction of the dominant negative hypothesis is that the ability to co-immunoprecipitate mGluR with Homer 1b/c or Homer 3 antibodies should be diminished in the transgenic mouse. As one of the controls for this experiment, we demonstrated by western blot that levels of expression of mGluR1a, mGluR5 and Homer 1b/c, 2a/b, 3 were unchanged in the transgenic mouse brain. We then performed IP experiments and observed the anticipated result; the co-immunoprecipitation of mGluR5 with CC-Homers from hippocampus was reduced in the transgenic mouse (Xiao et al., 1998). Similar co-immunoprecipitations of mGluR1a with Homer 3 from cerebellum was also reduced. As an additional control, we demonstrated that the ability to co-immunoprecipitate Homer 1b/c with Homer 3 was not altered in the transgenic mouse. This was the predicted result since the association between these proteins is mediated by their CC domains, and this interaction is not altered by the Homer 1a EVH1 domain. These observations support the hypothesis that Homer 1a functions as a natural dominant negative to regulate CC-Homer-dependent cross-linking.

Homer Binds a Proline Rich Sequence that is ~50 aa from the C-terminus of Group 1 mGluRs When we initially characterized the interaction between Homer and mGluR5, we anticipated that Homer might bind the free C-terminus. This surmise was based on the precedent of PDZ proteins such as PSD95 and GRIP, which bind the free C-terminus of NMDAR2 (Kornau, 1995) and AMPA receptors (Dong et al., 1997). Homer was noted to encode a GLGF sequence like the PDZ domain. Additionally, in GST pulldown assays that used brief washes, we noted a modest reduction of binding when the C-terminal 4 or 10 aa were deleted from mGluR5 Brakeman, 1997 #99. (In retrospect, this modest reduction of binding may be due to Homer pulldown of Shank which does bind the free C-terminus of mGluR5, but appears to be lower affinity than Homer-mGluR5 binding; see below.) However, with more standard wash conditions, it became clear that the 4 and 10 aa C-terminal deletion mutants of mGluR5 continued to bind avidly to Homer. We continued the deletion strategy until we found that a 50 aa C-terminal deletion of mGluR5 destroyed binding to Homer. By contrast, a 41 aa deletion of mGluR5 retained full binding activity. We noted that the intervening sequence was proline rich and shared sequence similarity with the previously described SH3 ligand sequence Yu, 1994 #166 We prepared a series of point mutants based on the known structure-function relationship for SH3 ligands. Binding assays confirmed general characteristics of SH3 ligand binding, but also demonstrated that that the Homer binding site is distinct in the positioning of critical amino acids (Tu et al., 1998). A consensus for binding was determined to be PPXXFR, consistent with the observation that mutation of either of the prolines or the phenylalanine, or a change in their relative position, interrupted binding. The arginine in the last position is preferred over other amino acids, but is not essential. Mutations were identically effective in interrupting binding to each of the Homer family members including Homer 1a, 1b/c, 2a/b, 3 and an EVH1 only fragment (110aa) of Homer 1. Thus, we conclude that the interaction with mGluR5 is mediated by the Homer EVH1 domain.

Mutations of mGluR5 were initially tested in the context of a 250aa C-terminal fragment, but were also determined to have an identical effect on binding when placed in the full length mGluR5 protein (Tu et al., 1998). This exquisite sensitivity of Homer binding to changes in single amino acid within the Homer-ligand site has been confirmed in other Homer-interacting proteins including mGluR1a (Tu et al., 1998), Shank (Tu et al., 1999) and I42 (see below). To further confirm that the interaction was mediated by a direct interaction at the Homer-ligand site (as opposed to a secondary allosteric effect on a remote binding site), we prepared synthetic 10 mer peptides with either the wild type, or F-to-R mutation, and demonstrated that the wild type peptide blocked binding of mGluR1a or mGluR5 to each of the Homer family members (Tu et al., 1998). Approximately half of the binding was blocked at a peptide concentration of 3.4 micromolar. By contrast, the F-to-R mutant peptide did not alter binding at concentrations as high as 340 micromolar.

Homer Binds the IP3 Receptor

Armed with a consensus sequence that predicted binding to Homer, we searched the NCBI data base for other proteins that might bind Homer. A Homer-ligand site was identified in the IP3R, dynamin III, a human alpha adrenergic receptor and the ryanodine receptor (Tu et al., 1998). Each of these interactions were determined to be consistent with the known topology of the candidate interacting protein, assuming that Homer proteins are cytosolic. We were able to confirm a biochemical interaction of Homer with the IP3R and dynamin III using GST pull down assays. More importantly, we demonstrated that the IP3R co-immunoprecipitates with each of the Homer 1b/c, 2a/b and 3 from detergent extracts of cerebellum (Tu et al., 1998). Homer appears to be associated with a substantial portion of IP3R in the cerebellum, since a cocktail of the three Homer antibodies is able to specifically (compared to a cocktail of preimmune serums) co-immunoprecipitate ~50% of the total IP3R in detergent extracts (CHAPS).

CC-Homers Function to Link mGluR5 and IP3R in a Signaling Complex

Based on the prior observations, we examined the hypothesis that CC-Homers might cross-link mGluR and IP3R. This notion was appealing in that the IP3R is part of the signaling network that is activated upon glutamate stimulation of mGluR1/5. Signaling complexes had previously been described including; AKAP proteins which function as scaffolds for specific kinases and their substrates Lester, 1997 #149, and the Drosophila protein InaD which couples the membrane light activated channel with its down stream effector enzyme, phospholipase C Tsunoda, 1997 #147. Unlike these other examples of signaling complexes, however, Homer would need to form a bridge between receptors in two different membranes. Functional mGluRs are in the plasma membrane while the IP3R is localized primarily to intracellular endoplasmic reticulum (ER). In support of the notion that ER and plasma membranes can come in close apposition in neurons, we noted that Dr. Kristin Harris (Harvard) described the presence of smooth ER (SER, or spine apparatus) in the spines of hippocampal and cerebellar neurons (Tu et al., 1998). Remarkably, the SER forms close appositions with the plasma membrane that were uniquely localized to the lateral margin of the PSD. These sites are precisely where the group 1 mGluRs are localized (Baude et al., 1993; Lujan et al., 1997; Nusser et al., 1994). The IP3R is present in spines of cerebellar Purkinje neurons where it is associated with the spine apparatus (Satoh et al., 1990). (Interestingly, in hippocampal neurons, the RYR is present in the spine apparatus while the IP3R appears to be restricted to the dendritic shaft reviewed in (Narasimhan et al., 1998). Homer 1b/c and 3 are also enriched in the cytosol at the lateral margin of the PSD (Xiao et al., 1998). Thus, available anatomic evidence supported the notion that synaptic mGluRs come in close apposition with SER-associated IP3Rs at sites that are enriched for CC-Homers.

As a first test of the hypothesis the CC-Homers cross-link mGluR and IP3R, we asked whether we could detect a trimolecular complex of mGluR, Homer and IP3R in brain. Indeed, IP3R antibody specifically co-immunoprecipitated Homer and mGluR1a from cerebellum (Narasimhan et al., 1998). Since IP3Rs are not known to directly interact with mGluR1a, this result supported the hypothesis that Homer bridges these proteins to form a trimolecular signaling complex. A further prediction of the "Homer hypothesis" is that Homer 1a should uncouple the putative mGluR-CC-Homer-IP3R complex. To test this, we monitored the effect of Homer 1a expression on glutamate-induced intracellular calcium release. Plasmids expressing Homer 1a or Homer 1b were transfected along with green fluorescent protein (gene gun) and identified Purkinje neurons were stimulated with quisqualate. A patch electrode containing the Ca2+ detector Fura-2 was attached to the soma and a holding potential of −60 mV was applied. Tetrodotoxin and picrotoxin were included in the bath to block synaptic input and EDTA/MgCl$_2$ was included to assure that measured Ca2+ increases in the cell were generated from intracellular stores. Under these conditions, quiqualate-induced Ca2+ increases are due to mGluR1-evoked release from IP3R pools (Roche et al., J Biol Chem (1999) 274:25953–259577). Expression of Homer 1b did not alter the induced Ca2+ transient compared to cells transfected with an empty vector. By contrast, neurons transfected with Homer 1a showed a Ca2+ transient that was reduced in amplitude and delayed in time to peak (Tu et al., 1998). This result is consistent with the notion that the IP3 generated by mGluR1a activation of phospholipase C is less effective in releasing Ca2+ from the Ip3R pools in neurons expressing Homer 1a, and is anticipated if Homer 1a disrupts the physical linkage between mGluR1a and IP3R. Released IP3 must diffuse further, thereby resulting in a lower effective concentration of IP3 at the receptor.

CC-Homers Alter Trafficking of mGluR1a/5 in Heterologous Cells

We initiated studies to examine the effect of Homer on mGluR5 expression. When wild type mGluR5 was expressed in heterologous cells (HEK293, COS or HeLa) the receptor reached the plasma membrane surface where it was diffusely localized. This was also true when mGluR5 was co-expressed with Homer 1a. However, we noted that co-expression of mGluR5 with Homer 1b resulted in intracellular inclusions of mGluR5 (Roche et al., 1999 supra). This effect of Homer 1b was dependent on the amount of transfected plasmid and was most obvious when equal amounts of Homer 1b and mGluR5 plasmids were co-transfected. There was a trend for higher level expression of mGluR5 when co-transfected with Homer 1b. When ratios of transfected plasmids were titrated so that total mGluR5 expression was the same (comparing expression with or without Homer 1b), a substantial portion of the total mGluR5 was associated with the intracellular pool when co-expressed with Homer 1b. In these cells, relatively less reached the plasma membrane compared to mGluR expressed alone, or co-expressed with Homer 1a. We further noted that at earlier times after transfection of Homer 1b and mGluR5, mGluR5 showed an enrichment in perinuclear organelles with a reticular pattern throughout the cell that resembled the ER. To assess the nature of the CC-Homer-dependent cellular accumulation, we compared the distribution of mGluR5 with the ER specific maker BIP B (Roche et al., 1999, supra). Staining with BIP antibodies revealed extensive ER present in both transfected and untransfected cells and co-localization with mGluR5. We also noted that the perinuclear organelles were not present within non-transfected cells and therefore appeared to be ER-derived structures unique to cells overexpressing mGluR5 and Homer 1b. These observations suggest that Homer 1b, but not Homer 1a, causes mGluR5 to be retained in the ER.

As an additional assay for ER retention, we examined the status of the carbohydrates present on mGluR5 in cells co-expressing Homer 1a or Homer 1b. If Homer 1b caused mGluR5 to be retained within the ER, then mGluR5 should contain immature, high mannose carbohydrates which are sensitive to digestion with the enzyme Endoglycosidase H (Endo H). Alternatively, if mGluR5 had successfully traveled through the ER and cis Golgi, it would possess mature, complex carbohydrates which would be Endo H resistant. Mature carbohydrates would be anticipated if mGluR5 was on the cell surface or if it was sequestered in a post-Golgi intracellular compartment such as endosomes. We determined that mGluR5 is Endo H resistant when expressed alone or with Homer 1a (Xiao et al., 1998). However, when expressed with H1b, mGluR5 is Endo H sensitive, consistent with the hypothesis that expression of H1b leads to the retention of group I mGluR in the ER.

The subcellular localization of the group II metabotropic glutamate receptor mGluR2 was the same whether expressed alone or with H1b. In addition, we used a series of mGluR5 constructs containing point mutations within the Homer binding site and found that mutations that disrupt mGluR5/Homer interactions in vitro also prevented ER retention of mGluR5 co-expressed with H1b (Takei et al., 1994). mGluR5 P1125L, which does not bind to Homer in vitro (Tu et al., 1998), was not retained in the ER when co-expressed with H1b. In contrast, mGluR5 S1126F, which does bind Homer in vitro, was ER retained when co-expressed with H1b. Other point mutations in adjacent residues were analyzed and the results were consistent with in vitro binding studies summarized in B (Ikeda et al., 1995), demonstrating that mGluR5 is retained within the ER by H1b only when its Homer binding site is intact.

While these experiments were performed in heterologous cells, we also noted enrichment of the group I metabotropic receptor mGluR1a in the ER of Purkinje cells (Kammermeier et al., submitted). Since Purkinje neurons express particularly high levels of CC-Homers (Xiao et al., 1998), this suggests Homer proteins may naturally regulate receptor trafficking through the ER. In this model, Homer 1a would be permissive for transfer through the ER Golgi system to insertion into the postsynaptic membrane. The ability of CC-Homers to alter the spatial distribution and metabolism of ER associated proteins may also impact the IP3R. IP3Rs in Purkinje neurons are associated with dense stacks of ER (Satoh et al., 1990) and this stacking morphology has been shown to be regulated by neural activity (Takei et al., 1994). Since a substantial portion of IP3R in cerebellum is associated with CC-Homers, it is possible that the ability of CC-Homer to crosslink interacting proteins on two adjacent membranes plays a regulatory role in ER morphology and function. Experiments in Aims 2 and 3 will examine this hypothesis.

Homer Modulates mGluR Coupling to Ion Channels

Group 1 mGluRs modulate ionic currents by activating pertussis toxin-sensitive and -insensitive G proteins (Naisbitt et al., 1999). Modulation of Ca2+ currents by heterologously expressed group 1 mGluRs in superior cervical ganglion (SCG) neurons proceeds through multiple pathways involving both the a and βg -subunits of G proteins. We examined the effect of Homer on mGluR coupling to Ca2+ and M-type potassium channels in SCG neurons. CC-Homers, including 1b, 2b and 3 produced a similar reduction of the effect of group 1 mGluRs (Kim et al., 1997; Naisbitt et al., 1999; Naisbitt et al., 1997; Takeuchi et al., 1997). By contrast, Homer Ia or an engineered short form of Homer 2 did not block group 1 mGluR effects, but were able to partially reverse the effect of the CC-Homers.

Homer Interacts with Shank Suggesting a Role Synaptogenesis and NMDAR Function

To gain further insight into the physiological function of Homer, we characterized a novel family of proteins that were identified based on their interaction with Homer 1a in a yeast 2-hybrid screen of a brain cDNA library. These Homer-interacting proteins were determined to be identical to the Shank family of PSD proteins that interact with GKAP and the PSD-95 complex (Tu et al., 1999). Shank proteins are specifically enriched at excitatory synapses and co-localize with NMDA receptors in primary neuronal cultures (Naisbitt et al., 1999). Shank proteins appear to be recruited to excitatory synapses by virtue of their interaction with GKAP, a synaptic protein that binds to the guanylate kinase domain of PSD-95 (Kim et al., 1997; Naisbitt et al., 1999; Naisbitt et al., 1997; Takeuchi et al., 1997). In addition to the PDZ domain which binds GKAP, Shank contains domains that mediate self-multimerization and interaction with cortactin (Golshani et al., 1998). Shank also directly interacts with Homer (Lujan et al., 1997). Homer and Shank proteins co-localize at the PSD of CA1 pyramidal neurons (Tu et al., 1999), and native Homer-Shank complexes were identified in brain using GST pull down assays of Shank with GKAP (Otani and Connor, 1998). Additionally, Homer and Shank co-immunoprecipitate from brain (Aniksztejn et al., 1991; Ben-Ari et al., 1992). These observations indicate that Shank and Homer naturally associate in brain. Biochemical studies indicate that the Shank-Homer interaction is mediated by the EVH1 domain of Homer which binds to a single Homer-ligand site present in the proline-rich domain of Shank proteins (Tu et al., 1999). A quaternary complex of Homer/Shank/GKAP/PSD-95 is assembled in heterologous cells, with Homer and PSD-95 co-localizing in large clusters (Berridge, 1998). Thus, Shank provides a molecular bridge that links the NMDA receptor complex with Homer and its associated proteins.

The Homer-Shank interaction also produces clustering of group 1 mGluRs (Satoh et al., 1990; Villa et al., 1992). Clustering molecules have previously been identified for a variety of receptors and ion channels (Selig et al., 1995), but Shank-Homer are the first clustering proteins for group 1 mGluR. It is notable that the mechanism of clustering involves a linkage of mGluRs with the previously defined NMDA receptor scaffold. Thus the Shank-Homer interaction could be relevant to synaptogenesis, by docking mGluRs to a preestablished "core" of NMDA receptors. In support of such a mechanism, functional NMDA receptors appear to precede the emergence of metabotropic receptors in the hippocampus and cerebellum (Xiao et al., 1998). Homer proteins, in association with Shank, could function to localize and cluster the mGluRs in proximity to NMDARs, and may contribute to the perisynaptic localization of group 1 metabotropic receptors (Lujan et al., 1997).

By linking NMDA and mGluR signaling pathways, the Shank-Homer interaction might also contribute to examples of glutamate receptor crosstalk for which physical proximity of molecules may be important, such as activation of phospholipase C (Beneken et al., submitted) or protein kinase C (Aniksztejn et al., 1991; Ben-Ari et al., 1992). Additionally, the Homer/Shank/GKAP/PSD-95 assembly may mediate physical association (and perhaps functional coupling) of the NMDAR with IP3R/RYR and intracellular Ca2+ stores. Consistent with such a functional interaction, recent studies indicate that NMDA receptor-dependent increases in spine Ca2+ may derive from intracellular stores by a mechanism of Ca2+-induced Ca2+ release (CICR) (Emptage et al., 1999) and reviewed by (Svoboda and Mainen, 1999). Both IP3R and ryanodine receptor channels possess CICR properties (Berridge, 1998), and are similarly localized in dendrites and spines of specific neuronal types (Satoh et al., 1990; Villa et al., 1992). The physical proximity of glutamate receptors with calcium pools may underlie synergistic effects of mGluRs on NMDA-dependent responses as reported in studies of LTP (Bashir et al., 1993; Bortolotto et al., 1994) but see also ((Selig et al., 1995), and is consistent with the reduction of LTP in group 1 mGluR mutant mice (Prehoda et al., 1999) but see also (Conquet et al., 1994).

The proposed model for Shank and Homer-dependent clustering requires that Homer be multivalent in order to cross-link Shank/GKAP/PSD95 to IP3R/RYRs and to mGluRs. This is achieved by multimerization of constitutively expressed CC-Homers (Xiao et al., 1998). In this context, the monovalent Homer 1a IEG product appears to function to uncouple proteins that are linked via the constitutively expressed CC-Homer multimers, and thereby dynamically regulate the assembly of this postsynaptic network. Cocaine-induced increases in Homer 1a may thus modulate both mGluR and NMDA Ca2+ responses in spines.

Homer EVH1 Domain Crystal Structure

To investigate the structural basis of interactions between EVH1 domains and ligands, we determined the high-resolution crystal structure of the EVH1 domain from rat Homer 1 ( ). Methods of protein purification and crystallization are described in our manuscript (Niebuhr et al., 1997; Tu et al., 1998). This structure revealed that the EVH1 module is homologous to both the plextrin homology (PH) domain and the phosphotyrosine binding (PTB) domain. (legend next page)

At the same time we were working to solve the structure of Homer 1 EVH1, Dr. Wendel Lim's group (at UCSF) solved the structure of the related EVH1 protein termed Mena (20% identical to Homer EVH1 domain) (Prehoda et al., 1999). Comparison of the Mena and Homer coordinates confirmed that these are related proteins despite the low degree of amino acid identity. The Mena crystal was solved with a 6mer peptide and identified a putative ligand binding surface. Both of our groups determined that co-crystals were not formed with longer synthetic peptides. One issue that concerned us regarding the putative ligand-binding site on Mena was that the affinity of the 6mer used for Mena was 100 fold less than that of a 10 mer (Prehoda et al., 1999). The measured affinity of the 6mer was ~600 micromolar. Additionally, within the EVH1 family, Homer is one of the most divergent members (Prehoda et al., 1999). One important difference between Mena and Homer EVH1 binding, is the orientation of the phenylalanine relative to the polyprolines. The optimal ligand for Mena is FPPPP while the consensus ligand for Homer is PPXXF. This may be important since the F is the single most critical side chain for the interaction when tested with larger peptides for both EVH1 domains (Niebuhr et al., 1997; Tu et al., 1998). In the Mena structure, the F side chain is not placed in a clear hydrophobic pocket (the ring appears to coordinate an arginine) and superposition of the ligand coordinates in Homer EVH1 is even less obviously stabilized.

To examine the predictive power of the Mena co-crystal for the ligand binding activity of Homer EVH1, we tested a series of missense mutations that targeted sites anticipated to contact the prolines of the ligand (PPXXF) sequence. Based on the homology of the EVH1 domain with the PTB domain, we also tested sites on Homer that would be critical if Homer mimicked the peptide binding surface of the PTB domain. This PTB ligand site is remote from the putative Mena EVH1 ligand site. Our mutation analysis also tested a series of mutants selected based on the homology between Homer and WASP. Genetic data from patients with Wiscott Aldrich syndrome defined a series of mutations in the EVH1 domain that map to sites that are distinct from both the PTB and the putative Mena ligand sites. Our selection of the mutational substitutions was based on the Homer EVH1 structure. Substituted amino acids were selected to be sufficiently conservative as not to disrupt the primary structure.

A total of 30 missense mutants of the Homer EVH1 domain were expressed in HEK293 cells and assayed for binding to either mGluR1a or Shank3 using GST pulldown assays. Surface-exposed mutations within the region homologous to the peptide binding site of PTB domains had no affect on peptide binding. Similarly, mutations based on the WASP data were also ineffective in disrupting binding. By contrast, certain of the mutants based the Mena ligand site did disrupt Homer EVH1 binding. Despite ambiguities involved with interpreting the effects of any single mutation, the nature and distribution of the effects of site-directed mutations in the Homer EVH1 domain on Homer-ligand interactions strongly implicate the Mena ligand region as mediating natural ligand binding by the Homer EVH1 domain.

One interesting finding from our analysis of mutant Homer EVH1 binding is that certain mutations disrupt binding specifically to mGluR1a, but not to Shank3 (and visa versa). One interpretation of this finding is that there are determinants of binding in addition to the core PPXXF motif. An important implication of this observation is that differences in critical determinants of Homer binding to its various targets may be exploited to develop pharmaceuticals that can selectively disrupt interactions with a particular target.

I42 Interacts with Homer

I42 (SEQ ID NOS:17 and 18) encodes a novel protein that was first identified in a Y2H screen of brain cDNA with the Homer EVH1 domain. Current information indicates that I42 functions with Homer at the excitatory synapse. We have generated I42 specific antisera and can demonstrate robust co-immunoprecipitation of I42 with Homer from brain. ImmunoEM analysis demonstrates that I42 is localized to the postsynaptic density. The predicted domain structure of I42 indicates that it shares certain properties with Shank including a N-terminal structural domain (a band 4.1 domain in I42), a single PDZ domain, and a central proline rich domain with a single Homer-ligand site. Additionally, there is a C-terminal type 1 PDZ ligand motif. We have identified a related sequence in the data base (KIAA sequence has several errors with frame shifts) suggesting that I42 may represent a gene family.

Current studies indicate a functional interaction of I42, Homer and mGluRs. We have performed a yeast 2-hybrid screen of the I42 PDZ domain and find it binds βB-Pix (also termed Cool-1) (Allen et al., 1998). β-Pix is a guanine nucleotide exchange factor (GEF) for Rac1/CDC42. This interaction appears robust using GST pulldown assays and we have recently confirmed the interaction using co-immunoprecipitation assays from brain. Biochemical assays indicate that the PDZ domain of I42 binds its own C-terminus (may be intra or inter molecular). Based on these observations, I42 functions as a scaffold/cytoskeletal regulatory protein that responds to specific signals and may link between mGluR activation and Rac-dependent cytoskeletal remodeling. This biochemical association may play a role in mGluR trafficking or synaptic remodeling. An additional functional consequence of the Homer I42 interaction is indicated by the demonstrated association of β-Pix with p21 activated kinase (Pak) (Tu et al., 1999). Paks are a family of kinase that can signal both locally and more distally to the nucleus. A mutation of Pak3 has recently been linked to mental retardation (Tu et al., 1998), confirming the importance of this regulated kinase to cognitive function. Accordingly, I42 appears to be part of a novel signaling pathway for the mGluRs that may be regulated by Homer proteins.

In preliminary studies, we observe that I42 co-immunoprecipitates with Homer from brain. Antibodies for I42 also co-immunoprecipitates mGluR1 from brain. In parallel studies, we observed the interaction between I42 and β-Pix ( ). These observations indicate the involvement of Homer in the function of I42/β-Pix and identify another signaling pathway that can be manipulated by agents that modulate Homer binding function.

ii) Ultrastructural localization of I42/β-Pix/Pak at synapses: We have performed preliminary immunoEM with I42 Ab and observes that it is associated with the PSD region. The methods and approach are identical to our studies of Shank (Naisbitt et al., 1999). This observation indicates that I42 is enriched at the excitatory synapse together with Homer, Shank and glutamate receptors.

Ryanodine Receptor (RYR) and Homer

The RYR encodes a potential Homer binding site near the N-terminus (Bhat et al., 1999) and using GST pulldown assays we observe that GSTHomer binds to the relevant fragment of RYR1. Importantly, we have demonstrated that the RYR co-immunoprecipitates with Homer from detergent extracts of skeletal muscle. The interaction between RYR and Homer is understood to be consistent with the function of Homer proteins to regulate the coupling of membrane receptors with intracellular calcium pools. Glutamate mediates an inhibitory postsynaptic potential in dopamine neurons of the midbrain and this is mediated by mGluR1 release of intracellular Ca2+ from RYR sensitive CICR pools (Bhat et al., 1999). RYR have recently been implicated as an important source of NMDAR-induced calcium rise in the post synaptic spine (Emptage et al., 1999). Since Shank is part of the NMDA receptor signaling complex (Naisbitt et al., 1999) and binds Homer, it is compelling to evaluate the possible interaction between RYR and Homer.

NMDA Receptor Type 2D (NR2D) and Homer

Independent Y2H screens of adult cortex and cerebellum identified several clones of the NMDA receptor type 2D (NR2D). NR2D has not been as extensively studied as NR2B but is expressed in developing cerebellum and interneurons in the forebrain (Dunah et al., 1998; Goebel and Poosch, 1999). NMDAR that include the NR2DR have slower channel properties (Cull-Candy et al., 1998; Okabe et al., 1998; Vicini et al., 1998). The C-terminus of NR2D is highly proline rich consistent with our observation that Homer binds a specific proline rich sequence. Thus, in the case of NR2D, Homer proteins form a direct coupling to CICR pools. This direct coupling would contrast with NMDAR that include NR2B which appear to couple to Homer indirectly via PSD95-GKAP-Shank (Naisbitt et al., 1999). In both cases, modification of Homer crosslinking activity will alter the intracellular release of calcium due to glutamate receptor activation. Because of the differences in the binding properties of the EVH1 domain of Homer to its different targets, it is anticipated that agents that specifically disrupt the linkage of NR2B or NR2D can be developed.

Mammalian InaD like Molecule Interaction with Homer

We have identified two distinct novel members of a family of proteins with similarity to the recently reported human InaD (Philipp and Flockerzi, 1997) and Drosophila Discs Lost DLT (Bhat et al., 1999). These proteins encode 5 and 4 PDZ domains, respectively, and a proline rich region that is shared in all clones that is presumed to mediate interaction with Homer. DLT has been demonstrated to be essential for establishment of epithelial cell polarity and binds to the C-terminus of Neurexin IV DLT (Bhat et al., 1999). We currently refer to our clones as rat InaD. In current studies, we observe that full length myc-tagged rInaD co-immunoprecipitates with Homer 2 from co-expressing HEK293 cells.

I30 Interaction with Homer

I30 is a novel member of the family of abl binding proteins. Related proteins function as adaptor proteins that regulate cell growth Ziemnicka-Kotula, 1998 #392; Biesova, 1997 #393 and are hypothesized . I30 encodes a SH3 domain and a Homer binding site. Accordingly, Homer is anticipated to link this protein to other Homer-interacting proteins including metabotropic glutamate receptors and IP3R. (See SEQ ID NOS: 15, 16, 19 and 20).

Cdc42-associated Tyrosine Kinase-2 (ACK-2) Interaction with Homer

ACK-2 is a non-receptor tyrosine kinase that is regulated by the Rho-related GTP-binding protein Cdc42 Yang, 1999 #391. ACK-2 is activated by signals that result from cell adhesion, by for example activation of the integrin receptor. One cellular consequence of ACK-2 activation is down stream activation of c-Jun kinase. Our observation that ACK-2 interacts with Homer indicates that this signaling pathway can be linked to other membrane receptors by Homer, and identifies another signaling cascade that can be manipulated by agents that alter Homer crosslinking function.

EXAMPLE 1

Identification and Sequencing of Homer Family Members

Low stringency screens of phage cDNA libraries and EST Database searches were performed to identify Homer family members. cDNA libraries were screened using the rat Homer 1a coding region as a probe. Screens of mouse and rat brain cDNA libraries identified two isoforms of Homer-1 (Homer-1b and Homer-1c).

Searches of EST Databases identified a mouse EST sequence (ID#442801) which is about 73% homologous to a portion of 5' coding region of Homer-1cDNA sequence. Based on the EST used RT-PCR (Forward: 5'-GAC AGC AGA GCC AAC ACC GTG-3'; (SEQ ID NO:49); Reverse: 5'-GTC TGC AGC TCC ATC TCC CAC-3'; (SEQ ID NO:50)) to amplify the corresponding region from various mouse tissues. The PCR products (~330 bp) consisted of two different sequences, one of which contains an additional insertion of 33 bp. A mixture of these two cDNA fragments were used as probes to screen an adult mouse brain cDNA library. Out of $10^6$ clones screened, five clones hybridized well to the probe. Sequence analysis of these clones indicated that they are five partial cDNA clones representing two isoforms of a Homer-2 gene. These clones are identical to the isoforms amplified by RT-PCR. The 5' region of Homer-2 was cloned using 5'-RACE technique. Total RNA from E14.5 mouse brain was reverse-transcribed using the reverse primer described above. Another gene-specific primer (5'-CAC GGT GTT GGC TCT GCT GTC-3'; (SEQ ID NO 51)) was used in the amplification of the 5' region of Homer-2. The sequence authenticity of the 5' RACE clones was further confirmed by sequencing a partial mouse EST clone #441857.

A search of the EST Database allowed the identification of several human EST's corresponding to mouse and rat Homer-1b, Homer-2a and 2b cDNA sequences. RT-PCR was used to clone the human Homer-1b and Homer 2a and 2b coding regions. A 5' degenerate primer (5'-ATG GG(A/G/C) GA(A/G) CA(A/G) CC(T/C/G) AT(T/C) TTC-3'; (SEQ ID NO:52)) was designed based on an amino-terminal seven residue amino acid sequence (MGEQPIF; (SEQ ID NO:53)) that is conserved among human EST clone #HCE003, mouse, rat, and Drosophila Homer homologue sequences. The 3' primers (5'-GAG GGT AGC CAG TTC AGC CTC-3';_(SEQ ID NO:54)) for human Homer-1 and human Homer-2 (5'-GTT GAT CTC ACT GCA TTG TTC-3'; (SEQ ID NO:55)) were made from the sequences of human EST clones #562862 and #HIBAB15 respectively. Human Homer-1b and Homer-2a and 2b were amplified from new born human frontal cortex. The sequences of human Homer 1b, Homer 2a and Homer 2b were derived from sequencing several PCR clones and EST clones and are shown in SEQ ID NO's:3, 7 and 9.

Human and mouse Homer-3 were identified by searching EST Database, using Homer-1 and Homer-2 sequences. Two full-length human Homer-3 clones were identified (Clone ID #284002 and #38753) and sequenced. Numerous mouse Homer-3 clones were found and one of them (Clone ID #1162828 ) contains an almost full-length coding region. Also identified were several Drosophila EST sequences exhibiting significant homology at the amino acid level to the N-terminal region of Homer family members. The sequence presented in SEQ ID NO:11 is derived from Clone #LD3829.

Expression Constructs Mammalian expression constructs were made by cloning cDNA into SalI and NotI sites of pRK5 (Genentech), so that the cDNA was fused in-frame to an N terminal c-Myc tag. GST-fusion constructs were made by cloning Homer cDNA into the SalI and NotI sites of pGEX4T-2 (Pharmacia). The full-length coding regions of mouse Homer-1b, rat Homer-1c, mouse Homer-2b and human Homer-3 were engineered with SalI and NotI sites at the 5' and 3' ends by PCR using high fidelity DNA polymerase Pfu (Stratagene). Various truncations of Homer-1b/c and Homer-2b coding regions were made by PCR with specific Primers containing SalI and NotI sites. All the PCR-based constructs were sequenced to confirm the sequences and in-frame fusion.

The sequence of Homer 1a was used to screen cDNA libraries prepared from rat and mouse brain for related gene products. Homer 1a sequence was also used to search GenBank data bases. Several related rodent and human sequences were identified.

cDNAs that are most closely related to Homer 1a appear to represent alternative splice forms. This inference is based on nucleotide sequence identity of their 5'UTRs and the first 175 amino acids of the open reading frames (ORF). The presumptive novel splice variants, termed Homer 1b and 1c, are completely divergent from Homer 1a after residue 175 of the ORF and they possess entirely distinct 3'UTRs. comparison at the point of sequence divergence indicates that Homer 1a encodes a unique eleven amino acid carboxy terminus of the ORF and about 5 kb 3' UTR region. The unique eleven amino acid carboxy-terminal sequence of Homer 1a does not possess a recognizable motif. In Homer 1b and 1c, an additional 168 and 180 amino acids are present that are predicted to possess coiled-coil (CC) secondary structure (Lupas, *Trends Biochem. Sci* 21:375 (1969)). While the 3'UTR sequence of Homer 1a includes multiple AUUUA repeats which are implicated in destabilizing mRNAs of intermediate early genes (IEG) (Shaw and Kamen, *Cell* 46:659 (1986)), the 3'UTR sequence of Homer 1b and 1c does not include this motif. The only difference between Homer 1b and 1c is the inclusion in Homer 1c of a twelve amino acid sequence insertion at residue 177, between the conserved amino-terminus and the CC domain. Thus, Homer 1b and 1c appear to be formed by a splicing event that substitutes a relatively long and unique carboxy-terminus of the ORF and shorter 3'UTR sequence that lacks the characteristic IEG motif. Multiple independent isolates of rat and mouse Homer 1b and 1c were identified and sequenced to confirm their natural expression in brain.

Further searches identified cDNA sequences that appear to represent two additional Homer genes, termed Homer 2 and Homer 3. The sequences of two splice forms of Homer 2 and one Homer 3 sequence is presented (See Figures section). The predicted size of the protein products and general domain structure are similar to Homer 1b and 1c. Like Homer 1b and 1c, each of the Homer 2 and Homer 3 proteins contain about 120 amino acids at the amino-terminal that is highly similar to the amino-terminal domain of Homer 1a . The degree of amino acid identity in these regions is about 88% between Homer 1 and Homer 2 and about 86% between Homer 1 and Homer 3. Many of the amino acid differences are conservative.

In contrast to the high degree of conservation in amino-terminal region, the carboxy-terminal regions of Homer 2 and 3 are only about 22% identical to Homer 1b, but like Homer 1b and 1c are predicted to possess a CC secondary structure. The CC domains of all Homer family members exhibit significant homology (about 40–45% amino acid similarity) to the CC regions of myosin heavy chain (Strehler et al., *J Mol Biol* 190:291 (1986)), kinesin heavy chain (Yang et al., *Cell* 56:879 (1989)) and dynactin (Gill et al, *J. Cell Biol* 115:1639 (1991)). The distinct splice forms of Homer 2, termed Homer 2a and Homer 2b, are differentiated by an eleven amino acid insertion at residue 131 in Homer 2b. Human Homer 1, 2 and 3 are mapped to chromosomes 5, 15 and 19, respectively by the Human Genome Project.

Drosophila Homer possess the basic domain structure of mammalian Homers. The amino-terminus is highly homologous to that of mammalian Homer and the carboxy terminus is predicted to form a CC secondary structure.

EXAMPLE 2

Generation and Characterization of Homer Antisera

Rabbit polyclonal antibodies were generated against synthetic peptides derived from the unique carboxy termini of Homer 1b/c, Homer 2a/b and Homer 3. Synthetic carboxy-terminal peptides of Homer 1, 2 or 3 were conjugated to thyroglobulin with glutaraldehyde and used to immunize rabbits according to a previously published protocol (Martin et al., *Neuron*, 9:259 1992). Peptide sequences used are contained in Homer-1b and 1c: IFELTELRDNLAKLLECS (SEQ ID NO:56); Homer-2a and 2b: GKIDDLHDFRRGL-SKLGTDN (SEQ ID NO:57); and Homer-3: RLFELSEL-REGLARLAEAA (SEQ ID NO:58). Detergent (2% SDS) extracts from rat cortex, hippocampus, and cerebellum were separated on 8% SDS-PAGE gels and transferred to nitrocellulose membranes. Blots was probed with polyclonal anti-Homer sera. Specificity was tested by incubating the antiserum with 10 µg/ml of relevant peptide at room temperature for 10 m prior to use. Rabbit polyclonal antiserum was also generated against the full length GST-Homer 1a fusion protein, as described previously (Brakeman, et al., *Cell* 87:227 1997). This antiserum recognizes all Homer 1 isoforms.

Unpurified antibodies were tested for their sensitivity and specificity in detecting heterologously expressed, full length Homer proteins with amino-terminal c-myc tags. Each Homer protein was selectively detected on Western blot by the appropriate Homer antibody in soluble extracts of transfected HEK293 cells. The myc-tagged Homer proteins migrated with an apparent molecular mass of 50 kDa. There was no cross reactivity between antibodies for one Homer form and other family members.

EXAMPLE 3

In Vitro Interaction of Homer Proteins with Cell-Surface mGlu Receptors

To examine the interaction of Homer proteins with mGluR1 and mGluR5, HEK293 cells were transiently transfected (using calcium phosphate) with full length mGluR1α and mGluR5 constructs in pRK5 (Brakeman et al., 1997). Cell lysates were made 24–48 h post-transfection. GST fusion proteins bound to glutathione agarose were prepared of Homer 1a , Homer 1c, Homer 2b, Homer 3 and two amino terminal fragments of Homer 2 according to the following procedure. GST fusion constructs were prepared by polymerase chain reaction with specific primers that included SalI and NotI sequences and subcloned into pGEX4T-2 vector (Pharmacia Biotech, Uppsala, Sweden). Constructs were confirmed by sequencing. GST-fusion proteins were expressed in BL21 bacterial strains. Bacteria were harvested and lysed in PBS, 1% Triton X100, 2 mM phenylmethyl-sulfonyl fluoride (PMSF) and pelleted at 13,000 rpm (Sorvall SS-34) at 4° C. for 5 m Proteins were purified by incubating 1 ml bed volume glutathione-sepharose (GST) beads (Sigma USA) with bacterial supernatant at 4° C. for 10 m, washing twice with PBS and PBS plus 1% Triton X-100. Protein was eluted with 10 mM glutathione and dialyzed against PBS at 4° C. Protein concentrations were measured by BCA (Pierce, Ill.). Cell lysates of the transfected cells were incubated with equivalent amounts of various Homer-GST fusion proteins at 4° C. for 2 h, washed with PBS and 1% Triton X-100. Proteins were eluted in 2% SDS sample buffer and separated on 8% or 2.5% SDS-PAGE gels and probed with appropriate antibody.

It has been previously demonstrated that the amino-terminal 131 amino acids of Homer 1a is sufficient to bind group I metabotropic glutamate receptors (Brakeman et al., *Nature* 386: 284 (1997)). In view of the high degree of sequence conservation in this region of Homer family members, the possibility that they would also bind group I receptors was examined. GST fusion proteins were prepared of Homer 1a, Homer 1 c, Homer 2b Homer 3 and two amino-terminal fragments of Homer 2. The fusion proteins were bound to glutathione agarose and assayed for binding to full length mGluR5 or full length mGluR1a expressed in HEK293 cells. These studies show that mGluR5 bound GST Homer 1a . mGluR5 also bound to all full length Homer constructs and to a Homer 2 amino-terminal fragment of about 141 residues but not to GST alone. The relative binding in the three assays were comparable for each of the three Homer types. A Homer 2 deletion mutant that includes only the amino-terminal 92 residues did not bind mGluR5. Similar binding of Homer proteins to mGluR1 was also observed.

EXAMPLE 4

In Vivo Interaction of Homer Proteins with Cell-Surface mGlu Receptors

To examine if Homer proteins are naturally associated with group I metabotropic receptors in the brain, immuno-precipitation studies were performed. Rat or mouse brain tissues were sonicated (3×10 s) in PBS (~200 mg/ml wet weight) containing 1% Triton-X100 with protease inhibitors and centrifuged for 10 m at 15,000 g. Three µl of antiserum directed against Homer 1b, Homer 1c, Homer 2a, Homer 2b or Homer 3 was added to 60 µl of tissue extract and incubated for 1½ h at 4° C. and then washed three times with PBS/Triton. Preimmune and peptide-blocked antisera were used as negative controls. Binding in tissue samples was analyzed by gel electrophoresis and western blot analysis. Proteins were eluted in 2% SDS loading buffer. mGluR1α monoclonal antibody was obtained from PharMingen (San Diego Calif.). Rabbit polyclonal mGluR5 antibody was a gift from Dr. Richard Huganir, Johns Hopkins School of Medicine.

Homer family members are naturally associated with group I metabotropic receptors in brain. This analysis was performed using cerebellum since all three Homer family members are expressed in this tissue. Detergent extracts of whole adult rat cerebellum were incubated with antibodies to Homer 1b/c. Homer 2a/b or Homer 3 and immunoprecipitates were blotted with a mouse monoclonal antibody to mGluR1α. mGluR1α co-immunoprecipitates with each of the antisera directed against Homer proteins. The predominate band after electrophoreses corresponded to the monomer form of mGluR1α (about 150 kDA) and other bands corresponding to multimers of mGluR1α are also observed.

EXAMPLE 5

In Vitro Interaction of Homer Proteins with Intracellular Inositol Trisphosphate Receptors To demonstrate that Homer proteins interact in vivo with inositol trisphosphate receptors immunoprecipitation studies were performed using brain tissue. Rats or mice were sacrificed by decapitation and the cerebella were dissected immediately. Cerebella were sonicated in TE buffer (50 mM Tris, 1 mM EDTA, pH 7.4) containing 1% CHAPS and protease inhibitor cocktail (~100 mg wet weight/ml). The homogenate was centrifuged at 90,000 rpm, 20 m, 4° C. in a TLA 100.3 rotor. 100 µl of the cerebellar extract was used for each immunoprecipitation assay with the following antibodies: 3 µl of crude Homer 1, Homer 2 or Homer 3 antibodies (Xiao et al., in press); 20 µg of affinity purified inositol trisphosphate antibody (gift from Alan Sharp). Antibodies and extract were incubated for 30 m at 4° C., then 60 µl of 1:1 protein A or protein G (for goat antibody) sepharose slurry was added. The antibody/extract/beads were incubated for an additional 90 m at 4° C. After washing 3×10 m in TE-CHAPS buffer, the proteins were eluted from the beads with 30 µl of 4% SDS loading buffer and analyzed by SDS-PAGE and immunoblot.

Results from these studies showed that the inositol trisphosphate receptor specifically co-precipitates with antisera directed against Homer 1, Homer 2 and Homer 3.

EXAMPLE 6

Calcium Mobilization is Decreased by Transient Expression of Homer Protein without a Coiled-Coil Domain To demonstrate that Homer cross-links metabotropic glutamate receptors and inositol trisphosphate receptors to provide or enhance a functional signaling complex, calcium mobilization was examined in cells transient expressing truncated forms of Homer protein. The truncated Homer protein used lacks the coiled-coil domain and is unable to form a bridge linking the mGluR at the cell surface with intracellular inositol trisphosphate receptors. The truncated form of Homer protein resembled Homer 1a with the exception of 11 residues at the carboxy-terminal. This form of Homer results in enhanced expression of Homer protein as compared with transfection of Homer 1a in heterologous cells. The Homer protein was introduced into Purkinje cells in primary cerebellar cultures and glutamate induced effects on calcium mobilization was measured.

Embryonic mouse cerebellar cultures were prepared and maintained according to the method of Schilling et al. (Schilling et al., Neuron 7:891 1991). At 4–5 DIV, cultures were transfected with plasmids coding for E-GFP (Clontech) and either full-length Homer 1b or an IEG form of Homer 1. The IEG form of Homer 1 was a 186 amino acid amino-terminal fragment of Homer 1b. Plasmids were purified by cesium banding. Three combinations of the plasmids were transfected. Group I (control), 20 µg of E-GFP and 40 µg of pRK5 vector; group II, 20 µg of E-GFP and 40 µg of pRK5 Homer 1 IEG; group III: 20 µg of E-GFP and 40 µg of pRK5 Homer 1b. Plasmid DNA was mixed with gold particles (0.6 micron), and coated onto plastic tubing. DNA was then ballistically transfected into cells according to the manufacturer's protocol (Helios Gene Gun System, BIO-RAD). After transfection, cultures were returned to the incubator and maintained for an additional 2 days for a total of 7–8 DIV at the time of use for imaging experiments.

Patch electrodes were attached to the somata of GFP-expressing Purkinje cells and a holding potential of –60 mV was applied. Micropressure electrodes (1 µm tip diameter) were filled with quisqualate (100 µm in external saline) and were positioned ~20 µm away from large-caliber dendrites. Test pulses were delivered using positive pressure (6 psi, 1 sec). Cells were bathed in a solution that contained (in mM) NaCl (140), KCl (5), EGTA (0.2), $MgCl_2$ (0.8), HEPES (10), glucose (10), tetrodotoxin (0.005), and picrotoxin (0.1), adjusted to pH 7.35 with NaOH, which flowed at a rate of 0.5 ml/m. The recording electrode contained CsCl (135), HEPES (10), fura-2 $K_5$ salt (0.2), and $Na_2$-ATP (4), adjusted to pH 7.35 with $C_5OH$. Patch electrodes yielded a resistance of 3–5 MΩ when measured with the internal and external salines described above.

Fura-2 ratio imaging of intracellular free $Ca^{2+}$, was accomplished by measuring the background corrected fluorescence ratio at 340 and 380 nm excitation using a cooled CCD camera system, as previously described (Linden et al., J Neurosci 15:5098 1995). Exposure times were 200 msec per single wavelength image. Experiments were conducted at room temperature. Enhanced GFP is weakly excited by illumination in the 380–400 nm spectrum. Based upon the bandpass characteristics of our 340HT15 and 380HT10 excitation filters and the absorption spectrum of enhanced GFP (Clontech), we estimate that <1% of the signal at 340 nm excitation and <5% of the signal at 380 nm excitation is contributed by GFP, even in those cells where the fura/GFP loading ratio is smallest. This could lead to a small (<5%) systemic underestimation of free calcium concentration that should distribute randomly across experimental groups.

Calcium mobilization in the absence of influx was measure by ratio imaging fura-2 in Purkinje cells bathed in $Ca^{+2}$-free external saline and stimulated with a micropressure pulse of quisqualate, a metabotropic glutamate receptor agonist (Linden, Neuron 17:483 1996). The resultant $Ca^{+2}$ transient is triggered by an mGluR and inositol trisphosphate pathway since it is completely blocked by either an mGluR antagonist ((+)-MCPG, 500 µM in the bath) or a novel specific inositol trisphosphate receptor-associated ion channel blocker, xestospongin C (1 µM in the internal saline). Purkinje cells transfected with a truncated form of Homer showed mGluR-evoked $Ca^{+2}$ responses with a decreased amplitude (170±9 nM, mean±SEM, n=30 cells) and an increased latency (10.5±1.8 sec) as compared with cells transfected with Homer 1b (244±17 nM, 4.2±0.9 sec, n=23) or an empty vector control (239±19 nM, 4.5±1.1 sec, n=15). The decay phase of the $Ca^{+2}$ response appeared somewhat slower in neurons transfected with the truncated form. While the total $Ca^{+2}$ flux appeared similar in cells transfected with truncated and complete Homer proteins and in empty vector controls, the measurement could not be made because the tail of the $Ca^{+2}$ response was abbreviated due to the constraints of the image buffer capacity.

EXAMPLE 7

Determination of the Crystal Structure of Homer Protein

The crystal structure of Homer protein and a Homer protein binding site were determined. Results of these experiments are presented in Table (a) Protein Expression and Purification Residues 1–120 of rat Homer 1a were expressed in Escherichia coli BL21 cells as a C-terminal fusion to glutathione-S-transferase (GST-1aEVH) as previously described (Tu et al., Neuron 21:717 1998). Selenomethionine-substituted (SeMet) GST-1aEVH was prepared by expression in the methionine auxotrophic strain B834 (DE3) (Novagen). 5 mL of an overnight culture grown at 37° C. in LB media supplemented with 100 µg/mL ampicillin (Sigma) was added to 4L M9 minimal media (Gibco BRL) supplemented with 100 μg/mL ampicillin, 0.05 mg/mL alanine, aspartic acid, glutamic acid, phenylalanine, glycine, histidine, isoleucine, lysine, asparagine, proline, glutamine, arginine, serine, threonine, valine, tryptophan, tyrosine, L-selenomethione, 1μ/mL thiamine (Sigma), 2 mM $MgSO_4$, 1% glucose, 100 μM $CaCl_2$. Cells were grown to an $A_{600}$ of 0.5 at which time IPTG (Calbiochem) was added to a final concentration of 0.2 mM. Cells were grown for an additional 3 hours, harvested by centrifugation, and resuspended in 1×PBS/1% Triton. Pepstatin A and leupeptin (Boehringer-Mannheim) were added to a final concentration of 1 μg/mL, and PMSF (Life Technologies) was added to 0.5 mM. Cells were lysed by sonication and centrifuged at 13,000 rpm in an SS-34 rotor to pellet cell debris. The cleared lysate was added to a 5 mL glutathione-agarose (Sigma) column. The column was washed in succession with twenty column volumes of 1×PBS/1% Triton, twenty column volumes of 1×PBS, and ten column volumes of cleavage buffer (50 mM Tris 7.4, 150 mM NaCl, 2.5 mM $CaCl_2$, 50 mM β-mercaptoethanol). All buffers were degassed. A 50% slurry of glutathione-agarose beads loaded with fusion protein was incubated with 20 U of biotinylated Thrombin (Novagen) for 16 h at room temperature. The released cleavage product (1a-EVH) was collected, and the biotinylated Thrombin was removed with streptavidin-agarose beads (Novagen). 1a-EVH was further purified by cation-exchange chromatography using a Resource S column (Amersham-Pharmacia).

(b) Crystallization and Data Collection

Crystals of native and SeMet protein were grown in hanging drops by the method of vapor diffusion (Wlodawer et al., *Proc Natl Acad Sci USA* 72:777 1975). 1 μl of a 9 mg/mL native or SeMet protein solution was mixed with a 1:1 dilution of reservoir buffer (30% PEG 3350, 87 mM $MgSO_4$, 50 mM HEPES, pH 7.3) with distilled water and equilibrated over I mL of reservoir buffer. All crystallization trials for the SeMet protein were set up under anaerobic conditions to minimize potential problems due to oxidation. Two different crystal forms were observed for both the native and the SeMet protein. Crystals in the orthorhombic space group $P2_12_12_1$, (unit cell dimensions a=33.79 Å, b=51.40 Å, c=66.30 Å) typically grew to a size of 0.5 mm×0.03 mm×0.03 mm. Crystals in the trigonal space group $P3_221$ (unit cell dimensions a=b=49.94 Å, c=80.91 Å) grew to a size of 0.4 mm×0.1 mm×0.1 mm. All data used for phasing and refinement were collected from a single trigonal SeMet crystal soaked in mother liquor plus 10% (v/v) ethylene glycol for approximately three minutes prior to flash freezing in a gaseous nitrogen stream at −180° C. X-ray diffraction data suitable for multiwavelength anomalous dispersion (MAD) phasing were collected at four wavelengths at or near the Se absorption edge. These data were collected at beamline X4A of the National Synchrotron Light Source at Brookhaven National Laboratory using an R-AXIS IV image plate detector. Nonoverlapping oscillations (2°) at φ and φ+180° were measured over a 90° rotation of the crystal, interleaving the four wavelengths. All data were processed and scaled using the DENZO/SCALEPACK programs (Otwinowski and Minor, *Meth Enzymol* 276:307 1997). Data collection statistics are shown in Table 1.

(c) Structure Solution and Refinement

The expected two selenium sites were determined and refined using the program SOLVE (Terwilliger and Berendzen, *Acta Crystallogr* D53:5711997; Terwilliger and Eisenberg, *Acta Crystallogr* A39:813 1983) and initial Se scattering factors from (Hall et al., *Cell* 91:85 1997). Values for the refined Se scattering factors as determined by SOLVE are shown in Table 1. The electron density maps calculated with the experimental MAD phases as determined by SOLVE were improved by solvent flattening and histogram matching using DM (Collaborative Computational Project, 1994). An initial model of residues 1–105 was built into 1.8 Å experimental electron density maps using the program O (Jones et al., *Acta Crystallogr* A47:110 1991). After one round of simulated annealing with bulk solvent correction and positional and B-factor refinement using CNS (Brünger et al., *Acta Crystallogr* D54:905 1998), residues 106–111 were built into $2F_0-F_c$ maps. The model was refined against the maximum-likelihood target (Pannu and Read, *Acta Crystallogr* A52:659 1996) using data to 1.7 Å Bragg spacing collected at 0.9879 Å. Eight rounds of model building and water addition alternated with B-factor and positional refinement yielded the current model, which includes residues 1–111 and 88 water molecules. No electron density was observed for residues 112–120. This model has a crystallographic R value of 25.3% and a free R value of 28.4%. The solvent content is ca. 40.6%, with one molecule per asymmetric unit. Fractional solvent accessibility for each residue was calculated in X-PLOR (Brünger, X-PLOR, Version 3.1: A system for X-ray crystallography and NMR (New Haven, Conn.: Yale Univ. 1992).

(d) Determination of Homer Site by Site Directed Mutagenesis

Point mutants of N-terminally myc-tagged, full-length Homer 1b and 1c and Homer 1 EVH1 were made using the QuikChange™ Site-Directed Mutagenesis Kit (Stratagene). Expression constructs were transiently transfected into HEK293 cells using calcium phosphate methods. About 24–48 h post-transfection, cell lysates were prepared in 1×PBS/1% Triton X-100 (Sigma) and protease inhibitors. GST pull-down assays were performed by mixing 100 μl of cell lysate with GST-mGluR5 or GST-Shank3 (residues 1143–1408) (Tu et al., in press) bound to glutathione-agarose, incubating at 4° C. for 2 h, and washing with 1×PBS and 1×PBS/1% Triton X-100. Bound products were eluted with 100 μl 2×SDS loading buffer and detected by SDS-PAGE and immunoblot using anti-myc antibody 9EI0 (Invitrogen) and ECL reagents (Amersham).

EXAMPLE 8

Homer Expression is Upregulated in Certain Brain Regions in Response to Electrically Induced Seizures Rat Homer 1a was cloned based on its rapid upregulation in hippocampal granule cell neurons following electrically-induced seizure (MECS; see Brakeman et al., *Nature* 3:284 1997) The expression of other members of the Homer family was examined in the brain following seizure. Radio-labeled riboprobes were prepared using unique sequences for Homer 1a, Homer 1b, Homer 1c, Homer 2a, Homer 2b and Homer 3. Probes used did not distinguish between the splice forms of Homer 1b and 1c or Homer 2 and 2b.

(a) In Situ Hybridization

Anti-sense and sense cRNA probes were generated from each mouse Homer plasmid by in vitro transcription in the presence of $^{35}$SUTP, as previously described (Lyford et al., *Neuron* 14:433 1995). Probe for Homer-1a (Xiao, 1998; GenBank # AF093257) was derived from nucleotides 1342 to 2140, for Homer 1b/c (Xiao, 1998; GenBank # AF093258) from nucleotides 785 to 1396, for Homer-2a/b (Xiao, 1998; GenBank # AF093260 submission) from nucleotides 486 to 1561, and for Homer-3 (GenBank #

AF093261) from nucleotides 371 to 2123. Probe (about $10^6$ cpm in 75 µl hybridization buffer) was applied to each slide. Coverslipped slides were then incubated in humidified chambers overnight at 56° C. Following completion of wash steps, slides were air dried and exposed to Kodak Biomax MR film for 2–3 days.

The anatomic distribution in unstimulated animals reveals that expression of Homer 1a is similar to the expression of Homer 1b and Homer 1c. High levels of expression of Homer 1a are observed in the hippocampus, striatum and cortex. In the cortex, there is laminar expression with the highest levels in the superficial and deep layers. Expression of Homer 2a and 2b is enriched in the thalamus, olfactory bulb and principle neurons of the hippocampus in contrast to the cortex where low levels of expression of Homer 2a and 2b are observed. Homer 3 is expressed primarily in the cerebellum and hippocampus.

In situ hybridization studies demonstrate the dramatic induction of Homer 1a in response to MECS. In the hippocampus, induction of expression is estimated to be greater than 20-fold compared to hippocampus from unstimulated animals. MECS induced an increase in Homer 1b and 1c expression of about 1.5 fold as determined by blot analysis. Expression of Homer 2 and Homer 3 is not altered in response to MECS.

EXAMPLE 9

Formation of Multimeric Complexes of Homer Proteins

The CC secondary structure is implicated in protein-protein interactions (Lupas, 1996 supra). Therefore, the possibility that this domain might confer the ability to form homo- or hetero-multimers between Homer family members was examined. For examining the coiled-coil interaction of Homer family members, myc-tagged Homer-1c and Homer-2b were transfected into HEK293 cells and cell extracts were made 2–3 days post-transfection. Cell lysates were treated as described above.

First, the ability of full length, bacterially-expressed GST fusion proteins of Homer to bind full length myc-tagged Homer proteins expressed in HEK293 cells was tested. myc Homer 1c bound Homer 1b, Homer 2b, Homer 3, Homer 1b and Homer 2b carboxy-terminal CC domain, but not Homer 1 a or Homer 2-amino-terminus. This is consistent with the notion that the CC domain is important in the interaction, since Homer 1a and Homer 2-amino-terminus doe not encode the CC domain. To test the specificity of the CC domain interactions, GST fusions of dynein IC-1a and dynein IC-2c were generated. The CC domains of these proteins show modest sequence to Homer family CC domains and bind to the CC domain of dynactin (Gill, 1991 supra). None of the myc-tagged Homer family members bound to either dynein IC-1a or dynein IC-2c.

To determine whether Homer family members naturally form multimers in brain, immunoprecipitates of cerebellum were examined. Extracts immunoprecipitated with Homer 1b/c antibody contained Homer 3, while extracts immunoprecipitated with Homer 3 contained Homer 1b/c. While it is possible that these co-immunoprecipitated Homer family members are associated by means other than their CC domains, the fact the amino-terminus of Homer is monovalent and cannot form extended concatomers supports a model of multimerization mediated by the CC domains. Homer 2 was not detected as a multimer with either Homer 1 or Homer 3 in these immunoprecipitation experiments.

EXAMPLE 10

Homer Family Proteins are Enriched at Brain Synaptic Fractions and are Expressed in Certain Peripheral Tissues The distribution and localization of Homer family proteins was examined at the using immunochemical methods. Tissue extracts were assayed using immunoblot analysis and tissue localization was examined using immunohistochemistry at the light and ultrastructural levels.

(a) Immunoblot Analysis

Immunoblot staining of SDS (2%) extracts of various brain regions were examined to assess the distribution of Homer proteins in the brain. Homer 1b/c antibody detected a single band of about 47 kDa in cortex, hippocampus and cerebellum. These regions have similar levels of expression. The Homer 2a/b antibody detected a single major band in each of cortex, hippocampus and cerebellum. Less intense, higher apparent molecular mass bands were detected at about 60 and about 80 kDa. Homer 3 immunoblots showed low level expression in cortex and hippocampus and intense staining of a single band in cerebellum (47 kDa). Immmunostaining was completely blocked by preincubating the antibody with 10 µl g/ml of the relevant peptide antigen.

(b) Immunohistochemistry

For light microscopy, rats were deeply anesthetized with sevoflurane and perfused through the aorta with 250 ml of saline followed by 400 cc each of 4% paraformaldehyde in 0.1% phosphate buffer (pH 6.5) and 4% paraformaldehyde in 0.1% phosphate buffer (pH 8.5). The rat was allowed to postfix for 1 hr. at room temperature and then prefused with 15% sucrose in 0.1% phosphate buffer (pH 7.4). The brain was removed and sectioned at 40 µm on a freezing sliding block microtome and collected in PBS. Tissue was stained with an immunoperoxidase technique, as follows. Brain sections were incubated in PBS containing 0.3% $H_2O_2$ and 0.25% Triton X-100 for 30 m and then washed 3×5 m in PBS. Sections were incubated in a buffer "PGT" containing 3% normal goat serum (Colorado Serum Co.) and 0.25% Triton X-100 in PBS for 1 hr. and then transferred to the primary antiserum diluted 1:750 in the same PGT buffer. Sections were gently shaken for 48 h at 4° C., washed 4×5 m in PBS and then incubated for 1 hr. at room temperature in a goat anti-rabbit IgG conjugated to horseradish peroxidase (Biosource International) diluted 1:100 in PGT. Sections were washed 4×5 m in PBS and incubated for 6 m at room temperature in 0.05% diaminobenzidine dihydrochloride (DAB:Sigma) and 0.01% $H_2O_2$ in 0.1 M phosphate buffer. Sections were washed in PBS, mounted onto gelatin chrome-alum subbed slides, dehydrated in a series of graded ethanol, cleared in xylene and coverslipped with DPX (BDH Limited).

Immunohistochemistry was performed to determine the cellular localization of Homer 1b/c and Homer 2a/b and Homer 3 in rat brain. Light microscopic examinations indicated that all three Homer proteins are enriched in Purkinje neurons. Immunoreactivity is present in the cytoplasmic region of the soma and extends prominently into the dendritic arbor. The nucleus is not stained. Little or no staining is detected in the contiguous granule cell layer. A similar light microscopic pattern of cellular localization was detected for Homer 3. Homer 2 immunostaining in cerebellum also showed staining in Purkinje neurons, but appeared technically less differentiated.

(c) Electron Microscopy

For EM, a postembedding immunogold method as described previously (Wang, et al., *J Neurosci* 18:1148

1998) was used and modified from the method of (Matsubara, et al., *J Neurosci* 16:4457 1996). Briefly, male Sprague-Dawley rats were perfused with 4% paraformaldehyde plus 0.5% glutaraldehyde in 0.1 M phosphate buffer. Two hundred micrometer parasagittal sections of the rostral cerebellum (folia III-V) were cryoprotected in 30% glycerol and frozen in liquid propane in a Leica EM CPC. Frozen sections were immersed in 1.5% uranyl acetate in methanol at −90° C. in a Leica AFS freeze-substitution instrument, infiltrated with Lowicryl HM 20 resin at −45° C., and polymerized with UV light. Thin sections were incubated in 0.1% sodium borohydride plus 50 mM glycine in Tris-buffered saline/0.1% Triton X-100 (TBST), followed by 10% normal goat serum (NGS) in TBST, primary antibody in 1% NGS/TBST, 10 nm immunogold (Amersham) in 1% NGS/TBST plus 0.5% polyethylene glycol, and finally staining in uranyl acetate and lead citrate. Primary antibodies were used at dilutions of 1:500 for Homer 1b and 1:100–1:400 for Homer 3.

Immunogold EM of Purkinje neurons of the cerebellum was performed to determine whether Homer family proteins are associated with synaptic structures. Homer 1b/c showed striking localization to the region of the postsynaptic spine. Gold particles are densely concentrated in the region of the postsynaptic density (PSD). A very similar distribution is noted for Homer 3 immunoreactivity. It is noted that rather than being concentrated directed over the PSD or the contiguous plasma membrane, the majority of the gold particles appear to be present in the cytoplasm immediately subjacent to these structures.

Peripheral Tissues

Homer proteins are expressed in peripheral tissues. In detergent extracts of heart and kidney, a single band at 47 kDa immunoreactive to Homer 1b and 1c is detected. In extracts of liver, a complex of three bands ranging from about 44 to 47 kDa is detected. In heart, liver, skeletal muscle and intestine, bands immunoreactive to Homer 2a and 2b are detected. Homer 3 immunoreactive bands are detected in extracts of lung and thymus.

Subcellular Distribution

To examine the subcellular distribution of Homer proteins, a biochemical fractionation of rat forebrain was performed and fractions were analyzed by Western blotting with Homer antibodies. Fractions were blotted for mGluR5, BIP and synaptophysin to monitor anticipated enrichment of fractions. Homer 1b/c, 2a/b and 3 were present in the crude nuclear pellet (P1), the medium spin crude synaptosomal pellet (P2), and the high speed microsomal pellet (P3). BIP is a 78 kDa ER resident protein (Munro and Pelham, Cell 48:899 (1987)). and was enriched in both the P3 and the S3 fractions. While Homer 1b/c and Homer 3 were not abundant in the soluble (S3) fraction, Homer 2 was enriched in the S3 fraction. The P2 fraction was subfractionated after hypotonic lysis. The 25,000×g pellet (LP1), which is enriched in PSDs (Huttner et al., *J Cell Biol* 96:1374 (1983)), showed enriched presence of mGluR5. The high speed pellet (165,000×g; LP2) showed the anticipated enrichment in the synaptic vesicle protein synaptophysin (P38). Each of the Homer proteins was enriched in the LP1 fraction relative to LP2. The final soluble fraction (LS2) was uniquely enriched in Homer 2.

EXAMPLE 11

Transgenic Mouse Model Demonstrates that Expression of Homer 1a Selectively Blocks Binding of Homer 1b/c to mGluR5 In Vivo N-terminal myc-tagged full-length Homer 1 a ORF was cloned into the expression vector pT2 (Gordon, et al., *Cell* 50:445 1987; Aigner, et al., *Cell* 83:269 1995). Transgenic mice were generated at the University of Alabama Transgenic Facility. Expression of the transgene protein was assayed by western blot with rabbit polyclonal antisera that recognizes all Homer 1 isoforms (pan-Homer 1 antibody) and myc antibody.

Homer 1a is unique within the family of Homer related proteins in that it is dynamically regulated and it lacks the CC domain. Accordingly, it was hypothesized that the IEG would bind to group 1 metabotropic receptors and disrupt the formation of multivalent complexes of Homer and mGluR. To examine this hypothesis, a transgenic mouse was generated that expresses Homer 1a under the control of a modified Thy-1 promoter (Gordon et al., 1987, supra), which drives neuron-specific expression in postnatal brain (Aigner et al., 1995, supra). Transgenic mice expressed Homer 1a at high levels in cortex, hippocampus, cerebellum and thalamus/brainstem relative to levels in wild type litter mate controls. The pattern of Homer 1a transgene expression is consistent with the previously reported activity of this promoter (Gordon et al, 1987, supra). As expected, antibodies for both Homer 1b/c and Homer 2a/b co-immunoprecipitated mGluR5 from detergent extracts of wild type forebrain. By contrast, Homer 1b/c antibody did not co-immunoprecipitates mGluR5 from transgenic mice. The effect of Homer 1 a transgene expression was selective in that it did not disrupt the co-immunoprecipitation of Homer 3 with Homer 1b/c. The latter observation is consistent with the notion that the Homer 1b/c-Homer 3 interaction is mediated by the CC domain and is predicted not to be altered by Homer 1a expression. Homer 1a was not part of the complex co-immunoprecipitated with Homer 1b/c, consistent with the notion that the CC is necessary for association with the complex. The effect of the Homer 1 a transgene in blocking the in vivo coupling of mGluR5 and Homer 1b/c was additionally selective in that Homer 2 antibody co-immunoprecipitated mGluR5 similarly from extracts of wild type and transgenic mice. Thus Homer 1a appears to selectively disrupt the interaction of Homer 1b/c with mGluR5 but not Homer 2 with mGluR5. Homer 3 is less highly expressed in forebrain than Homer 1b/c or Homer 2a/b and co-immunoprecipitates of mGluR5 with Homer 3 antibody were less clean. Accordingly, it could not be determined in these experiments whether Homer 1a also competes with Homer 3. Identical results were obtained in tow independent mouse lines that express Homer 1a transgene. The Homer 1a expressing transgenic mice have not been behaviorally characterized but appear normal in size and gross motor activity.

EXAMPLE 12

Yeast Two-Hybrid Screen

To examine the physiological functions of Homer, a novel family of proteins was identified based on its ability to interact with Homer family proteins in a yeast two-hybrid screen of a brain cDNA library. Homer 1a was subcloned into pPC97 (Chevray and Nathans, *Proc. Natl. Acad. Sci. U.S.A.*, 89:5789 (1992)) and used to screen a random primed cDNA library prepared from seizure-stimulated rat hippocampus and cortex cloned in pPC86 (Chevray and Nathans, 1992, id.) as described previously (Brakeman et al., *Nature*, 386:284 (1997)). The same library was rescreened using the PDZ domain of Shank 3 (amino acid residues 559–673) cloned into pPC86. The Shank 3 PDZ domain was also tested for interaction with mGluR constructs in pPC86. mGluR5 constructs included a wild type C-terminal 241 amino acid fragment and a four amino acid carboxy-terminal deletion of the same fragment.

Using Homer as "bait" in a yeast two-hybrid screen of a rat cortex and hippocampus cDNA library, multiple cDNA isolates of two novel genes were obtained. Sequencing and full length cloning identified these as distinct members of a gene family, termed Shank 1 and 3 (Naisbitt et al., Neuron (1999) 23:569–82). Shank family proteins are closely related to a previously described protein, termed Cortactin Binding protein (CortBP-1; Du et al., *Mol. Cell. Biol.*, 18:5838 (1998)).

EXAMPLE 13

Interactions Between Homer Proteins and Shank Proteins In Vitro and In Vivo

To characterize the interaction between Homer proteins and Shank proteins, the Shank cDNAs isolated from the yeast two-hybrid screen (Example 10)) were expressed in HEK293 for GST pulldown assays with GST-Homer 1a. The interaction between Homer and Shank proteins was further characterized by co-immunoprecipitation assays.

(a) Expression Constructs

Expression constructs were transiently transfected into HEK293 cells using the calcium phosphate method. Cells were lysed 24–48 h post-transfection with PBS plus 1% Triton X-100. GST pull down assays were performed by mixing 100 µl cell lysates with beads charged with GST fusion proteins (1–3 µg/50 µl bed vol.) at 4° C. for 2 h followed by washing once with PBS, once with PBS plus 1% Triton X-100. Bound proteins were eluted with 100 µl 2×SDS loading buffer and detected by SDS-PAGE and immunoblotting using ECL reagents (Amersham). GST pull down assays of mGluR1a and mGluR5 from brain lysates were performed by sonicating rat cerebellum or cortex in 50 mM Tris, 1 mM EDTA, 1% CHAPS (Sigma), 0.5% deoxycholic acid (Sigma) and proteinase inhibitors with GST-proteins and these tissue extracts were then processed as above. For immunoprecipitation from COS7 cells, transfected cells were extracted in RIPA (see Naisbitt et al., 1999, supra). Soluble extracts were precipitated with 2 µg control non-immune IgG, Myc or Shank 1 (56/e) antibodies (Naisbitt et al., 1999, supra).

(b) GST Pulldown and Co-immunoprecipitation Assays

Expression constructs were transiently transfected into HEK293 cells using the calcium phosphate method. Cells were lysed 24–48 h post-transfection with PBS plus 1% Triton X-100. GST pull down assays were performed by mixing 100 µl cell lysates with beads charged with GST fusion proteins (1–3 µg/50 µl bed vol.) at 4° C. for 2 h followed by washing once with PBS, once with PBS plus 1% Triton X-100. Bound proteins were eluted with 100 µl 2×SDS loading buffer and detected by SDS-PAGE and immunoblotting using ECL reagents (Amersham). GST pull down assays of mGluR1a and mGluR5 from brain lysates were performed by sonicating rat cerebellum or cortex in 50 mM Tris, 1 mM EDTA, 1% CHAPS (Sigma), 0.5% deoxycholic acid (Sigma) and proteinase inhibitors with GST-proteins and these tissue extracts were then processed as above. For immunoprecipitation from COS7 cells, transfected cells were extracted in RIPA (see Naisbitt et al., in press). Soluble extracts were precipitated with 2 µg control non-immune IgG, Myc or Shank 1 (56/e) antibodies (Naisbitt et al., in press).

Extracts of forebrain crude synaptosomes for immunoprecipitation were prepared using deoxycholic acid as described previously (Dunah et al., *Mol. Pharmacol.* 53429 (1998)). Forebrain P2 fraction was extracted in 1% deoxycholic acid, dialyzed over night into 0.1% Triton X-100, 50 mM Tris, pH 7.4. Concurrently, 5 g of each antibody was pre-incubated overnight with 10 µl bed volume protein A-sepharose. After centrifugation at 100,000 g for 1 h, 50 µg of extract was incubated with antibody-protein A in 100 µl 0.1% Triton X-100, 50 mM Tris, pH 7.4 for 2 h at 4° C. Pellets were washed 4 times with 1 ml incubation buffer, and bound proteins were analyzed by immunoblotting.

Antibodies Shank antibodies were raised in rabbits immunized with GST-fusions of Shank 3 residues 1379–1740 and 1379–1675 (Covance, Denver, Pa.). Similar bands were seen on rat brain immunoblots with both antisera. GKAP, PSD 95 and Shank 1 (56/e) antibodies are described in (Naisbitt et al., 1999, supra). Homer antibodies are described above. Anti-mGluR 1a monoclonal antibody is from Pharmingen and rabbit polyclonal mGluR5 antiserum was obtained from Dr Richard Huganir (Johns Hopkins University).

Shank cDNAs derived from the yeast two-hybrid screen were expressed in HEK293 cells for GST pulldown assays with GST-Homer 1a. Each of the Shank polypeptides specifically bound Homer 1a. Based on the finding that the Homer EVH1 domain binds a specific proline-rich motif, three potential Homer binding sites (or Homer "ligands") that are conserved in Shank 1, 2, 3 and CortBP-1 were identified. (Naisbitt et al., 1999, supra). To define the Homer binding site on Shank family proteins, three deletion fragments of Shank 3 that included, respectively, amino acid residues 559–908, amino acid residues 1143–1408, and amino acid residues 1379–1740 were testing for their ability to bind to Homer 1b, Homer 1c, Homer 2 and Homer 3 in GST pulldown assays. Similar binding specificity was detected with each of the Homer proteins. Only Shank3 fragment 1143–1408 bound to Homer. This region contains the amino acid sequence that most closely resembles the Homer ligand peptide consensus (LVPPPEEFAN; residues 1307–1316). A similar sequence is present in Shank1 (PLPPPLEFSN 1563–1572; see Naisbitt et al., 1999, supra). CortBP possesses two similar sites; (PLPPPLEFAN; residues 813–822) and (FLPPPESFDA residues 878–887). Fragments of Shank3 containing amino acid residues located nearer the amino-terminal of the protein such as Shank 3 fragment 559–908 (which includes the PDZ domain and the first proline-rich motif) did not bind to Homer, but did bind to GKAP (Naisbitt et al., 1999, supra). Similarly, Shank3 fragment 1379–1740, which includes the carboxy-terminal proline-rich sequence and the SAM domain, did not bind to Homer, though it is capable of binding itself and cortactin (Naisbitt et al., 1999, supra). These studies identify the Homer binding site as being distinct from either the PDZ domain that binds GKAP, or the proline-rich binding site that binds cortactin and which is located nearer to the carboxy-terminal (Naisbitt et al., 1999, supra).

To confirm the site of Homer interaction, site directed point mutants of the putative Homer ligand in Shank3 were assessed for their ability to bind to GST-Homer 1c. Full length wild type Shank 3, Shank3(P1311L), and Shank3 (F1314C) were expressed in HEK293 cells and assayed for binding to GST-Homer 1c. Compared to wild type Shank 3, both point mutants showed dramatically reduced binding to Homer., These experiments provide further confirmation that the Homer ligand in Shank3 is the principle site of interaction.

It has been previously demonstrated that amino acids 1–110 of the Homer EVH1 domain are necessary and sufficient for binding to Homer ligands (Brakeman et al., 1997, supra; Tu et al., 1998, supra). To confirm that the EVH1 domain of Homer mediates interactions with Shank, a series of point mutants of the Homer 1 EVH1 domain were generated. Mutations that disrupted binding to mGluR5 disrupted binding to Shank 3 in an identical manner, indicating Homer binds both proteins via a similar EVH1-dependent mechanism (Beneken et al., 2000, supra).

To confirm the interaction between Homer and Shank in a mammalian cell context, co-immunoprecipitation experiments were performed in heterologous cells. COS7 cell were transfected with Myc tagged-Homer 1b, Shank 1, or Shank 1 plus myc-Homer 1b. Detergent extracts of cells were subjected to immunoprecipitation and blotted with myc, shank, or control (non-immune IgG) antibodies. Homer 1b was used in these experiments because it expresses more efficiently in mammalian cells than Homer 1a. There is co-immunoprecipitation of Homer with Shank antibody and of Shank with myc antibody only from cells expressing both Shank and myc-Homer 1b.

To demonstrate the in vivo relevance of the Homer-Shank interaction, co-immunoprecipitation experiments were performed using detergent extracts of rat brain. Detergent extracts of rat forebrain fractions were immunoprecipitated with Shank and control (non-immune) antisera. Immunoprecipitates were blotted for Homer, Shank and GRIP antibodies. Antibodies raised against a fusion protein of Shank 1 immunoprecipitated Homer 1b and 1c proteins as well as Shank from rat forebrain. GRIP was not co-immunoprecipitated with Shank and neither Shank or Homer were precipitated by non-immune IgGs. Furthermore, another Shank antibody, generated against Shank 3 fragment 1379–1675, co-immunoprecipitated Homer 1b and 1c extracted from both cerebellum and cortex.

EXAMPLE 14

Homer and Shank Mediate Clustering of Cell-Surface Receptors

Shank proteins may link Homer proteins with components of a cell-surface clustering complex, such as the NMDA clustering complex.

COS7 cells were transfected using the Lipofectamine method (GIBCO-BRL) on poly-lysine coated coverslips for clustering experiments, as described in Naisbitt et al. ([in press] 1999, supra) and Kim et al. (*Neuron* 17:103 1996). Primary antibodies were used as follows: GKAP C9589, 1 $\mu$g/ml (Naisbitt et al., 1999, supra); Shank 56/e 0.5 $\mu$g/ml (Naisbitt et al., 1999, supra), PSD-95, 1:1000 diluted guinea pig serum (Kim et al., *Neuron* 378:85 1995). Cy3 and (fluoroscein isothiocyanate conjugate (FITC)- conjugated secondary antibodies (Jackson Immunoresearch) were used at dilutions of 1:500 and 1:100 respectively.

Yeast two-hybrid screens were performed as described in Example 10.

A yeast two-hybrid screen of the same rat brain cDNA library was performed using the PDZ domain of Shank3 as bait. From this screen, two identical clones of the carboxy-terminus of GKAP-3/SAPAP3 were isolated. In a reciprocal screen, Naisbitt et al., 1999, supra) isolated multiple clones of Shank1, 2 and 3 using GKAP as bait. This result provides independent confirmation of the specificity of the interaction between the Shank and GKAP/SAPAP families of proteins.

The cDNA from the yeast two-hybrid screen encoding the carboxy-terminal 347 amino acids of GKAP-3 was expressed with an amino-terminal myc tag in HEK293 cells and tested for binding to GST fusion constructs of Shank3 and other PDZ containing proteins. The GST fusion of Shank3 fragments containing just the PDZ domain (residues 559–673) was sufficient to bind GKAP3, while a Shank3 construct lacking the PDZ domain (residues 665–908) failed to bind. Additionally, PDZ domains of GRIP and SAP102 failed to pull down GKAP3, demonstrating the specificity of the Shank-GKAP interaction.

The above findings suggest that Homer, Shank and GKAP may assemble into a ternary complex. To explore this further, GST pull-down assays were performed using rat brain extracts. The carboxy-terminal 76 amino acids of GKAP 1a, containing the Shank PDZ-binding sequence -QTRL, was fused to GST GST-GKAP(carboxy-terminal). GST-GKAP(carboxy-terminal) specifically pulled down both Shank and Homer 1b and 1c, but not GKAP1 or several other proteins (Naisbitt et al., 1999, supra). Since GKAP binds directly to Shank but not to Homer (Naisbitt et al., 1999, supra), the results suggest that the GKAP pulldown of Homer is mediated by Shank. These findings corroborate the co-immunoprecipitation experiments of Shank and Homer from brain extracts and confirm that Homer is associated with Shank in a native complex.

Since Shank proteins may link Homer proteins with components of the NMDA clustering complex, co-clustering of these proteins in transfected COS cells was assessed. In cells co-expressing Homer 1b and PSD-95, both proteins showed a diffuse distribution in the cytoplasm. This is not surprising, since Homer and PSD-95 do not interact directly. When cells were transfected with Shank1 and GKAP in addition to Homer and PSD-95, Homer and PSD-95 redistributed into plaque-like clusters in which both proteins were exactly co-localized. By contrast, co-clustering of Homer and PSD-95 was not observed following co-transfection of Homer and PSD-95 with either Shank1 or GKAP alone. Thus, Homer and PSD-95 co-cluster only upon co-expression of Shank and GKAP. Therefore, Shank and GKAP may mediate the formation of a quaternary protein complex containing PSD-95 and Homer (see also Naisbitt et al., 1999, supra). Other types of macromolecular complexes may also form when Homer and Shank proteins interact. Cells expressing Homer 1b and Shank 1 (without GKAP or PSD-95) exhibited a redistribution of Homer 1b into a reticular filamentous pattern, as well as into clusters; in both kinds of structures Shank and Homer immunoreactivities were co-localized. These findings provide further evidence for an interaction between Homer and Shank, and suggest that Homer 1b and Shank can co-assemble into higher order macrocomplexes. This result is consistent with the biochemical properties of Shank that include its ability to self-multimerize and bind cortactin (Naisbitt et al., 1999, supra). Since Shank, GKAP, and PSD-95 are components of NMDA receptor-associated complex (Naisbitt et al., 1999, supra), the identification of Homer as a Shank-binding protein invokes a molecular link between the NMDA receptor complex and Homer-associated synaptic proteins such as mGluR1a and 5 and the inositol trisphosphate receptor.

Group 1 Metabotropic Receptors

Based on the observations in heterologous cells that Shank clusters with Homer 1b and that Shank together with GKAP can mediate the co-clustering of Homer and PSD-95 Shank may mediate clustering of group 1 metabotropic glutamate receptors (mGluRs). Co-expression of Shank1 and mGluR5 in COS cells did not result in obvious clustering of either protein. Similarly, Homer and mGluR5 do not form co-clusters. Co-expression of the three proteins Homer, Shank 1, and mGluR5, however, resulted in conspicuous co-clustering of mGluR5 with Shank 1. Clustering of mGluR5 in these triply transfected cells was dependent on the ability of Homer to bind the receptor since a point mutant of mGluR5 that does not interact with Homer failed to co-cluster with Shank. Thus, both Homer and Shank are required to mediate the clustering of mGluR5.

EXAMPLE 15

The Shank 3 PDZ Domain Binds the Carboxy-Terminus of Group 1 Metabotropic Receptors Directly at a Site Distinct from the Homer Binding Site The Shank PDZ domain shows selective binding to the GKAP carboxy-terminus (Naisbitt et al., 1999, supra). The carboxy-terminal sequence of GKAP (-QTRL) finds similarities with that of the group 1 mGluRs (mGluR1a -SSSL; mGluR5 -SSTL) and therefore it was determined whether the PDZ domain of Shank can directly bind the carboxy-terminus of group 1 mGluRs. GST-pulldown assays were performed using extracts from heterologous cells expressing a recombinant mGluR5 carboxy-terminal 241 amino acid peptide. The mGluR5 carboxy-terminal tail bound two partially overlapping constructs of Shank 3 that included the PDZ domain (559–908; and 559–673), but not a construct from which the PDZ domain was deleted (amino acids 665–908). Binding of mGluR to the Shank3 PDZ domain was qualitatively similar to mGluR5 binding to Homer 1c and Homer 2. Negative controls included absence of binding of mGluR to SAP102 PDZ1–3 and GRIP PDZ 4–6. Furthermore, a deletion mutant of the mGluR5 polypeptide that lacked the carboxy-terminal four amino acids failed to bind to the PDZ domain of Shank3. Identical interactions between Shank PDZ and mGluR5 C-terminal tail were detected in a yeast two-hybrid analysis. These studies indicate that the PDZ domain of Shank 3 can bind the carboxy-terminus of group 1 metabotropic receptors via a PDZ-mediated interaction with the carboxy-terminal sequence —S S/T L.

To confirm that Shank3 PDZ domain can bind full length native mGluRs, GST pull down assays were performed with detergent extracts of forebrain or cerebellum. The PDZ domain of Shank 3 bound specifically to mGluR1a and mGluR5 from cerebellum and forebrain, respectively. (Cerebellum predominantly expresses mGluR1, while forebrain expresses predominantly mGluR5.) While it is possible that the Shank3 PDZ pulldown of mGluRs from brain extracts is indirect, via Shank PDZ pulling down a GKAP-Shank-Homer-mGluR complex, this extended complex is unlikely given the more modest ability of GST-GKAP to pull down Homer.

These studies suggest that Shank may interact with the cytoplasmic tail of mGluR1a/5 both directly, via its PDZ domain, and indirectly, via Homer. The inability of Shank 1 to cluster mGluR5 in the absence of Homer indicates that the direct PDZ-dependent Shank-mGluR interaction is contingent upon a co-incident Homer interaction. Both modes of interaction with mGluR may be involved in mGluR clustering by Shank and contribute to physiological regulation.

EXAMPLE 16

Shank and Homer Co-Localization at Specific Post Synaptic Densities

Immuno Electron Microscopy A postembedding immunogold method (Petralia et al., Nature Neurosci 2:31 1999; Zhao et al., J Neurosci 18:5517 1998) was used. Male Sprague-Dawley rats was perfused with 4% paraformaldehyde plus 0.5% glutaraldehyde in 0.1 M phosphate buffer (PBS). Parasagittal sections (250 μm) of the hippocampus were cryoprotected in 30% glycerol and frozen in liquid propane in a Leica EM CPC. Frozen sections were immersed in 1.5% uranyl acetate in methanol at −90° C. in a Leica AFS freeze-substitution instrument, infiltrated with Lowicryl HM 20 resin at −45° C., and polymerized with UV light. Thin sections were incubated in 0.1% sodium borohydride plus 50 mM glycine in Tris-buffered saline/0.1% Triton X-100 (TBST), followed by incubations in 10% normal goat serum (NGS) in TBST, primary antibody in 1% NGS/TBST, 10 nm immunogold (Amersham) in 1% NGS/TBST plus 0.5% polyethylene glycol, and finally staining with uranyl acetate and lead citrate. For double labeling, the first primary antibody (e.g., Shank; Shank3 1379–1675 antigen) and corresponding immunogold-conjugated antibody (10 nm gold) were applied, sections were exposed to paraformaldehyde vapors at 80° C. for one hour, and the second primary (Homer 1b and 1c) and secondary (20 nm gold; Ted Pella/BBI International) antibodies were applied the following day. Controls (showing little or no gold labeling) included absence of the primary antibody for single labeling and absence of the second primary antibody for double labeling. Primary antibodies were used at dilutions of 1:100–1:300 for Shank and 1:400 for Homer 1b and 1c.

An antibody generated against a carboxy-terminal region of Shank 3 (amino acids 1379–1675) was used to examine the ultrastructural distribution of the Shank proteins in brain. This antibody recognizes multiple bands on brain immunoblots, including major bands of ~160–180 kD and ~210 kD in forebrain and cerebellum, similar to those seen with other Shank antibodies (see Naisbitt et al., 1999, supra). The different size bands presumably derive from the multiple Shank genes and splice variants. All Shank immunoreactivity is blocked by incubation of the Shank antibody with the Shank fusion protein antigen.

Immunogold electron microscopy revealed intense Shank immunoreactivity at the PSD of CA1 pyramidal neurons. Gold particles were distributed over the entire region of the PSD. In the same preparations, Homer 1b/1c was found to co-distribute with Shank. In all profiles with immunostaining for both Shank and Homer, gold particles were present over the PSD but also extended into the region subjacent to the PSD. This distribution is similar to the distribution of NMDA receptors associated with the postsynaptic membrane (Petralia et al., 1999, supra) and distinct from the distribution of mGluR5 which are most prevalent in the perisynaptic membrane region just outside the PSD (Lujan et al., Eur J Neurosci 8:1488 1996). This spatial localization is consistent with the idea that Shank 3 and Homer interact with components of both the NMDA receptor and metabotropic receptor signaling complexes.

This family of proteins that interact with Homer are identical to the Shank family of postsynaptic density (PSD) proteins that interact with GKAP and PSD-95 complex (Naisbitt et al., 1999, supra). Shank uses distinct domains to bind to GKAP and to Homer, and thus can form a bridge between proteins of this family. Shank/GKAP is also associated with NMDA receptors through the PSD-complex (Naisbitt et aL, 1999, supra) and thus the Homer-Shank interaction indicates a molecular link between NMDA receptors and Homer-associated proteins such as mGlu receptors and inositol trisphosphate receptors. This linkage has important implications for the coupling of NMDA receptors to intracellular calcium release pools and for excitatory synapse assembly in general.

REFERENCES CITED

Allen, K. M., Gleeson, J. G., Bagrodia, S., Partington, M. W., MacMillan, J. C., Cerione, R. A., Mulley, J. C., and Walsh, C. A. (1998). PAK3 mutation in nonsyndromic X-linked mental retardation. Nat Genet 20, 25–30.

Bagrodia, S., Taylor, S. J., Jordon, K. A., Van Aelst, L., and Cerione, R. A. (1998). A novel regulator of p21-activated kinases. J Biol Chem 273, 23633–6.

Biesova, Z., Piccoli, C., and Wong, W. T. (1997). Isolation and characterization of e3B1, an eps8 binding protein that regulates cell growth. Oncogene 14, 233–41.

Yang, W., Lin, Q., Guan, J. L., and Cerione, R. A. (1999). Activation of the Cdc42-associated tyrosine kinase-2 (ACK-2) by cell adhesion via integrin beta1. J Biol Chem 274, 8524–30.

Ziemnicka-Kotula, D., Xu, J., Gu, H., Potempska, A., Kim, K. S., Jenkins, E. C., Trenkner, E., and Kotula, L. (1998). Identification of a candidate human spectrin Src homology 3 domain- binding protein suggests a general mechanism of association of tyrosine kinases with the spectrin-based membrane skeleton. J Biol Chem 273, 13681–92.

Abel, T., Nguyen, P. V., Barad, M., Deuel, T. A., Kandel, E. R., and Bourtchouladze, R. (1997). Genetic demonstration of a role for PKA in the late phase of LTP and in hippocampus-based long-term memory. Cell 88, 615–26.

Aiba, A., Chen, C., Herrup, K., Rosenmund, C., Stevens, C. F., and Tonegawa, S. (1994). Reduced hippocampal long-term potentiation and context-specific deficit in associative learning in mGluR1 mutant mice. Cell 79, 365–75.

Aigner, L., Arber, S., Kapfhammer, J. P., Laux, T., Schneider, C., Botteri, F., Brenner, H. R., and Caroni, P. (1995). Overexpression of the neural growth-associated protein GAP-43 induces nerve sprouting in the adult nervous system of transgenic mice. Cell 83, 269–78.

Allen, K. M., Gleeson, J. G., Bagrodia, S., Partington, M. W., MacMillan, J. C., Cerione, R. A., Mulley, J. C., and Walsh, C. A. (1998). PAK3 mutation in nonsyndromic X-linked mental retardation. Nat Genet 20, 25–30.

Aniksztejn, L., Bregestovski, P., and Ben-Ari, Y. (1991). Selective activation of quisqualate metabotropic receptor potentiates NMDA but not AMPA responses. Eur J Pharmacol 205, 327–8.

Arai, I., Shimazoe, T., Shibata, S., Inoue, H., Yoshimatsu, A., and Watanabe, S. (1996). Enhancement of dopamine release from the striatum through metabotropic glutamate receptor activation in methamphetamine sensitized rats. Brain Res 729, 277–80.

Arai, I., Shimazoe, T., Shibata, S., Inoue, H., Yoshimatsu, A., and Watanabe, S. (1997). Methamphetamine-induced sensitization of dopamine release via a metabotropic glutamate receptor mediated pathway in rat striatal slices. Jpn J Pharmacol 73, 243–6.

Bagrodia, S., Taylor, S. J., Jordon, K. A., Van Aelst, L., and Cerione, R. A. (1998). A novel regulator of p21-activated kinases. J Biol Chem 273, 23633–6.

Banno, T., and Kohno, K. (1998). Conformational changes of the smooth endoplasmic reticulum are facilitated by L-glutamate and its receptors in rat Purkinje cells. J Comp Neurol 402, 252–63.

Barnes, C. A., Jung, M. W., McNaughton, B. L., Korol, D. K., Andreasson, K., and Worley, P. F. (1994). LTP saturation and spatial learning disruption: Effects of task variables and saturation levels. Journal of Neuroscience 14, 5793–5806.

Bashir, Z. I., Bortolotto, Z. A., Davies, C. H., Berretta, N., Irving, A. J., Seal, A. J., Henley, J. M., Jane, D. E., Watkins, J. C, and Collingridge, G. L. (1993). Induction of LTP in the hippocampus needs synaptic activation of glutamate metabotropic receptors. Nature 363, 347–50.

Baude, A., Nusser, Z., Roberts, J. D., Mulvihill, E., McIlhinney, R. A., and Somogyi, P. (1993). The metabotropic glutamate receptor (mGluR1 alpha) is concentrated at perisynaptic membrane of neuronal subpopulations as detected by immunogold reaction. Neuron 11, 771–87.

Ben-Ari, Y., Aniksztejn, L., and Bregestovski, P. (1992). Protein kinase C modulation of NMDA currents: an important link for LTP induction. Trends Neurosci 15, 333–9.

Beneken, J., Tu, J. C., Xiao, B., Yuan, J. P., Worley, P. F., and Leahy, D. J. (submitted). Crystal structure of the Homer EVH1 Domain: A versitile binding module with unexpected homology to PH domains. Neuron.

Berke, J. D., Paletzki, R. F., Aronson, G. J., Hyman, S. E., and Gerfen, C. R. (1998). A complex program of striatal gene expression induced by dopaminergic stimulation. J Neurosci 18, 5301–10.

Berridge, M. J. (1998). Neuronal Calcium Signaling. Neuron 21, 13–26.

Bhat, M. A., Izaddoost, S., Lu, Y., Cho, K. O., Choi, K. W., and Bellen, H. J. (1999). Discs Lost, a novel multi-PDZ domain protein, establishes and maintains epithelial polarity. Cell 96, 833–45.

Blue, M. E., and Parnavelas, J. G. (1983). The formation and maturation of synapses in the visual cortex of the rat. I. Qualitative analysis. J Neurocytol 12, 599–616.

Bonci, A., and Williams, J. T. (1996). A common mechanism mediates long-term changes in synaptic transmission after chronic cocaine and morphine. Neuron 16, 631–9.

Bootman, M. D., Berridge, M. J., and Lipp, P. (1997). Cooking with calcium: the recipes for composing global signals from elementary events. Cell 91, 367–73.

Bortolotto, Z. A., Bashir, Z. I., Davies, C. H., and Collingridge, G. L. (1994). A molecular switch activated by metabotropic glutamate receptors regulates induction of long-term potentiation. Nature 368, 740–3.

Brakeman, P. R., Lanahan, A. A., O'Brien, R., Roche, K., Barnes, C. A., Huganir, R. L., and Worley, P. F. (1997). Homer: a protein that selectively binds metabotropic glutamate receptors. Nature 386, 284–8.

Carlezon, W. A., Jr., Thome, J., Olson, V. G., Lane-Ladd, S. B., Brodkin, E. S., Hiroi, N., Duman, R. S., Neve, R. L., and Nestler, E. J. (1998). Regulation of cocaine reward by CREB. Science 282, 2272–5.

Chevray, P. M., and Nathans, D. (1992). Protein interaction cloning in yeast: identification of mammalian proteins that react with the leucine zipper of Jun. Proc Natl Acad Sci U S A 89, 5789–93.

Cole, A., Saffen, D., Baraban, J., and Worley, P. (1989). Rapid increase of an immediate early gene mRNA in hippocampal neurons by synaptic NMDA receptor activation. Nature 340, 474–476.

Conquet, F., Bashir, Z. I., Davies, C. H., Daniel, H., Ferraguti, F., Bordi, F., Franz-Bacon, K., Reggiani, A., Matarese, V., Conde, F., and et, a. (1994). Motor deficit and impairment of synaptic plasticity in mice lacking mGluR1. Nature 372, 237–43.

Cull-Candy, S. G., Brickley, S. G., Misra, C., Feldmeyer, D., Momiyama, A., and Farrant, M. (1998). NMDA receptor diversity in the cerebellum: identification of subunits contributing to functional receptors. Neuropharmacology 37, 1369–80.

Daniels, R. H., Zenke, F. T., and Bokoch, G. M. (1999). alphaPix stimulates p21-activated kinase activity through exchange factor-dependent and -independent mechanisms. J Biol Chem 274, 6047–50.

Dong, H., O'Brien, R. J., Fung, E. T., Lanahan, A. A., Worley, P. F., and Huganir, R. L. (1997). GRIP: a synaptic PDZ domain-containing protein that interacts with AMPA receptors [see comments]. Nature 386, 279–84.

DuBois, R. N., and Smalley, W. E. (1996). Cyclooxygenase, NSAIDs, and colorectal cancer. J Gastroenterol 31, 898–906.

Dudek, S. M., and Bear, M. F. (1989). A biochemical correlate of the critical period for synaptic modification in the visual cortex. Science 246, 673–5.

Dunah, A. W., Luo, J., Wang, Y. H., Yasuda, R. P., and Wolfe, B. B. (1998). Subunit composition of N-methyl-D-aspartate receptors in the central nervous system that contain the NR2D subunit. Mol Pharmacol 53, 429–37.

Eck, M. J., Dhe-Paganon, S., Trub, T., Nolte, R. T., and Shoelson, S. E. (1996). Structure of the IRS-1 PTB domain bound to the juxtamembrane region of the insulin receptor. Cell 85, 695–705.

Elmer, G. I., Gorelick, D. A., Goldberg, S. R., and Rothman, R. B. (1996). Acute sensitivity vs. context-specific sensitization to cocaine as a function of genotype. Pharmacol Biochem Behav 53, 623–8.

Emptage, N., Bliss, T. V., and Fine, A. (1999). Single synaptic events evoke NMDA receptor-mediated release of calcium from internal stores in hippocampal dendritic spines [In Process Citation]. Neuron 22, 115–24.

Fields, S., and Song, O. (1989). A novel genetic system to detect protein-protein interactions. Nature 340, 245–6.

Fiorillo, C. D., and Williams, J. T. (1998). Glutamate mediates an inhibitory postsynaptic potential in dopamine neurons [In Process Citation]. Nature 394, 78–82.

Fitzgerald, L. W., Ortiz, J., Hamedani, A. G., and Nestler, E. J. (1996). Drugs of abuse and stress increase the expression of GluR1 and NMDAR1 glutamate receptor subunits in the rat ventral tegmental area: common adaptations among cross-sensitizing agents. J Neurosci 16, 274–82.

Fosnaugh, J. S., Bhat, R. V., Yamagata, K., Worley, P. F., and Baraban, J. M. (1995). Activation of Arc, a putative "effector" immediate early gene, by cocaine in rat brain. J. Neurochemistry 64, 2377–2380.

Gertler, F. B., Niebuhr, K., Reinhard, M., Wehland, J., and Soriano, P. (1996). Mena, a relative of VASP and Drosophila Enabled, is implicated in the control of microfilament dynamics. Cell 87, 227–39.

Goebel, D. J., and Poosch, M. S. (1999). NMDA receptor subunit gene expression in the rat brain: a quantitative analysis of endogenous mRNA levels of NR1 Com, NR2A, NR2B, NR2C, NR2D and NR3A [In Process Citation]. Brain Res Mol Brain Res 69, 164–70.

Golshani, P., Warren, R. A., and Jones, E. G. (1998). Progression of change in NMDA, non-NMDA, and metabotropic glutamate receptor function at the developing corticothalamic synapse. J Neurophysiol 80, 143–54.

Haffner, C., Jarchau, T., Reinhard, M., Hoppe, J., Lohmann, S. M., and Walter, U. (1995). Molecular cloning, structural analysis and functional expression of the proline-rich focal adhesion and microfilament-associated protein VASP. Embo J 14, 19–27.

Harris, K. M., and Stevens, J. K. (1989). Dendritic spines of CA 1 pyramidal cells in the rat hippocampus: serial electron microscopy with reference to their biophysical characteristics. J Neurosci 9, 2982–97.

Harris, K. M., and Stevens, J. K. (1988). Dendritic spines of rat cerebellar Purkinje cells: serial electron microscopy with reference to their biophysical characteristics. J Neurosci 8,4455–69.

Henry, D. J., and White, F. J. (1991). Repeated cocaine administration causes persistent enhancement of D1 dopamine receptor sensitivity within the rat nucleus accumbens. J. Pharmacol. Exp. Ther. 258, 882–890.

Herschman, H. R. (1994). Regulation of prostaglandin synthase-1 and prostaglandin synthase-2. Cancer and Metastasis Reviews 13, 241–256.

Hope, B. T., Kosofsky, B., Hyman, S. E., and Nestler, E. J. (1992). Regulation of IEG expression and AP-1 binding by chronic cocaine in the rat nucleus accumbens. Proc. Natl. Acad. Sci. USA 89, 5764–5768.

Hsueh, Y. P., and Sheng, M. (1998). Anchoring of glutamate receptors at the synapse. Prog Brain Res 116, 123–31.

Hyman, S. E. (1996). Addiction to cocaine and amphetamine. Neuron 16, 901–4.

Hyvönen, M., Macias, M. J., Nilges, M., Oschkinat, H., Sarastre, M., and Wilmanns, M. (1995). Structure of the binding site for inositol phosphates in a PH domain. EMBO J. 14, 4676–4685.

Ikeda, S. R., Lovinger, D. M., McCool, B. A., and Lewis, D. L. (1995). Heterologous expression of metabotropic glutamate receptors in adult rat sympathetic neurons: subtype-specific coupling to ion channels. Neuron 14, 1029–38.

Ingi, T., Krumins, A. M., Chidiac, P., Brothers, G. M., Chung, S., Snow, B. E., Barnes, C. A., Lanahan, A. A., Siderovski, D. P., Ross, E. M., Gilman, A. G., and Worley, P. F. (1998). Dynamic Regulation of RGS2 Suggests a Novel Mechanism in G-Protein Signaling and Neuronal Plasticity. J. Neurosci. 18, 7178–7188.

Kammermeier, P., Xiao, B., Tu, J., Worley, P., and Ikeda, S. (submitted). A functional role for the interaction of Homer proteins with group 1 mGluRs. J. Neuroscience.

Kaufmann, W. E., Worley, P. F., Pegg, J., Bremer, M., and Isakson, P. (1996). COX-2, a synaptically induced enzyme, is expressed by excitatory neurons at postsynaptic sites in rat cerebral cortex. Proc Natl Acad Sci U S A 93, 2317–21.

Kim, E., Naisbitt, S., Hsueh, Y. P., Rao, A., Rothschild, A., Craig, A. M., and Sheng, M. (1997). GKAP, a novel synaptic protein that interacts with the guanylate kinase-like domain of the PSD-95/SAP90 family of channel clustering molecules. J Cell Biol 136, 669–78.

Kim, J. H., and Vezina, P. (1998). Metabotropic glutamate receptors are necessary for sensitization by amphetamine. Neuroreport 9, 403–6.

Koff, J. M., Shuster, L., and Miller, L. G. (1994). Chronic cocaine administration is associated with behavioral sensitization and time-dependent changes in striatal dopamine transporter binding. J Pharmacol Exp Ther 268, 277–82.

Kombian, S. B., and Malenka, R. C. (1994). Simultaneous LTP of non-NMDA- and LTD of NMDA-receptor-mediated responses in the nucleus accumbens. Nature 368, 242–6.

Kornau, H. C., Schenker, L. T., Kennedy, M. B., and Seeburg, P. H. (1995). Domain interaction between NMDA receptor subunits and the postsynaptic density protein PSD-95. Science 269, 1737–40.

Kraulis, P. J. (1991). MOLSCRIPT: a program to produce both detailed and schematic plots of protein structures. J. Appl. Cryst. 24, 946–950

Lanahan, A., Lyford, G., Stevenson, G. S., Worley, P. F., and Barnes, C. A. (1997). Selective alteration of long-term potentiation-induced transcriptional response in hippocampus of aged, memory-impaired rats. Journal of Neuroscience 1 7, 2876–2885.

Lanahan, A., and Worley, P. (1998). Immediate-Early Genes and Synaptic Function. Neurobiol Learn Mem 70, 37–43.

Lau, L. F., and Nathans, D. (1991). Genes induced by serum growth factors. In The Hormonal Control of Gene Transcription. Vol. 6. Molecular Aspects, P. Cohen and J. G. Foulkes, eds. (Amsterdam: Elsevier Science Publishers B.V.), pp. 257–293.

Le Moal, M. (1995). Mesocorticolimbic Dopaminergic Neurons; Functional and Regulatory Roles. In Psychopharmacology: The Fourth Generation of Progress, F. B. a. D. Kupfer, ed. (New York: Raven Press Ltd.), pp. 283–294.

Leanna, C., and Hannink, M. (1996). The reverse two-hybrid system: a genetic scheme for selection against specific protein/protein interactions. Nucleic Acids Res. 24, 3341–3347.

Leong, P., and MacLennan, D. H. (1998). Complex interactions between skeletal muscle ryanodine receptor and dihydropyridine receptor proteins [In Process Citation]. Biochem Cell Biol 76, 681–94.

Leong, P., and MacLennan, D. H. (1998). The cytoplasmic loops between domains II and III and domains III and IV in the skeletal muscle dihydropyridine receptor bind to a contiguous site in the skeletal muscle ryanodine receptor. J Biol Chem 273, 29958–64.

Lester, L. B., and Scott, J. D. (1997). Anchoring and scaffold proteins for kinases and phosphatases. Recent Prog Horm Res 52, 409–29; discussion 429–30.

Linden, D. J. (1999). The return of the spike: postsynaptic action potentials and the induction of LTP and LTD. Neuron 22, 661–6.

Lu, Y. M., Jia, Z., Janus, C., Henderson, J. T., Gerlai, R., Wojtowicz, J. M., and Roder, J. C. (1997). Mice lacking metabotropic glutamate receptor 5 show impaired learning and reduced CA1 long-term potentiation (LTP) but normal CA3 LTP. J Neurosci 17, 5196–205.

Lujan, R., Nusser, Z., Roberts, J. D., Shigemoto, R., and Somogyi, P. (1996). Perisynaptic location of metabotropic glutamate receptors mGluR1 and mGluR5 on dendrites and dendritic spines in the rat hippocampus. Eur J Neurosci 8, 1488–500.

Lujan, R., Roberts, J. D., Shigemoto, R., Ohishi, H., and Somogyi, P. (1997). Differential plasma membrane distribution of metabotropic glutamate receptors mGluR1 alpha, mGluR2 and mGluR5, relative to neurotransmitter release sites. J Chem Neuroanat 13, 219–41.

Lyford, G., Yamagata, K., Kaufmann, W. E., Barnes, C. A., Sanders, L. K., Copeland, N. G., Gilbert, D. J., Jenkins, N. A., Lanahan, A. A., and Worley, P. F. (1995). Arc, a growth factor and activity-regulated gene encodes a novel cytoskeleton-associated protein that is enriched in neuronal dendrites. Neuron 14, 433–445.

Lyford, G. L., Yamagata, K., Kaufmann, W. E., Barnes, C. A., Sanders, L. K., Copeland, N. G., Gilbert, D. J., Jenkins, N. A., Lanahan, A. A., and Worley, P. F. (1995). Arc, a growth factor and activity-regulated gene, encodes a novel cytoskeleton-associated protein that is enriched in neuronal dendrites. Neuron 14, 433–45.

Manser, E., Loo, T. H., Koh, C. G., Zhao, Z. S., Chen, X. Q., Tan, L., Tan, I., Leung, T., and Lim, L. (1998). PAK kinases are directly coupled to the PIX family of nucleotide exchange factors. Mol Cell 1, 183–92.

Martin, L. J., Blackstone, C. D., Huganir, R. L., and Price, D. L. (1992). Cellular localization of a metabotropic glutamate receptor in rat brain. Neuron 9, 259–70.

Marx, S. O., Ondrias, K., and Marks, A. R. (1998). Coupled gating between individual skeletal muscle Ca2+ release channels (Ryanodine receptors) [In Process Citation]. Science 281, 818–21.

Matsui, T., Maeda, M., Doi, Y., Yonemura, S., Amano, M., Kaibuchi, K., Tsukita, S., and Tsukita, S. (1998). Rho-kinase phosphorylates COOH-terminal threonines of ezrin/radixin/moesin (ERM) proteins and regulates their head-to-tail association. J Cell Biol 140, 647–57.

Miserendino, M., Guitart, X., Terwilliger, R., Chi, S., and Nestler, E. J. (1993). Individual differences in locomotor activity are associated with levels of tyrosine hydroxylase and neurofilament proteins in the ventral tegmental area of Sprague Dawley rats. Mol. Cell. Neurosci. 4, 440–448.

Moratalla, R., Elibol, B., Vallejo, M., and Graybiel, A. M. (1996). Network-level changes in expression of inducible Fos-Jun proteins in the striatum during chronic cocaine treatment and withdrawal. Neuron 17, 147–56.

Morgan, J. I., and Curran, T. (1991). Stimulus-transcription coupling in the nervous system. Ann. Rev. Neurosci. 14, 421–452.

Naisbitt, S., Kim, E., Tu, J., Xiao, B., Sala, C., Valtschanoff, J., Weinberg, R., Worley, P., and Sheng, M. (1999). Shank, a novel family of postsynaptic density proteins that binds to the NMDA receptor/PSD-95/GKAP complex and cort-actin. Neuron 23, 569–582.

Naisbitt, S., Kim, E., Weinberg, R. J., Rao, A., Yang, F. C., Craig, A. M., and Sheng, M. (1997). Characterization of guanylate kinase-associated protein, a postsynaptic density protein at excitatory synapses that interacts directly with postsynaptic density-95/synapse-associated protein 90. J Neurosci 17, 5687–96.

Nakanishi, S., Masu, M., Bessho, Y., Nakajima, Y., Hayashi, Y., and Shigemoto, R. (1994). Molecular diversity of glutamate receptors and their physiological functions. [Review]. Exs 71, 71–80.

Narasimhan, K., Pessah, I. N., and Linden, D. J. (1998). Inositol-1,4,5-trisphosphate receptor-mediated Ca mobilization is not required for cerebellar long-term depression in reduced preparations. J Neurophysiol 80, 2963–74.

Nestler, E. J., and Aghajanian, G. K. (1997). Molecular and cellular basis of addiction. Science 278, 58–63.

Nestler, E. J., Hope, B. T., and Widnell, K. L. (1993). Drug addiction: a model for the molecular basis of neural plasticity. Neuron 11, 995–1006.

Nestler, E. J., Terwilliger, R. Z., Walker, J. R., Servarino, K. A., and Duman, R. S. (1990). Chronic cocaine treatment decreases levels of the G-protein subunits Gia and Goa in discrete regions of rat brain. J. Neurochem. 55, 1079–1082.

Niebuhr, K., Ebel, F., Frank, R., Reinhard, M., Domann, E., Carl, U. D., Walter, U., Gertler, F. B., Wehland, J., and Chakraborty, T. (1997). A novel proline-rich motif present in ActA of Listeria monocytogenes and cytoskeletal proteins is the ligand for the EVH1 domain, a protein module present in the Ena/VASP family. EMBO J 16, 5433–44.

Nusser, Z., Mulvihill, E., Streit, P., and Somogyi, P. (1994). Subsynaptic segregation of metabotropic and ionotropic glutamate receptors as revealed by immunogold localization. Neuroscience 61, 421–7.

O'Brien, R. J., Xu, D., Petralia, R. S., Steward, O., Huganir, R. L., and Worley, P. F. (1999). Synaptic clustering of AMPA receptors by the extracellular immediate-early gene product Narp. Neuron 23, 309–323.

O'Rourke, B., Kass, D. A., Tomaselli, G. F., Kaab, S., Tunin, R., and Marban, E. (1999). Mechanisms of altered excitation-contraction coupling in canine tachycardia-induced heart failure, I: experimental studies. Circ Res 84, 562–70.

Okabe, S., Collin, C., Auerbach, J. M., Meiri, N., Bengzon, J., Kennedy, M. B., Segal, M., and McKay, R. D. (1998). Hippocampal synaptic plasticity in mice overexpressing an embryonic subunit of the NMDA receptor. J Neurosci 18, 4177–88.

Otani, S., and Connor, J. A. (1998). Requirement of rapid Ca2+ entry and synaptic activation of metabotropic glutamate receptors for the induction of long-term depression in adult rat hippocampus. J Physiol (Lond) 511, 761–70.

Petralia, R., Esteban, J., Wang, Y.-X., Partridge, J., Zhao, H.-M., Wenthold, R., and Malinow, R. (1999). Selective acquisition of AMPA receptors over postnatal development suggests a molecular basis for silent synapses. Nature Neurosci. 2, 31–36.

Philipp, S., and Flockerzi, V. (1997). Molecular characterization of a novel human PDZ domain protein with homology to INAD from Drosophila melanogaster. FEBS Lett 413, 243–8.

Piazza, P. V., Deminiere, J.-M., LeMoal, M., and Simon, H. (1989). Factors that predict individual vulnerability to amphetamine self-administration. Science 245, 1511–1513.

Pin, J. P., and Duvoisin, R. (1995). The metabotropic glutamate receptors: structure and functions. [Review]. Neuropharmacology 34, 1–26.

Pisabarro, M. T., Serrano, L., and Wilmanns, M. (1998). Crystal Structure of the Ab1-SH3 Domain Complexed with a Designed High- affinity Peptide Ligand: Implications for SH3-Ligand Interactions. J Mol Biol 281, 513–21.

Ponting, C. P., and Phillips, C. (1997). Identification of homer as a homologue of the Wiskott-Aldrich syndrome protein suggests a receptor-binding function for WH1 domains. J Mol Med 75, 769–71.

Prehoda, K. E., Lee, D. J., and Lim, W. A. (1999). Strucute of the Enabled/VASP Homology 1 domain-peptide complex: A key component in the spatial control of actin assembly. Cell 97, 471–480.

Qian, Z., Gilbert, M. E., Colicos, M. A., Kandel, E. R., and Kuhl, D. (1993). Tissue-plasminogen activator is induced as an immediate-early gene during seizure, kindling and long-term potentiation. Nature 361, 453–457.

Riedel, G. (1996). Function of metabotropic glutamate receptors in learning and memory. Trends in Neurosciences 19, 219–224.

Robinson, T. E., and Kolb, B. (1999). Alterations in the morphology of dendrites and dendritic spines in the nucleus accumbens and prefrontal cortex following repeated treatment with amphetamine or cocaine. Eur J Neurosci 11, 1598–604.

Roche, K., Tu, J., Petralia, R., Xiao, B., Wenthold, R., and Worley, P. (accepted). Homer 1b regulates the surface expression of type I metabotropic glutamate receptors. J. Biol. Chem.

Romano, C., Sesma, M. A., McDonald, C. T., O'Malley, K., Van den Pol, A. N., and Olney, J. W. (1995). Distribution of metabotropic glutamate receptor mGluR5 immunoreactivity in rat brain. J Comp Neurol 355, 455–69.

Ross, C. A., Meldolesi, J., Milner, T. A., Satoh, T., Supattapone, S., and Snyder, S. H. (1989). Inositol 1,4, 5-trisphosphate receptor localized to endoplasmic reticulum in cerebellar Purkinje neurons. Nature 339, 468–70.

Saffen, D. W., Cole, A. J., Worley, P. F., Christy, B. A., Ryder, K., and Baraban, J. M. (1988). Convulsant-induced increase in transcription factor messenger RNAs in rat brain. Proceedings of the National Academy of Sciences (USA) 85, 7795–7799.

Saiki, Y., El-Hayek, R., and Ikemoto, N. (1999). Involvement of the Glu724-Pro760 region of the dihydropyridine receptor II-III loop in skeletal muscle-type excitation-contraction coupling. J Biol Chem 274, 7825–32.

Satoh, T., Ross, C. A., Villa, A., Supattapone, S., Pozzan, T., Snyder, S. H., and Meldolesi, J. (1990). The inositol 1,4,5,-trisphosphate receptor in cerebellar Purkinje cells: quantitative immunogold labeling reveals concentration in an ER subcompartment. J Cell Biol 111 , 615–24.

Seibert, K., Zhang, Y., Leahy, K., Hauser, S., Masferrer, J., Perkins, W., Lee, L., and Isakson, P. (1994). Pharmacological and biochemical demonstration of the role of cyclooxygenase 2 in inflammation and pain. Proc Natl Acad Sci U S A 91, 12013–7.

Selig, D. K., Lee, H. K., Bear, M. F., and Malenka, R. C. (1995). Reexamination of the effects of MCPG on hippocampal LTP, LTD, and depotentiation. J Neurophysiol 74, 1075–82.

Shatz, C. J. (1990). Impulse activity and the patterning of connections during CNS development. Neuron 5, 745–756.

Shaw, R. J., Henry, M., Solomon, F., and Jacks, T. (1998). RhoA-dependent phosphorylation and relocalization of ERM proteins into apical membrane/actin protrusions in fibroblasts. Mol Biol Cell 9, 403–19.

Sheng, M., and Wyszynski, M. (1997). Ion channel targeting in neurons. Bioessays 19, 847–53.

Shih, H., Goldman, P., DeMaggio, A., Hollenberg, S., Goodman, R., and Hoekstra, M. (1996). A positive genetic selection for disrupting protein-protein interactions:Identification of CREB mutations that prevent association with the coactivator CBP. Proc. Natl. Acad. Sci. USA 93, 13896–13901.

Spacek, J., and Harris, K. M. (1997). Three-dimensional organization of smooth endoplasmic reticulum in hippocampal CA1 dendrites and dendritic spines of the immature and mature rat. J Neurosci 17, 190–203.

Steward, O., Wallace, C. S., Lyford, G. L., and Worley, P. F. (1998). Synaptic activation causes the mRNA for the immediate early gene Arc to localize selectively near activated postsynaptic sites on neuronal dendrites. Neuron 21, 741–751.

Stewart, W. F., Kawas, C., Corrada, M., and Metter, E. J. (1997). Risk of Alzheimer's disease and duration of NSAID use [see comments]. Neurology 48, 626–32.

Storck, T., Kruth, U., Kolhekar, R., Sprengel, R., and Seeburg, P. H. (1996). Rapid construction in yeast of complex targeting vectors for gene manipulation in the mouse. Nucleic Acids Res 24, 4594–6.

Svoboda, K., and Mainen, Z. F. (1999). Synaptic [Ca2+]: intracellular stores spill their guts. Neuron 22, 427–30.

Symons, M., Derry, J. M., Karlak, B., Jiang, S., Lemahieu, V., McCormick, F., Francke, U., and Abo, A. (1996). Wiskott-Aldrich syndrome protein, a novel effector for the GTPase CDC42Hs, is implicated in actin polymerization. Cell 84, 723–34.

Taber, M. T., and Fibiger, H. C. (1995). Electrical stimulation of the prefrontal cortex increases dopamine release in the nucleus accumbens of the rat: modulation by metabotropic glutamate receptors. J Neurosci 15, 3896–904.

Takei, K., Mignery, G. A., Mugnaini, E., Sudhof, T. C., and De Camilli, P. (1994). Inositol 1,4,5-trisphosphate receptor causes formation of ER cisternal stacks in transfected fibroblasts and in cerebellar Purkinje cells. Neuron 12, 327–42.

Takeuchi, M., Hata, Y., Hirao, K., Toyoda, A., Irie, M., and Takai, Y. (1997). SAPAPs. A family of PSD-95/SAP90-associated proteins localized at postsynaptic density. J Biol Chem 272, 11943–51.

Testa, C. M., Standaert, D. G., Landwehrmeyer, G. B., Penney, J., Jr., and Young, A. B. (1995). Differential expression of mGluR5 metabotropic glutamate receptor mRNA by rat striatal neurons. J Comp Neurol 354, 241–52.

Tolliver, B. K., and Carney, J. M. (1994). Comparison of cocaine and GBR 12935: effects on locomotor activity and stereotypy in two inbred mouse strains. Pharmacol Biochem Behav 48, 733–9.

Tsui, C. C., Copeland, N. G., Gilbert, D. J., Jenkins, N. A., Barnes, C., and Worley, P. F. (1996). Narp, a novel member of the pentraxin family, promotes neuite outgrowth and is dynamically regulated by neuronal activity. Journal of Neuroscience 16, 2463–2478.

Tsunoda, S., Sierralta, J., Sun, Y., Bodner, R., Suzuki, E., Becker, A., Socolich, M., and Zuker, C. S. (1997). A multivalent PDZ-domain protein assembles signalling complexes in a G- protein-coupled cascade. Nature 388, 243–9.

Tu, J. C., Bo Xiao, B., Naisbitt, S., Yuan, J. P., Petralia, R. S., Brakeman, P. R., Aakalu, V. K., Lanahan, A. A., Sheng, M., and Worley, P. (1999). mGluR/Homer and PSD-95 Complexes Are Linked by the Shank Family of Postsynaptic Density Proteins. Neuron 23, 583–592.

Tu, J. C., Xiao, B., Yuan, J., Lanahan, A., Leoffert, K., Li, M., Linden, D., and Worley, P. F. (1998). Homer binds a novel proline rich motif and links group1 metabotropic glutamate receptors with IP3 receptors. Neuron 21, 717–726.

Ujike, H., Okumura, K., Zushi, Y., Akiyama, K., and Otsuki, S. (1992). Persistent supersensitivity of sigma receptors develops during repeated methamphetamine treatment. Eur J Pharmacol 211, 323–8.

Vicini, S., Wang, J. F., Li, J. H., Zhu, W. J., Wang, Y. H., Luo, J. H., Wolfe, B. B., and Grayson, D. R. (1998). Functional and pharmacological differences between recombinant N-methyl-D-aspartate receptors. J Neurophysiol 79, 555–66.

Vidal, M., Brachmann, R., Fattaey, A., Harlow, E., and Boeke, J. (1996). Reverse two-hybrid and one-hybrid systems to detect dissociation of protein-protein and DNA-protein interactions. Proc. Natl. Acad. Sci. USA 93, 10315–10320.

Vidal, M., Pascal, B., Chen, E., Boeke, J., and Harlow, E. (1996). Genetic characterization of a mammalian proteinprotein interaction domain by using a yeast reverse two-hybrid system. Proc. Natl. Acad. Sci. USA 93, 10321–10326.

Villa, A., Sharp, A. H., Racchetti, G., Podini, P., Bole, D. G., Dunn, W. A., Pozzan, T., Snyder, S. H., and Meldolesi, J. (1992). The endoplasmic reticulum of Purkinje neuron body and dendrites: molecular identity and specializations for Ca2+ transport. Neuroscience 49, 467–77.

Vrana, S. L., Vrana, K. E., Koves, T. R., Smith, J. E., and Dworkin, S. I. (1993). Chronic cocaine administration increases CNS tryosine hydroxylase enzyme activity and mRNA levels and trypophan hydroxylase enzyme activity levels. J. Neurochem. 61, 2262–2268.

Wlodawer, A., Hodgson, K. O., and Shooter, E. M. (1975). Crystallization of nerve growth factor from mouse submaxillary glands. Proc Natl Acad Sci U S A 72, 777–9.

Wolf, M. E. (1998). The role of excitatory amino acids in behavioral sensitization to psychomotor stimulants. Prog Neurobiol 54, 679–720.

Worley, P. F., Baraban, J. M., Colvin, J. S., and Snyder, S. H. (1987). Inositol trisphosphate receptor localization in brain: variable stoichiometry with protein kinase C. Nature 325, 159–161.

Worley, P. F., Baraban, J. M., Supattapone, S., Wilson, V. S., and Snyder, S. H. (1987). Characterization of inositol trisphosphate receptor binding in brain: Regulation by calcium and pH. Journal Biological Chemistry 262, 12132–12136.

Worley, P. F., Cole, A. J., Saffen, D. W., and Baraban, J. M. (1990). Transcription factor regulation in brain: focus on activity and NMDA dependent regulation. In Molecular mechanisms of aging, K. Beyreuther and G. Schettler, eds. (Heidelberg: Springer-Verlag), pp. 62–76.

Xiao, B., Tu, J. C., Petralia, R. S., Yuan, J., Doan, A., Breder, C., Ruggiero, A., Lanahan, A. A., Wenthold, R. J., and Worley, P. F. (1998). Homer regulates the association of Group 1 metabotropic receptors with multivalent complexes of Homer-related, synaptic proteins. Neuron 21, 707–716.

Yamagata, K., Andreasson, K. I., Kaufmann, W. E., Barnes, C. A., and Worley, P. F. (1993). Expression of a Mitogen-Inducible Cyclooxygenase in Brain Neurons: Regulation by Synaptic Activity and Glucocorticoids. Neuron 11, 371–386.

Yamagata, K., Sanders, L. K., Kaufmann, W. E., Barnes, C. A., Nathans, D., and Worley, P. F. (1994). Rheb, a growth factor and synaptic activity regulated gene, encodes a novel Ras-related protein. Journal of Biological Chemistry 269, 16333–16339.

Yee, W., and Worley, P. F. (1997). Rheb interacts with Raf-1 kinase and may function to integrate growth factor- and protein kinase A-dependent signals. Molecular and Cellular Biology 17, 921–933.

Yu, H., Chen, J. K., Feng, S., Dalgarno, D. C., Brauer, A. W., and Schreiber, S. L. (1994). Structural basis for the binding of proline-rich peptides to SH3 domains. Cell 76, 933–45.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Data Collection, Phase Calculation, and Refinement Statistics

| Wavelength (λ) | 0.9879 | 0.9793 | 0.9790 | 0.9611 |
|---|---|---|---|---|
| MAD Data Collection Statistics | | | | |
| Unique reflections | 24051 | 24179 | 24226 | 24481 |
| Redundancy | 6.2 | 6.2 | 6.2 | 6.3 |
| Completeness (%) | 96.8 | 97.2 | 97.3 | 98.4 |
| Signal (<I>/σ<I>)[a] | 21.5 (2.3) | 21.0 (2.1) | 20.9 (2.0) | 20.4 (1.9) |
| $R_{sym}$ (%) | 8.1 | 8.7 | 9.1 | 8.8 |
| Overall figure of merit | 0.71 | | | |
| MAD Structure Factor Ratios[b] and Anomalous Scattering Factors[c] | | | | |
| 0.9879 | 0.033 | 0.040 | 0.032 | 0.026 |
| 0.9793 | | 0.047 | 0.029 | 0.044 |
| 0.9790 | | | 0.063 | 0.036 |
| 0.9611 | | | | 0.050 |
| f' (e) | −4.87 | −9.96 | −8.06 | −4.15 |
| f" (e) | 0.47 | 3.77 | 6.28 | 4.12 |
| Refinement Statistics | | | | |
| $R_{cryst}$ (%) | 25.3 | | | |
| $R_{free}$ (%) | 28.4 | | | |
| Average B (Å$^2$) | 24.8 protein/31.7 solvent | | | |
| No. of water molecules | 88 | | | |
| RMSD bond lengths (Å) | 0.0126 | | | |
| RMSD bond angles (°) | 1.745 | | | |
| RMSD B values (Å$^2$) | 0.837/1.487 bonds/angles main chain | | | |
| | 1.0211/1.594 bonds/angles side chains | | | |

[a]Values in parentheses are for the highest resolution shell (1.73–1.70Å).
$R_{sym}$ = 100 × Σ | I − <I>|/ ΣI where I is the integrated intensity of a given reflection.

TABLE 1-continued

Data Collection, Phase Calculation, and Refinement Statistics

| Wavelength (λ) | 0.9879 | 0.9793 | 0.9790 | 0.9611 |
|---|---|---|---|---|

[b]RMS (Δ |F|) /RMS (|F |) where Δ |F | is the Bijvoet difference at one wavelength (values on the diagonal) or the dispersive differences between two wavelength (values off the diagonal).
[c]Anomalous components of the Se scattering factors as a function of wavelength as determined by SOLVE (Terwilliger and Eisenberg, 1983).
[d]All rounds of refinement included data for which |F |>2.0σ. R value = $\Sigma |F_p(\text{obs}) - F_p(\text{calc})| / \Sigma F_p(\text{obs})$, where $F_p$ is the structure factor amplitude. The free R value was calculated from 10% of the data that was excluded from the refinement (Brünger, 1992).

Amino Acid Residues and the Homer Binding Domain

| Mutation | Expression Level (Western Blot) | Binding[a] |
|---|---|---|
| Homer 2 EVH WT | ++ | +- |
| F7A | − | ND |
| F7R | + | + |
| S8L | + | − |
| N23A | ++ | + |
| S28A | + | − |
| V34M | ++ | + |
| S35V | ++ | + |
| D39A | ++ | − |
| R42E | ++ | − |
| R42A | ++ | + |
| R46A | ++ | − |
| R46C | ++ | + |
| I48A | ++ | + |
| N58A | ++ | + |
| N64G | ++ | + |
| F67S | + | − |
| K69A | ++ | + |
| Q72A | ++ | + |
| F74A | ++ | + |
| F74L | ++ | + |
| F90S | ++ | + |
| E93K | + | + |
| H95A | ++ | + |
| L96S | + | + |
| F109C | ++ | + |

[a](−) indicates substantially reduced binding relative to wild-type (+).

TABLE 2

WASP EVH1 Mutations

| WASP Residue/Mutation | Homer Residue |
|---|---|
| Table 2A - β1 region | |
| *Exposed* | |
| L39M | Met 1 |
| C43W | Pro 5 |
| L46P | Ser 8 |
| T48I | Arg 10 |
| E133K | His 95 |
| *Buried/partially buried* | |
| T45M | Phe 7 |
| A47D | Thr 9 |
| A49E | Ala 11 |
| Table 2B - β3 region | |
| *Exposed* | |
| S82P/F | Arg 42 |
| *Buried/partially buried* | |
| F84L | Val 44 |
| R86C/H/P/L | Arg 46 |
| G89D | Ser 49 |
| Table 2C - Other mutations | |
| *Exposed* | |
| P58L | Pro 18 |
| E131K | Glu 93 |
| *Buried/partially buried* | |
| H68P | Ser 28 |
| V75M | Ser 35 |
| Y107S/C | Phe 67 |
| G125R | Gly 87 |
| F128S | Phe 90 |
| A134T/V | Leu 96 |
| *Other* | |
| A56V | — |
| W97C | — |

Homer Sequence Listing

| SEQ ID No. | Sequence |
|---|---|
| 1 | Human Homer 1a (nucleic acid) |
| 2 | Human Homer 1a (amino acid) |
| 3 | Human Homer 1b (nucleic acid) |
| 4 | Human Homer 1b (amino acid) |
| 5 | Homer 1c (nucleic acid) |
| 6 | Homer 1c (amino acid) |
| 7 | Human Homer 2a (nucleic acid) |
| 8 | Human Homer 2a (amino acid) |
| 9 | Human Homer 2b (nucleic acid) |
| 10 | Human Homer 2b (amino acid) |
| 11 | Human Homer 3 (nucleic acid) |
| 12 | Human Homer 3 (amino acid) |
| 13 | peptide binding—core region: PPXXFR |
| 14 | peptide binding—extended region: ALTPPSPFRD |
| 15 | Homer interacting protein: rat I30 (nucleic acid) |
| 16 | Homer interacting protein: rat I30 (arnino acid) |
| 17 | Homer interacting protein: rat I42 (nucleic acid) |
| 18 | Homer interacting protein: rat I42 (amino acid) |
| 19 | Homer interacting protein: human I30 (nucleic acid) |
| 20 | Homer interacting protein: human I30 (amino acid) |
| 21 | Homer interacting protein: human I42 (nucleie acid) |
| 22 | Homer interacting protein: human I42 (amino acid) |
| 23 | Mouse Homer 1 a (nucleic acid) |
| 24 | Mouse Homer 1 a (amino acid) |
| 25 | Mouse Homer 1b (nucleic acid) |
| 26 | Mouse Homer 1b (amino acid) |
| 27 | Mouse Homer 2a (nucleic acid) |
| 28 | Mouse Homer 2a (amino acid) |
| 29 | Mouse Homer 2b (nucleic acid) |
| 30 | Mouse Homer 2b (amino acid) |
| 31 | Mouse Homer 3 (nucleic acid) |
| 32 | Mouse Homer 3 (amino acid) |
| 33 | Rat Homer 1a (nucleic acid) |
| 34 | Rat Homer 1a (amino acid) |
| 35 | Rat Homer 1b (nucleic acid) |
| 36 | Rat Homer 1b (amino acid) |
| 37 | Rat Homer 1c (nucleic acid) |
| 38 | Rat Homer 1c (amino acid) |
| 39 | Rat Shank 3a (nucleic acid) |
| 40 | Rat Shank 3a (amino acid) |
| 41 | Human Homer 3a (nucleic acid) |

-continued

| Homer Sequence Listing | | |
|---|---|---|
| SEQ ID No. | Sequence | |
| 42 | Human Homer 3a (amino acid) | |
| 43 | Rat NADL partial nucleic acid sequence | |
| 44 | Rat NADL partial amino acid sequence | |

What is claimed is:

1. An isolated nucleic acid encoding Homer protein 1b, wherein said nucleic acid has the nucleotide sequence set forth in SEQ ID NO:3.

2. An expression vector encoding a polynucleotide of claim 1.

3. The expression vector of claim 2, wherein the vector is virus-derived.

4. The expression vector of claim 2, wherein the vector is a plasmid.

5. A host cell comprising a vector of claim 2.

6. The host cell of claim 5, wherein the host cell is a prokaryotic cell.

7. The host cell of claim 5, wherein the host cell is a eukaryotic cell.

* * * * *